(12) United States Patent
Chung et al.

(10) Patent No.: US 10,593,891 B2
(45) Date of Patent: Mar. 17, 2020

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Yeonsook Chung, Seoul (KR); Sangmo Kim, Hwaseong-si (KR); Hyunjung Kim, Suwon-si (KR); Soonok Jeon, Seoul (KR); Yongsik Jung, Yongin-si (KR); Miyoung Chae, Suwon-si (KR); Dalho Huh, Suwon-si (KR); Hosuk Kang, Suwon-si (KR); Jongsoo Kim, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 155 days.

(21) Appl. No.: 15/234,089

(22) Filed: Aug. 11, 2016

(65) Prior Publication Data

US 2017/0047526 A1 Feb. 16, 2017

(30) Foreign Application Priority Data

Aug. 13, 2015 (KR) .................. 10-2015-0114548

(51) Int. Cl.
*H01L 51/54* (2006.01)
*C09K 11/06* (2006.01)
*H01L 51/00* (2006.01)
*C07D 405/14* (2006.01)
*C07D 405/10* (2006.01)
*C07D 495/04* (2006.01)
*C07D 409/10* (2006.01)
*C07D 491/048* (2006.01)
*C09K 11/02* (2006.01)
(Continued)

(52) U.S. Cl.
CPC ........ *H01L 51/0072* (2013.01); *C07D 405/10* (2013.01); *C07D 405/14* (2013.01); *C07D 409/10* (2013.01); *C07D 491/048* (2013.01); *C07D 495/04* (2013.01); *C09K 11/025* (2013.01); *C09K 11/06* (2013.01); *H01L 51/008* (2013.01); *H01L 51/009* (2013.01); *H01L 51/0067* (2013.01); *H01L 51/0071* (2013.01); *H01L 51/0073* (2013.01); *H01L 51/0074* (2013.01); *H01L 51/0085* (2013.01); *C09K 2211/1007* (2013.01); *C09K 2211/1022* (2013.01); *C09K 2211/1044* (2013.01); *H01L 51/506* (2013.01); *H01L 51/5016* (2013.01); *H01L 51/56* (2013.01)

(58) Field of Classification Search
CPC .. C07D 417/00; C07D 417/02; C07D 417/04; C07D 417/10; C07D 417/14; C07D 491/00; C07D 491/02; C07D 491/04; C07D 491/044; C07D 491/048; C07D 493/00; C07D 493/02; C07D 493/04; C07D 495/00; C07D 495/02; C07D 495/04; C09K 11/025; C09K 11/06; C09K 2211/00; C09K 2211/10; C09K 2211/1007; C09K 2211/1022; C09K 2211/1044; H01L 51/0032; H01L 51/005; H01L 51/0059; H01L 51/006; H01L 51/0061; H01L 51/0067; H01L 51/0071; H01L 51/0072; H01L 51/0073; H01L 51/0074; H01L 51/0079; H01L 51/008; H01L 51/0084; H01L 51/0085; H01L 51/009; H01L 51/50; H01L 51/5012; H01L 51/5016; H01L 51/506; H01L 51/5056; H01L 51/56
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2009/0030202 A1 1/2009 Iwakuma et al.
2009/0072727 A1* 3/2009 Takeda .................. C09K 11/06
313/504

FOREIGN PATENT DOCUMENTS

EP 2878599 A1 6/2015
EP 2966146 A1 1/2016
EP 3015457 A1 5/2016
(Continued)

OTHER PUBLICATIONS

Deng et al. J. Mater. Chem. C 2013, 1, 8140-8145. (Year: 2013).*
(Continued)

*Primary Examiner* — Andrew K Bohaty
(74) *Attorney, Agent, or Firm* — Cantor Colburn LLP

(57) ABSTRACT

A condensed cyclic compound represented by Formula 1:

Formula 1

(Continued)

wherein, in Formula 1, groups and variables are the same as described in the specification.

21 Claims, 1 Drawing Sheet

(51) Int. Cl.
    *H01L 51/50*     (2006.01)
    *H01L 51/56*     (2006.01)

(56)     References Cited

FOREIGN PATENT DOCUMENTS

| KR | 10-2011-0088427 A | 8/2011 |
| WO | 2012-093862 A2 | 7/2012 |
| WO | 2014-208698 A1 | 12/2014 |

OTHER PUBLICATIONS

Lee et al. Organic Electronics 2013, 14, 1009-1014. (Year: 2013).*
Lin et al. J. Mater. Chem. 2012, 22, 16114-16120. (Year: 2012).*
Extended Search Report dated Oct. 21, 2016, issued by the European Patent Office for Application No. 16183873.5-1462.
English Translation of WO 2014-208698, 42 pp.
Office Action issued by the European Patent Office dated Jul. 25, 2018 in the examination of the European Patent Application No. 16183873.5-1110.

* cited by examiner

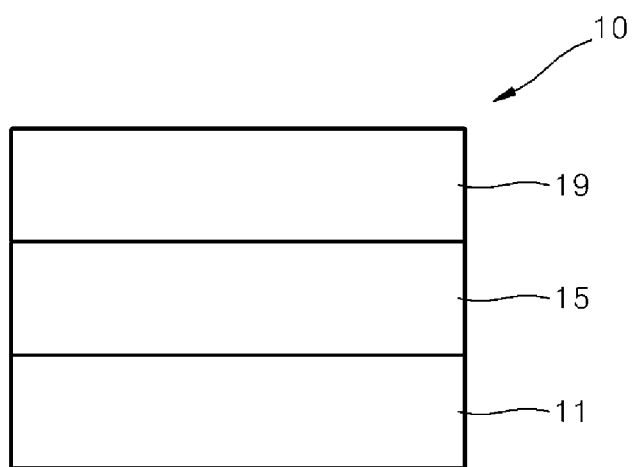

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0114548, filed on Aug. 13, 2015, in the Korean Intellectual Property Office, the content of which is incorporated herein in its entirety by reference.

BACKGROUND

1. Field

The present disclosure relates to a condensed cyclic compound and an organic light-emitting device including the condensed cyclic compound.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons change from an excited state to a ground state to thereby generate light.

Different types of organic light emitting devices are known. However, there still remains a need in OLEDs having low driving voltage, high efficiency, high brightness, and long lifespan.

SUMMARY

Provided are a condensed cyclic compound and an organic light-emitting device including the condensed cyclic compound.

Additional aspects will be set forth in part in the description which follows and, in part, will be apparent from the description, or may be learned by practice of the presented exemplary embodiments.

According to an aspect of an exemplary embodiment, provided is a condensed cyclic compound represented by Formula 1:

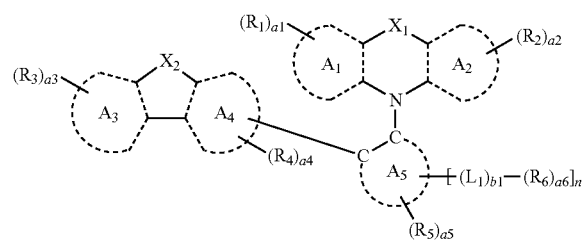

Formula 1 wherein, in Formula 1, $X_1$ may be selected from a single bond, O, S, N($R_{11}$) and C($R_{12}$)($R_{13}$), $X_2$ may be O or S, ring $A_1$ to ring $A_4$ may each independently be a $C_5$-$C_{60}$ carbocyclic group or a $C_2$-$C_{60}$ heterocyclic group, ring $A_5$ may be selected from a benzene, a pyridine, a pyrimidine, a pyrazine, a pyridazine and a triazine, $R_1$ to $R_6$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$) and —B($Q_6$)($Q_7$), a1 may be an integer of 1 to 4, a2 to a6 may be each independently an integer of 0 to 4, $L_1$ may be selected from a phenylene group, a pyridinylene group, a pyrimidinylene group, a pyrazinylene group, a pyridazinylene group and a triazinylene group; and a phenylene group, a pyridinylene group, a pyrimidinylene group, a pyrazinylene group, a pyridazinylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$), b1 may be an integer of 1 to 3, n may be an integer of 0 to 3, the number of cyano groups in Formula 1 may be 1, 2, 3 or 4, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group and substituted monovalent non-aromatic condensed heteropolycyclic group may be selected from a deuterium, —F, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group and a C$_1$-C$_{60}$ alkoxy group;

a C$_1$-C$_{60}$ alkyl group, a C$_2$-C$_{60}$ alkenyl group, a C$_2$-C$_{60}$ alkynyl group and a C$_1$-C$_{60}$ alkoxy group, each substituted with at least one selected from a deuterium, —F, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_1$-C$_{60}$ heteroaryloxy group, a C$_1$-C$_{60}$ heteroarylthio group, a C$_2$-C$_{60}$ heteroarylalkyl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$) and —B(Q$_{16}$)(Q$_{17}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_1$-C$_{60}$ heteroaryloxy group, a C$_1$-C$_{60}$ heteroarylthio group, a C$_2$-C$_{60}$ heteroarylalkyl group, a monovalent non-aromatic condensed polycyclic group and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_1$-C$_{60}$ heteroaryloxy group, a C$_1$-C$_{60}$ heteroarylthio group, a C$_2$-C$_{60}$ heteroarylalkyl group, a monovalent non-aromatic condensed polycyclic group and a monovalent non-aromatic condensed heteropolycyclic group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_7$-C$_{60}$ arylalkyl group, a C$_1$-C$_{60}$ heteroaryl group, a C$_1$-C$_{60}$ heteroaryloxy group, a C$_1$-C$_{60}$ heteroarylthio group, a C$_2$-C$_{60}$ heteroarylalkyl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$) and —B(Q$_{26}$)(Q$_{27}$), and —Si(Q$_{31}$)(Q$_{32}$)(Q$_{33}$), —N(Q$_{34}$)(Q$_{35}$) and —B(Q$_{36}$)(Q$_{37}$), Q$_1$ to Q$_{10}$, Q$_{11}$ to Q$_{17}$, Q$_{21}$ to Q$_{27}$ and Q$_{31}$ to Q$_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_7$-C$_{60}$ arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group and a substituted or unsubstituted monovalent non-aromatic condensed heteropolycyclic group.

According to an aspect of another exemplary embodiment, provided is an organic light-emitting device including:

a first electrode;

a second electrode; and an organic layer disposed between the first electrode and the second electrode, wherein the organic layer includes an emission layer and at least one condensed cyclic compound represented by Formula 1.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 illustrates a schematic view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect, provided is a condensed cyclic compound represented by Formula 1:

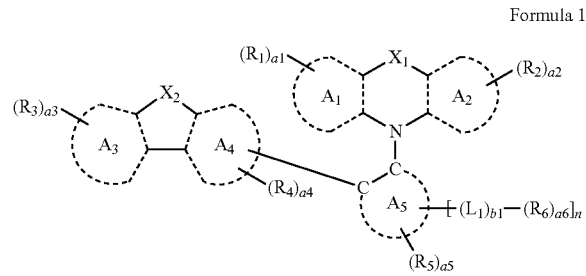

Formula 1

$X_1$ in Formula 1 may be selected from a single bond, O, S, $N(R_{11})$ and $C(R_{12})(R_{13})$, and $X_2$ may be O or S. Descriptions of $R_{11}$ to $R_{13}$ may be understood by referring to the descriptions below.

According to an embodiment, $X_1$ in Formula 1 may be a single bond, but embodiments are not limited thereto.

Ring $A_1$ to ring $A_4$ in Formula 1 may each independently be a $C_5$-$C_{60}$ carbocyclic group or a $C_2$-$C_{60}$ heterocyclic group.

For example, ring $A_1$ to ring $A_4$ in Formula 1 may be each independently selected from a benzene, a pyridine, a pyrimidine, a pyrazine, a pyridazine, a naphthalene, a quinoline, an isoquinoline, a quinoxaline, a quinazoline, a cinnoline, an indene, an indole, a benzofuran, a benzothiophene, a fluorene, a carbazole, a dibenzofuran and a dibenzothiophene.

According to an embodiment, ring $A_1$ to ring $A_4$ in Formula 1 may be each independently selected from a benzene, a benzofuran, a benzothiophene, a fluorene, a carbazole, a dibenzofuran and a dibenzothiophene.

In some embodiments, ring $A_1$ to ring $A_4$ in Formula 1 may be each independently selected from a benzene, a fluorene, a carbazole, a dibenzofuran and a dibenzothiophene.

In some embodiments, ring $A_1$ to ring $A_4$ in Formula 1 may be each independently selected from a benzene, a fluorene, a carbazole, a dibenzofuran and a dibenzothiophene, at least one of ring $A_1$ and ring $A_2$ may be a benzene, and at least one of ring $A_3$ and ring $A_4$ may be a benzene.

In some embodiments, in Formula 1, ring $A_1$ and ring $A_2$ may be each independently selected from a benzene, a dibenzofuran and a dibenzothiophene; ring $A_3$ and ring $A_4$ may be each independently selected from a benzene, a fluorene, a carbazole, a dibenzofuran and a dibenzothiophene; at least one of ring $A_1$ and ring $A_2$ may be a benzene; and at least one of ring $A_3$ and ring $A_4$ may be a benzene, but embodiments are not limited thereto.

Ring $A_5$ in Formula 1 may be selected from a benzene, a pyridine, a pyrimidine, a pyrazine, a pyridazine and a triazine. For example, ring $A_5$ may be a benzene, but embodiments are not limited thereto.

$R_1$ to $R_6$ and $R_{11}$ to $R_{13}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$) and —B($Q_6$)($Q_7$).

For example, $R_1$ to $R_6$ and $R_{11}$ to $R_{13}$ in Formula 1 may be each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group and a quinazolinyl group.

According to an embodiment, $R_1$ to $R_6$ and $R_{11}$ to $R_{13}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, a pyridinyl group, a pyrimidinyl group, a pyrazinyl group, a pyridazinyl group and a triazinyl group;

a phenyl group, a naphthyl group, a pyridinyl group, a pyrimidinyl group, a pyrazinyl group, a pyridazinyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group and a triazinyl group, but embodiments are not limited thereto.

In some embodiments, $R_1$ to $R_6$ and $R_{11}$ to $R_{13}$ in Formula 1 may be each independently selected from a hydrogen, a deuterium, a cyano group, a $C_1$-$C_{10}$ alkyl group and a $C_1$-$C_{10}$ alkoxy group;

a $C_1$-$C_{10}$ alkyl group and a $C_1$-$C_{10}$ alkoxy group, each substituted with at least one selected from a deuterium and a cyano group;

a phenyl group, a pyridinyl group, a pyrimidinyl group and a triazinyl group;

a phenyl group, a pyridinyl group, a pyrimidinyl group and a triazinyl group, each substituted with at least one selected from a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group.

a1 in Formula 1 denotes the number of $R_{1(s)}$ and may be an integer of 1 to 4. When a1 is 2 or more, two or more $R_{1(s)}$ may be the same or different. Descriptions of a2 to a6 may be understood by referring to the description of a1 and Formula 1.

a1 in Formula 1 may be an integer of 1 to 4 and a2 to a6 in Formula 1 may each independently be an integer of 0 to 4. For example, a1 in Formula 1 may be 1, 2 or 3 and a2 to a6 in Formula 1 may each independently be 0, 1, 2 or 3.

$L_1$ in Formula 1 may be selected from a phenylene group, a pyridinylene group, a pyrimidinylene group, a pyrazinylene group, a pyridazinylene group and a triazinylene group; and a phenylene group, a pyridinylene group, a pyrimidinylene group, a pyrazinylene group, a pyridazinylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$).

For example, $L_1$ in Formula 1 may be selected from a phenylene group, a pyridinylene group, a pyrimidinylene group and a triazinylene group; and a phenylene group, a pyridinylene group, a pyrimidinylene group and a triazinylene group, each substituted with at least one selected from a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$), wherein $Q_8$ to $Q_{10}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group, but embodiments are not limited thereto.

According to an embodiment, $L_1$ in Formula 1 may be selected from groups represented by Formulae 3-1 to 3-40:


Formula 3-1

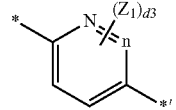

Formula 3-2

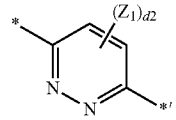

Formula 3-3

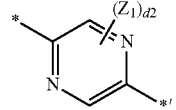

Formula 3-4

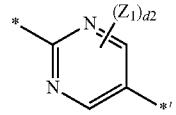

Formula 3-5


Formula 3-6

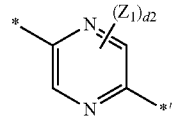

Formula 3-7

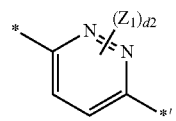

Formula 3-8

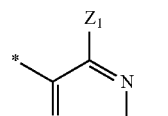

Formula 3-9

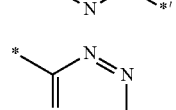

Formula 3-10

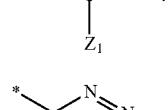

Formula 3-11

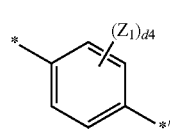

Formula 3-12

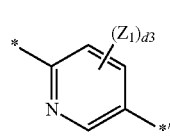

Formula 3-13

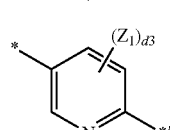

Formula 3-14

Formula 3-15

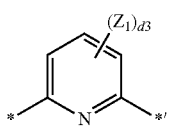
Formula 3-16
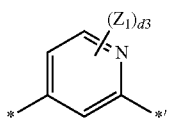
Formula 3-17
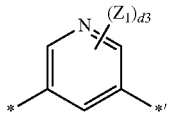
Formula 3-18
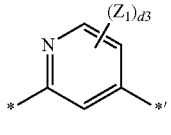
Formula 3-19
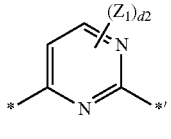
Formula 3-20
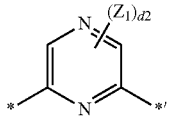
Formula 3-21
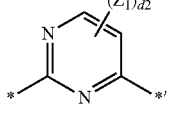
Formula 3-22
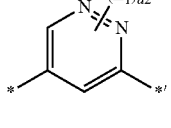
Formula 3-23
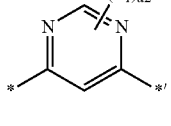
Formula 3-24

Formula 3-25
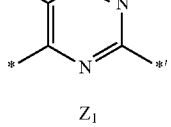
Formula 3-26
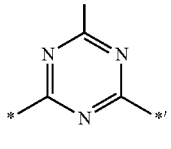
Formula 3-27
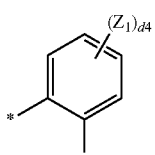
Formula 3-28
Formula 3-29
Formula 3-30
Formula 3-31
Formula 3-32
Formula 3-33
Formula 3-34
Formula 3-35
Formula 3-36

-continued

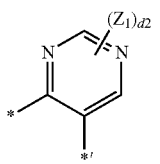
Formula 3-37

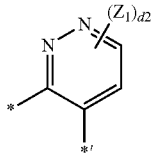
Formula 3-38

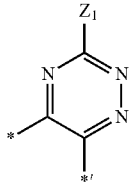
Formula 3-39

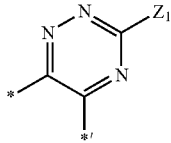
Formula 3-40

In Formulae 3-1 to 3-40, $Z_1$ may be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$) (for example, a hydrogen, a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$)), $Q_8$ to $Q_{10}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group, d4 may be an integer of 0 to 4, d3 may be an integer of 0 to 3, d2 may be an integer of 0 to 2, and each of * and *' is a binding site to a neighboring atom.

According to an embodiment, at least one of groups $L_1$ in the number of b1 may be selected from groups represented by Formulae 3-15 to 3-40.

In some embodiments, all of groups $L_1$ in the number of b1 may be each independently selected from groups represented by Formulae 3-15 to 3-40.

b1 in Formula 1 denotes the number of groups $L_1$ and may be integer of 1 to 3. When b1 is 2 or more, two or more groups $L_1$ may be the same or different.

According to an embodiment, a group represented by *-($L_1$)$_{b1}$-*' in Formula 1 may be selected from groups represented by Formulae 4-1 to 4-39:

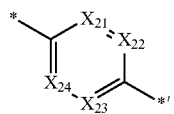
Formula 4-1

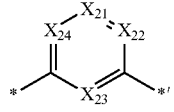
Formula 4-2

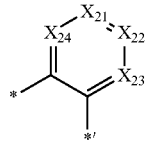
Formula 4-3

Formula 4-4

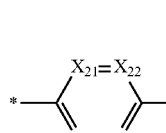
Formula 4-5

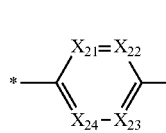
Formula 4-6

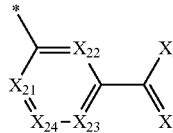
Formula 4-7

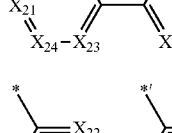
Formula 4-8

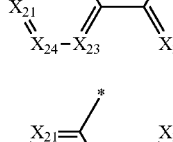
Formula 4-9

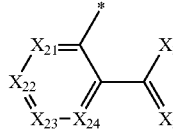
Formula 4-10

Formula 4-11

Formula 4-12
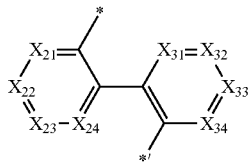
Formula 4-13
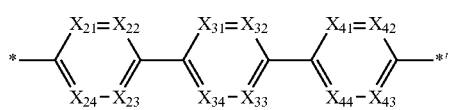
Formula 4-14
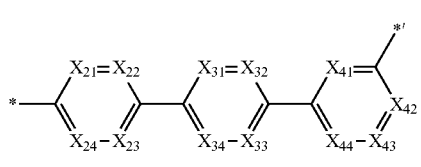
Formula 4-15
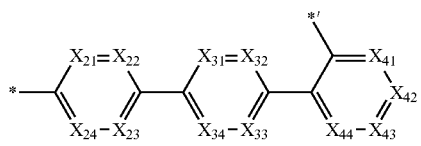
Formula 4-16
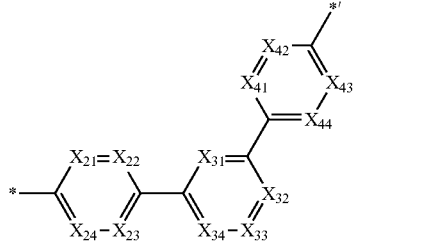
Formula 4-17
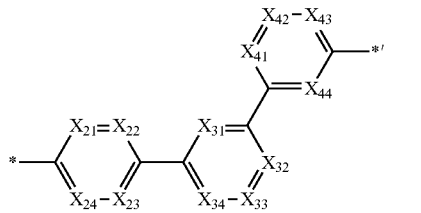
Formula 4-18
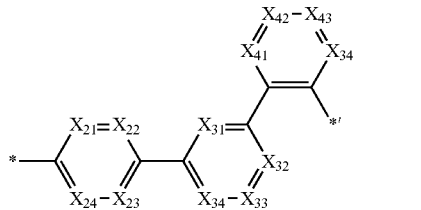
Formula 4-19
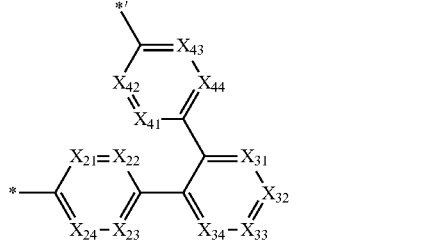
Formula 4-20
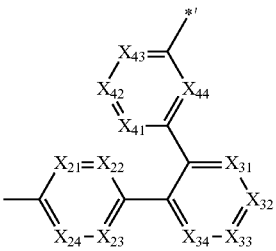
Formula 4-21
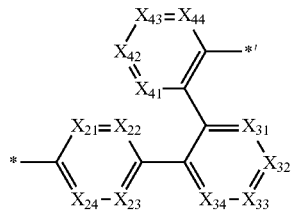
Formula 4-22
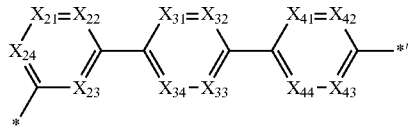
Formula 4-23
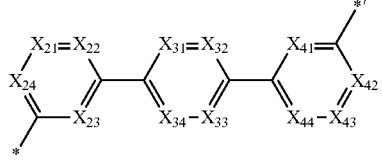
Formula 4-24
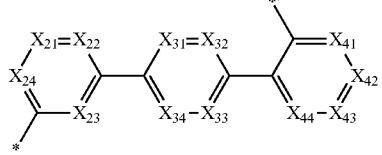
Formula 4-25
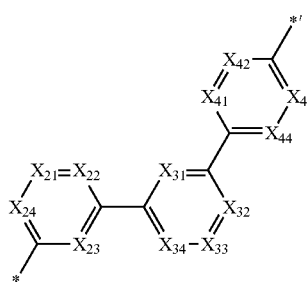
Formula 4-26
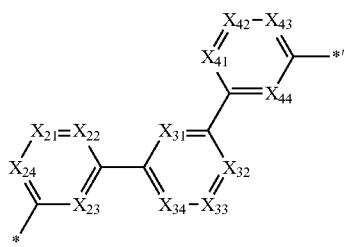

Formula 4-27
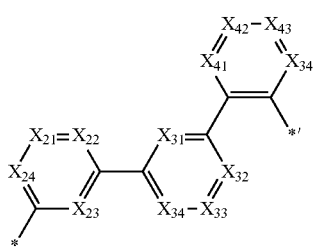
Formula 4-28
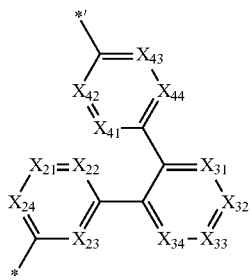
Formula 4-29
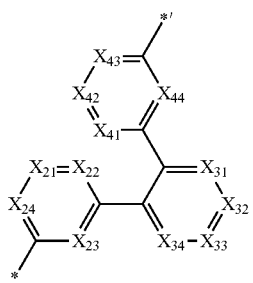
Formula 4-30
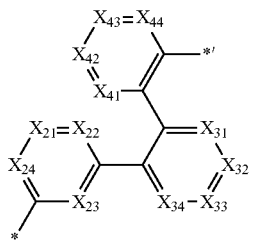
Formula 4-31
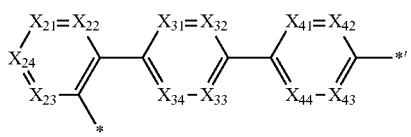
Formula 4-32
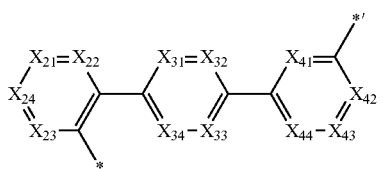
Formula 4-33
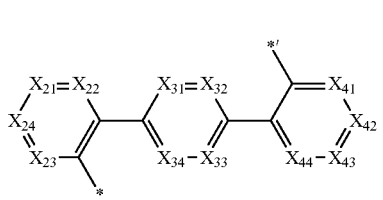
Formula 4-34
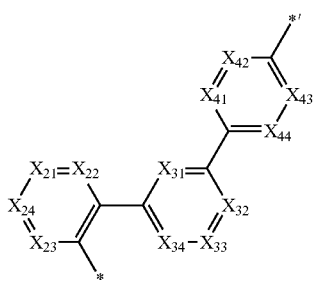
Formula 4-35
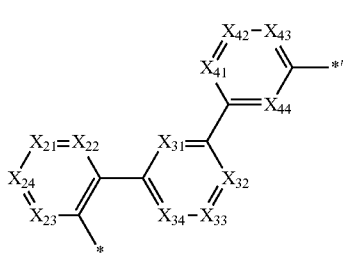
Formula 4-36
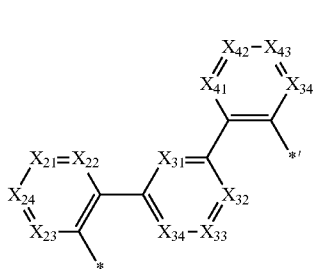
Formula 4-37
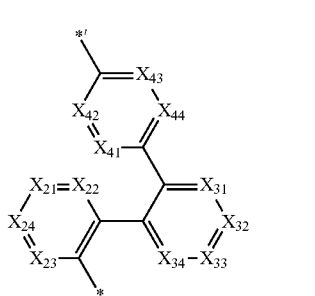
Formula 4-38
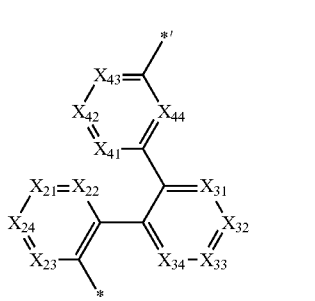
Formula 4-39
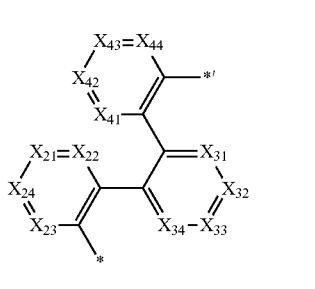

In Formula 4-1 to 4-39, $X_{21}$ may be N or $C(Z_{21})$, $X_{22}$ may be N or $C(Z_{22})$, $X_{23}$ may be N or $C(Z_{23})$, $X_{24}$ may be N or $C(Z_{24})$, $X_{31}$ may be N or $C(Z_{31})$, $X_{32}$ may be N or $C(Z_{32})$, $X_{33}$ may be N or $C(Z_{33})$, $X_{34}$ may be N or $C(Z_{34})$, $X_{41}$ may be N or $C(Z_{41})$, $X_{42}$ may be N or $C(Z_{42})$, $X_{43}$ may be N or $C(Z_{43})$, $X_{44}$ may be N or $C(Z_{44})$, provided that all of $X_{21}$ to $X_{24}$ are not N, provided that all of $X_{31}$ to $X_{34}$ are not N, and provided that all of $X_{41}$ to $X_{44}$ are not N, $Z_{21}$ to $Z_{24}$, $Z_{31}$ to $Z_{34}$, and $Z_{41}$ to $Z_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —$Si(Q_8)(Q_9)(C)_{10}$) (for example, a hydrogen, a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —$Si(Q_8)(Q_9)(Q_{10})$), $Q_8$ to $Q_{10}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group, and each of * and *' is a binding site to a neighboring atom.

For example, in Formulae 4-1 to 4-39, $X_{21}$ may be $C(Z_{21})$, $X_{22}$ may be $C(Z_{22})$, $X_{23}$ may be $C(Z_{23})$, $X_{24}$ may be $C(Z_{24})$, $X_{31}$ may be $C(Z_{31})$, $X_{32}$ may be $C(Z_{32})$, $X_{33}$ may be $C(Z_{33})$, $X_{34}$ may be $C(Z_{34})$, $X_{41}$ may be $C(Z_{41})$, $X_{42}$ may be $C(Z_{42})$, $X_{43}$ may be $C(Z_{43})$, and $X_{44}$ may be $C(Z_{44})$.

In some embodiments, one of $X_{21}$ to $X_{24}$ in Formulae 4-1 to 4-3 may be N, and the others thereof may not be N.

n in Formula 1 denotes the number of groups represented by *-$(L_1)_{b1}$-$(R_6)_{a6}$ and may be an integer of 0 to 3. For example, n in Formula 1 may be 0 or 1, but embodiments are not limited thereto.

The number of cyano groups in Formula 1 may be 1, 2, 3 or 4. For example, the number of cyano groups in Formula 1 may be 1 or 2, but embodiments are not limited thereto.

When the number of cyano groups in Formula 1 is 1, a cyano group in Formula 1 may be included in one of ring $A_2$, ring $A_3$, ring $A_4$, ring $A_5$, groups $L_1$ in the number of b1 and groups $R_6$ in the number of a6.

When the number of cyano groups in Formula 1 is 2, cyano groups in Formula 1 may be included in two of ring $A_2$, ring $A_3$, ring $A_4$, ring $A_5$, $L_1$ in the number of b1 and $R_6$ in the number of a6.

According to an embodiment, in Formula 1, one to four of groups $R_2$ in the number of a2 may be each independently a cyano group or a cyano group-substituted $C_6$-$C_{10}$ aryl group;

one to four of groups $R_3$ in the number of a3 may be each independently a cyano group or a cyano group-substituted $C_6$-$C_{10}$ aryl group;

one to three of groups $R_4$ in the number of a4 may be each independently a cyano group or a cyano group-substituted $C_6$-$C_{10}$ aryl group;

one to three of groups $R_5$ in the number of a5 may be each independently a cyano group or a cyano group-substituted $C_6$-$C_{10}$ aryl group;

i) one or two of groups $R_5$ in the number of a5 and ii) one or two of groups $R_2$ in the number of a2 may be each independently a cyano group or a cyano group-substituted $C_6$-$C_{10}$ aryl group;

i) one or two of groups $R_5$ in the number of a5 and ii) one or two of groups $R_3$ in the number of a3 may be each independently a cyano group or a cyano group-substituted $C_6$-$C_{10}$ aryl group;

i) one or two of groups $R_5$ in the number of a5 and ii) one or two of groups $R_4$ in the number of a4 may be each independently a cyano group or a cyano group-substituted $C_6$-$C_{10}$ aryl group;

i) one or two of groups $R_2$ in the number of a2 and ii) one or two of groups $R_3$ in the number of a3 may be each independently a cyano group or a cyano group-substituted $C_6$-$C_{10}$ aryl group;

i) one or two of groups $R_2$ in the number of a2 and ii) one or two of groups $R_4$ in the number of a4 may be each independently a cyano group or a cyano group-substituted $C_6$-$C_{10}$ aryl group; or i) one or two of groups $R_3$ in the number of a3 and ii) one or two of groups $R_4$ in the number of a4 may be each independently a cyano group or a cyano group-substituted $C_6$-$C_{10}$ aryl group.

Detailed examples of "a cyano group-substituted $C_6$-$C_{10}$ aryl group" as described herein may include a phenyl group substituted with at least one cyano group, but embodiments are not limited thereto.

A condensed cyclic compound represented by Formula 1 may be represented by one of Formulae 1A to 1H:

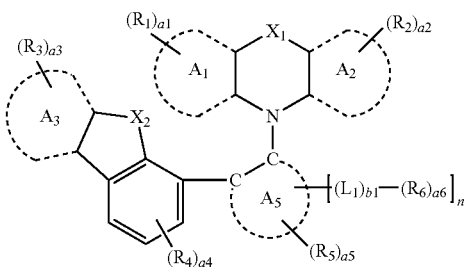

Formula 1A

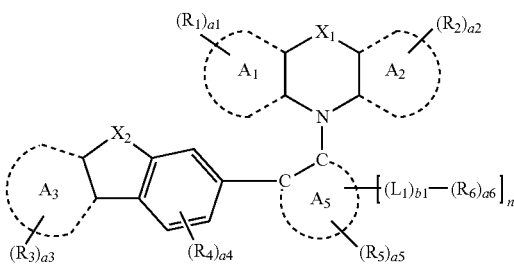

Formula 1B

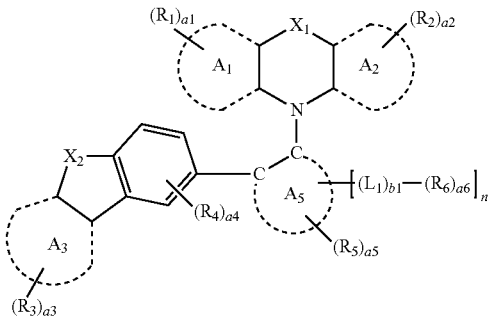

Formula 1C

-continued

Formula 1D

Formula 1E

Formula 1F

Formula 1G

-continued

Formula 1H

Formula 2A

Formula 2B

In Formulae 1A to 1H, 2A and 2B, descriptions of $X_1$, $X_2$, ring $A_1$, ring $A_2$, ring $A_5$, $R_1$ to $R_6$, a1 to a6, $L_1$, b1 and n are the same as described herein, ring $A_3$ may be selected from a benzene, a pyridine, a pyrimidine, a pyrazine, a pyridazine, an indene, an indole, a benzofuran, a benzothiophene, a fluorene, a carbazole, a dibenzofuran and a dibenzothiophene, ring $A_6$ may be represented by Formula 2A, ring $A_7$ may be represented by Formula 2B, $X_4$ may be selected from O, S, N($R_{4c}$) and C($R_{4d}$)($R_{4e}$), descriptions of $R_{4a}$ to $R_{4e}$ are the same as the description of $R_4$, aa4 may be an integer of 0 to 3, and ab4 may be an integer of 0 to 2.

According to an embodiment, in Formulae 1A to 1H, $X_1$ may be a single bond, ring $A_1$ and ring $A_2$ may be each independently selected from a benzene, a fluorene, a carbazole, a dibenzofuran and a dibenzothiophene, and at least one of ring $A_1$ and ring $A_2$ may be a benzene, ring $A_3$ in Formulae 1A to 1D may be each independently selected from a benzene, a fluorene, a carbazole, a dibenzofuran and a dibenzothiophene, and ring $A_3$ in Formulae 1E to 1H may be a benzene, ring $A_5$ may be a benzene, $R_1$ to $R_6$ and $R_{4a}$ to $R_{4e}$ may be each independently selected from a hydrogen, a deuterium, a cyano group, a $C_1$-$C_{10}$ alkyl group and a $C_1$-$C_{10}$ alkoxy group;

a $C_1$-$C_{10}$ alkyl group and a $C_1$-$C_{10}$ alkoxy group, each substituted with at least one selected from a deuterium and a cyano group;

a phenyl group, a pyridinyl group, a pyrimidinyl group and a triazinyl group;

a phenyl group, a pyridinyl group, a pyrimidinyl group and a triazinyl group, each substituted with at least one selected from a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_{31}$)($Q_{32}$)($Q_{33}$); and —Si(Q$_1$)(Q$_2$)(Q$_3$), a1 may be an integer of 1 to 3, a2 to a6 may each independently be an integer of 0 to 3, aa4 and ab4 may each independently be an integer of 0 to 2, L$_1$ may be selected from a phenylene group, a pyridinylene group, a pyrimidinylene group and a triazinylene group; and a phenylene group, a pyridinylene group, a pyrimidinylene group and a triazinylene group, each substituted with at least one selected from a deuterium, a cyano group, a C$_1$-C$_{10}$ alkyl group, a C$_1$-C$_{10}$ alkoxy group, a phenyl group, a pyridinyl group, a pyrimidinyl group, a triazinyl group and —Si(Q$_8$)(Q$_9$)(Q$_{10}$), b1 may be 1 or 2, and n may be 0 or 1, wherein Q$_1$ to Q$_3$, Q$_{31}$ to Q$_{33}$, and Q$_8$ to Q$_{10}$ may be each independently selected from a hydrogen, a C$_1$-C$_{10}$ alkyl group, a C$_1$-C$_{10}$ alkoxy group, a phenyl group, a pyridinyl group, a pyrimidinyl group and a triazinyl group.

In Formulae 1A to 1H, one to three of groups R$_2$ in the number a2 may be each independently a cyano group or a cyano group-substituted C$_6$-C$_{10}$ aryl group;

one to three of groups R$_3$ in the number of a3 may be each independently a cyano group or a cyano group-substituted C$_6$-C$_{10}$ aryl group;

one to three of groups R$_4$ in the number of a4 (or, one to three of groups R$_{4a}$ in the number of aa4) may be each independently a cyano group or a cyano group-substituted C$_6$-C$_{10}$ aryl group;

one to three of groups R$_5$ in the number of a5 may be each independently a cyano group or a cyano group-substituted C$_6$-C$_{10}$ aryl group;

i) one or two of groups R$_5$ in the number of a5 and ii) one or two of groups R$_2$ in the number of a2 may be each independently a cyano group or a cyano group-substituted C$_6$-C$_{10}$ aryl group;

i) one or two of groups R$_5$ in the number of a5 and ii) one or two of groups R$_3$ in the number of a3 may be each independently a cyano group or a cyano group-substituted C$_6$-C$_{10}$ aryl group;

i) one or two of groups R$_5$ in the number of a5 and ii) one or two of groups R$_4$ in the number of a4 (or, one or two of groups R$_{4a}$ in the number of aa4) may be each independently a cyano group or a cyano group-substituted C$_6$-C$_{10}$ aryl group;

i) one or two of groups R$_2$ in the number of a2 and ii) one or two of groups R$_3$ in the number of a3 may be each independently a cyano group or a cyano group-substituted C$_6$-C$_{10}$ aryl group;

i) one or two of groups R$_2$ in the number of a2 and ii) one or two of groups R$_4$ in the number of a4 (or, one or two of groups R$_{4a}$ in the number of aa4) may be each independently a cyano group or a cyano group-substituted C$_6$-C$_{10}$ aryl group; or i) one or two of groups R$_3$ in the number of a3 and ii) one or two of groups R$_4$ in the number of a4 (or, one or two of groups R$_{4a}$ in the number of aa4) may be each independently a cyano group or a cyano group-substituted C$_6$-C$_{10}$ aryl group.

For example, a condensed cyclic compound represented by Formula 1 may be represented by one of Formulae 1-1 to 1-19:

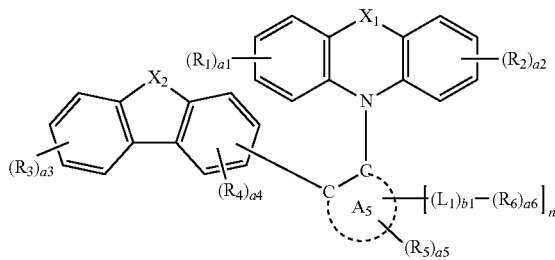

Formula 1-1

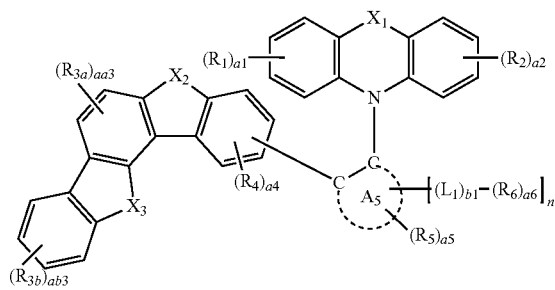

Formula 1-2

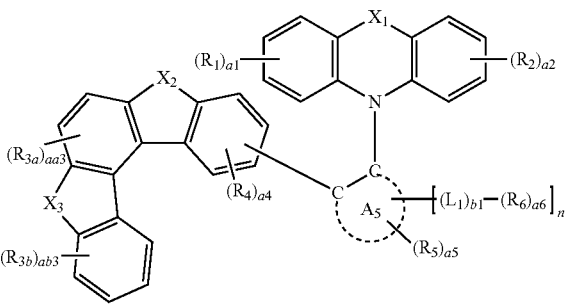

Formula 1-3

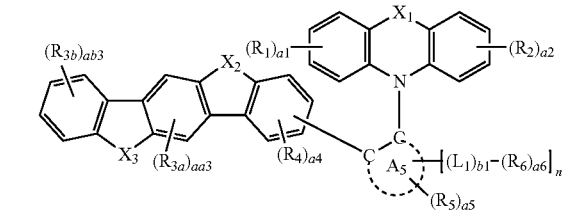

Formula 1-4

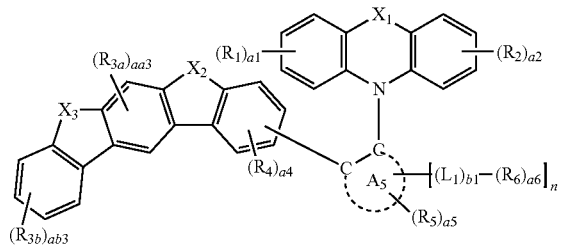

Formula 1-5

Formula 1-6
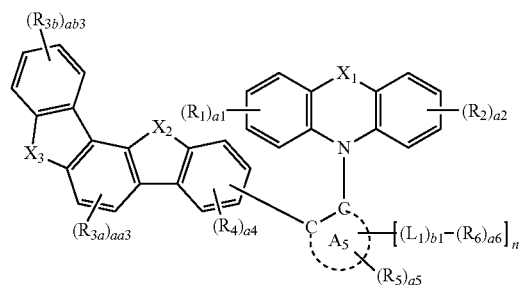
Formula 1-7
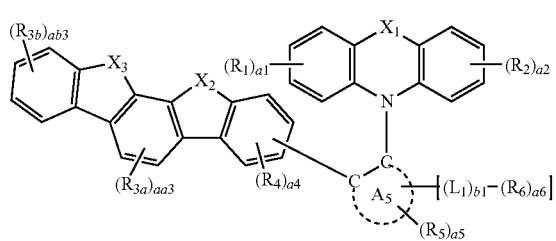
Formula 1-8
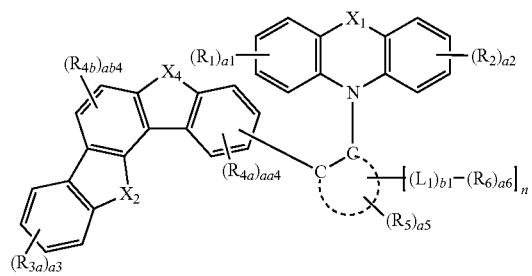
Formula 1-9
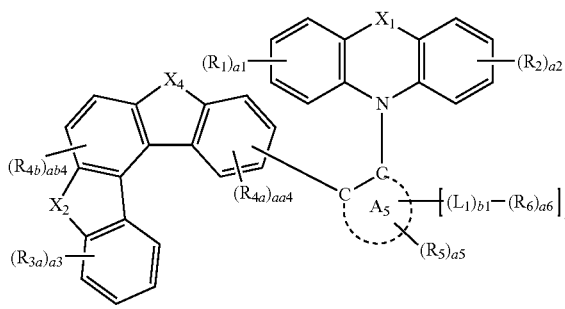
Formula 1-10
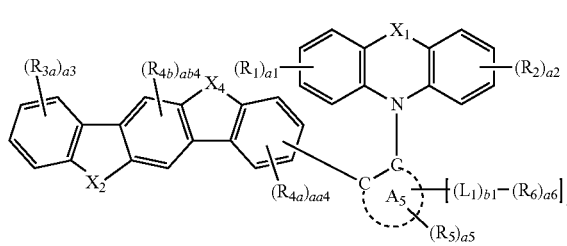
Formula 1-11
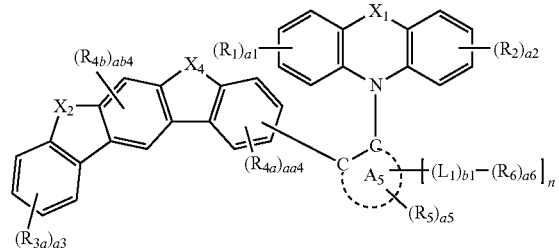
Formula 1-12
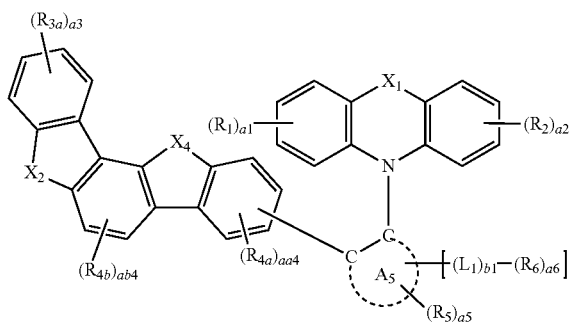
Formula 1-13
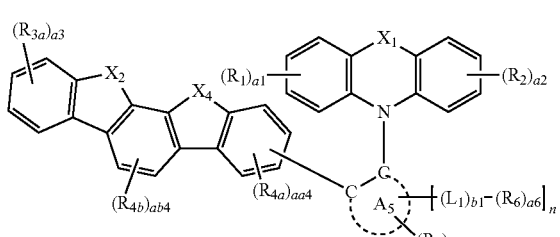
Formula 1-14
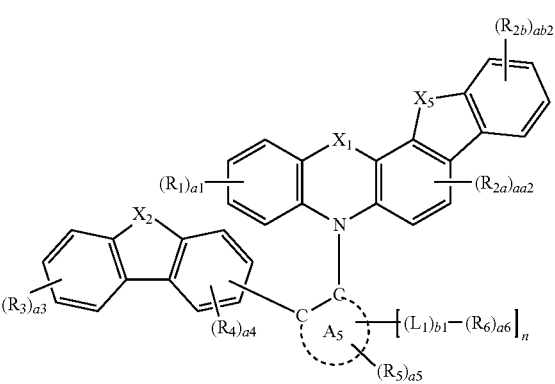

-continued

Formula 1-15

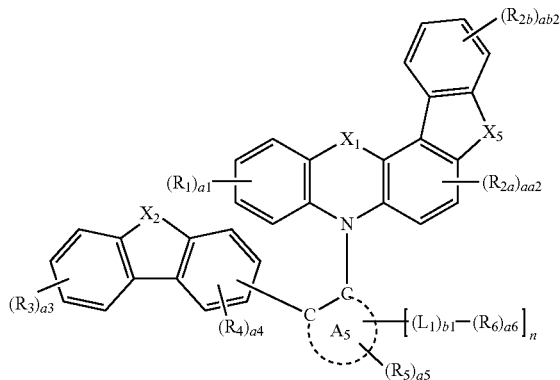

Formula 1-16

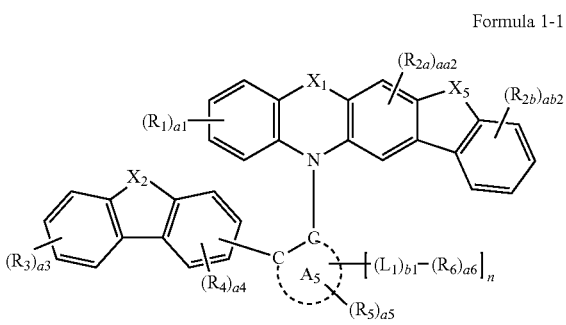

Formula 1-17

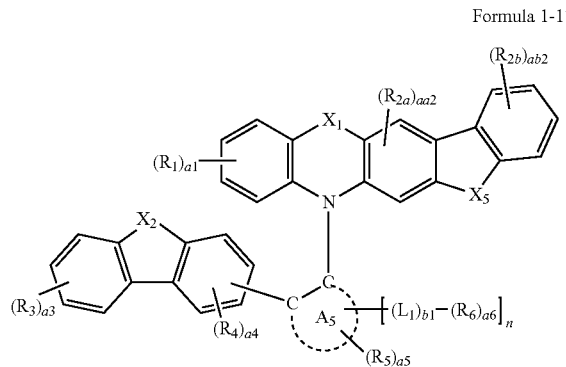

Formula 1-18

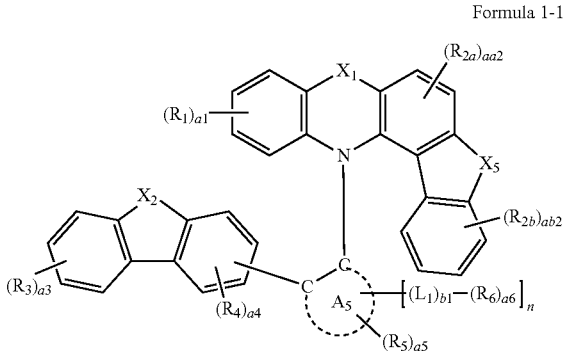

Formula 1-19

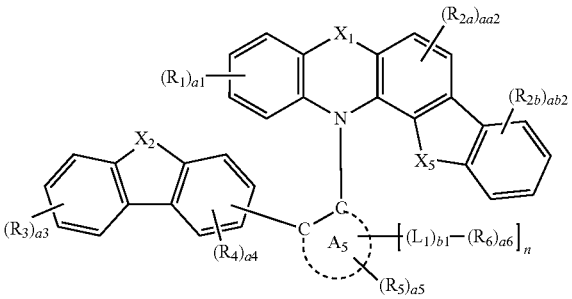

In Formulae 1-1 to 1-19, descriptions of $X_1$, $X_2$, ring $A_5$, $R_1$ to $R_6$, a1 to a6, $L_1$, b1 and n are the same as described herein, $X_3$ may be selected from O, S, $N(R_{3c})$ and $C(R_{3d})(R_{3e})$, $X_4$ may be selected from O, S, $N(R_{4c})$ and $C(R_{4d})(R_{4e})$, $X_5$ may be selected from O, S, $N(R_{2c})$ and $C(R_{2d})(R_{2e})$, descriptions of $R_{2a}$ to $R_{2e}$ are the same as the description of $R_2$, descriptions of $R_{3a}$ to $R_{3e}$ are the same as the description of $R_3$, descriptions of $R_{4a}$ to $R_{4e}$ are the same as the description of $R_4$, aa2 and aa3 may be an integer of 0 to 2, ab2 and ab3 may be an integer of 0 to 4, aa4 may be an integer of 0 to 3, and ab4 may be an integer of 0 to 2.

According to an embodiment, in Formulae 1-1 to 1-19, $X_1$ may be a single bond, $X_3$ may be selected from O, S, $N(R_{3c})$ and $C(R_{3d})(R_{3e})$, $X_4$ may be selected from O, S, $N(R_{4c})$ and $C(R_{4d})(R_{4e})$, $X_5$ may be O or S, ring $A_5$ may be a benzene, $R_1$ to $R_6$, $R_{2a}$ to $R_{2e}$, $R_{3a}$ to $R_{3e}$, and $R_{4a}$ to $R_{4e}$ may be each independently selected from a hydrogen, a deuterium, a cyano group, a $C_1$-$C_{10}$ alkyl group and a $C_1$-$C_{10}$ alkoxy group;

$C_1$-$C_{10}$ alkyl group and $C_1$-$C_{10}$ alkoxy group, each substituted with at least one selected from a deuterium and a cyano group;

a phenyl group, a pyridinyl group, a pyrimidinyl group and a triazinyl group;

a phenyl group, a pyridinyl group, a pyrimidinyl group and a triazinyl group, each substituted with at least one selected from a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_{31}$)($Q_{32}$)($Q_{33}$); and —Si($Q_1$)($Q_2$)($Q_3$), a1 may be an integer of 1 to 3, a2 to a6 may each independently be an integer of 0 to 3, $L_1$ may be selected from a phenylene group, a pyridinylene group, a pyrimidinylene group and a triazinylene group; and a phenylene group, a pyridinylene group, a pyrimidinylene group and a triazinylene group, each substituted with at least one selected from a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$), b1 may be 1 or 2, n may be 0 or 1, and $Q_1$ to $Q_3$, $Q_{31}$ to $Q_{33}$, and $Q_8$ to $Q_{10}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group.

In Formulae 1-1 to 1-19, one to three of groups $R_2$ in the number of a2 (or, one to three of groups $R_{2b}$ in the number of ab2) may be each independently a cyano group or a cyano group-substituted $C_6$-$C_{10}$ aryl group;

one to three of groups $R_3$ in the number of a3 (or, one to three of groups $R_{3b}$ in the number of ab3) may be each independently a cyano group or a cyano group-substituted $C_6$-$C_{10}$ aryl group;

one to three of groups $R_4$ in the number of a4 (or, one to three of groups $R_{4a}$ in the number of aa4) may be each independently a cyano group or a cyano group-substituted $C_6$-$C_{10}$ aryl group;

one to three of groups $R_5$ in the number of a5 may be each independently a cyano group or a cyano group-substituted $C_6$-$C_{10}$ aryl group;

i) one or two of groups $R_5$ in the number of a5 and ii) one or two of groups $R_2$ in the number of a2 (or, one or two of groups $R_{2b}$ in the number of ab2) may be each independently a cyano group or a cyano group-substituted $C_6$-$C_{10}$ aryl group;

i) one or two of groups $R_5$ in the number of a5 and ii) one or two of groups $R_3$ in the number of a3 (or, one or two of groups $R_{3b}$ in the number of ab3) may be each independently a cyano group or a cyano group-substituted $C_6$-$C_{10}$ aryl group;

i) one or two of groups $R_5$ in the number of a5 and ii) one or two of groups $R_4$ in the number of a4 (or, one or two of groups $R_{4a}$ in the number of aa4) may be each independently a cyano group or a cyano group-substituted $C_6$-$C_{10}$ aryl group;

i) one or two of groups $R_2$ in the number of a2 (or, one or two of groups $R_{2b}$ in the number of ab2) and ii) one or two of groups $R_3$ in the number of a3 (or, one or two of groups $R_{3b}$ in the number of ab3) may be each independently a cyano group or a cyano group-substituted $C_6$-$C_{10}$ aryl group;

i) one or two of groups $R_2$ in the number of a2 (or, one or two of groups $R_{2b}$ in the number of ab2) and ii) one or two of groups $R_4$ in the number of a4 (or, one or two of groups $R_{4a}$ in the number of aa4) may be each independently a cyano group or a cyano group-substituted $C_6$-$C_{10}$ aryl group; or i) one or two of groups $R_3$ in the number of a3 (or, one or two of groups $R_{3b}$ in the number of ab3) and ii) one or two of groups $R_4$ in the number of a4 (or, one or two of groups $R_{4a}$ in the number of aa4) may be each independently a cyano group or a cyano group-substituted $C_6$-$C_{10}$ aryl group.

In some embodiments, a condensed cyclic compound represented by Formula 1 may be represented by Formulae 1(1) to 1(12):

Formula 1(1)

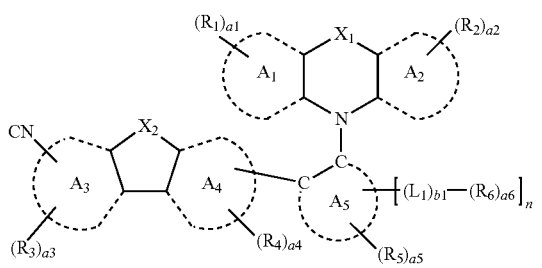

Formula 1(2)

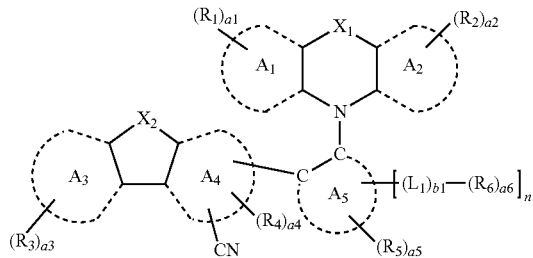

Formula 1(3)

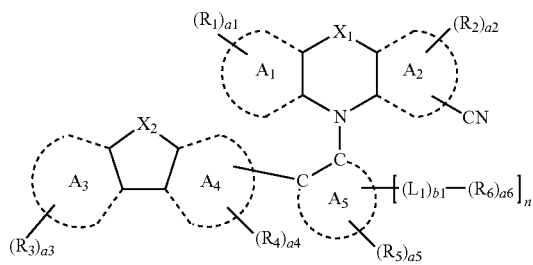

Formula 1(4)

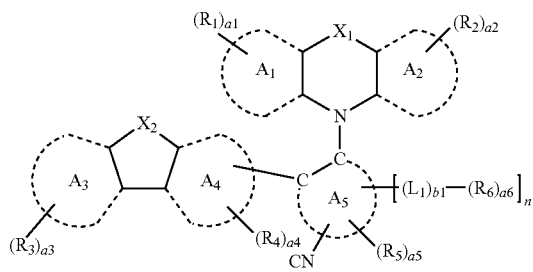

Formula 1(5)

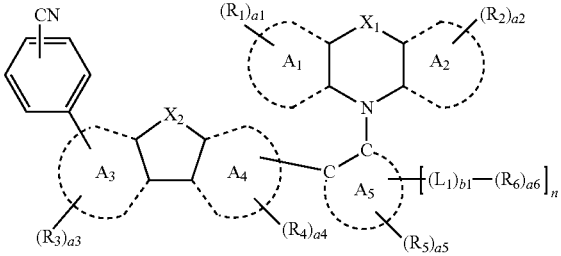

Formula 1(6)

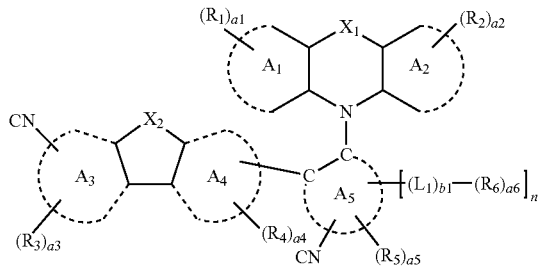

-continued

Formula 1(7)
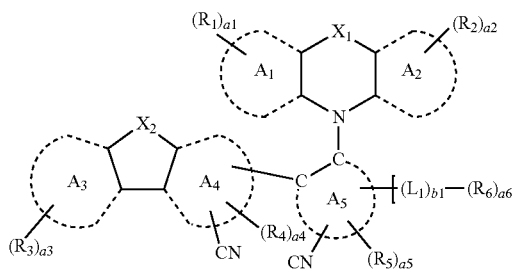

Formula 1(8)
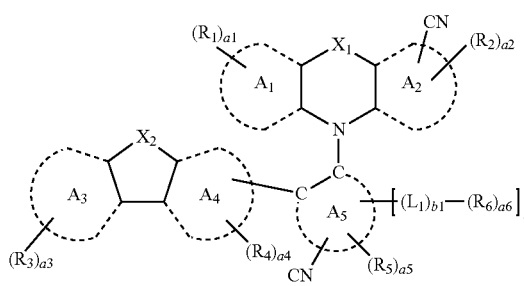

Formula 1(9)
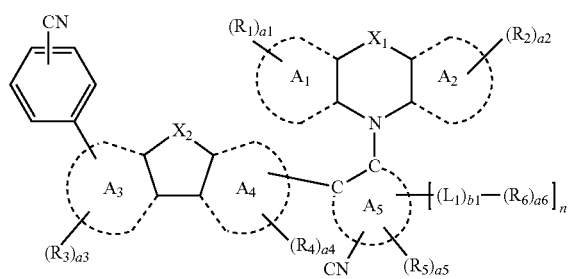

Formula 1(10)
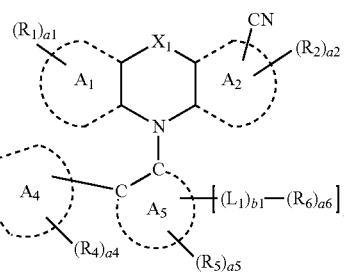

Formula 1(11)
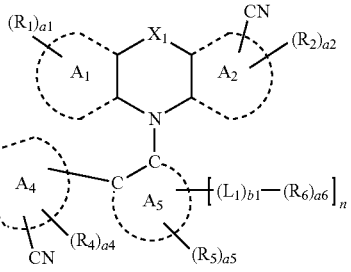

-continued

Formula 1(12)
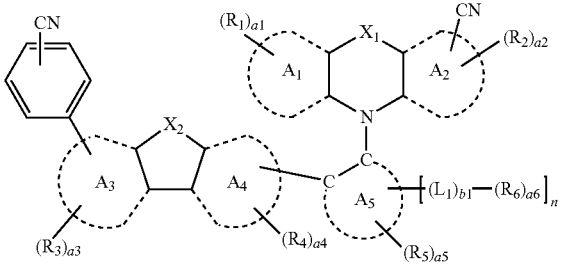

Descriptions of $X_1$, $X_2$, ring $A_1$ to ring $A_5$, $R_1$ to $R_6$, $L_1$, b1 and n in Formulae 1(1) to 1(12) are the same as described herein, a1 may be an integer of 1 to 3 and a2 to a6 may each independently be an integer of 0 to 3.

For example, in Formulae 1(1) to 1(12), $X_1$ may be a single bond, ring $A_1$ and ring $A_2$ may be each independently selected from a benzene, a fluorene, a carbazole, a dibenzofuran and a dibenzothiophene, and at least one of ring $A_1$ and ring $A_2$ may be a benzene, ring $A_3$ and ring $A_4$ may be each independently selected from a benzene, a fluorene, a carbazole, a dibenzofuran and a dibenzothiophene, and at least one of ring $A_3$ and ring $A_4$ may be a benzene, ring $A_5$ may be a benzene, $R_1$ to $R_6$ may be each independently selected from a hydrogen, a deuterium, a $C_1$-$C_{10}$ alkyl group and a $C_1$-$C_{10}$ alkoxy group;

a $C_1$-$C_{10}$ alkyl group and a $C_1$-$C_{10}$ alkoxy group, each substituted with at least one deuterium;

a phenyl group, a pyridinyl group, a pyrimidinyl group and a triazinyl group;

a phenyl group, a pyridinyl group, a pyrimidinyl group and a triazinyl group, each substituted with at least one selected from a deuterium, a $C_1$-$C_{10}$ alkyl group, a $C_1$-$C_{10}$ alkoxy group, a phenyl group, a pyridinyl group, a pyrimidinyl group, a triazinyl group and —Si($Q_{31}$)($Q_{32}$)($Q_{33}$); and —Si($Q_1$)($Q_2$)($Q_3$), $L_1$ may be selected from a phenylene group, a pyridinylene group, a pyrimidinylene group and a triazinylene group; and a phenylene group, a pyridinylene group, a pyrimidinylene group and a triazinylene group, each substituted with at least one selected from a deuterium, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$), b1 may be 1 or 2, n may be 0 or 1, and $Q_1$ to $Q_3$, $Q_{31}$ to $Q_{33}$, and $Q_8$ to $Q_{10}$ may be each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group, but embodiments are not limited thereto.

The condensed cyclic compound may be one of Compounds 1 to 482 below, but embodiments are not limited thereto:

1
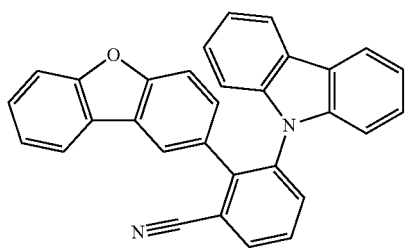
2
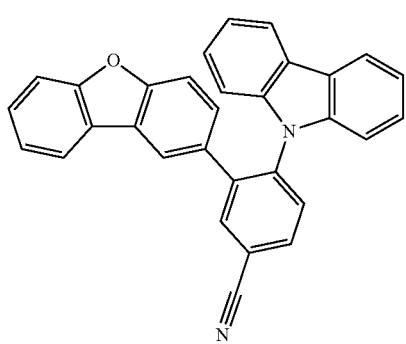
3
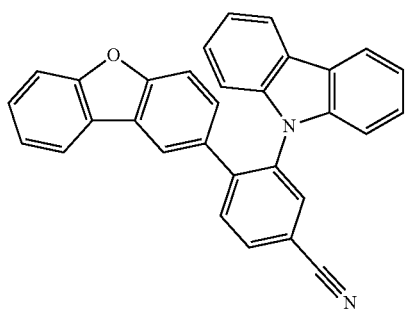
4
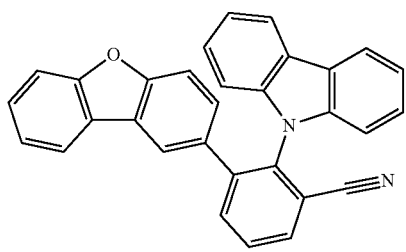
5
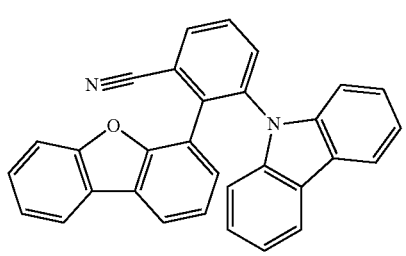
-continued
6
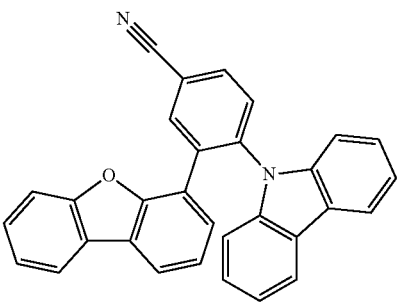
7
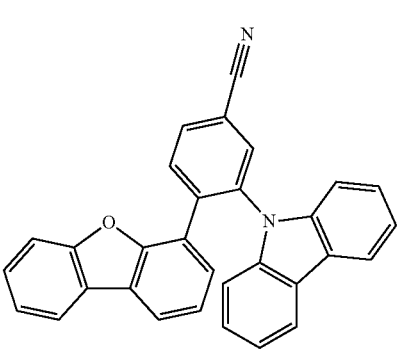
8
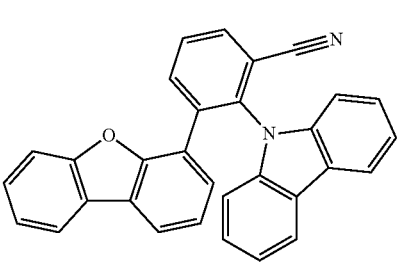
9
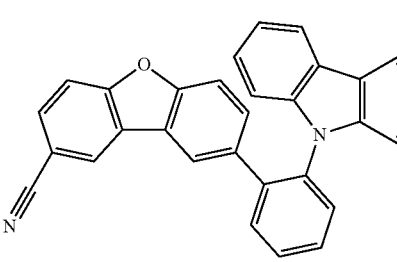
10
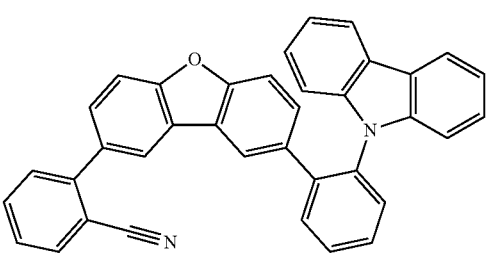

11
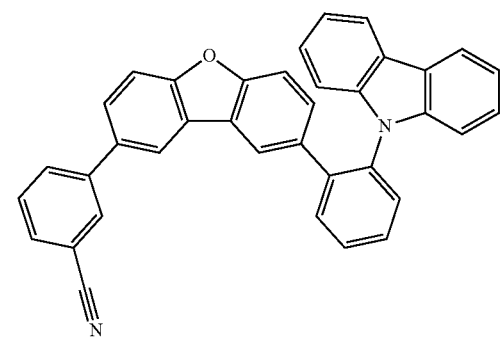
12
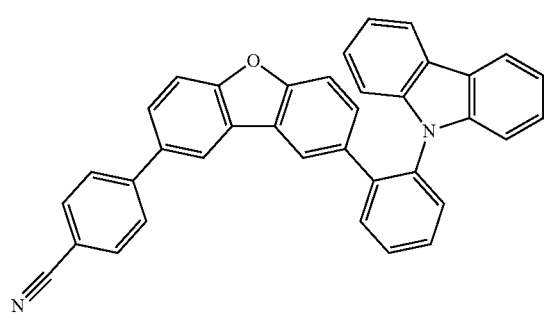
13
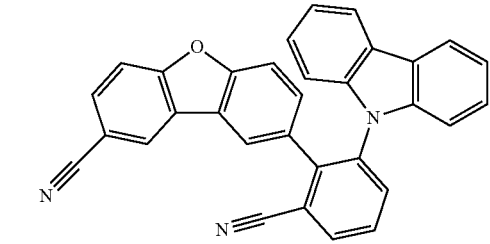
14
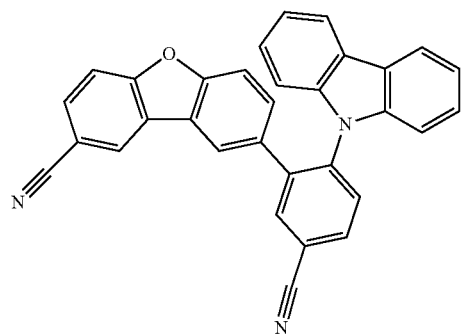
15
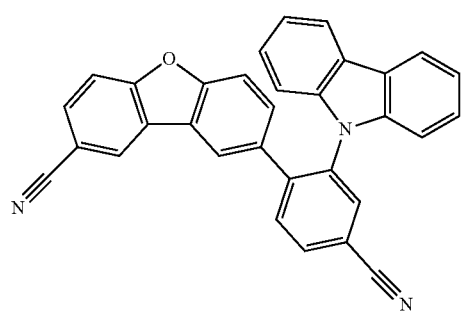
16
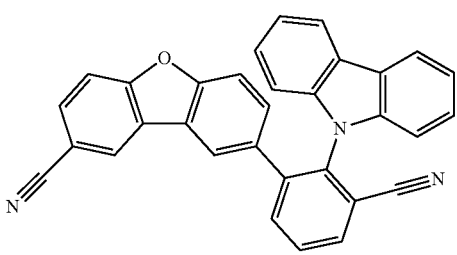
17
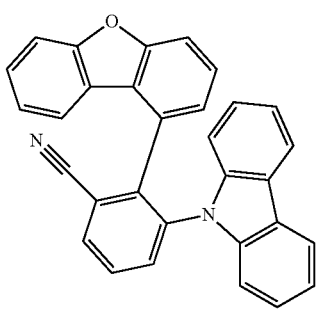
18
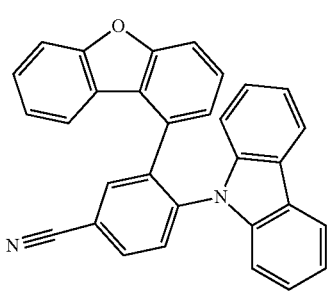
19
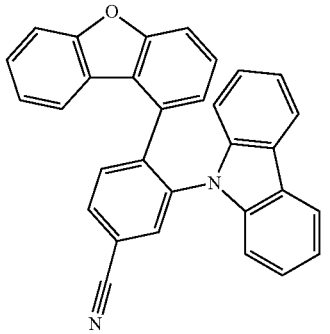
20
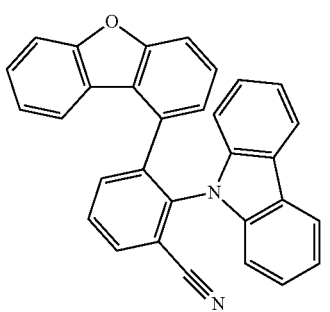

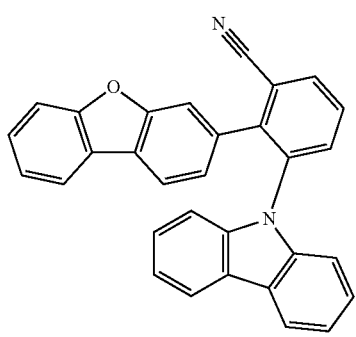
21
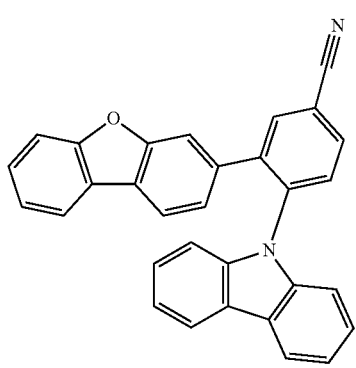
22
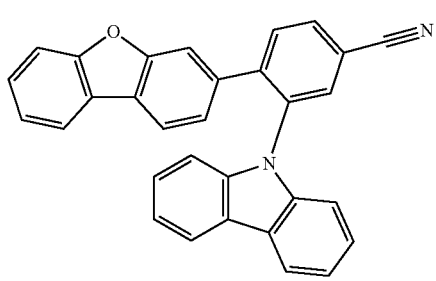
23
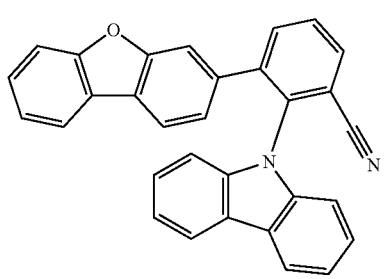
24
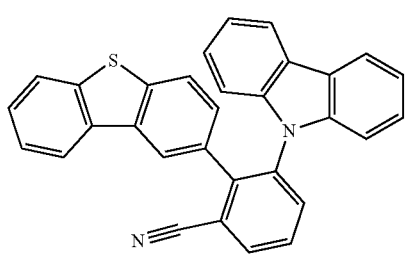
25
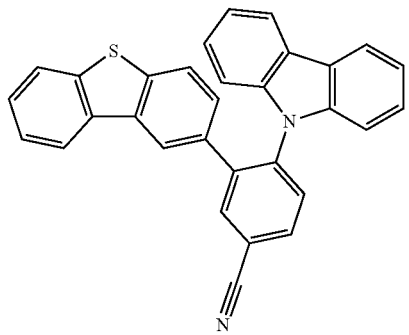
26
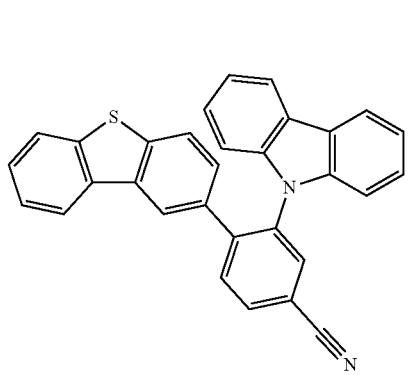
27
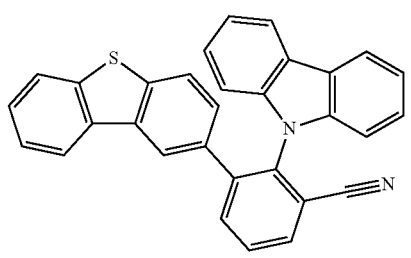
28
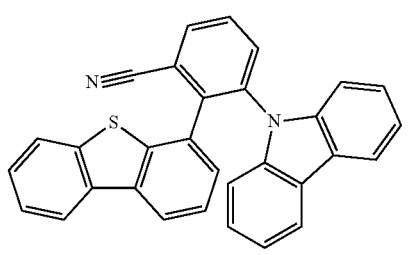
29
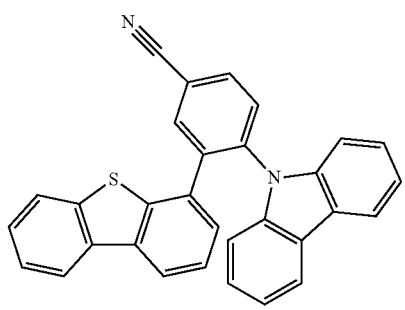
30

31 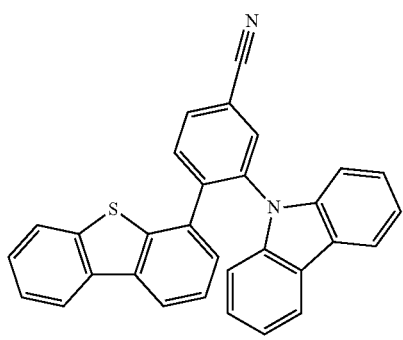
32 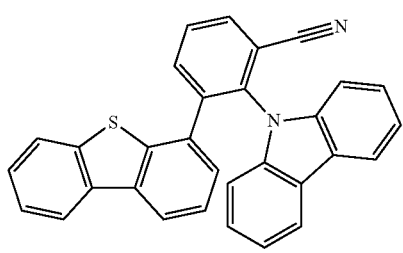
33 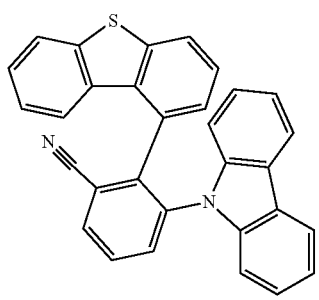
34 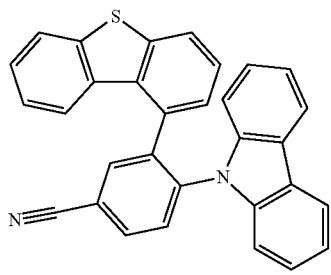
35 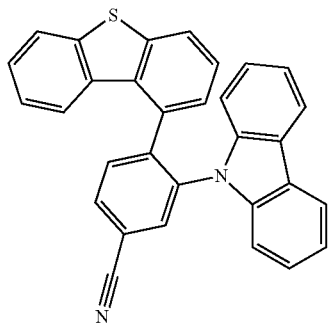
36 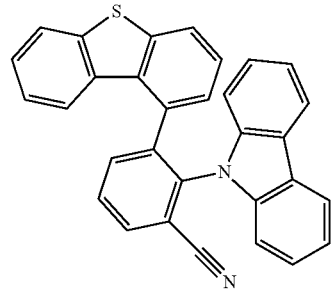
37 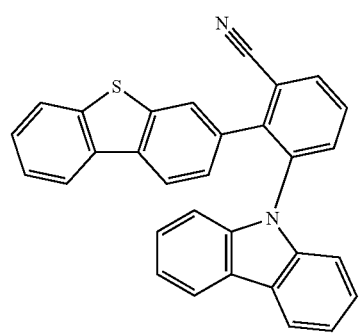
38 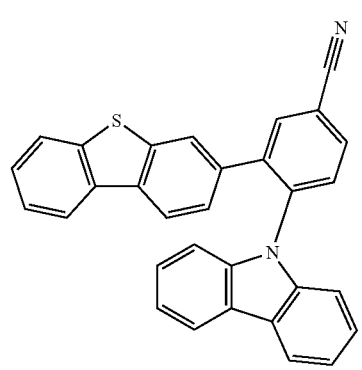
39 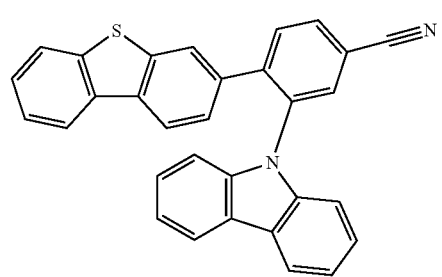
40 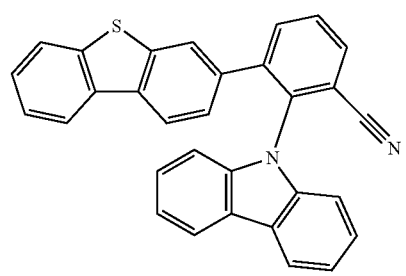

41
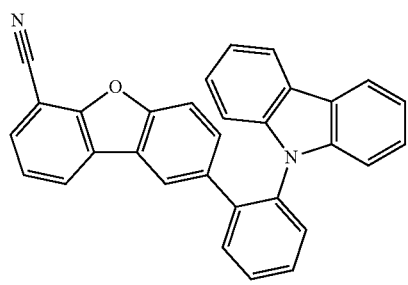
42
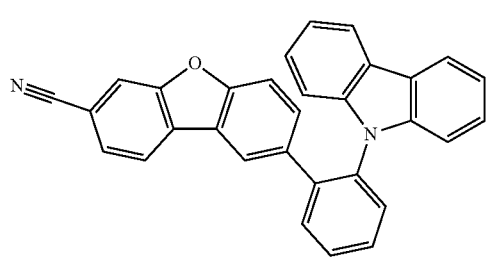
43
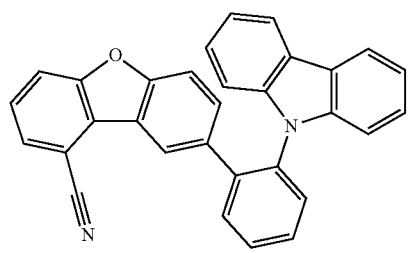
44
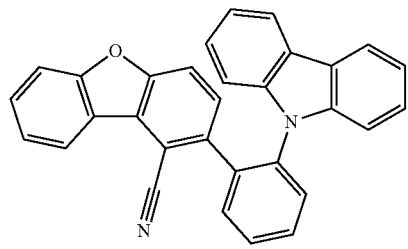
45
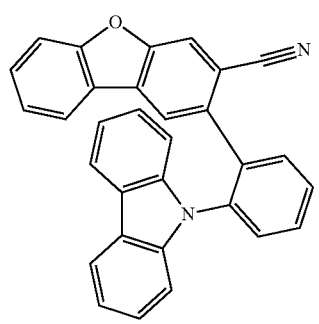
46
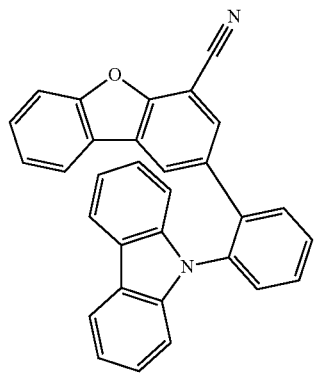
47
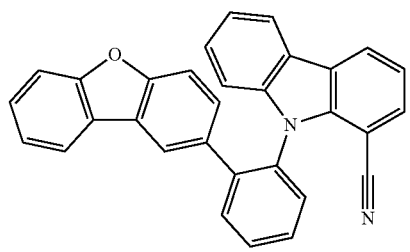
48
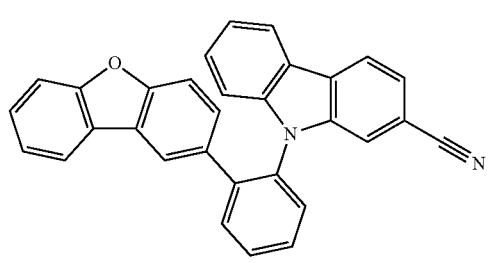
49
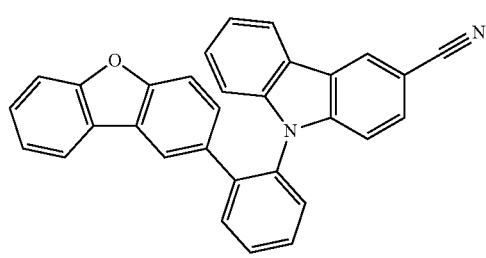
50
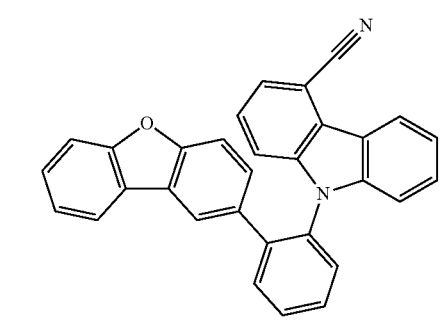

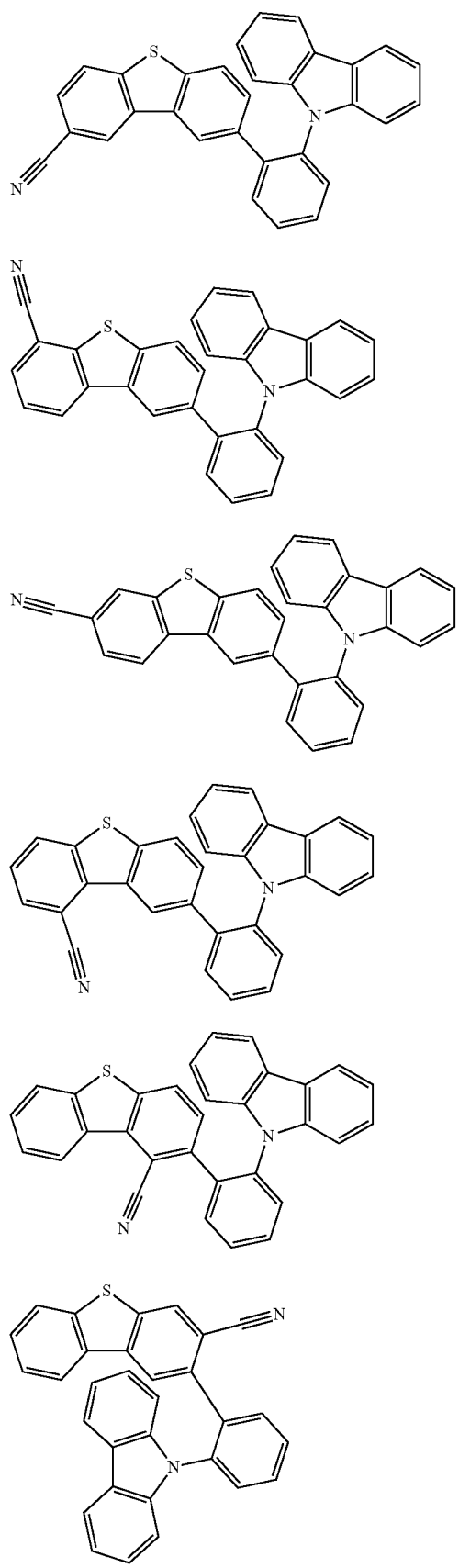
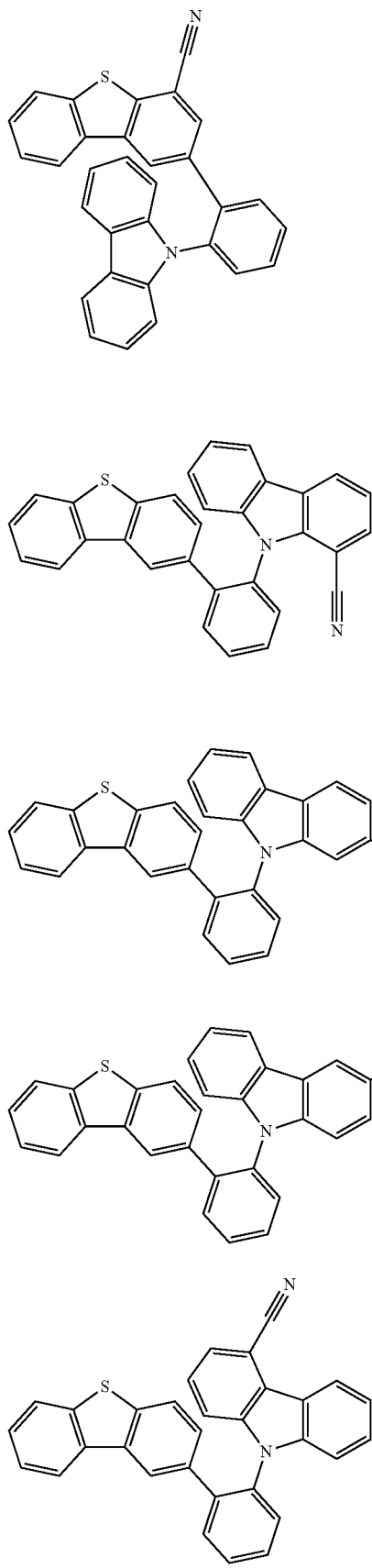

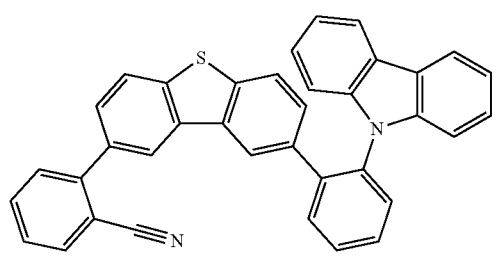
62
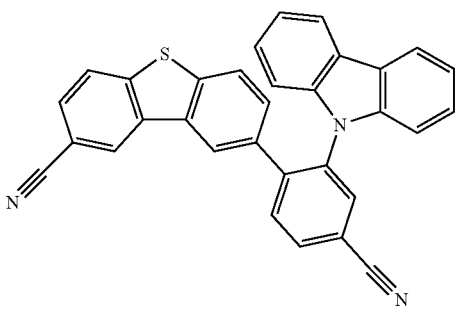
67
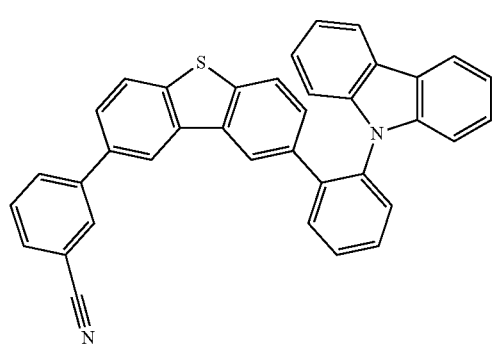
63
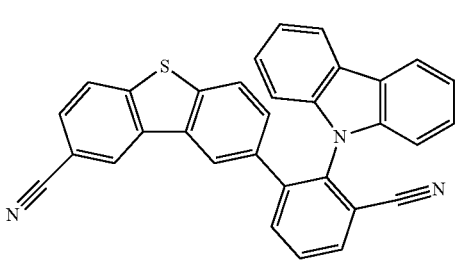
68
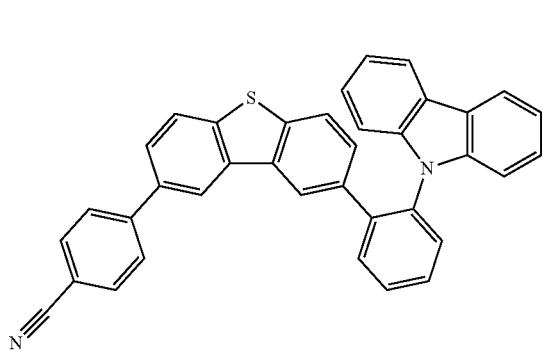
64
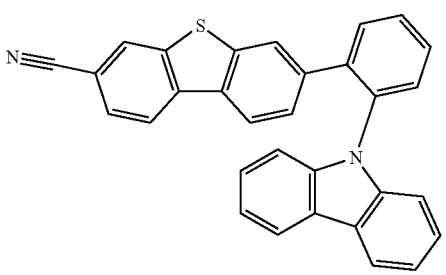
69
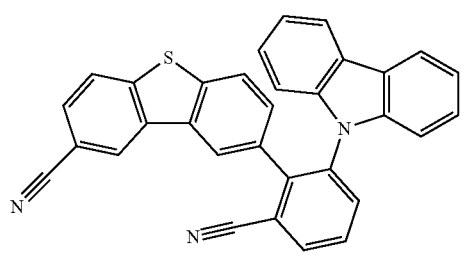
65
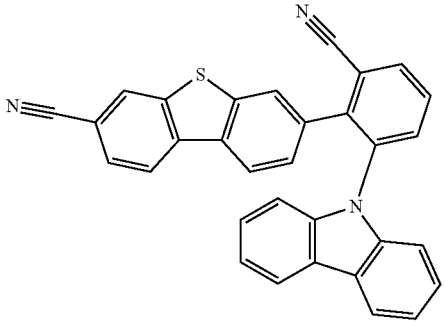
70
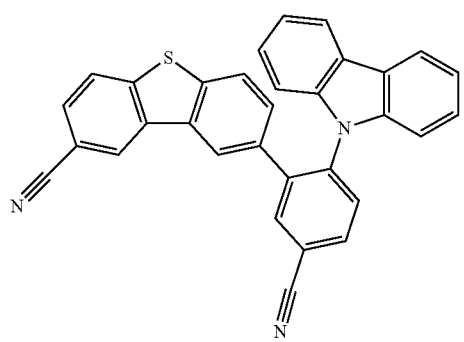
66
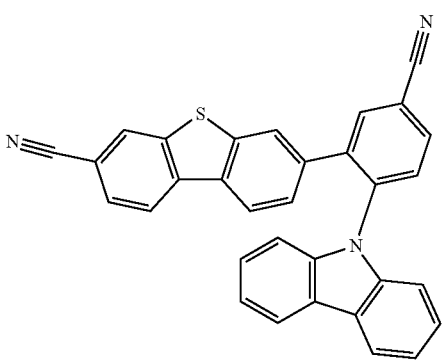
71

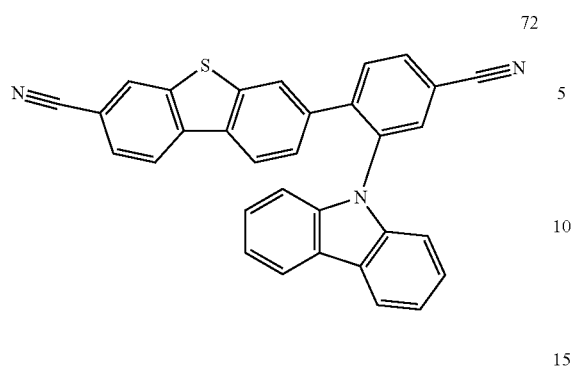
72
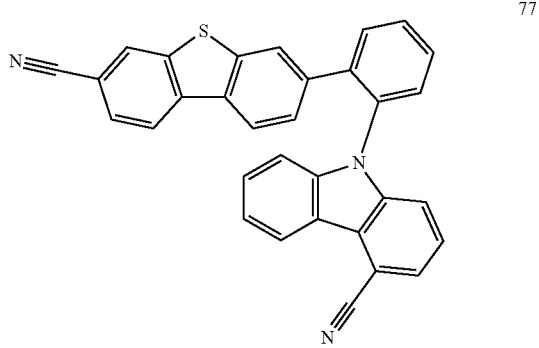
77
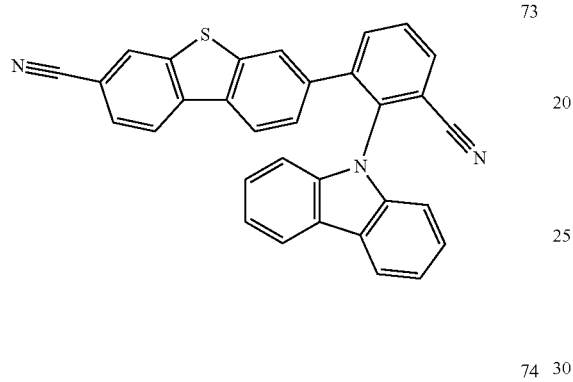
73
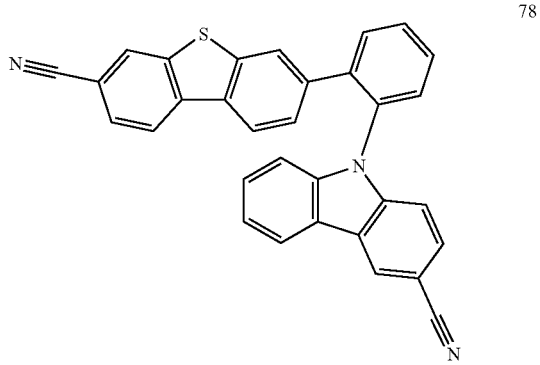
78
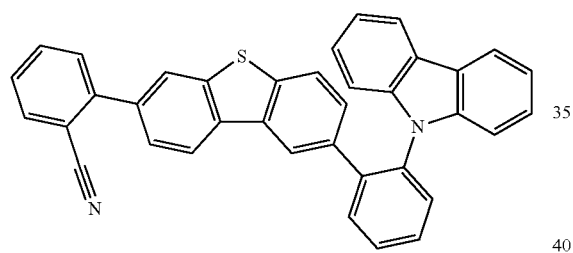
74
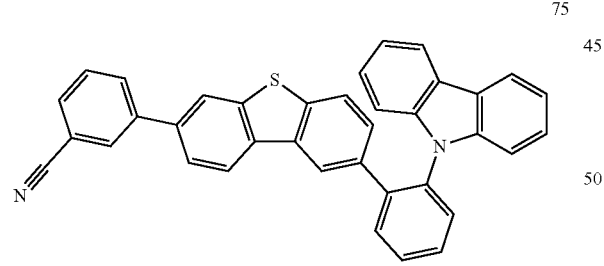
75
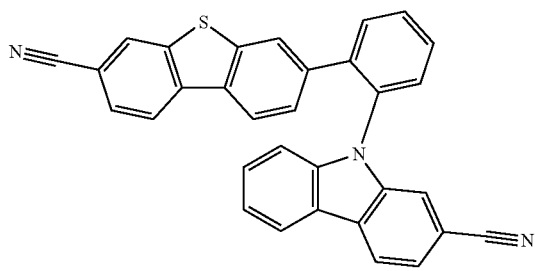
79
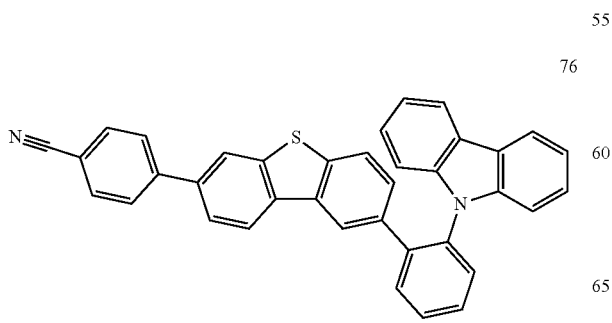
76
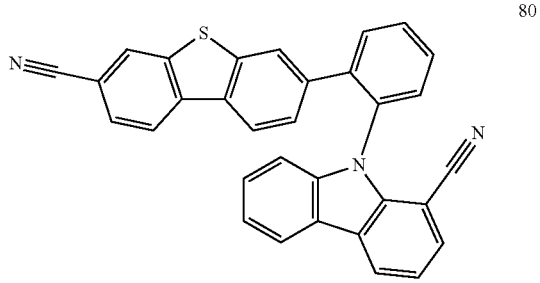
80

81
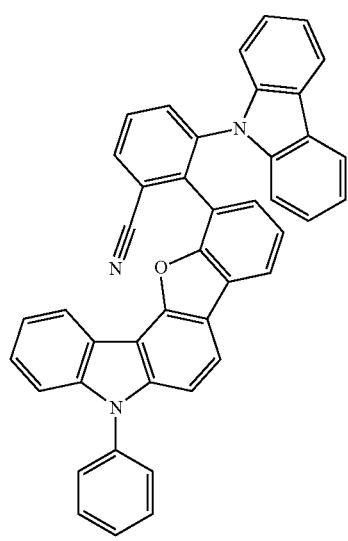
82
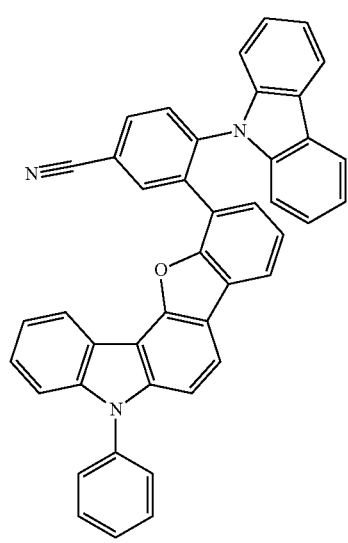
83
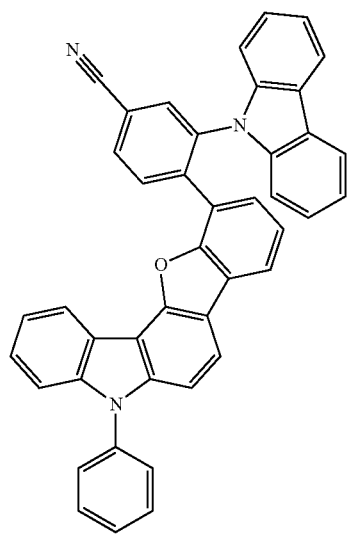
84
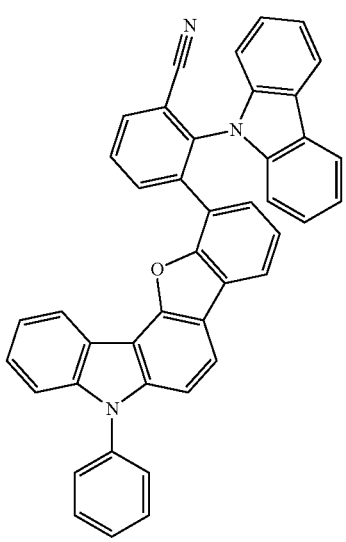
85
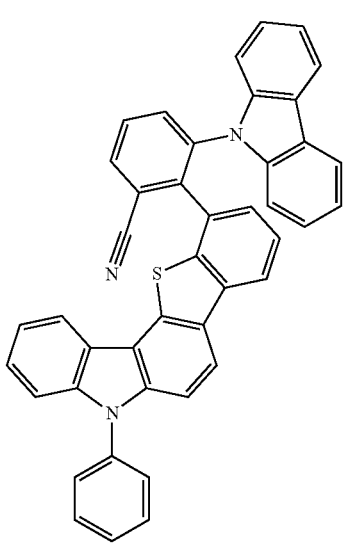
86
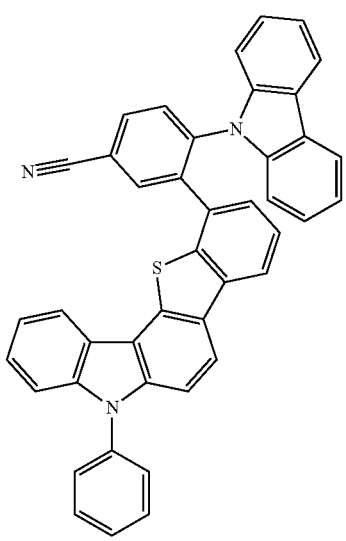

87
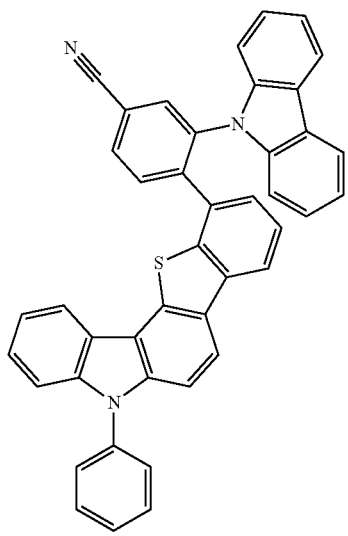
88
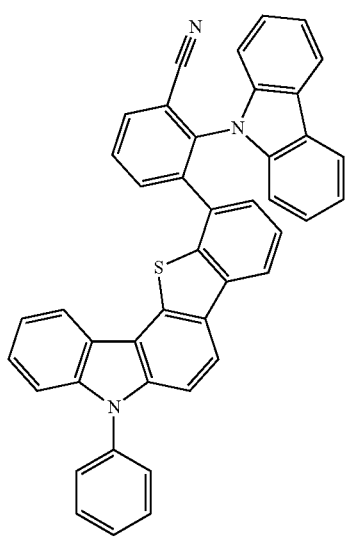
89
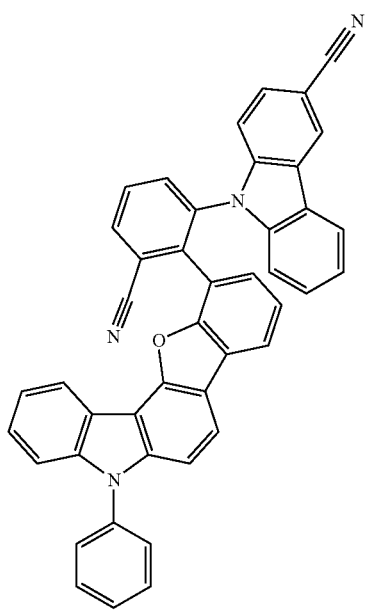
90
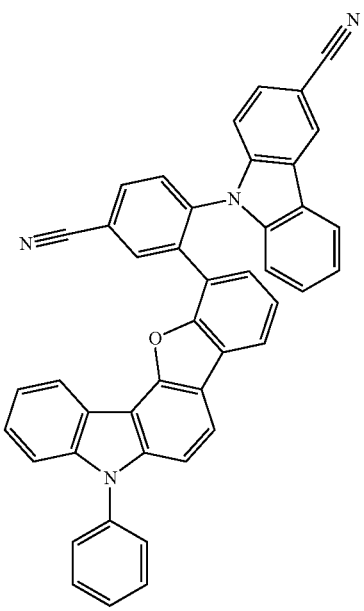
91

92
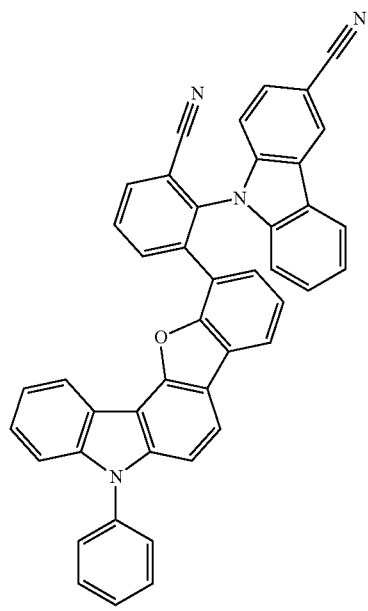
93
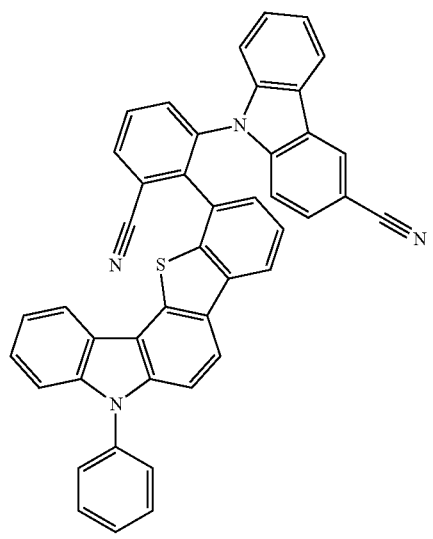
94
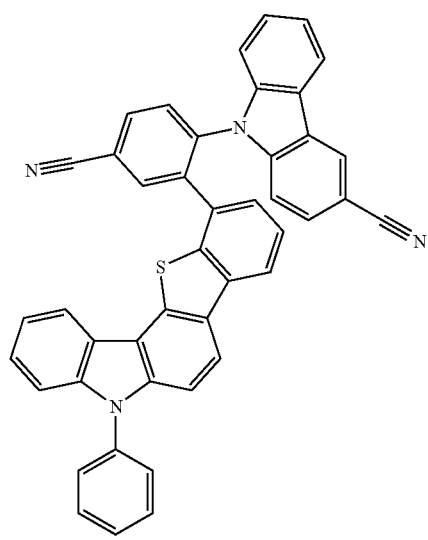
95
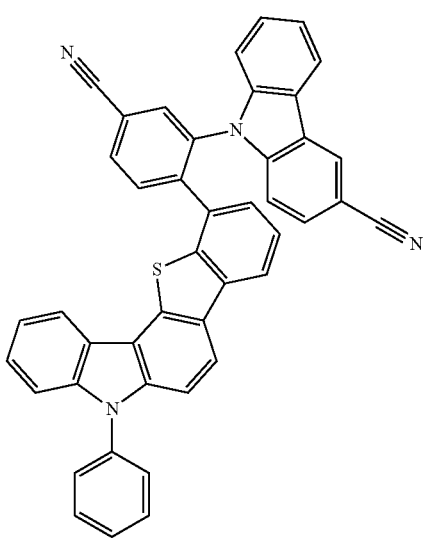
96
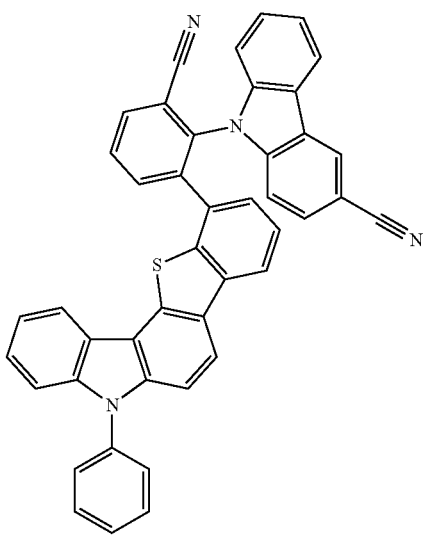
97
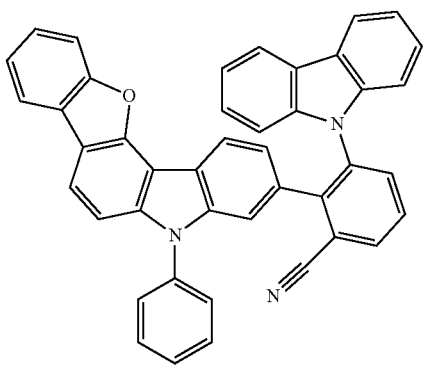

98
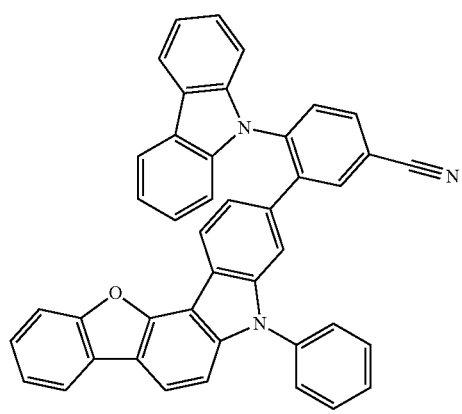
99
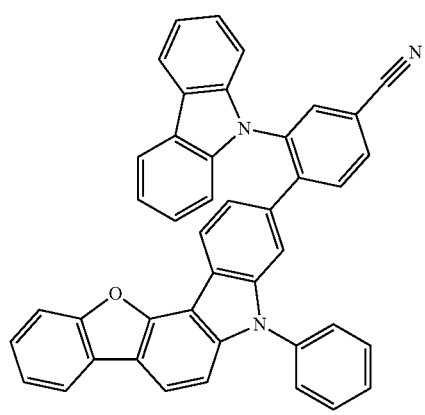
100
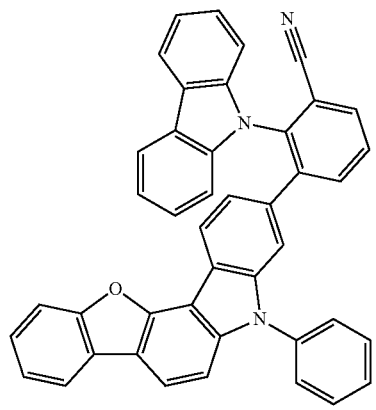
101
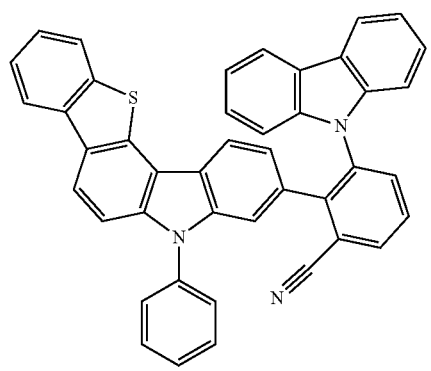
102
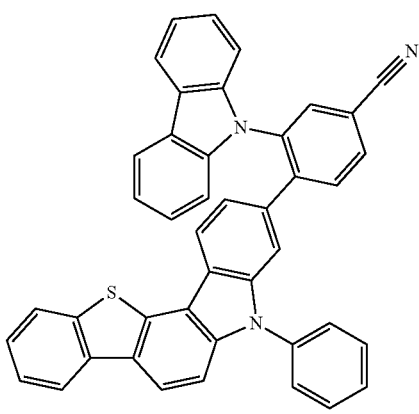
103
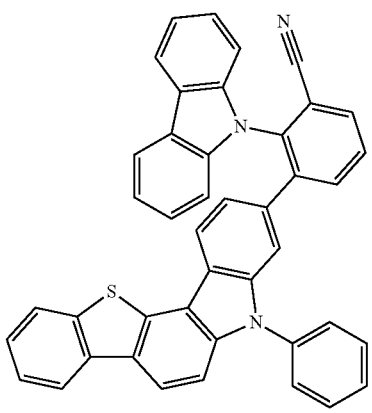
104
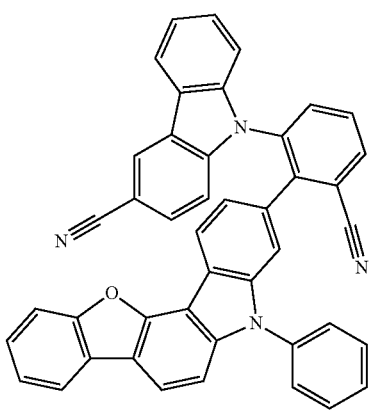
105
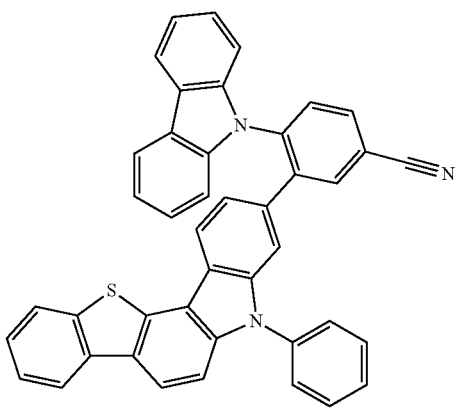

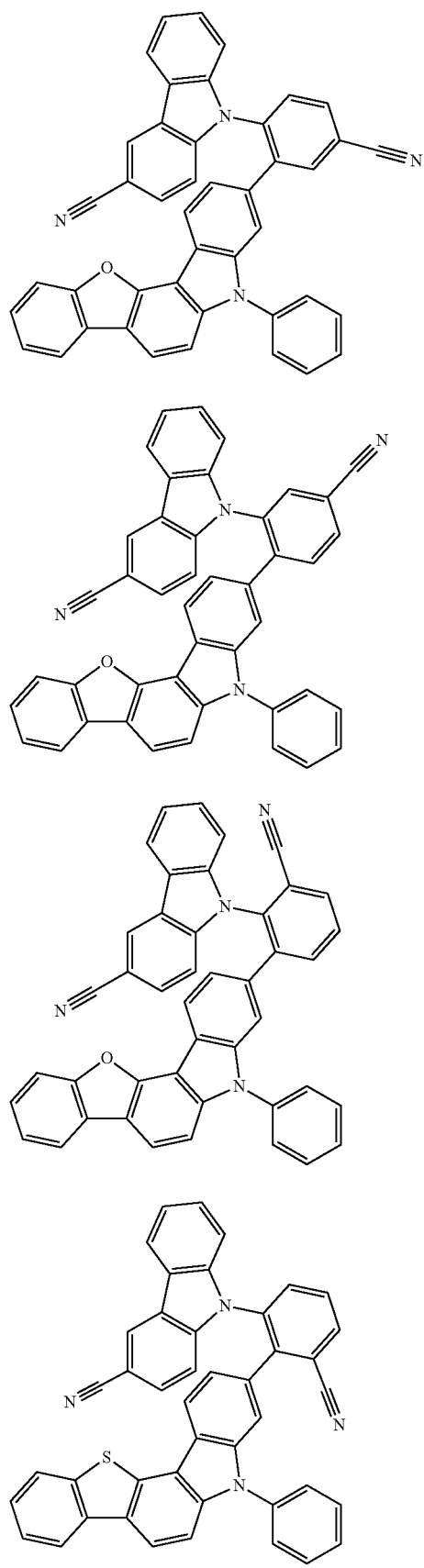
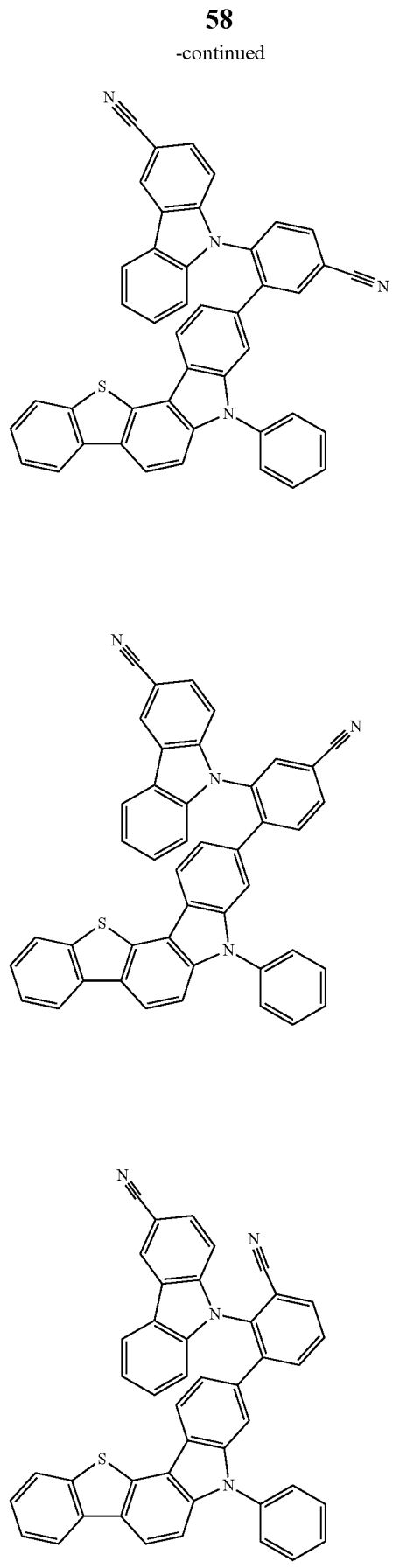

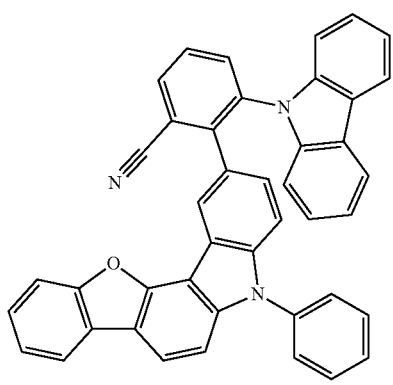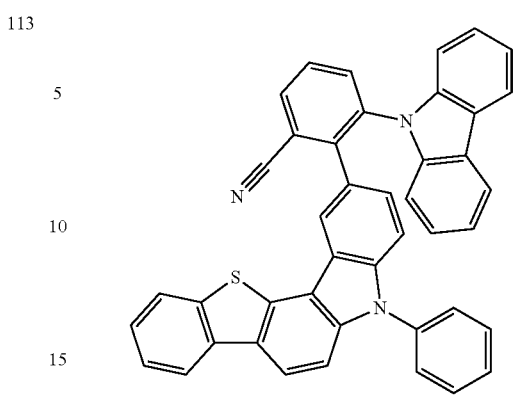

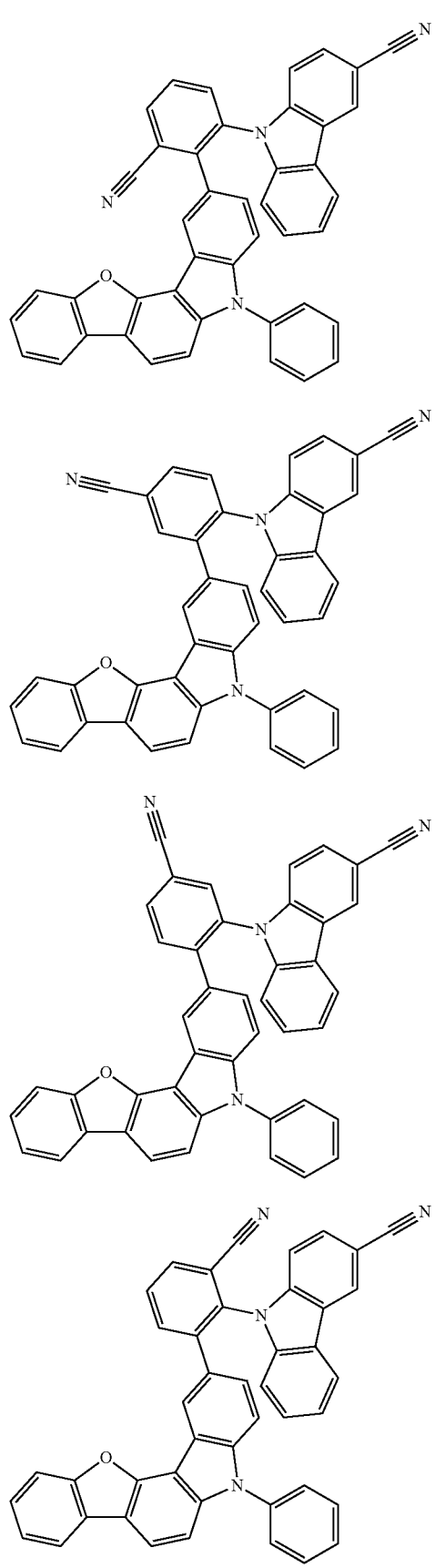
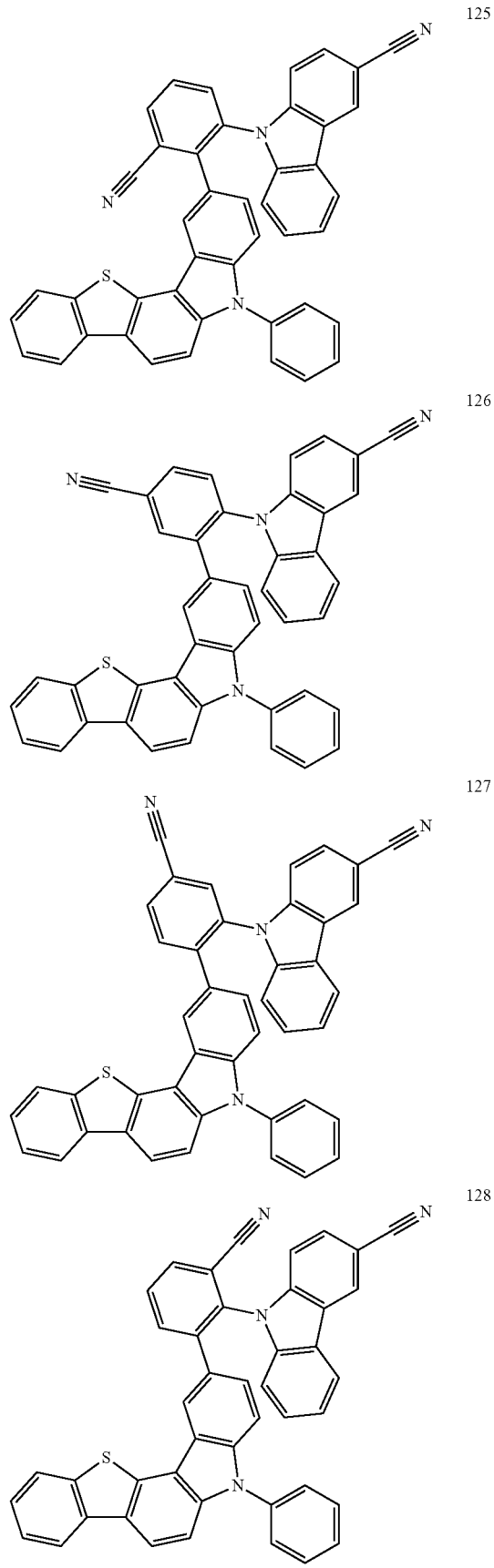

129
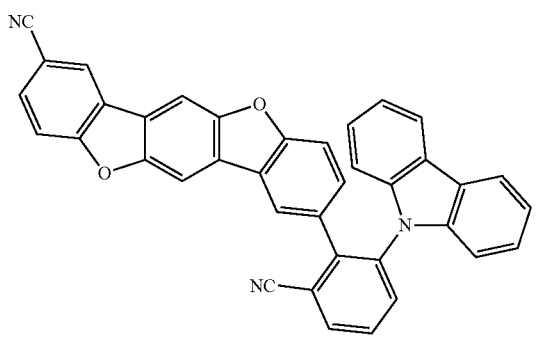
130
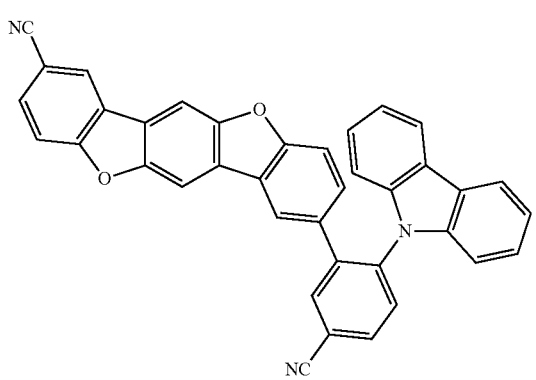
131
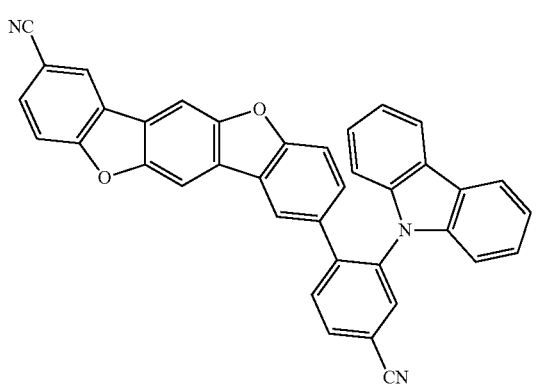
132
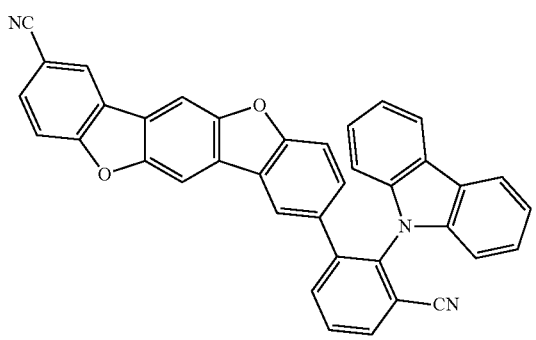
133
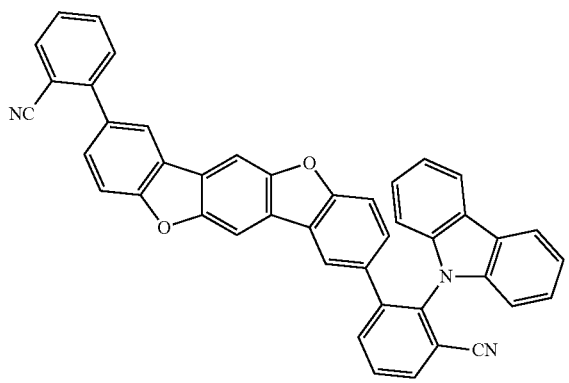
134
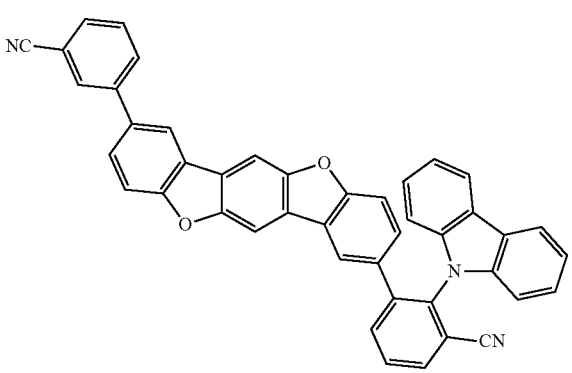
135
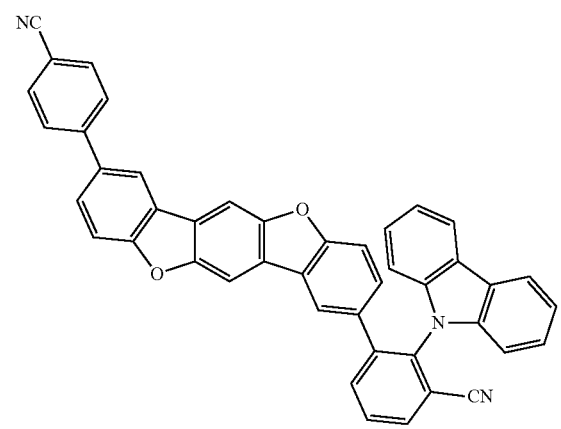
136
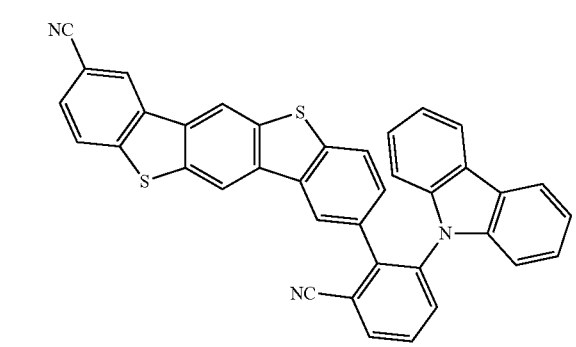

-continued
137
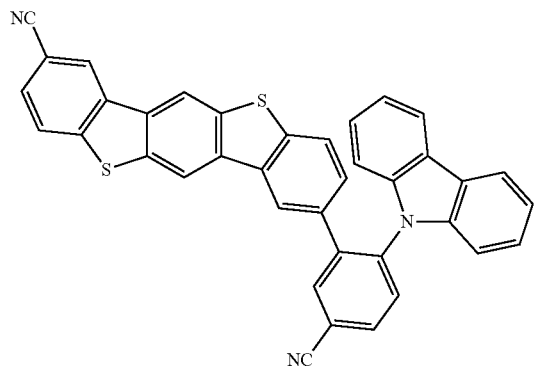
138
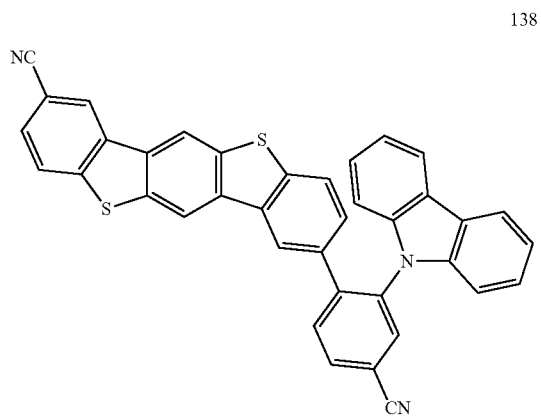
139
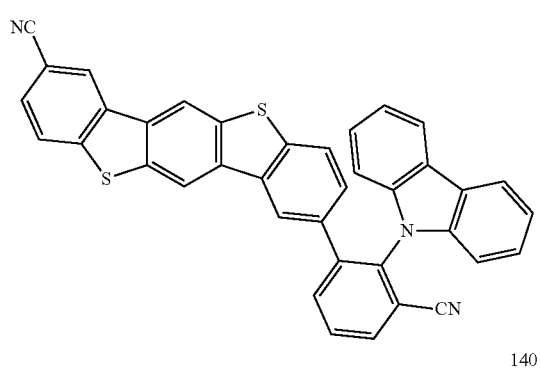
140
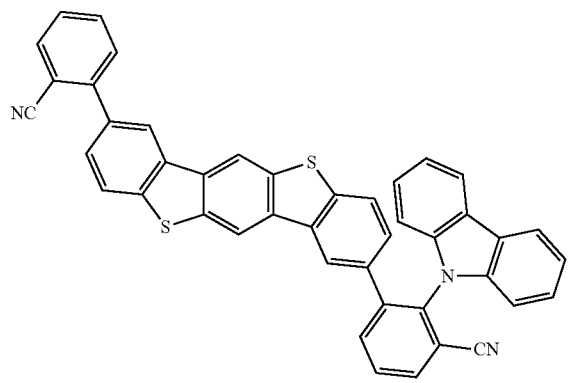
-continued
141
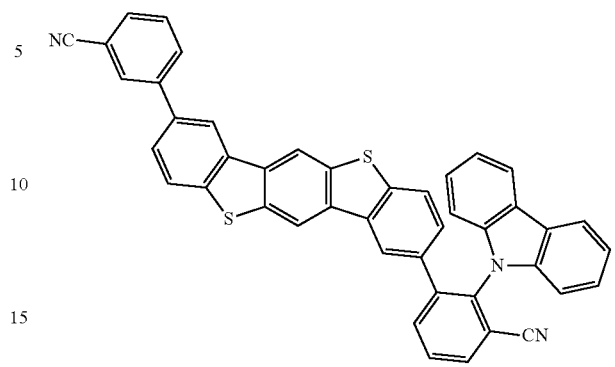
142
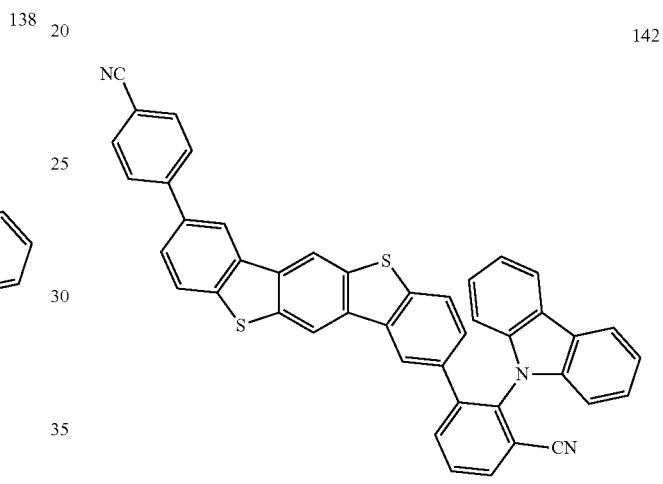
143
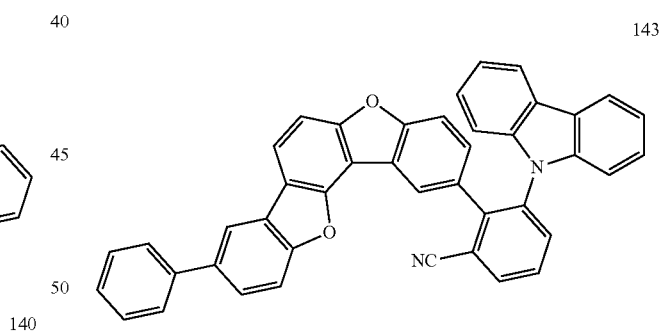
144
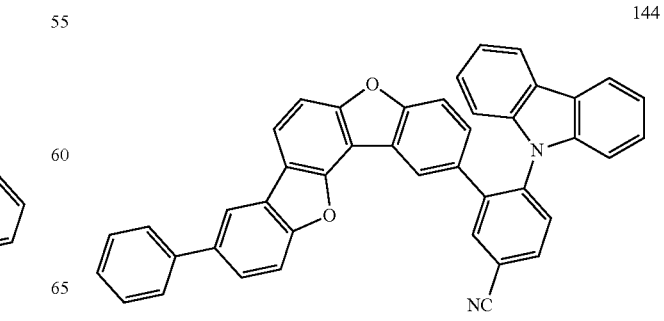

-continued
145
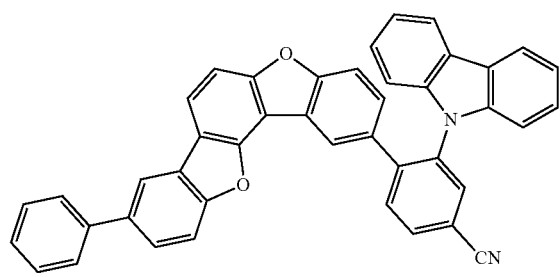
146
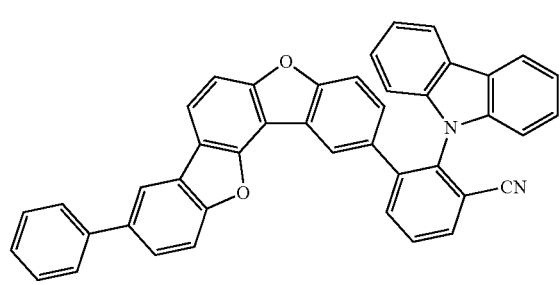
147
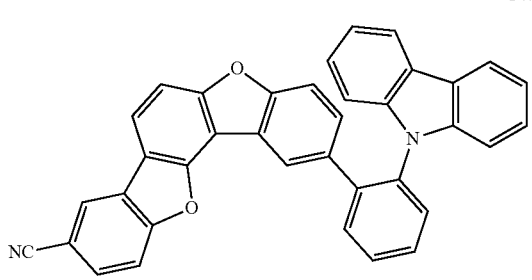
148
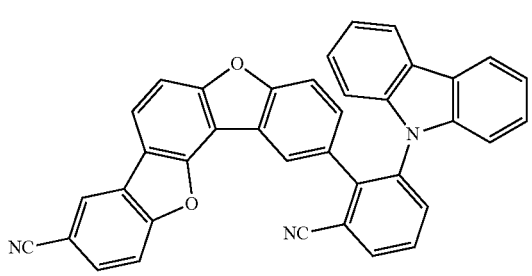
149
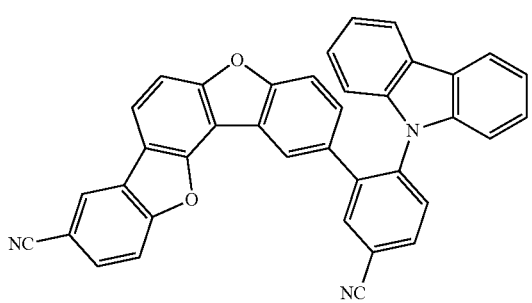
-continued
150
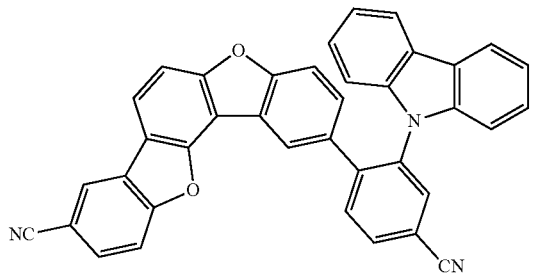
151
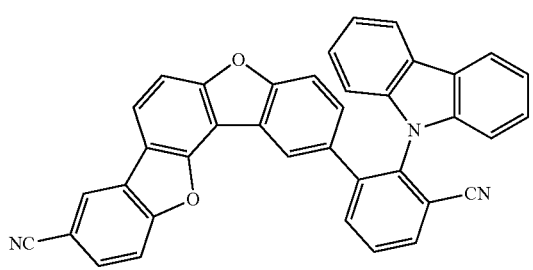
152
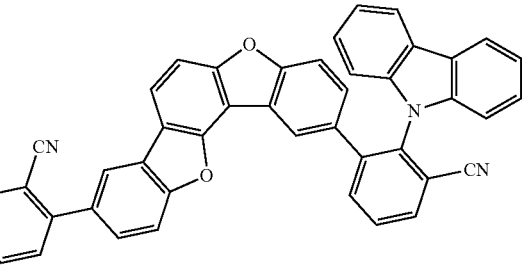
153
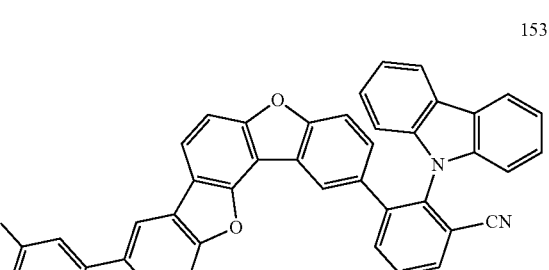
154
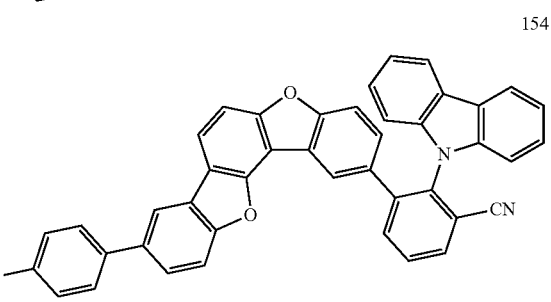

-continued
155
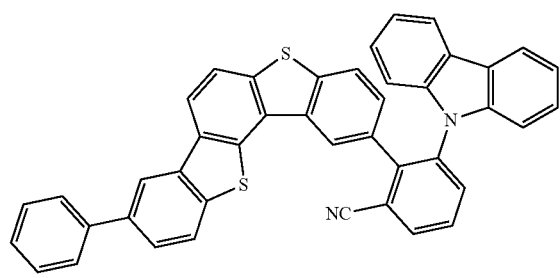
156
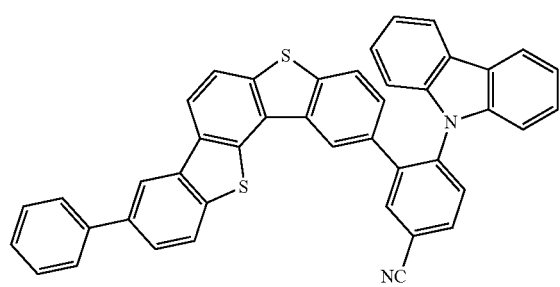
157
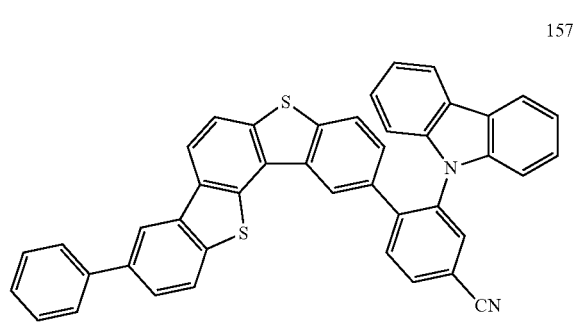
158
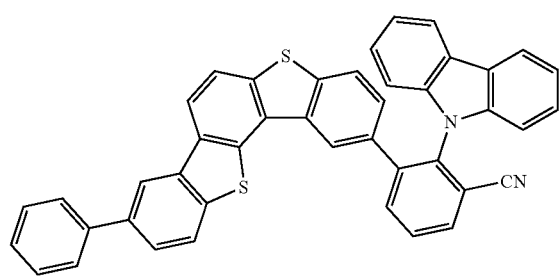
159
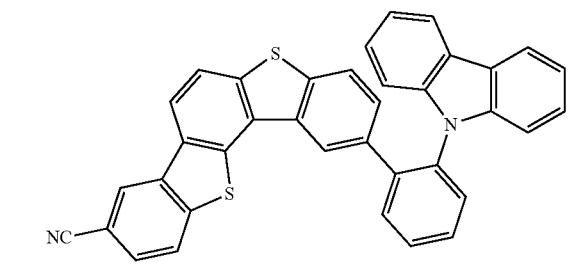
-continued
160
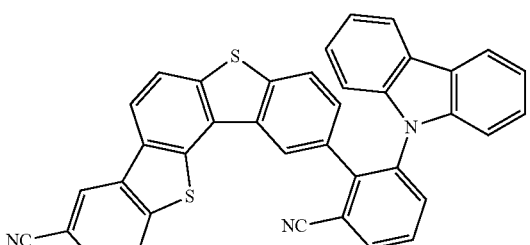
161
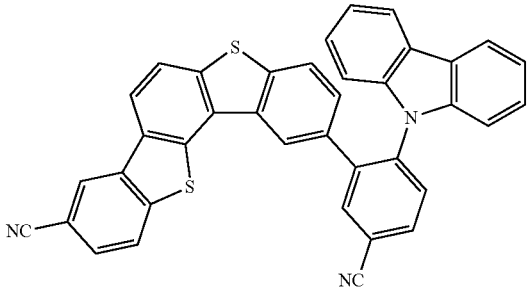
162
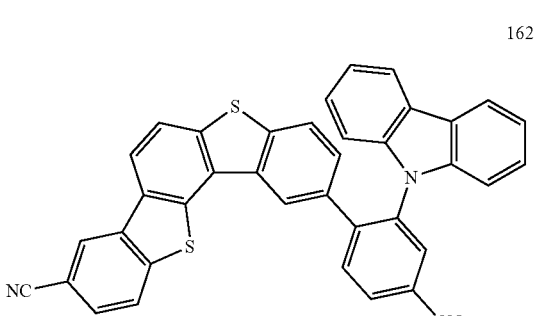
163
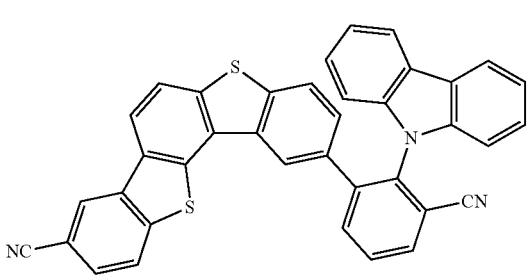
164
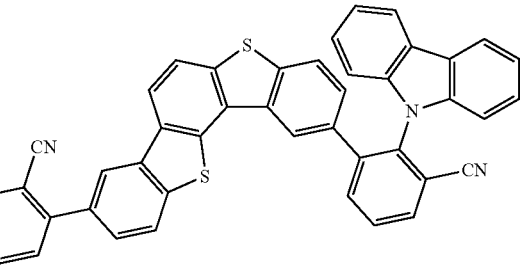

165
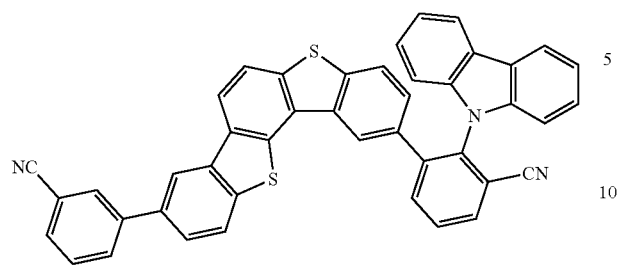
166
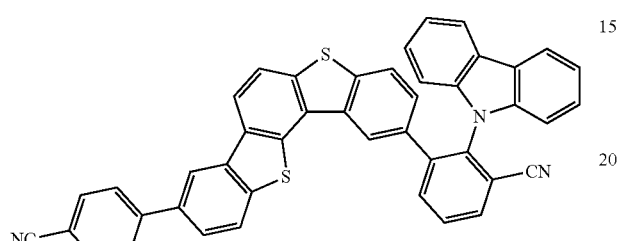
167
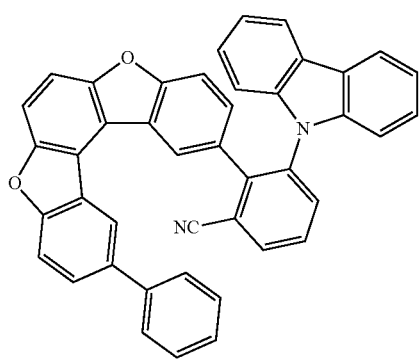
168
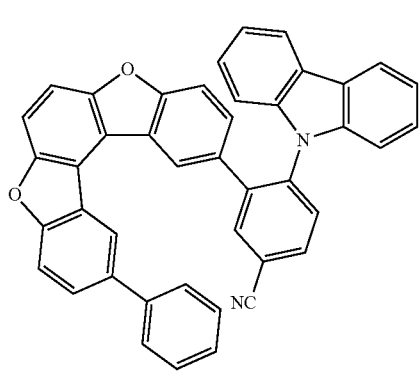
169
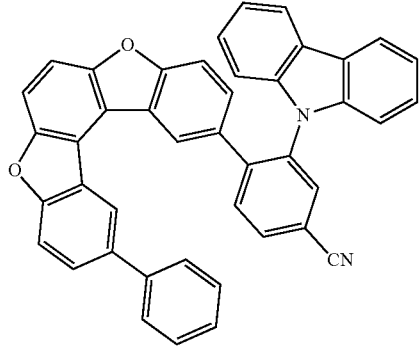
170
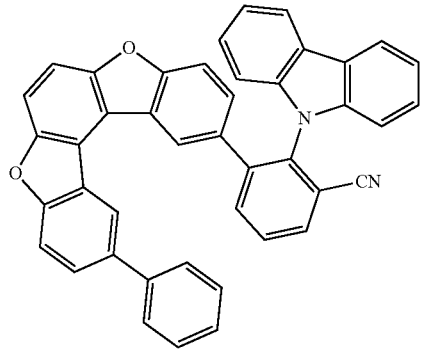
171
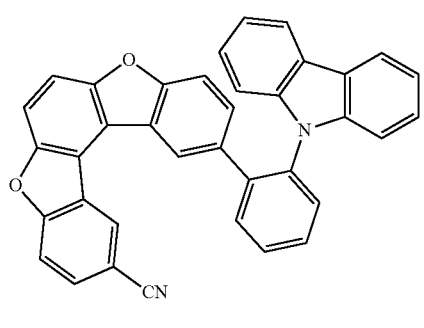
172
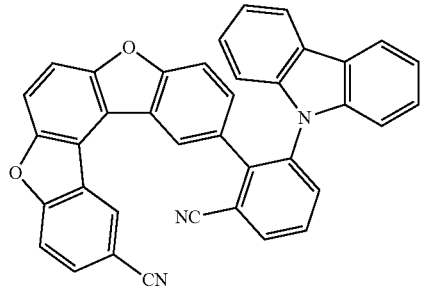
173
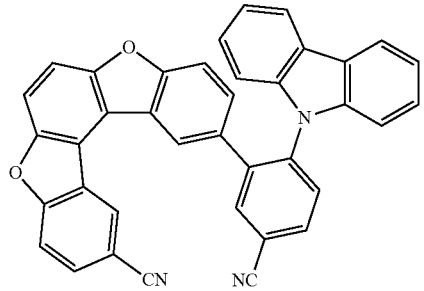
174
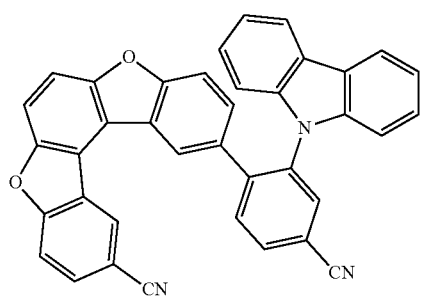

175 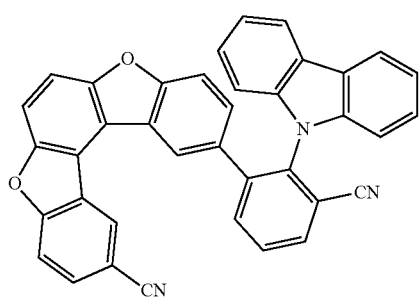
176 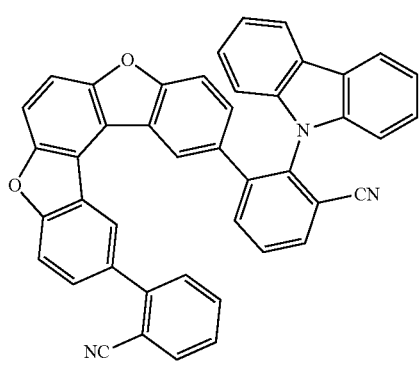
177 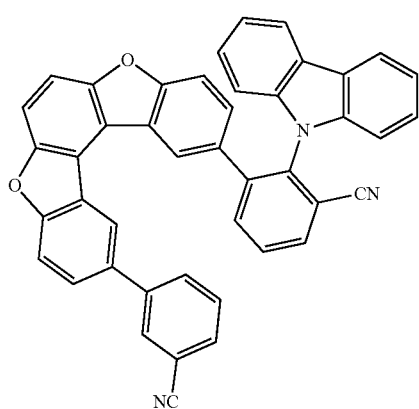
178 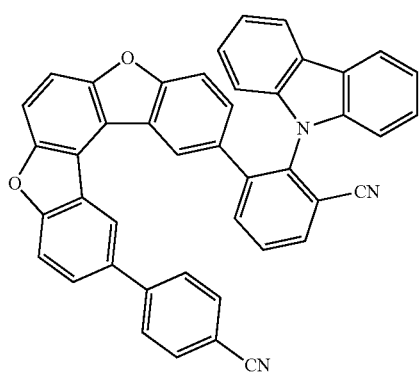
179 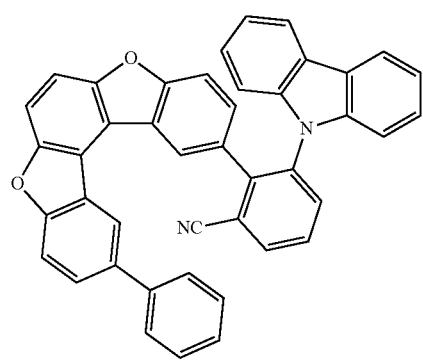
180 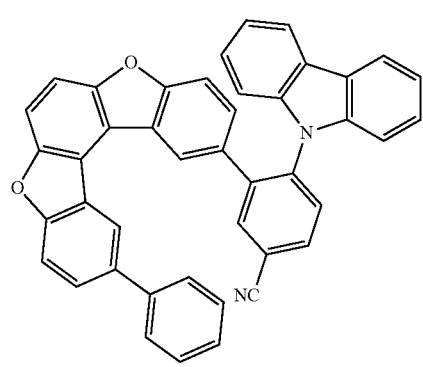
181 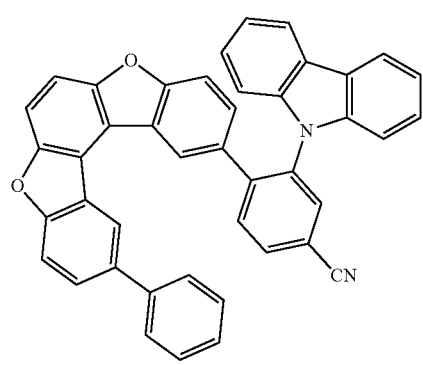
182 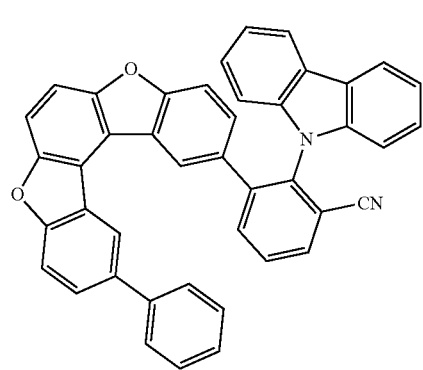

-continued
183
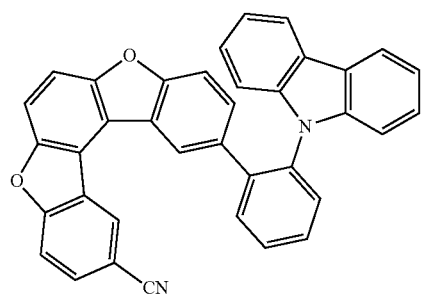
184
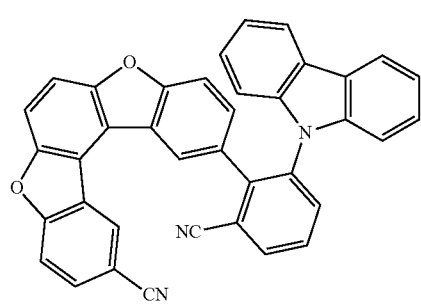
185
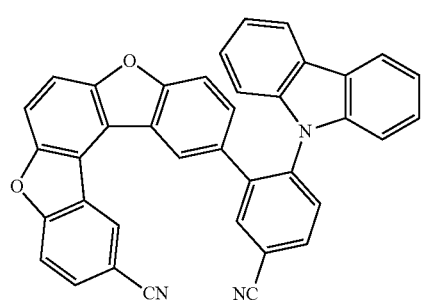
186
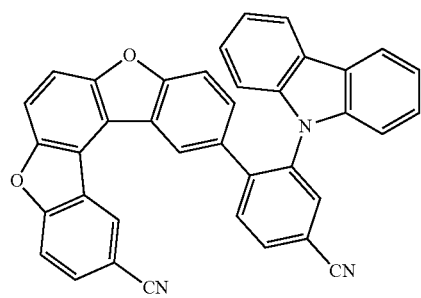
187
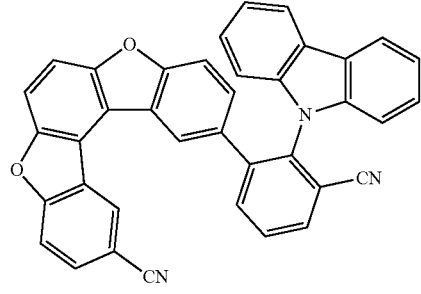
-continued
188
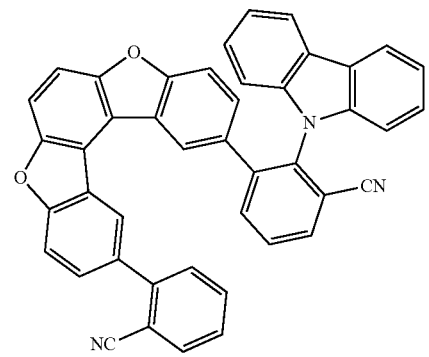
189
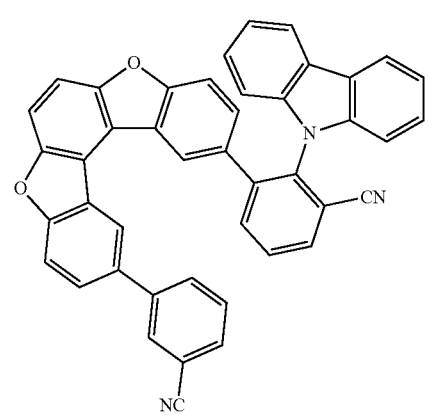
190
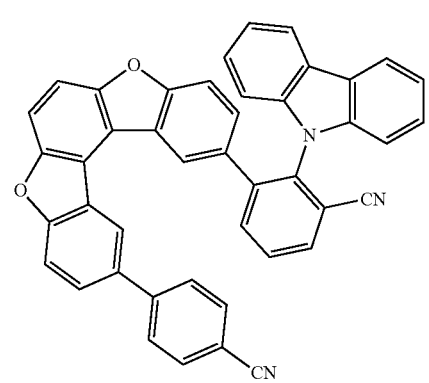
191
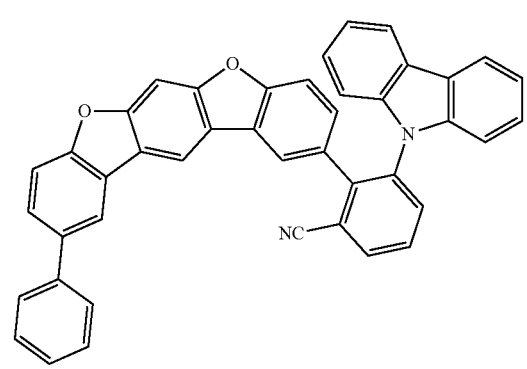

192
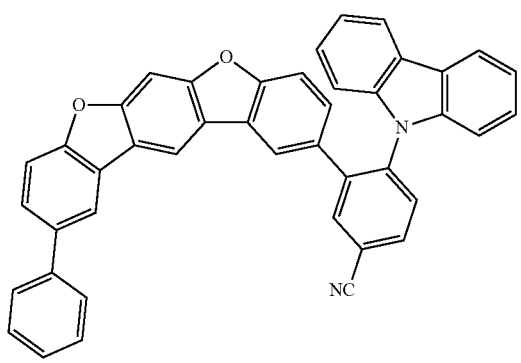
193
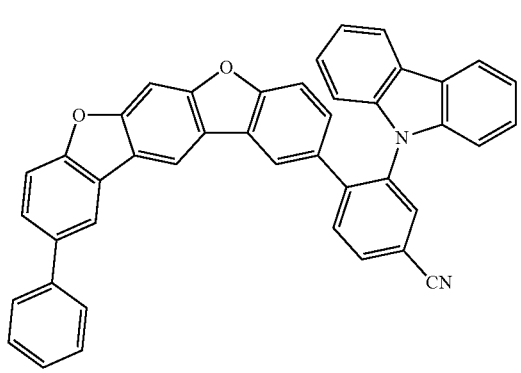
194
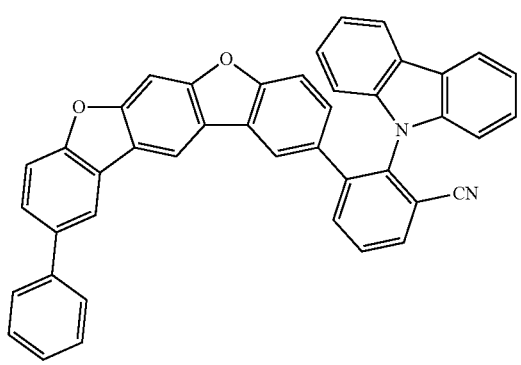
195
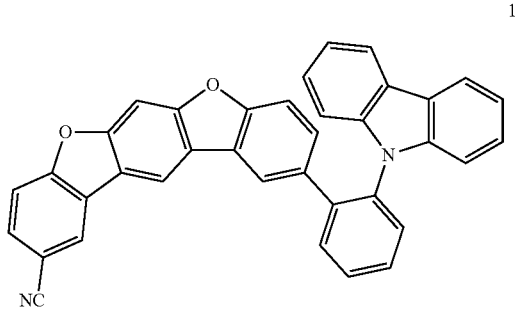
196
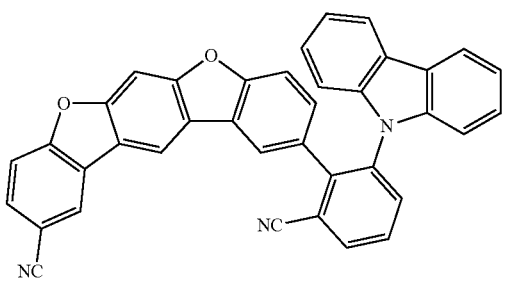
197
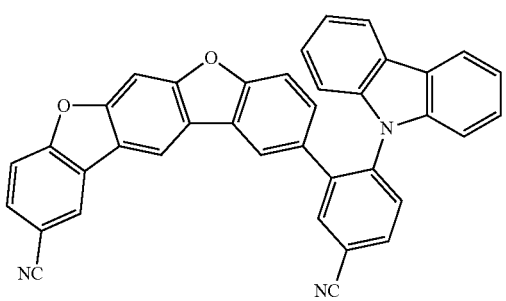
198
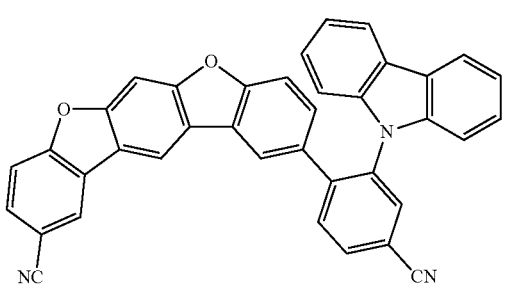
199
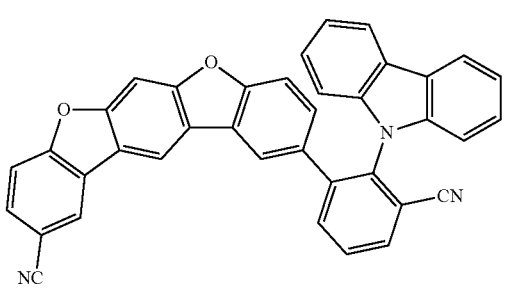
200
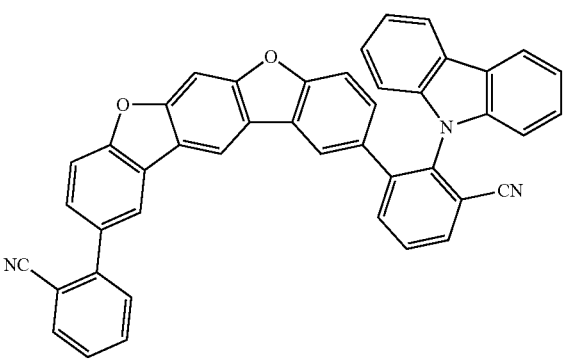

-continued
201
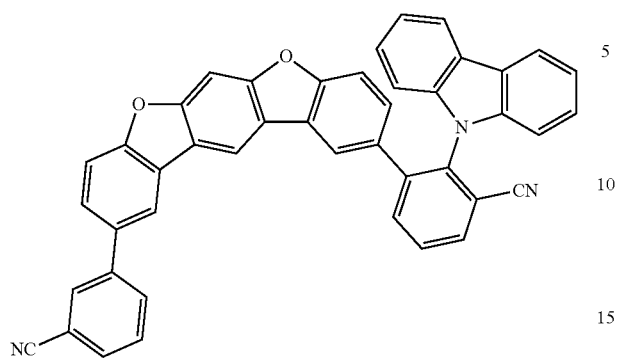
202
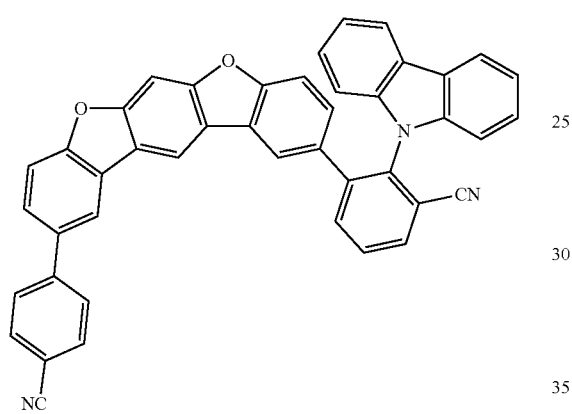
203
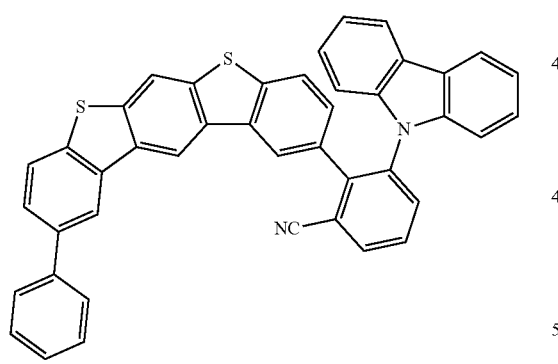
204
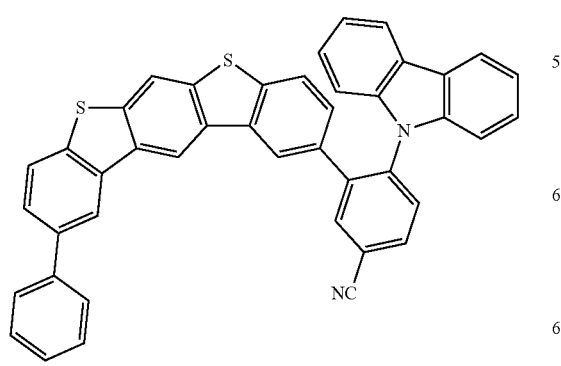
-continued
205
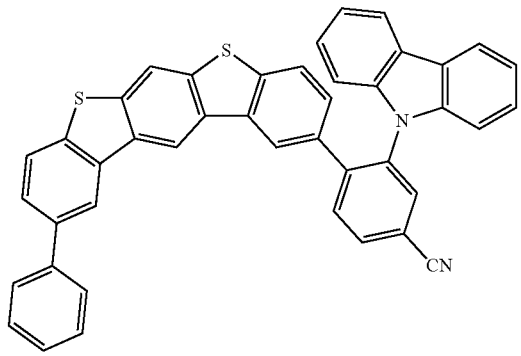
206
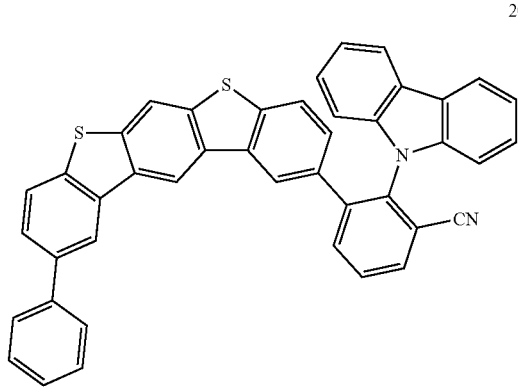
207
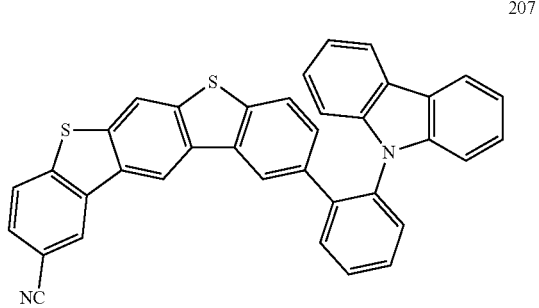
208
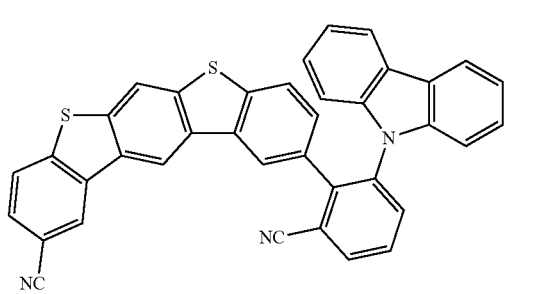

-continued
209
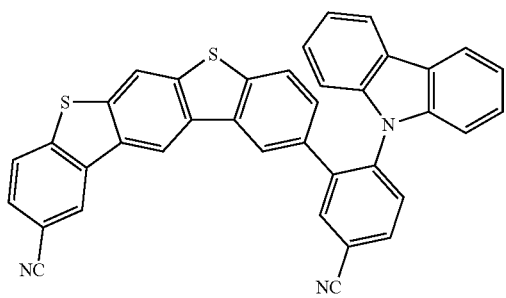
210
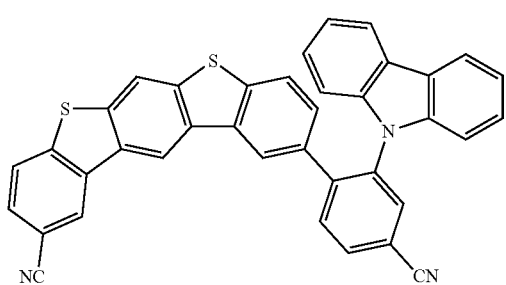
211
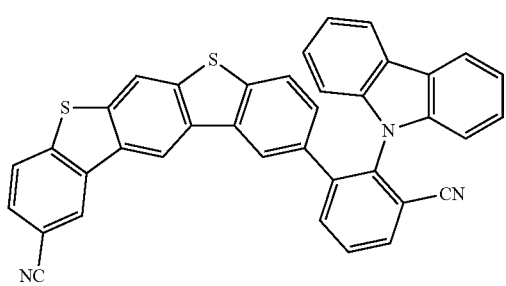
212
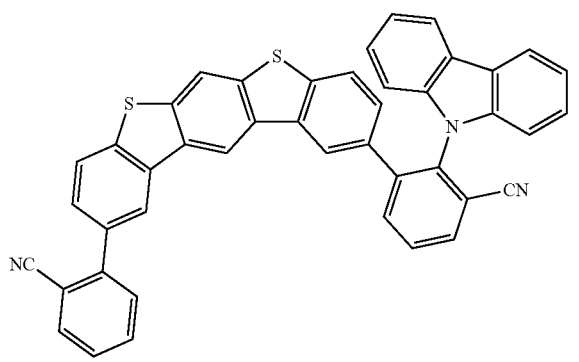
-continued
213
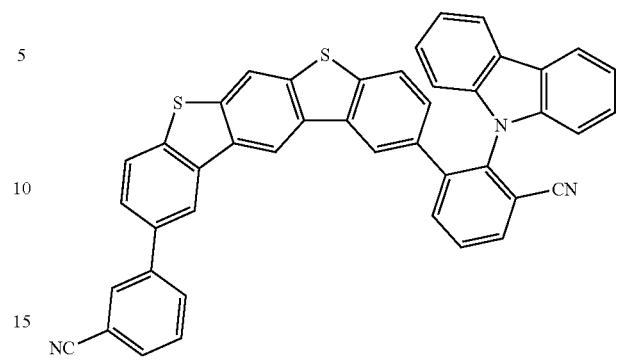
214
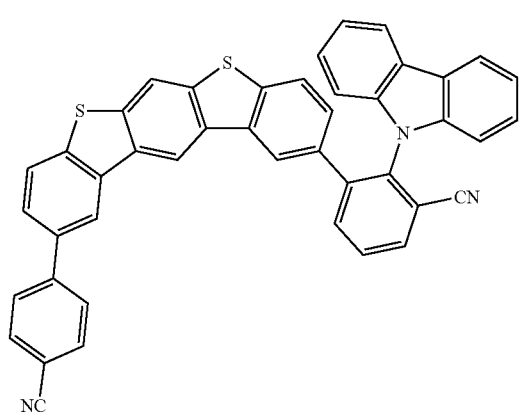
215
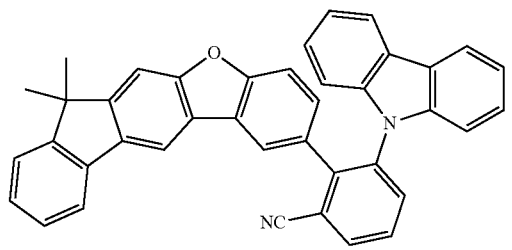
216
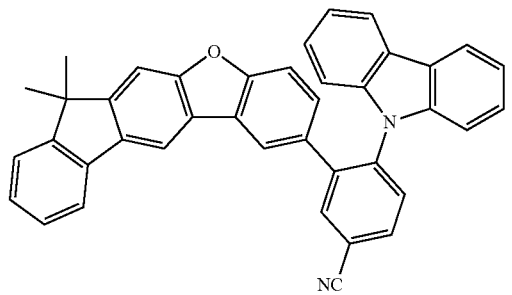

217
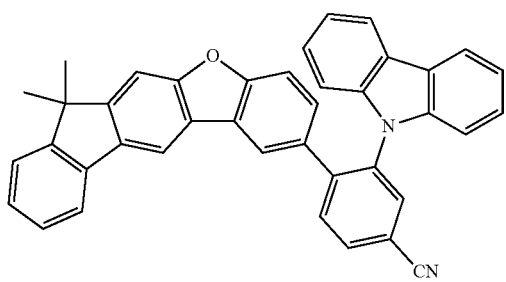
218
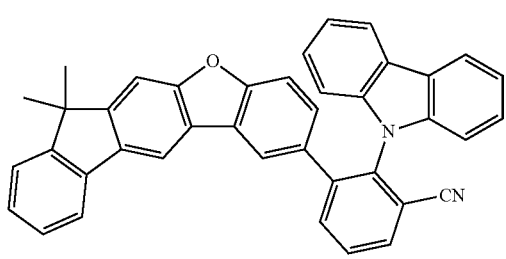
219
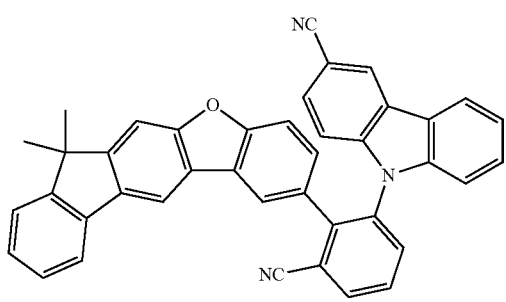
220
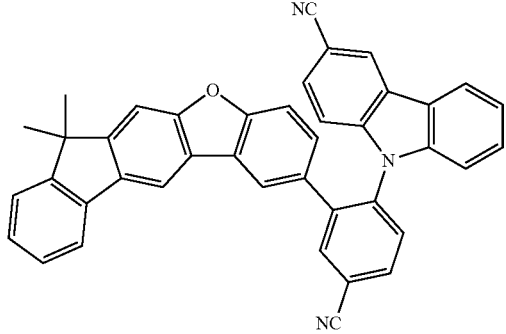
221
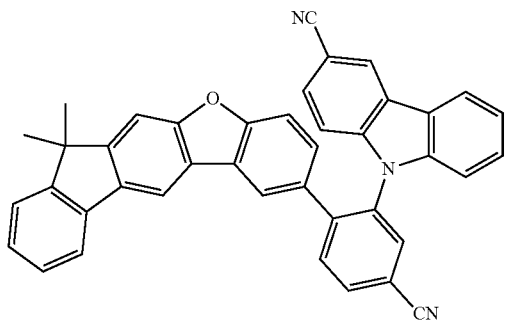
222
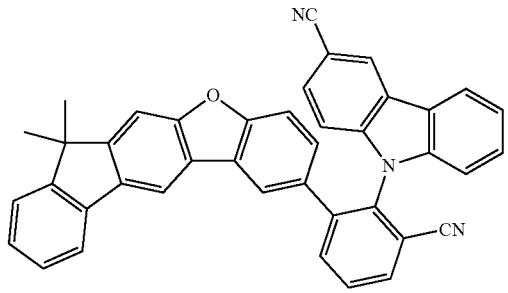
223
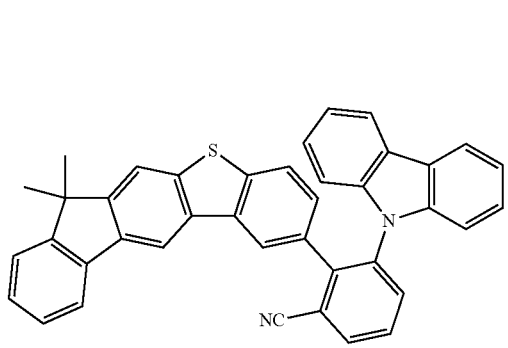
224
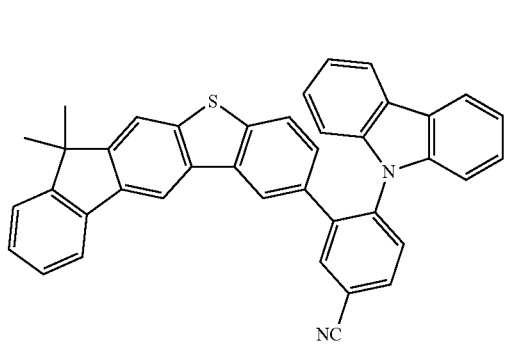
225
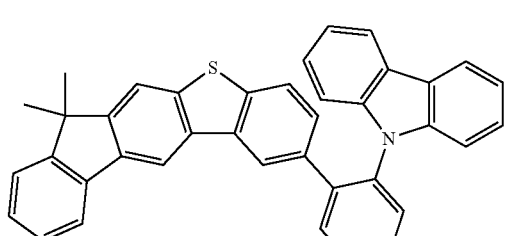
226
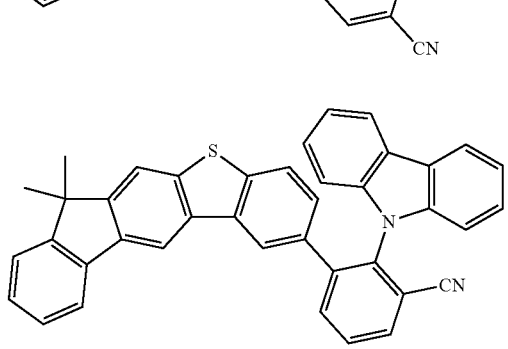

-continued
227
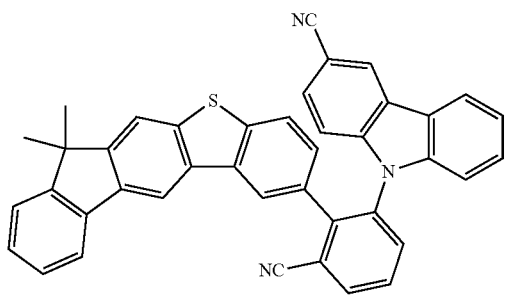
228
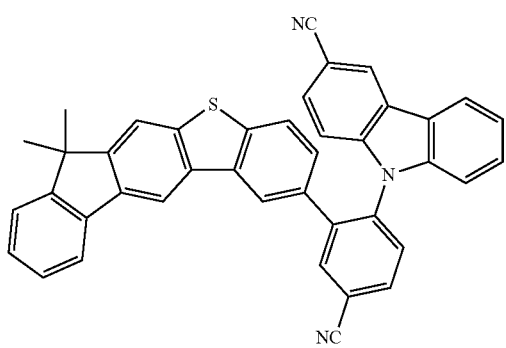
229
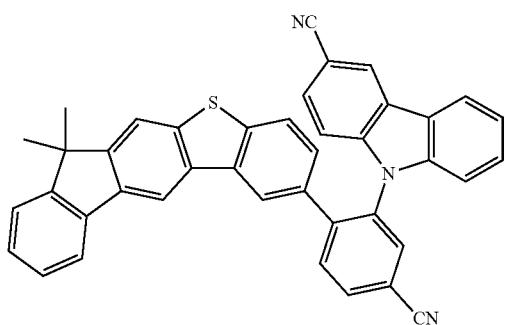
230
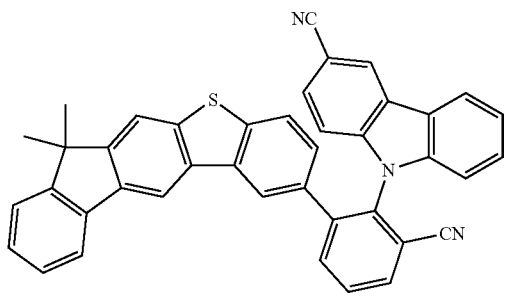
231
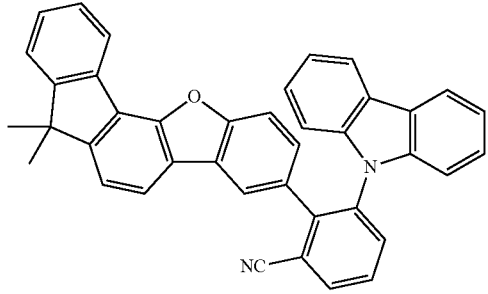
-continued
232
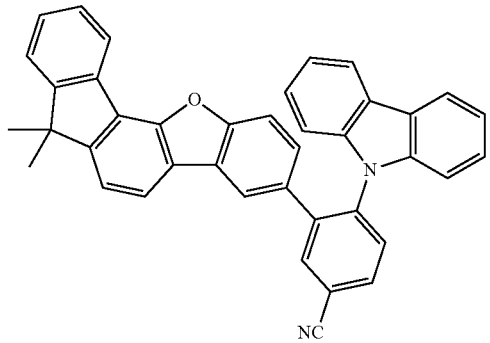
233
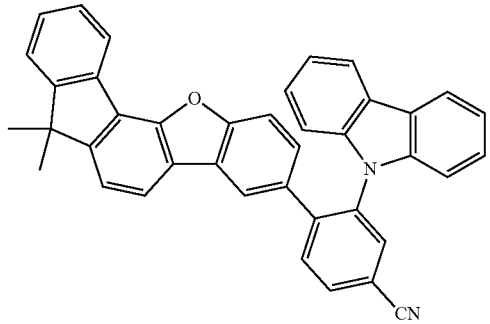
234
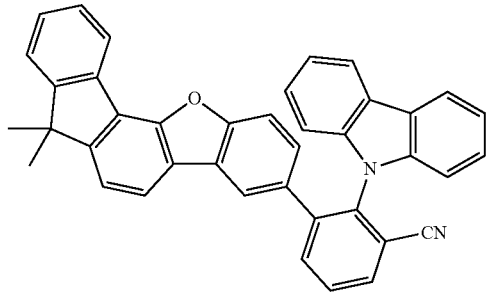
235
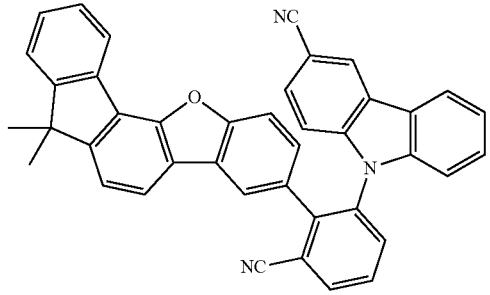
236
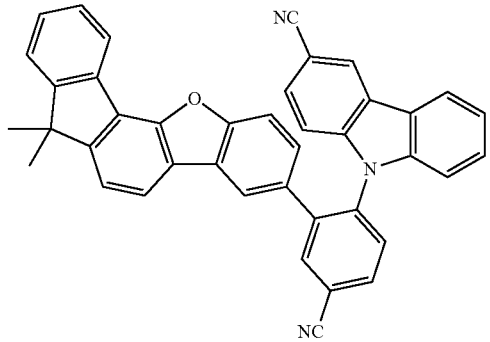

237
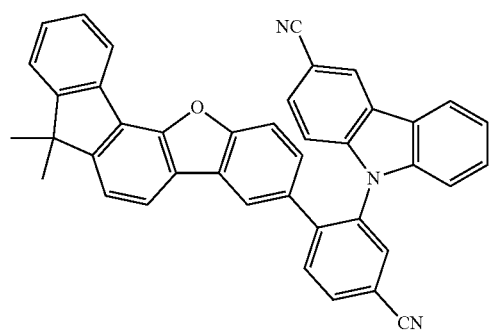
238
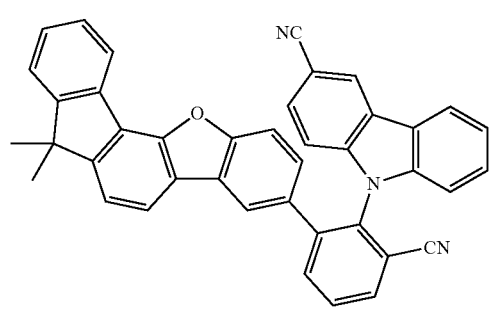
239
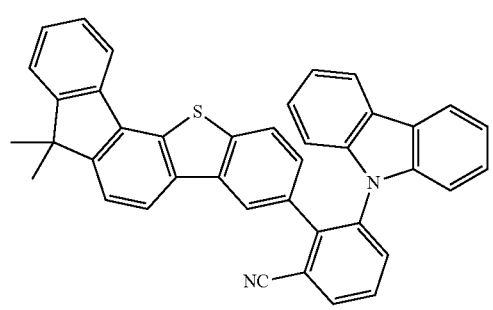
240
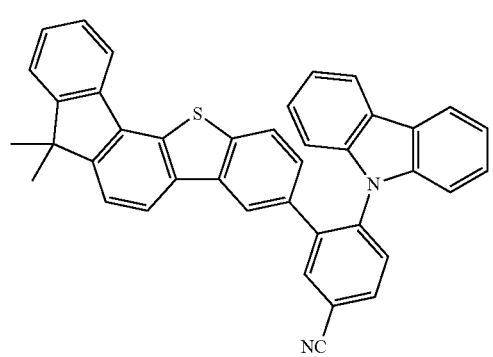
241
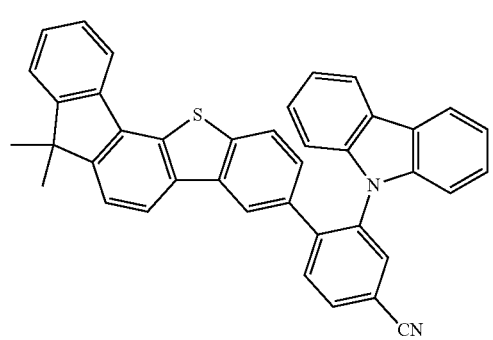
242
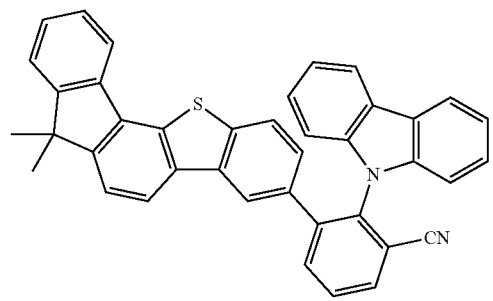
243
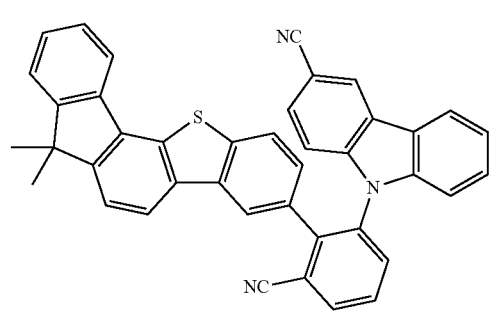
244
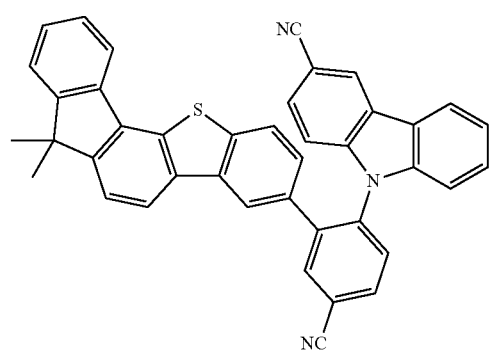
245
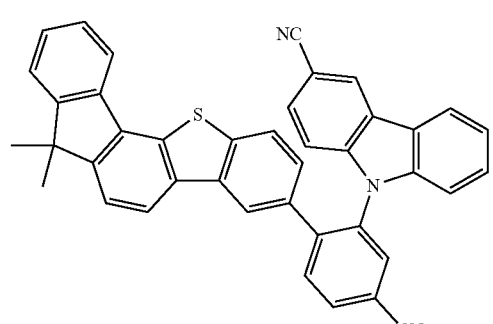
246
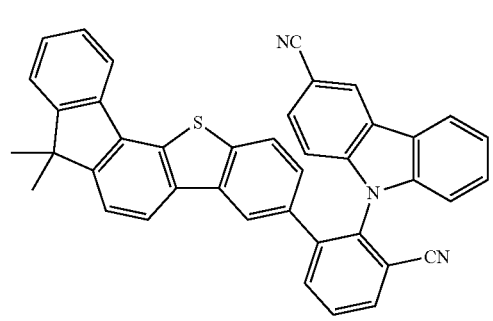

247
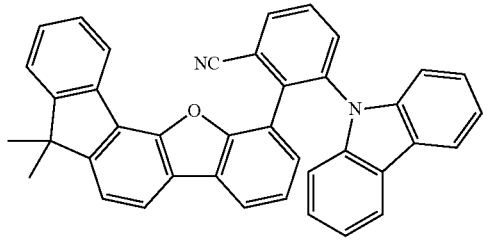
248
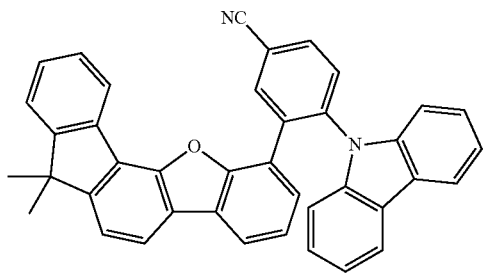
249
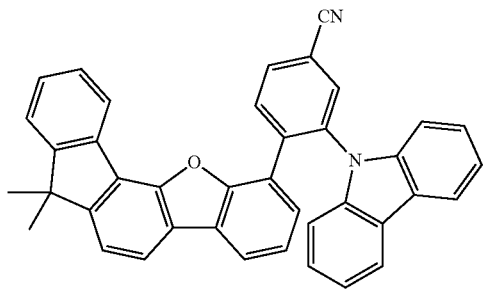
250
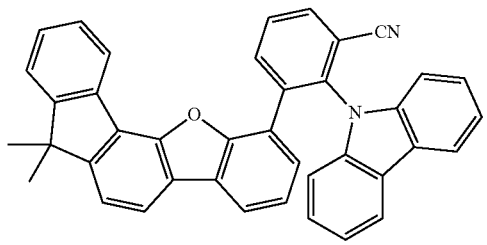
251
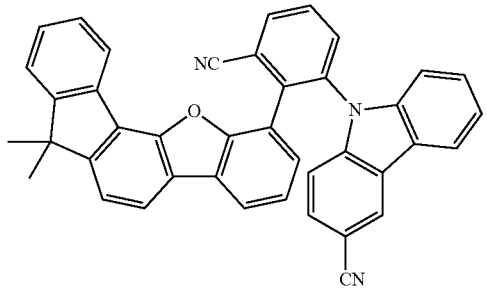
252
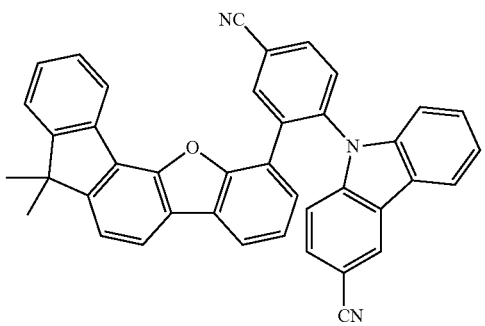
253
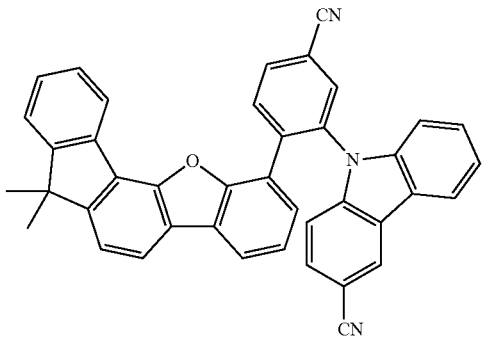
254
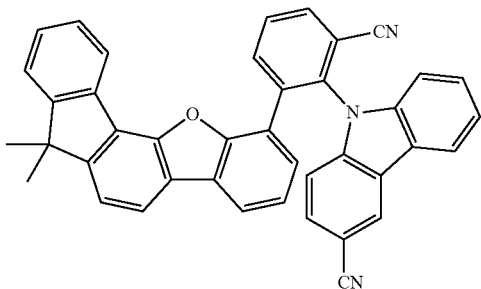
255
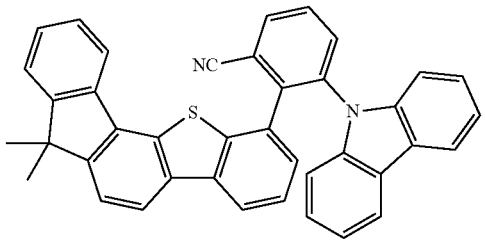
256
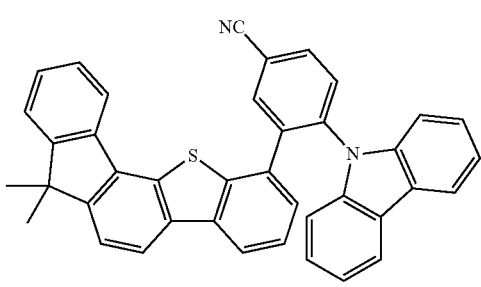

257
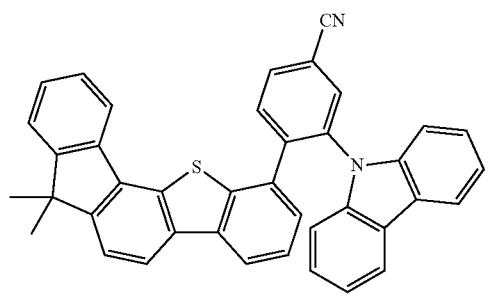
258
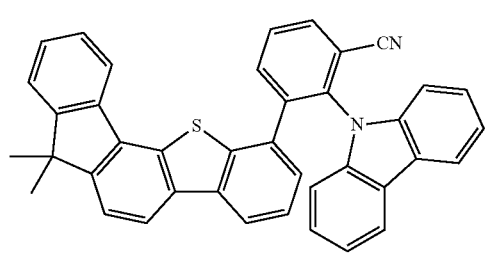
259
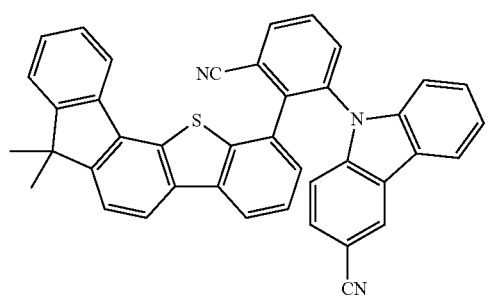
260
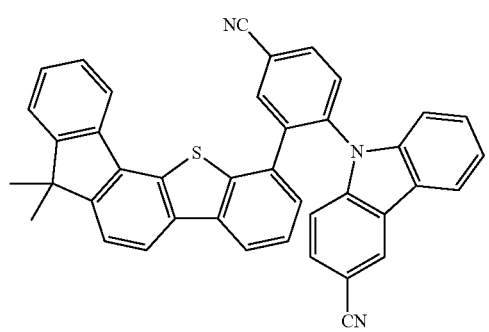
261
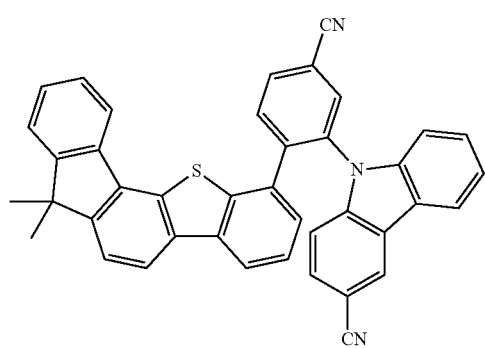
262
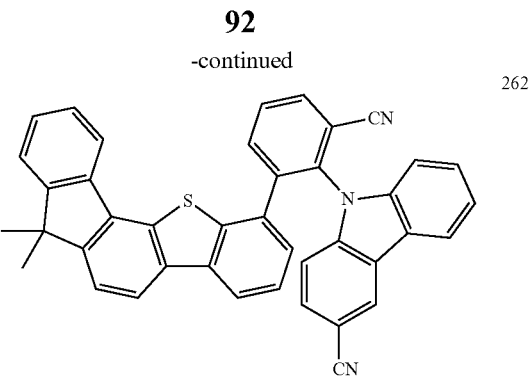
263
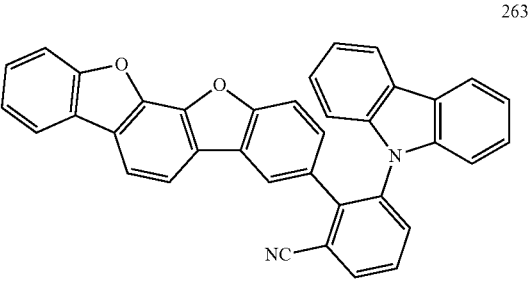
264
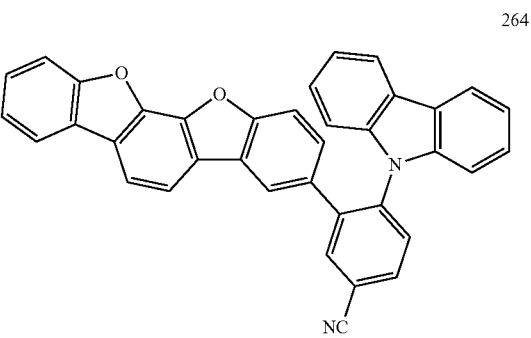
265
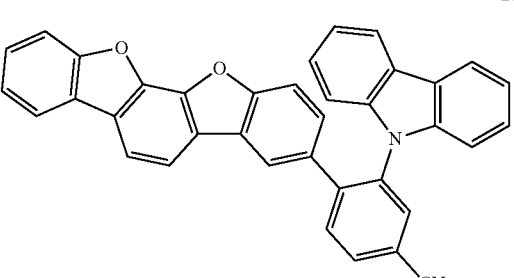
266
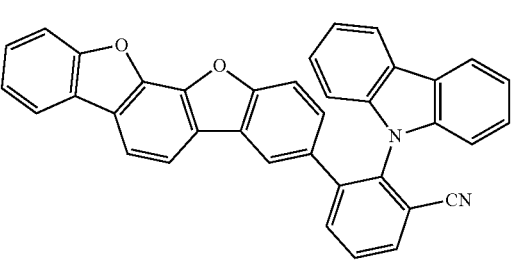

267
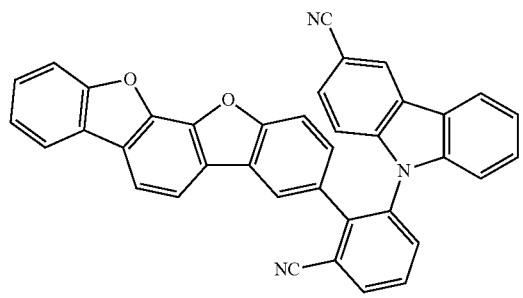
268
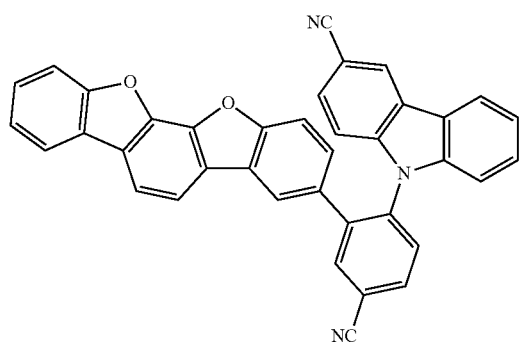
269
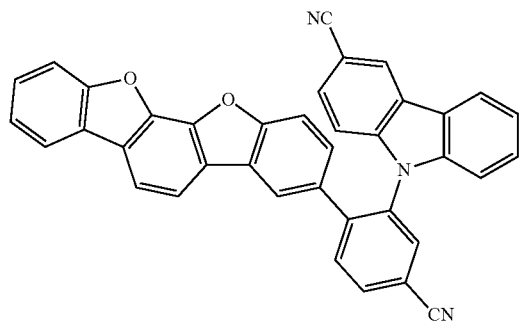
270
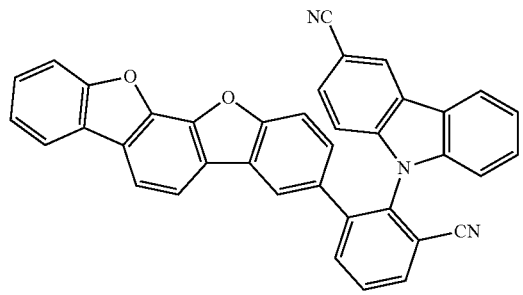
271
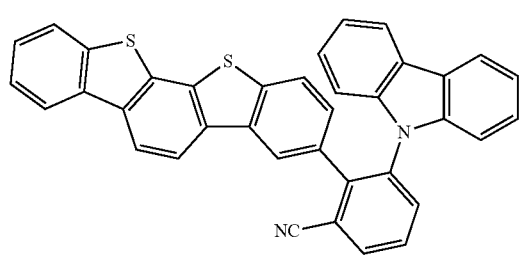
272
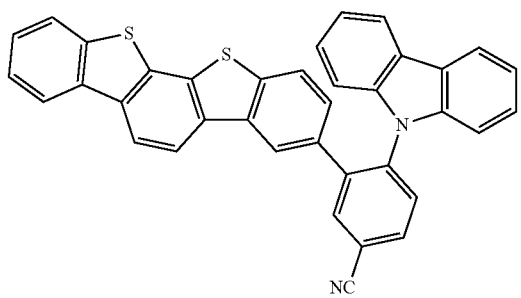
273
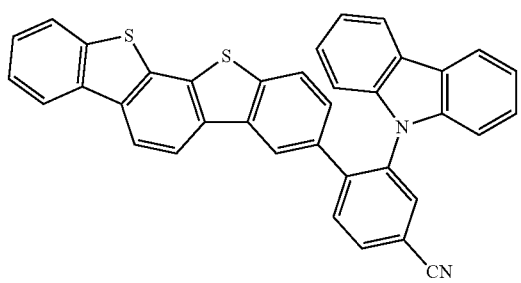
274
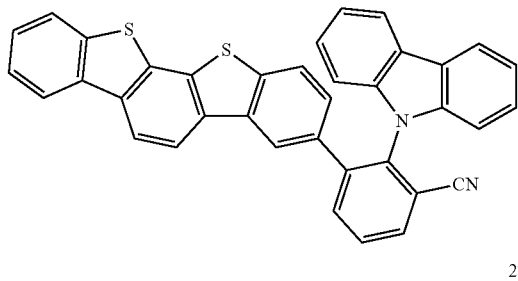
275
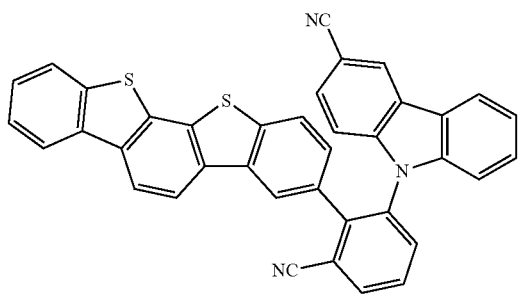
276
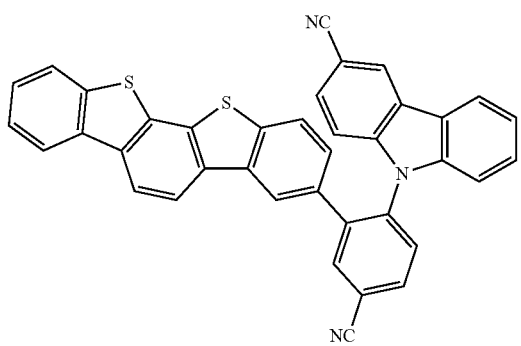

-continued
277
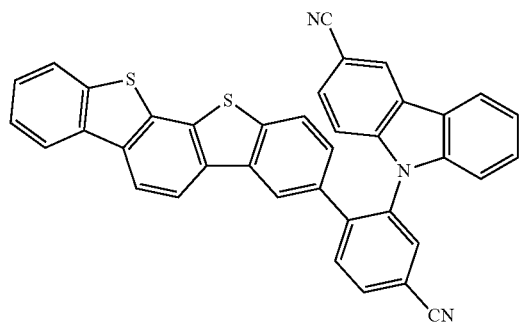
278
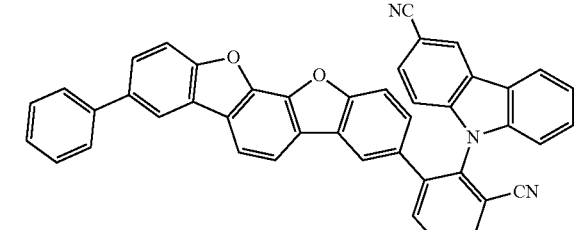
279
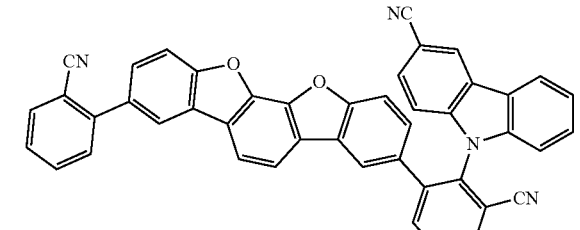
280
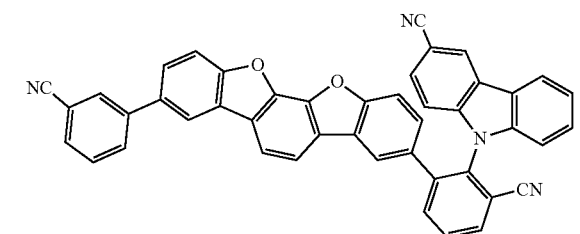
281
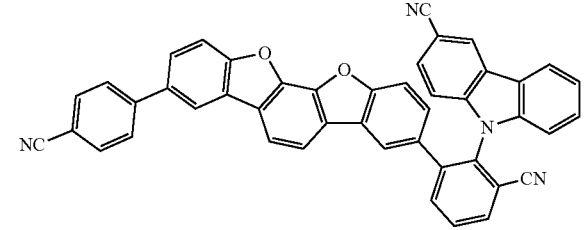
-continued
282
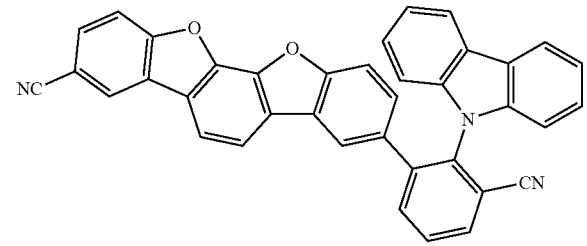
283
284
285
286
287
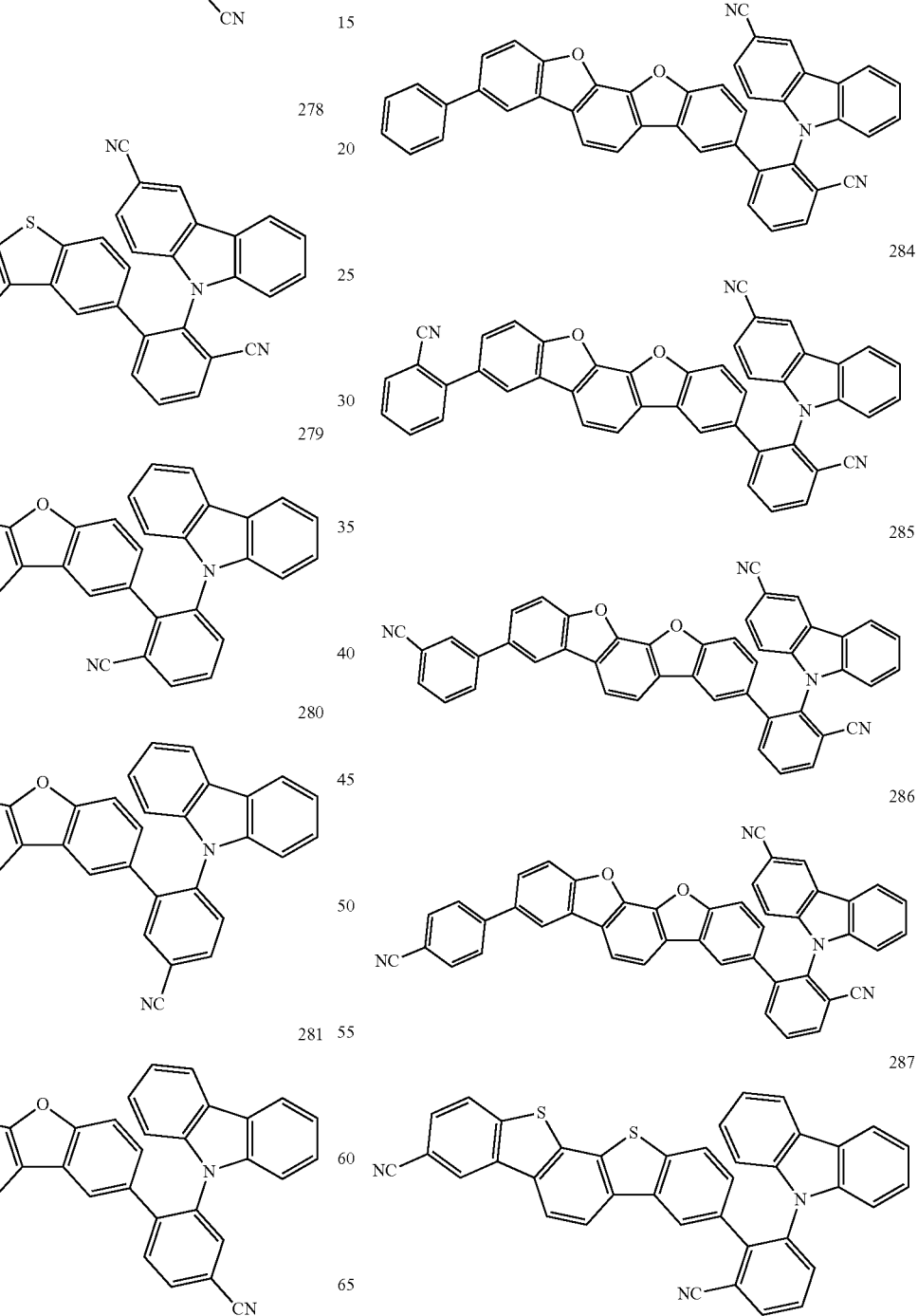

-continued
288
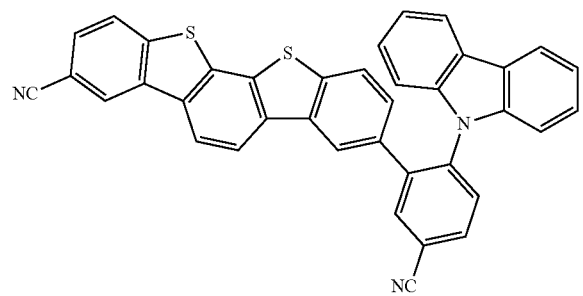
289
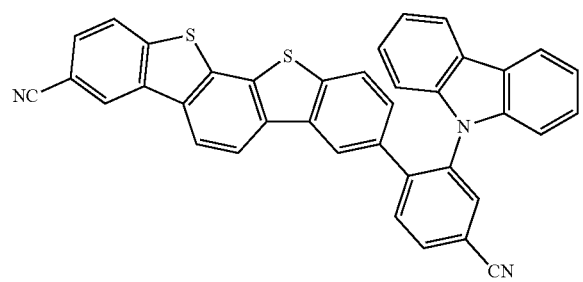
290
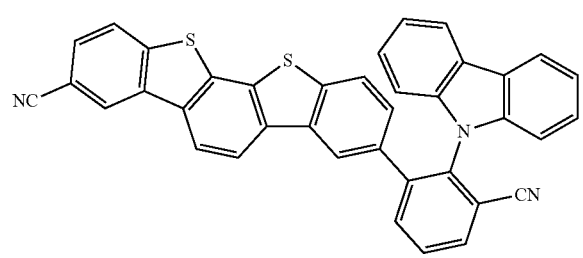
291
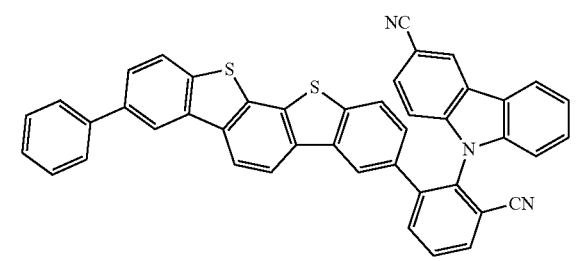
292
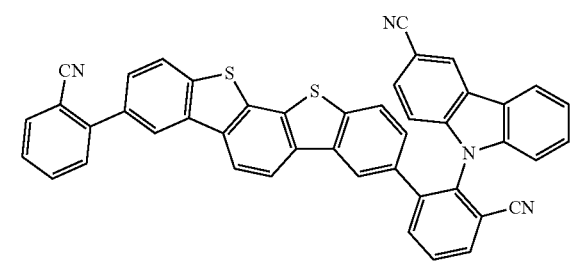
-continued
293
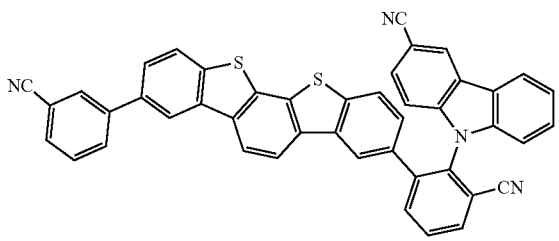
294
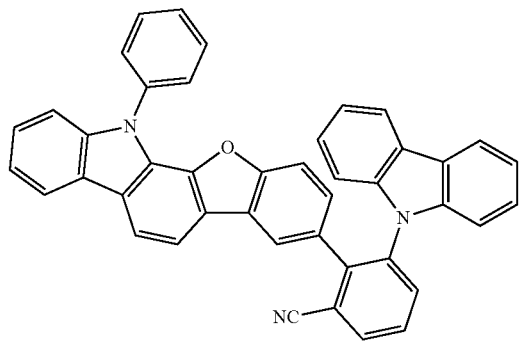
295
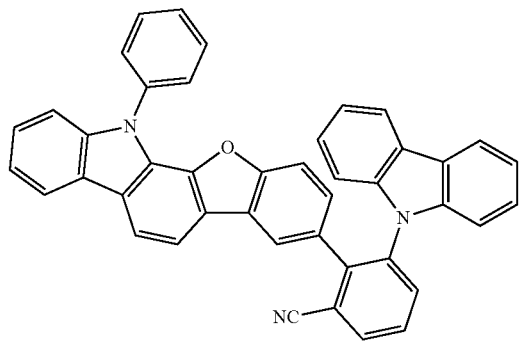
296
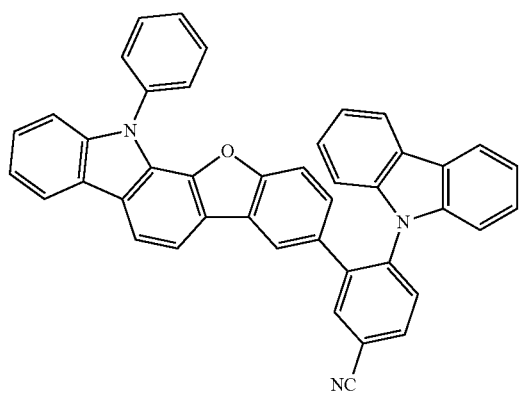

297
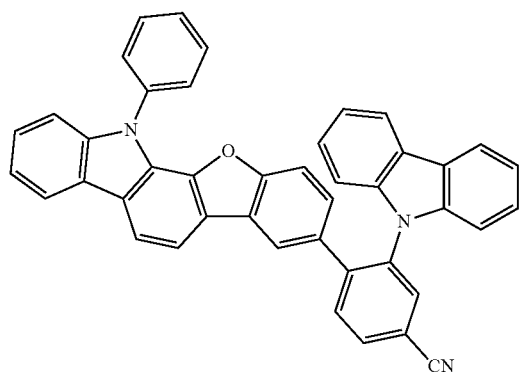
298
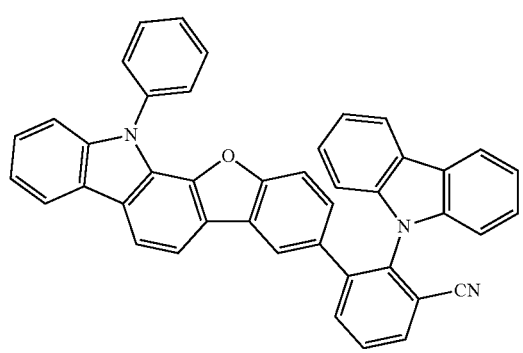
299
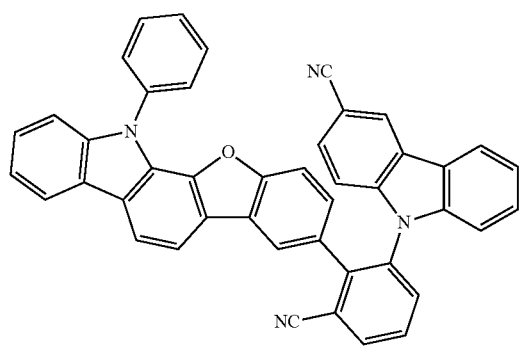
300
301
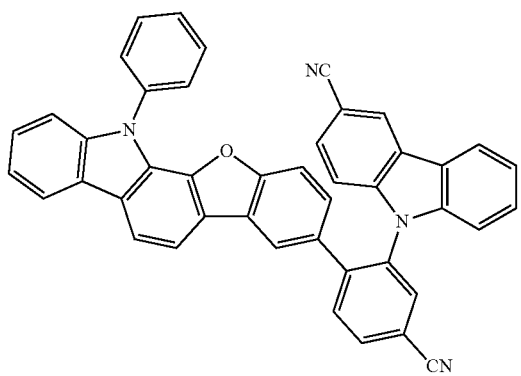
302
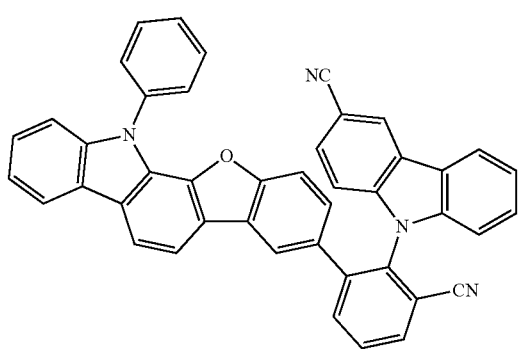
303
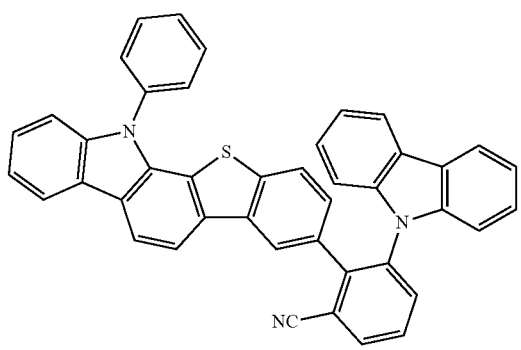
304
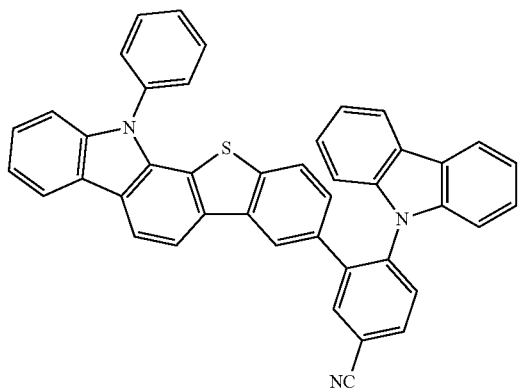

305
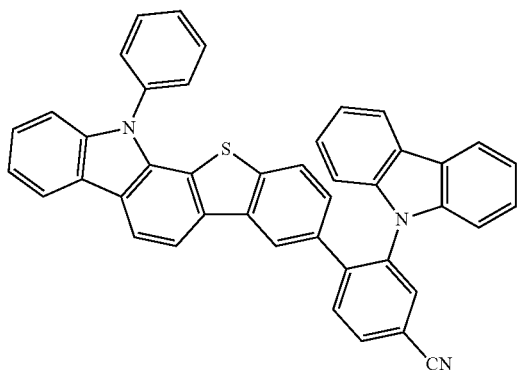
306
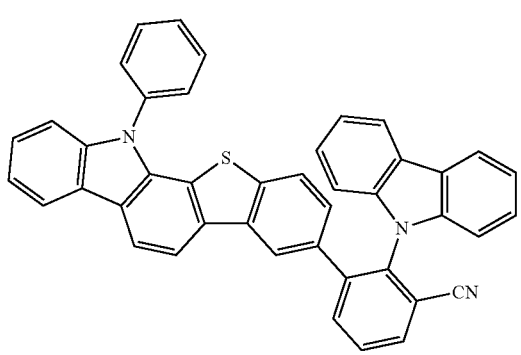
307
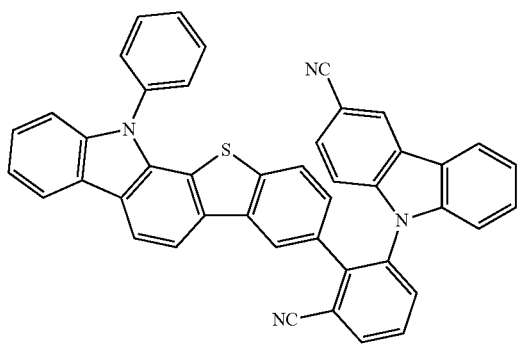
308
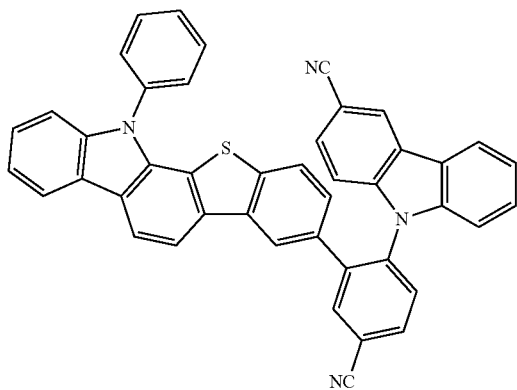
309
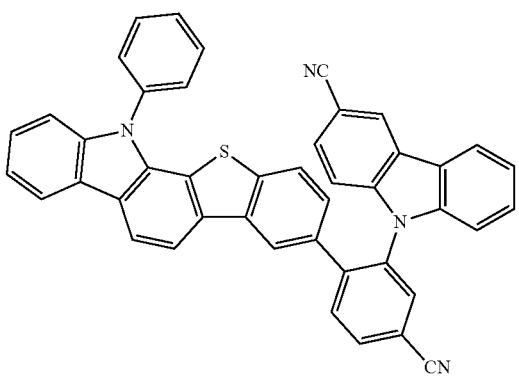
310
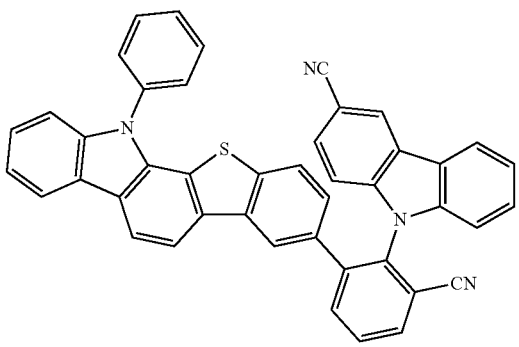
311
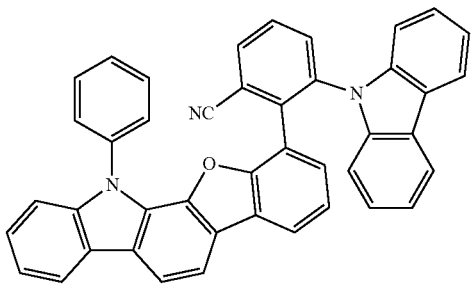
312
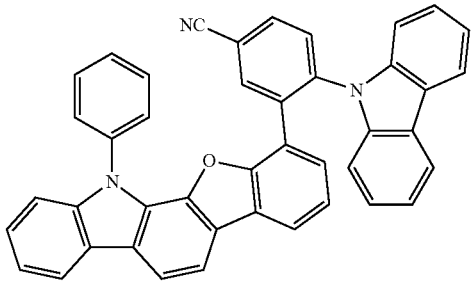

103
-continued
313
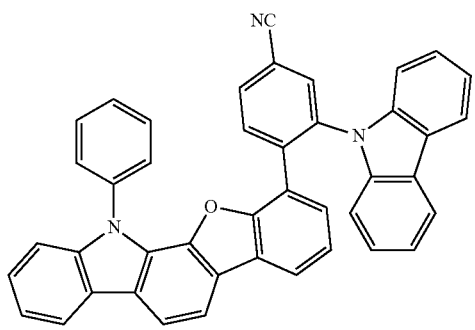
314
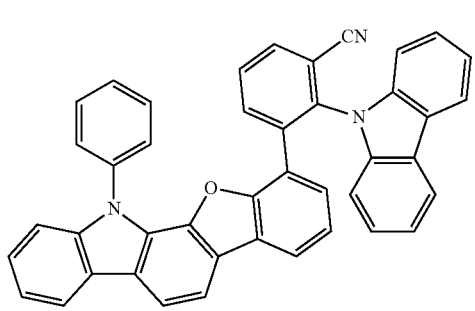
315
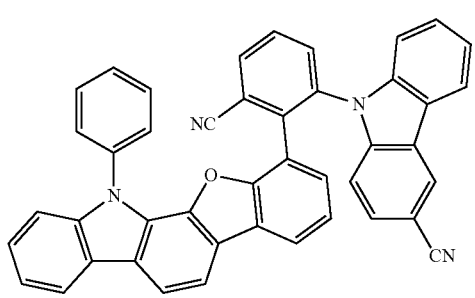
316
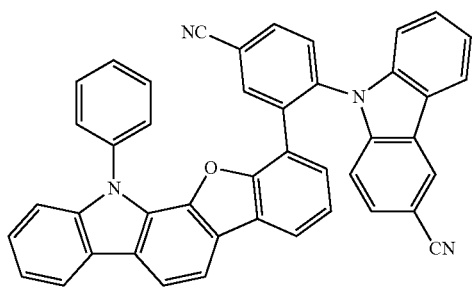
317
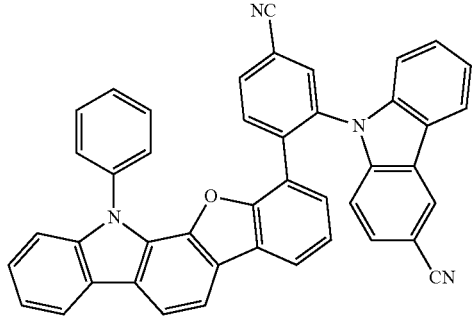
104
-continued
318
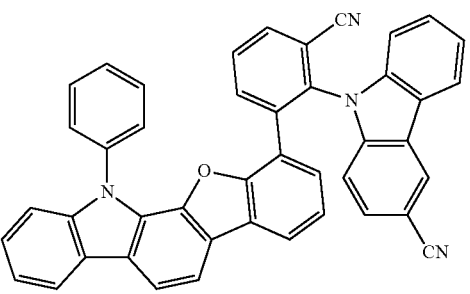
319
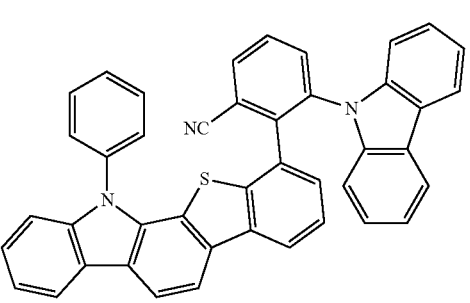
320
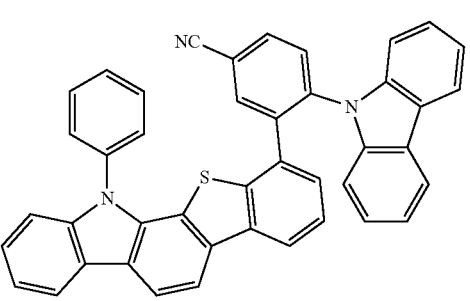
321
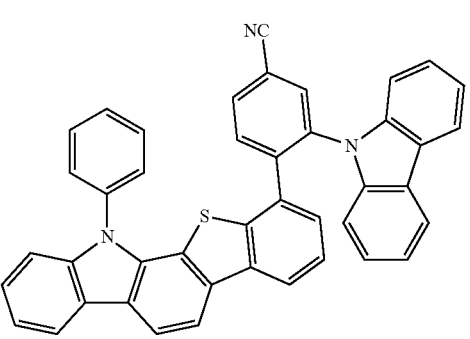
322
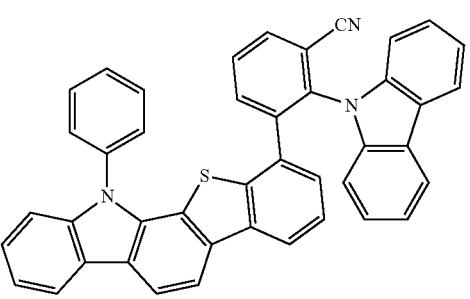

323
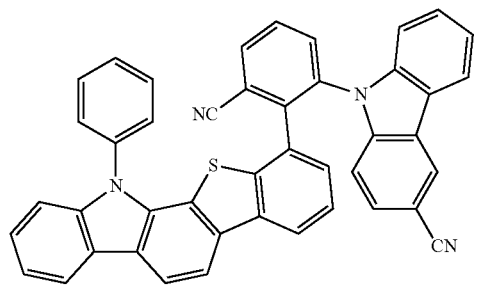
324
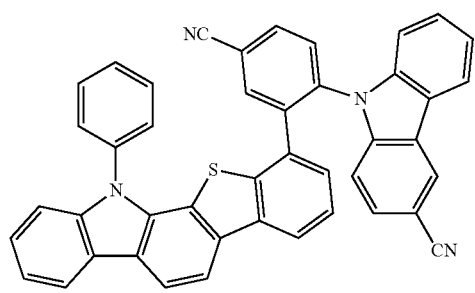
325
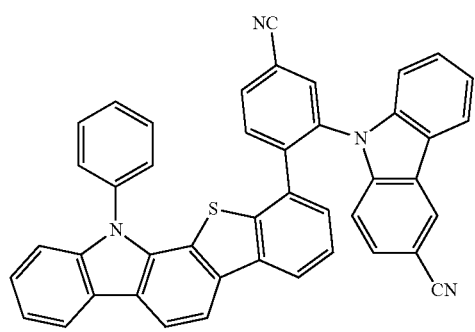
326
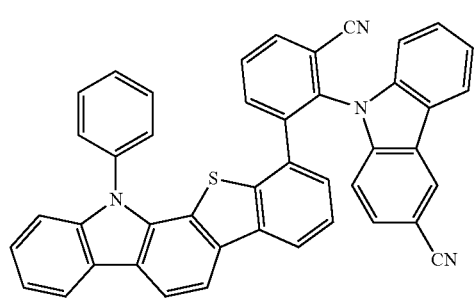
327
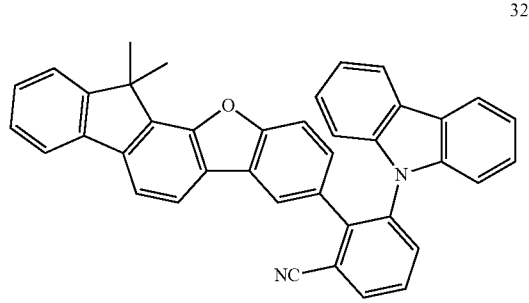
328
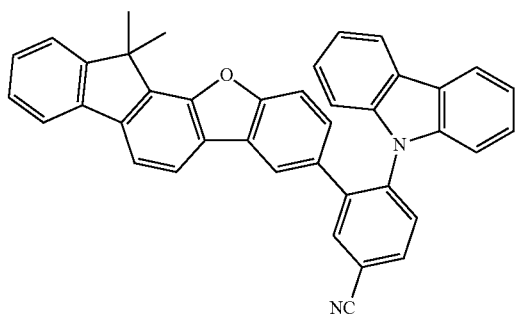
329
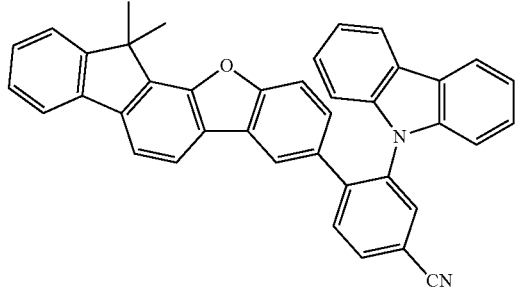
330
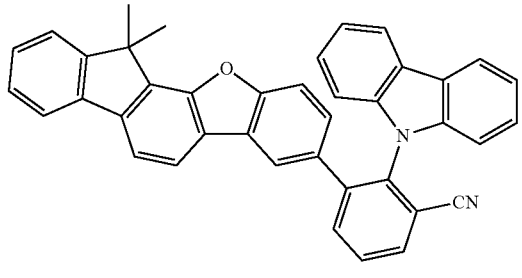
331
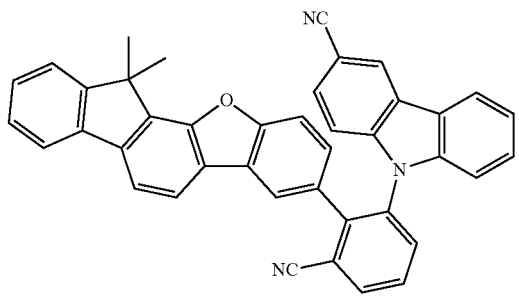
332
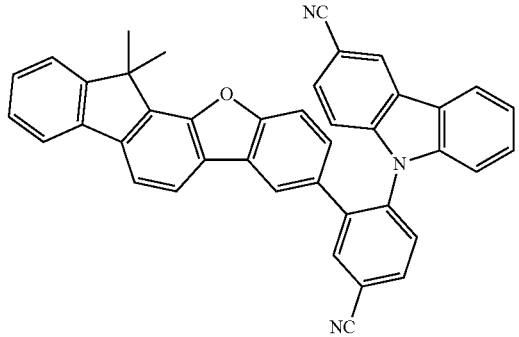

333
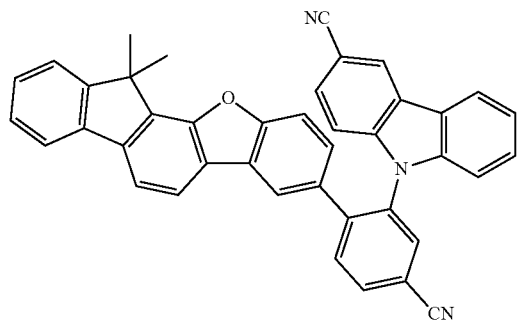
334
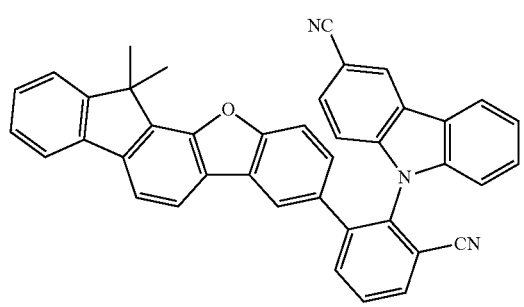
335
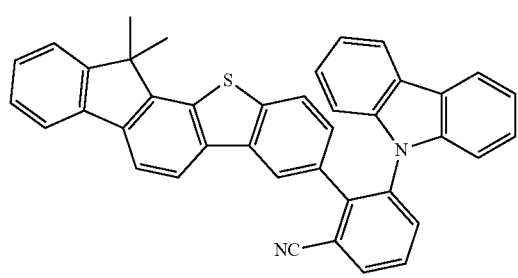
336
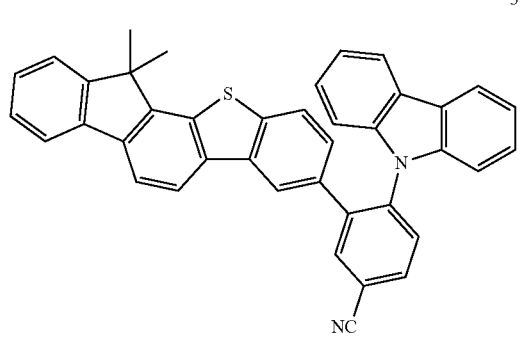
337
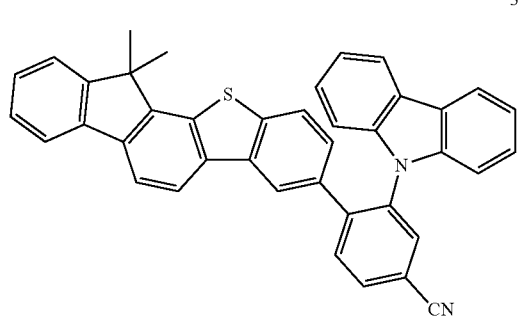
338
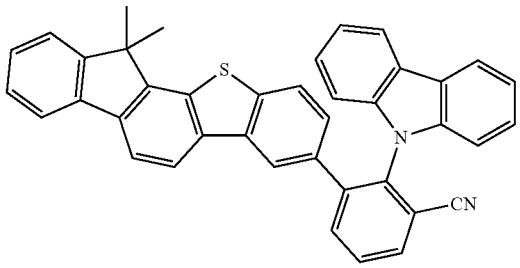
339
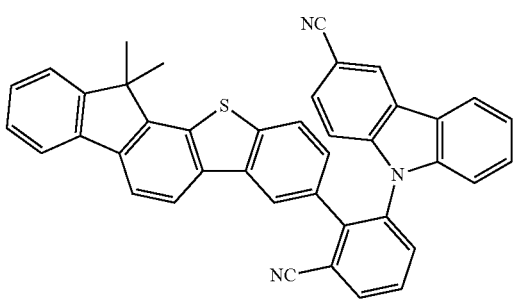
340
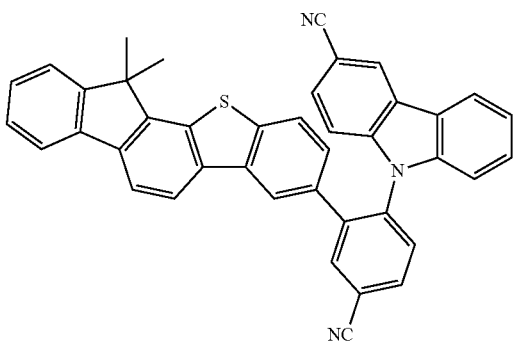
341
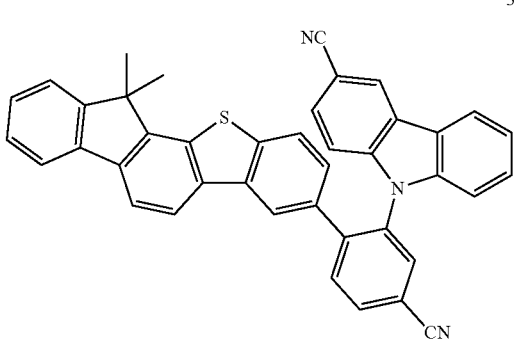
342
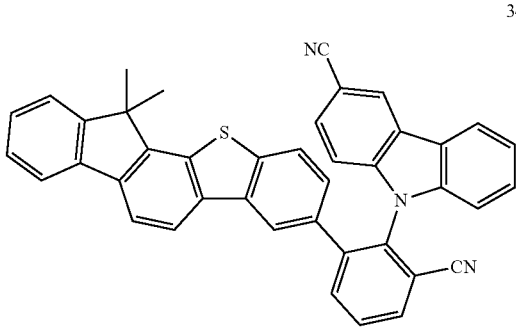

343
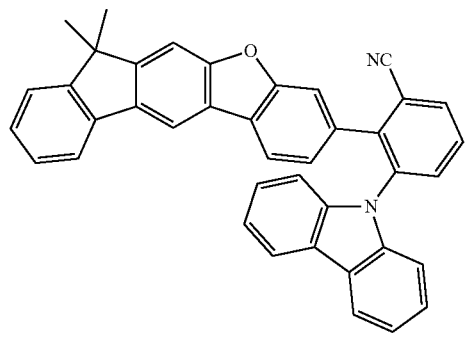
344
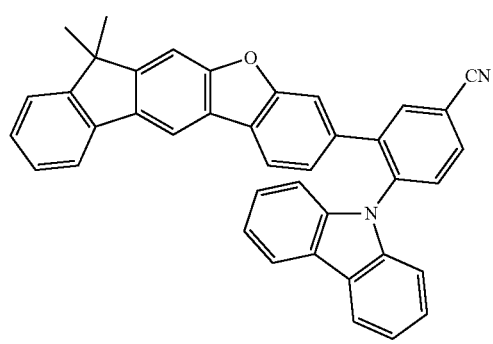
345
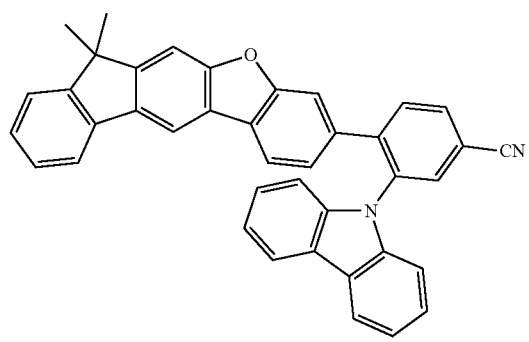
346
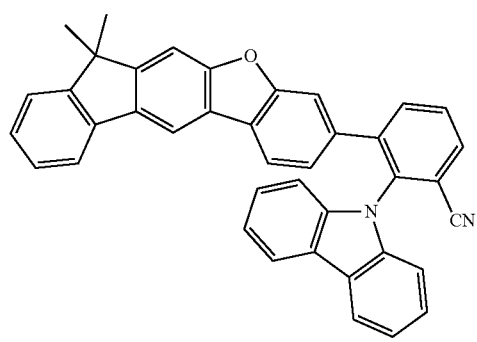
347
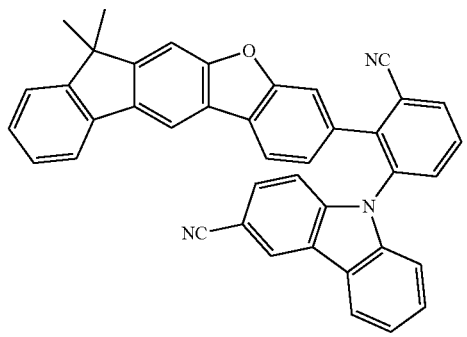
348
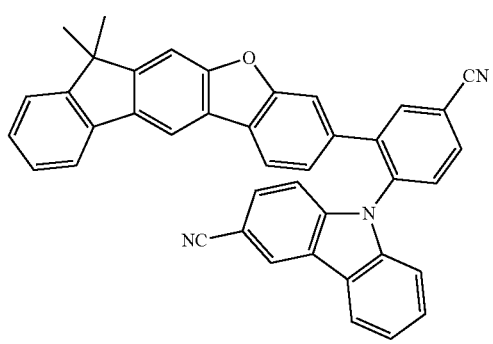
349
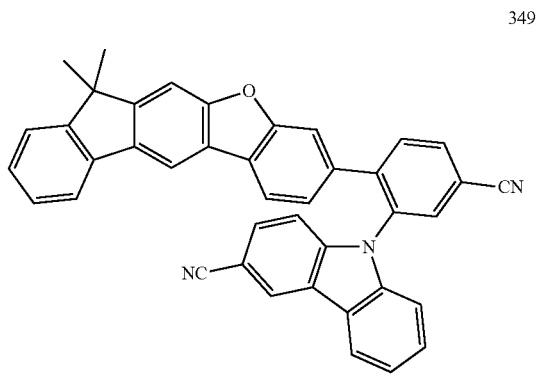
350
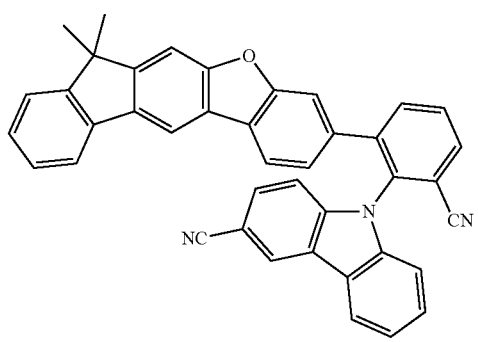

111
-continued
351
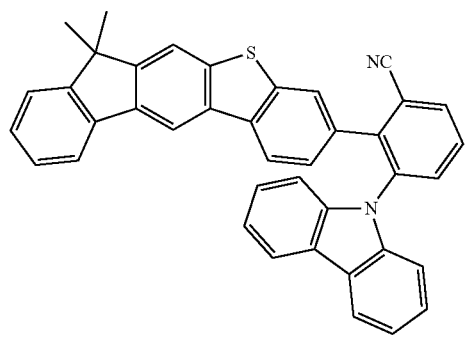
352
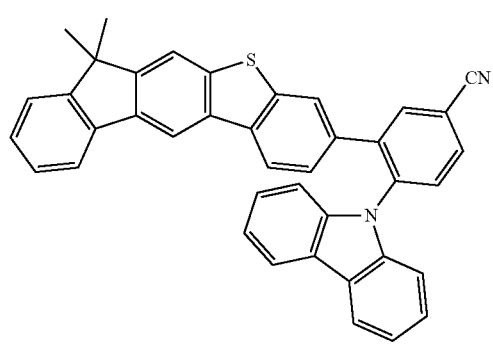
353
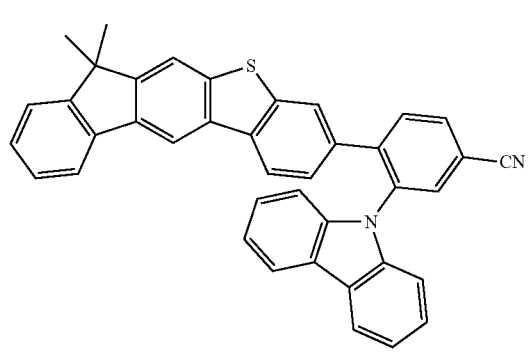
354
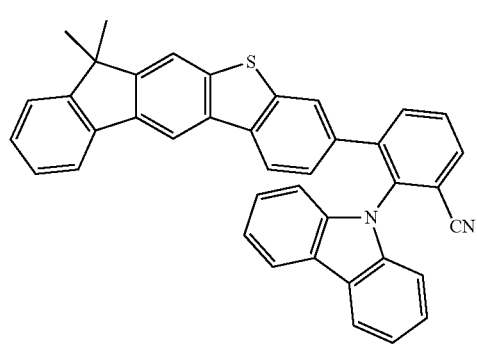
112
-continued
355
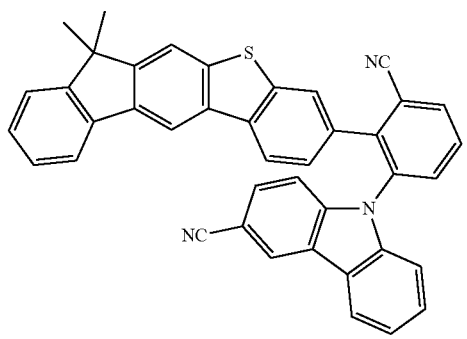
356
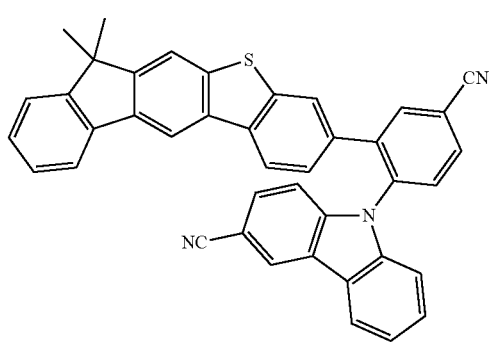
357
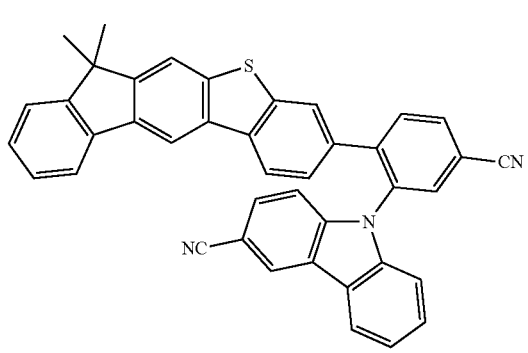
358
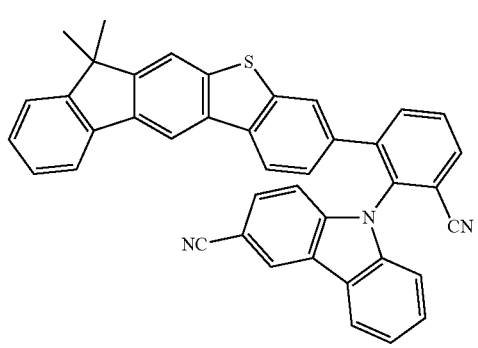

359 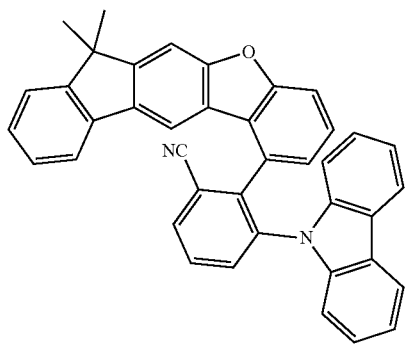
363 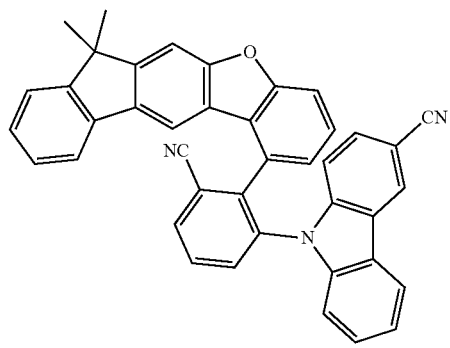
360 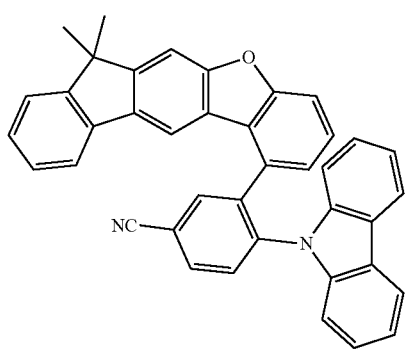
364 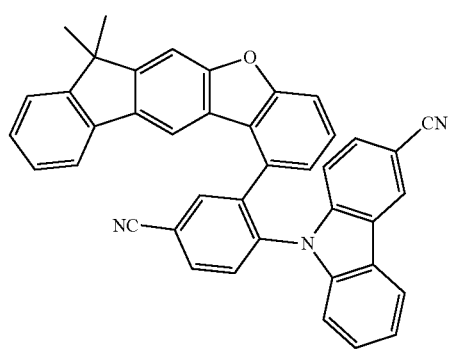
361 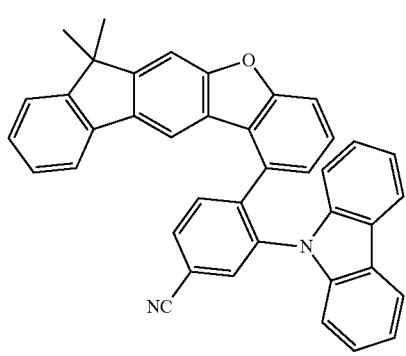
365 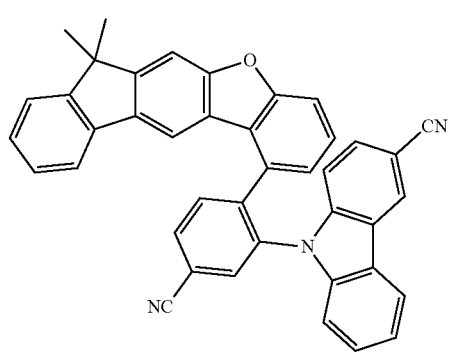
362 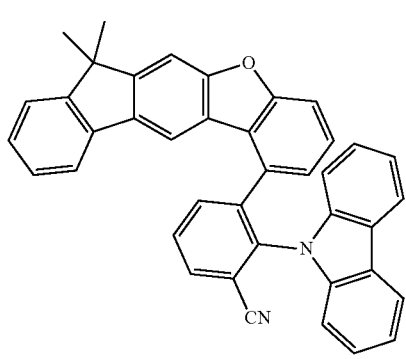
366 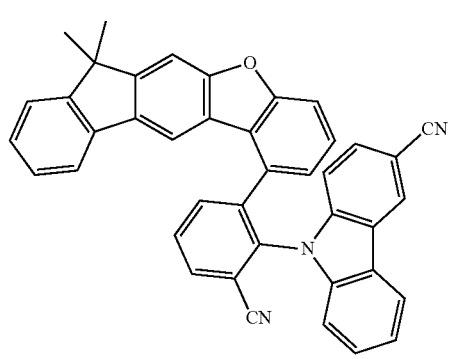

367
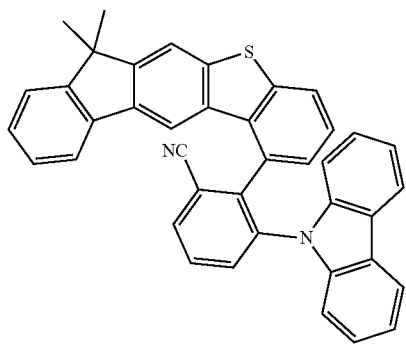
368
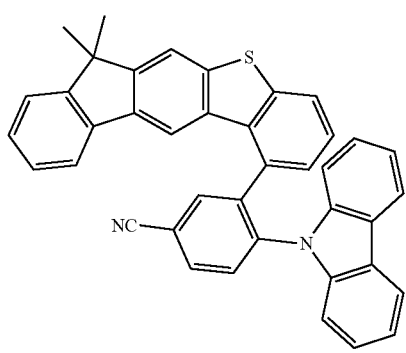
369
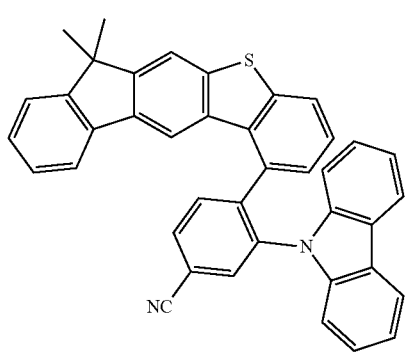
370
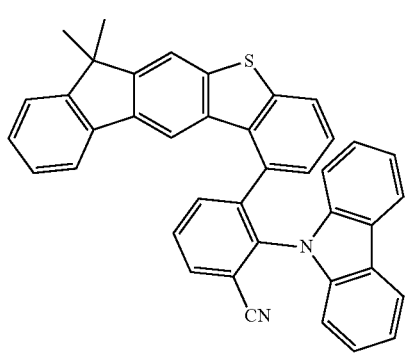
371
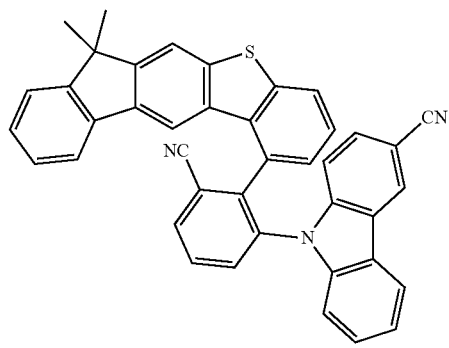
372
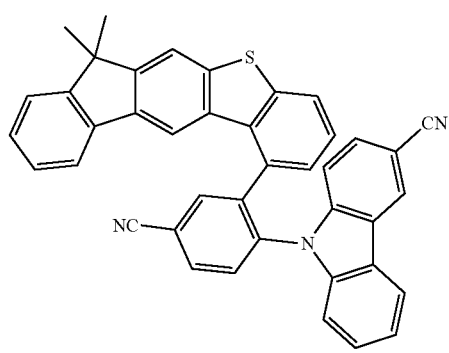
373
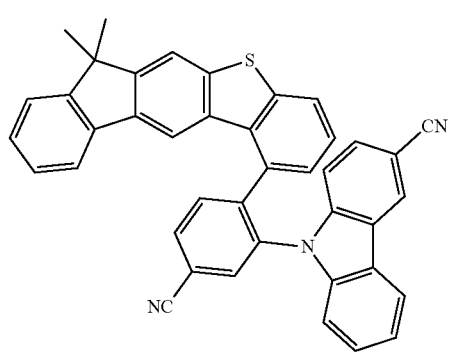
374
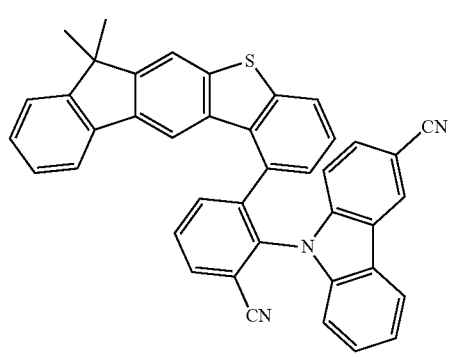

375
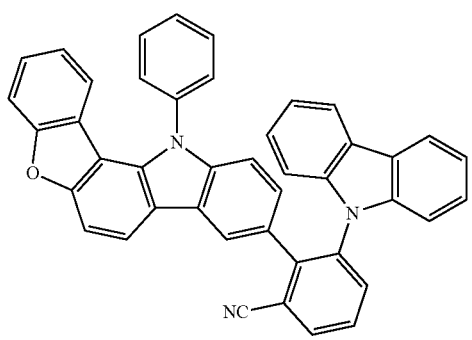
376
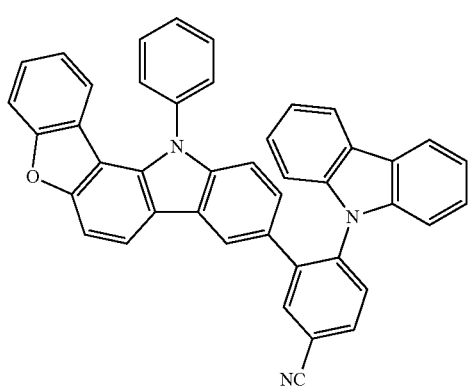
377
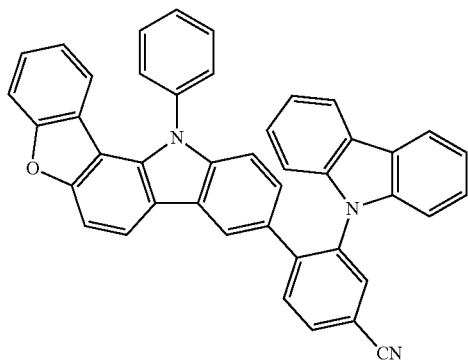
378
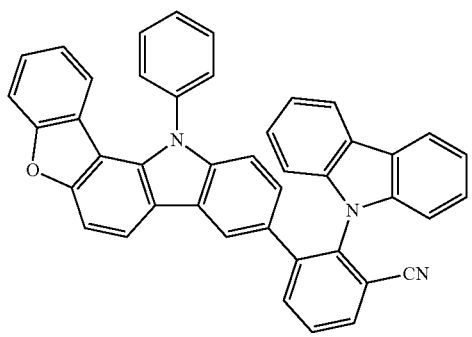
379
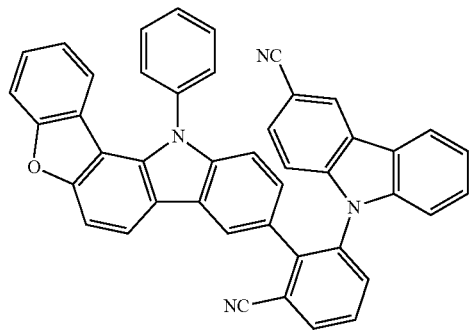
380
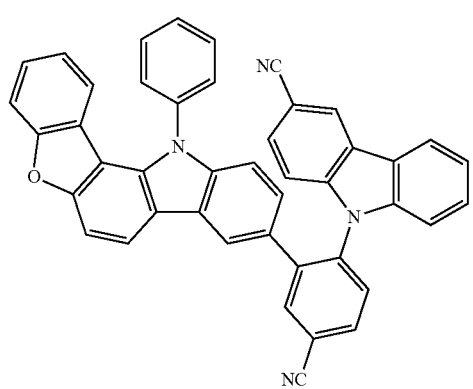
381
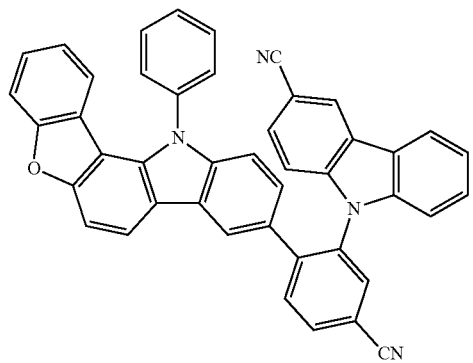
382
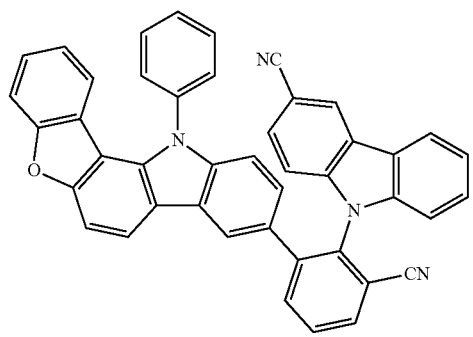

383
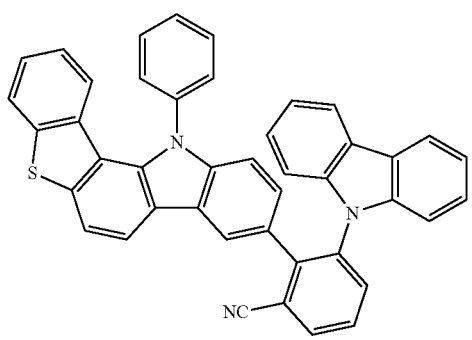
384
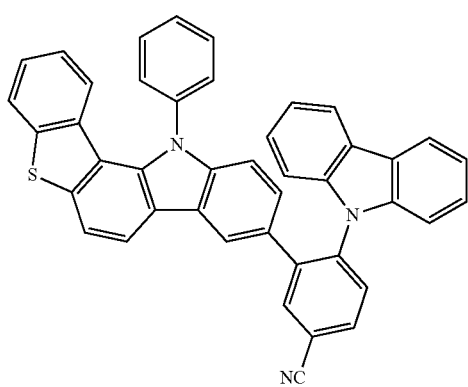
385
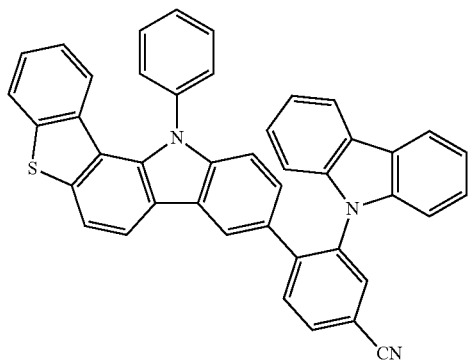
386
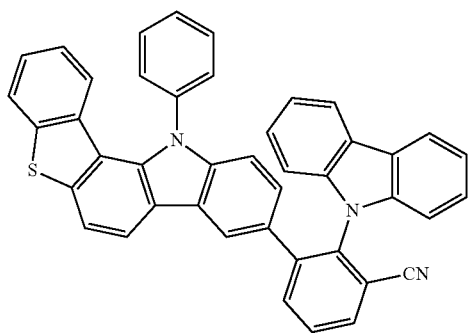
387
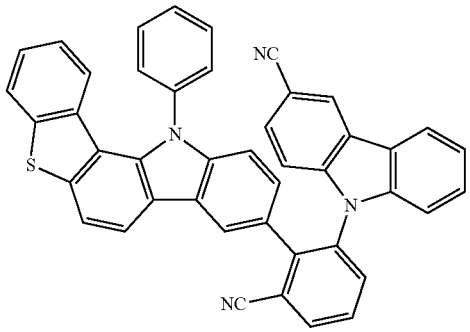
388
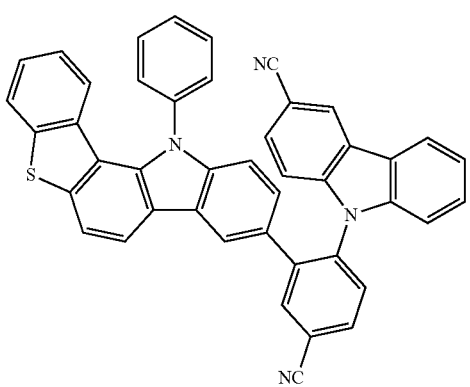
389
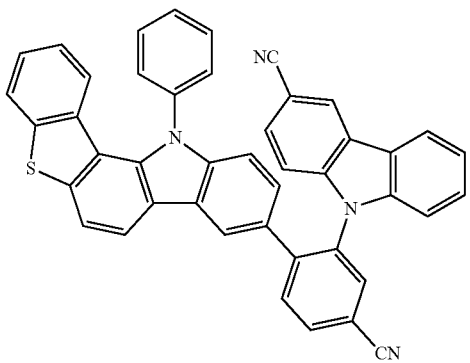
390
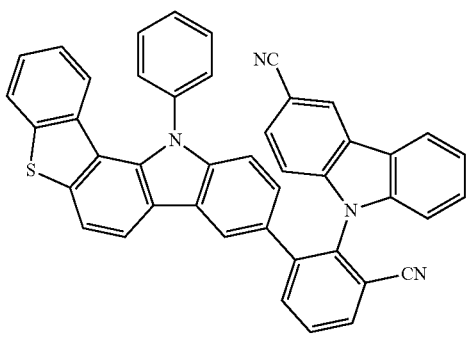

-continued
391
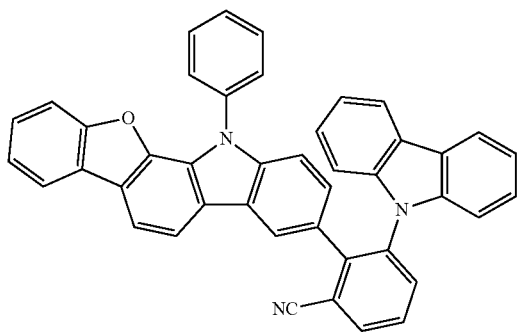
392
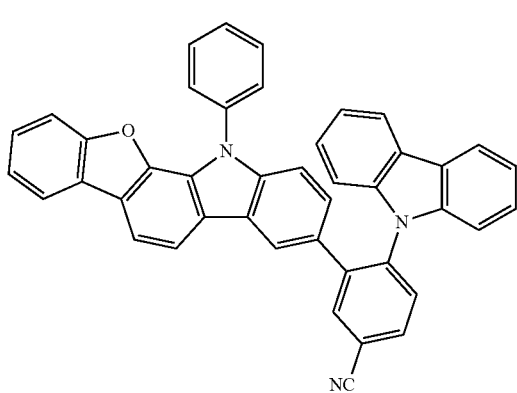
393
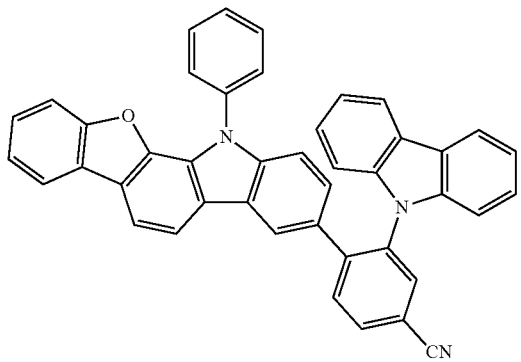
394
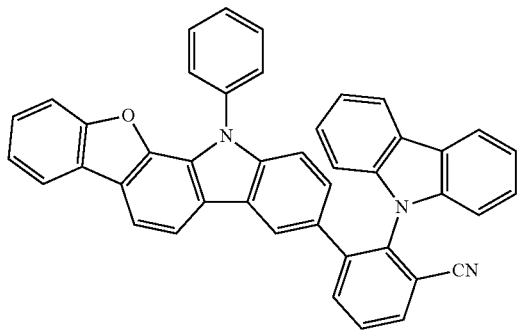
-continued
395
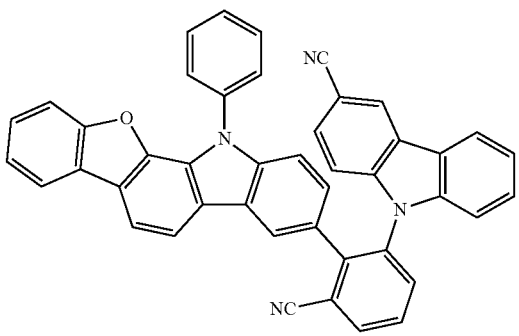
396
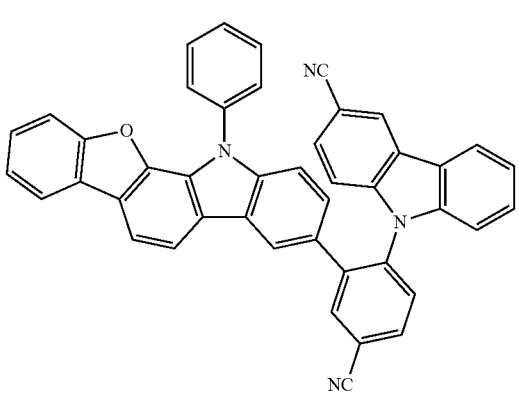
397
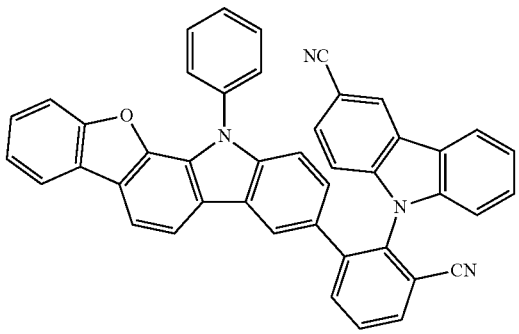
398

123
-continued
399
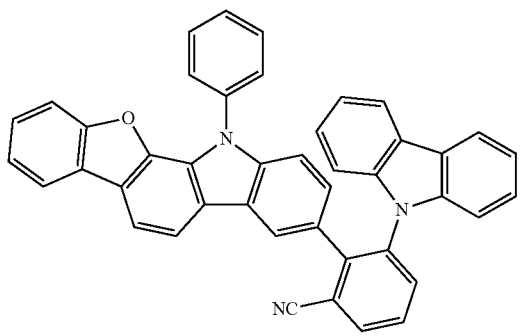
400
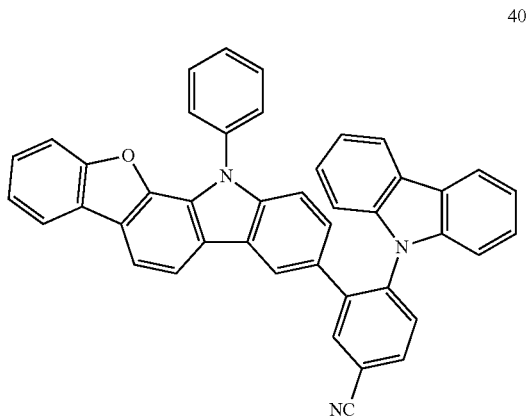
401
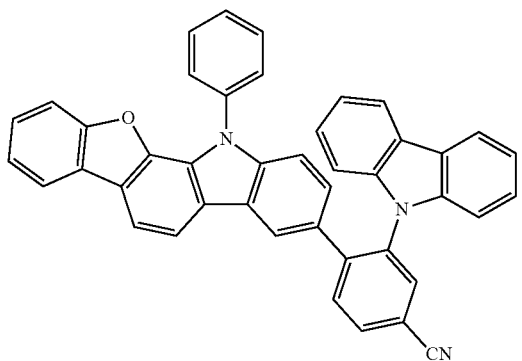
402
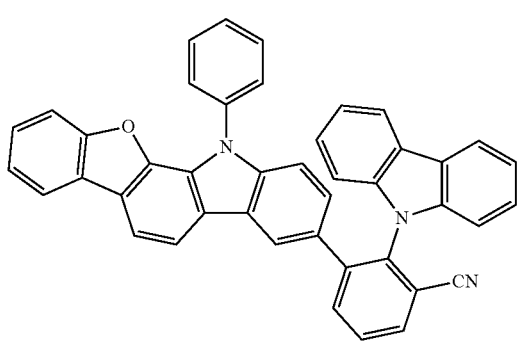
124
-continued
403
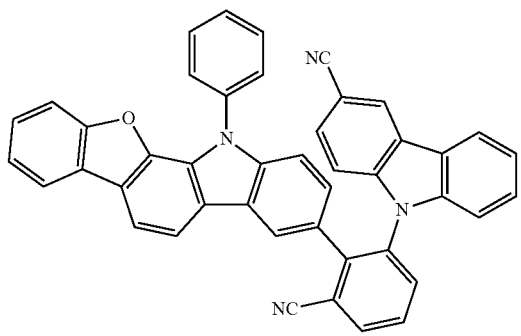
404
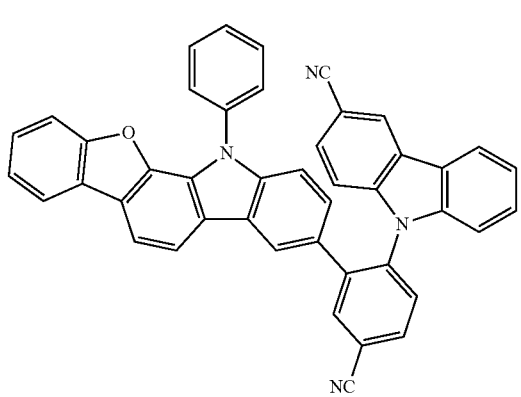
405
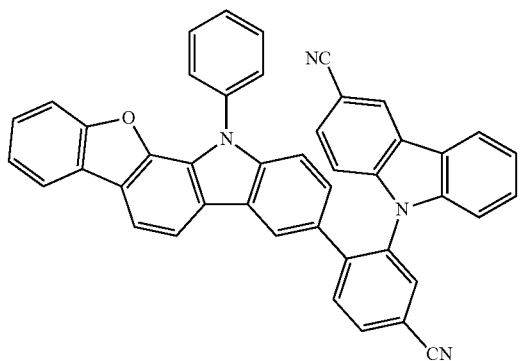
406
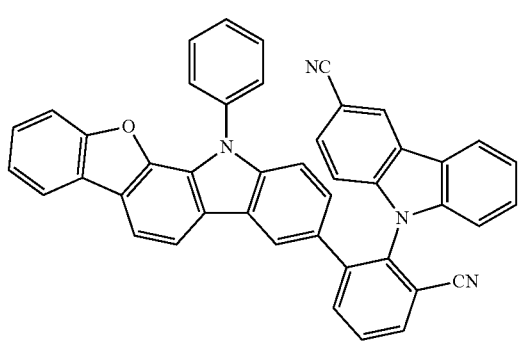

407
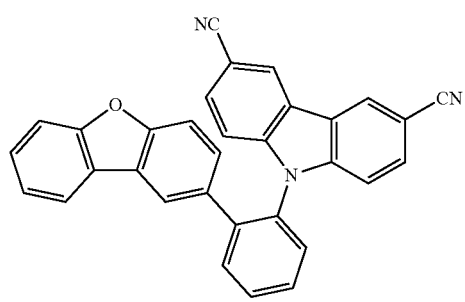
408
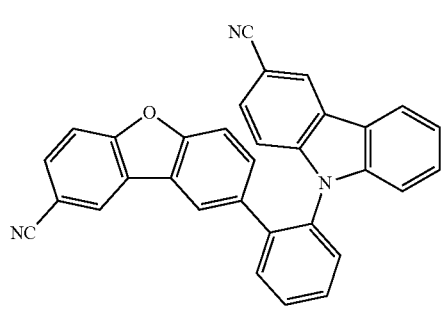
409
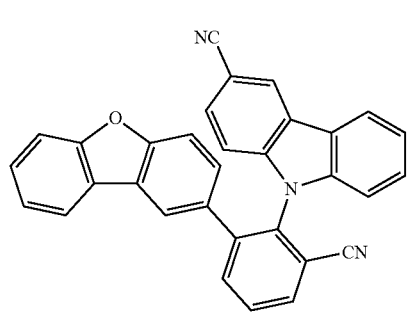
410
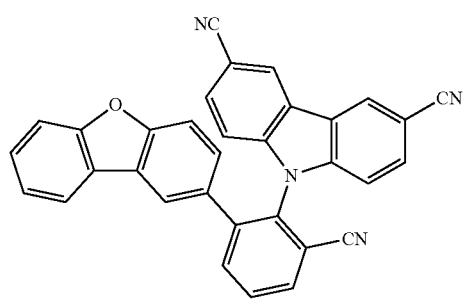
411
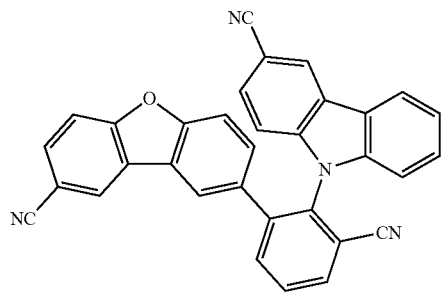
412
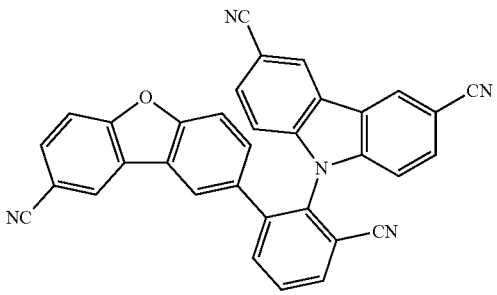
413
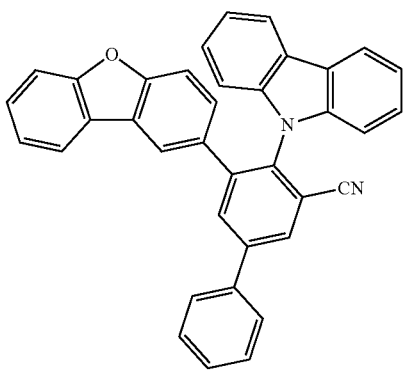
414
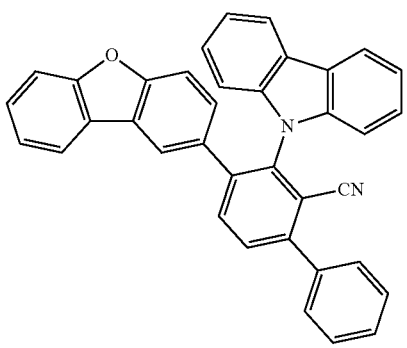
415
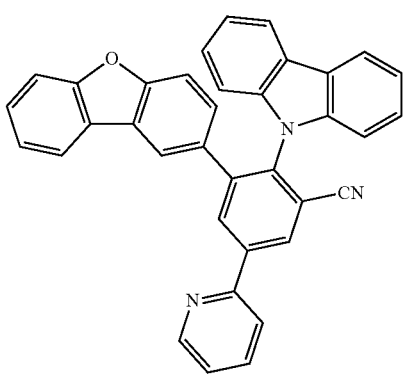

| 127 -continued | 128 -continued |
|---|---|
| 416 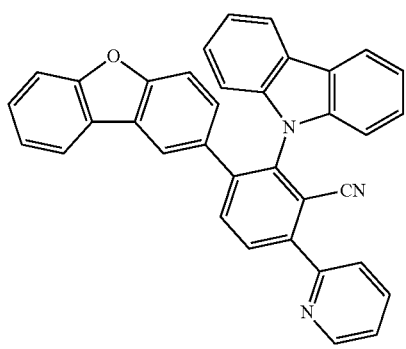 | 420 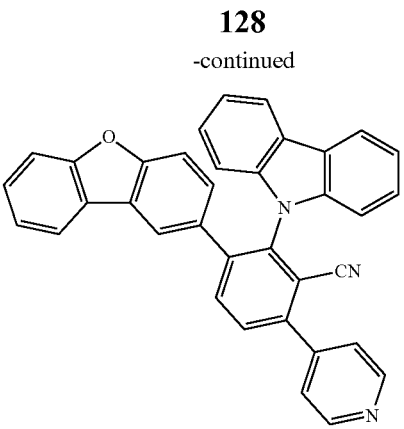 |
| 417 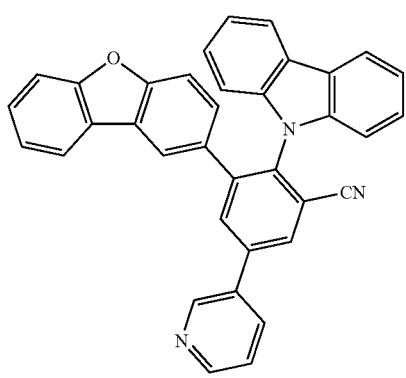 | 421 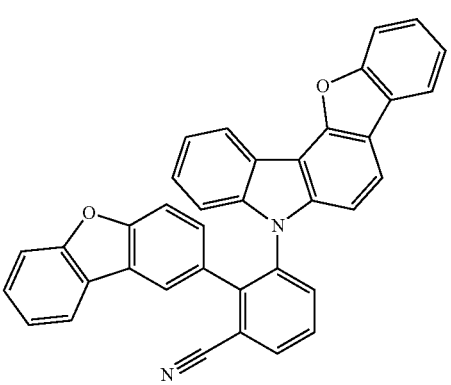 |
| 418 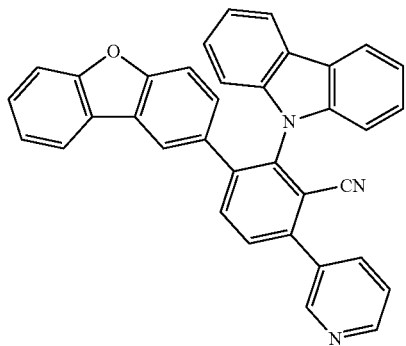 | 422 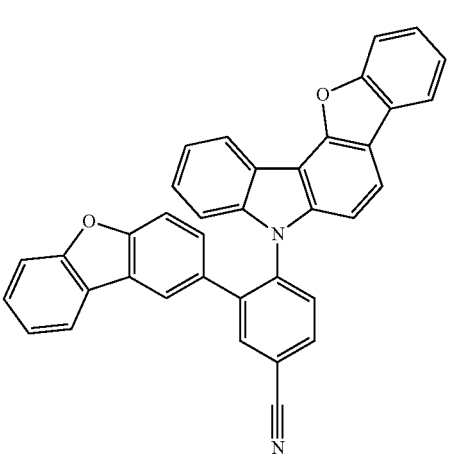 |
| 419 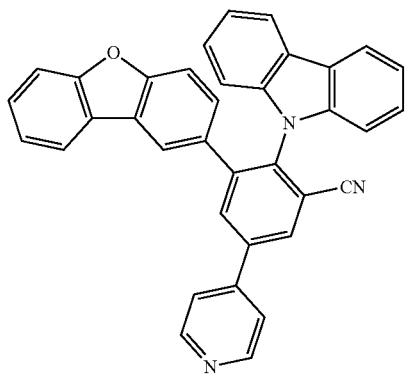 | 423 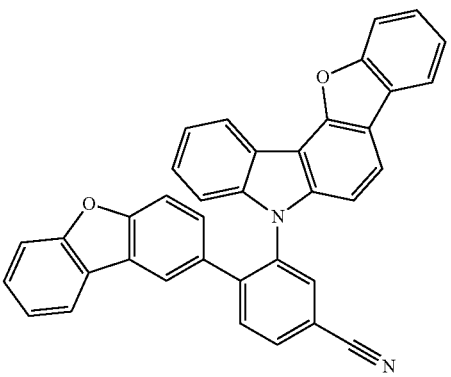 |

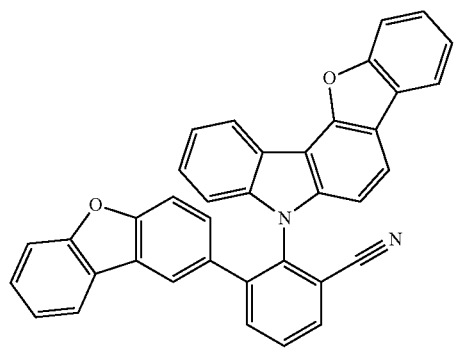
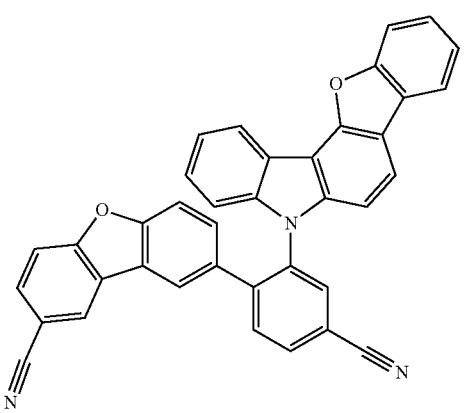
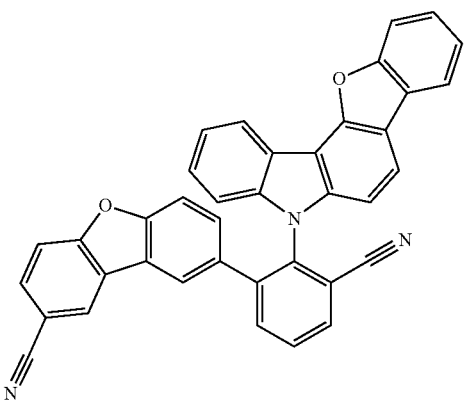
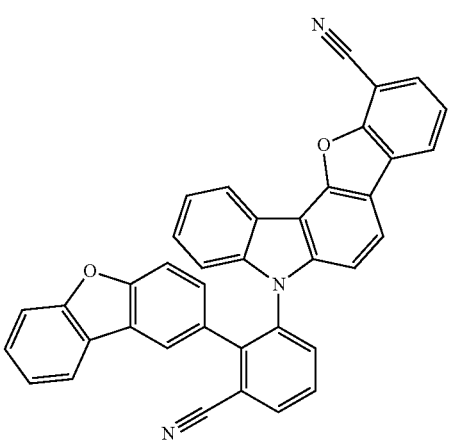

431 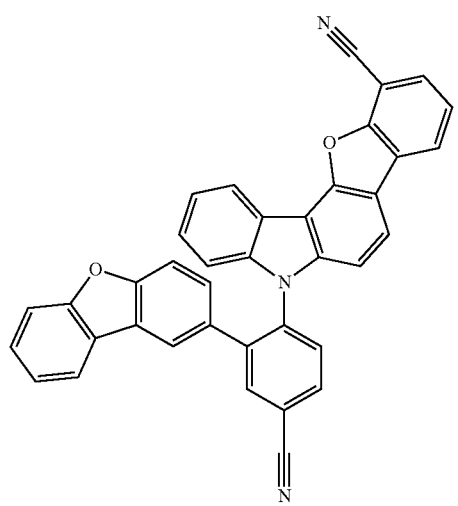
432 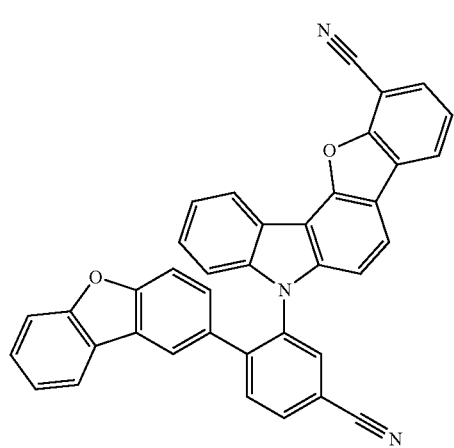
433 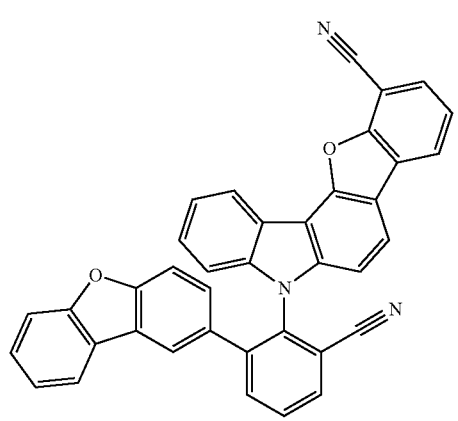
434 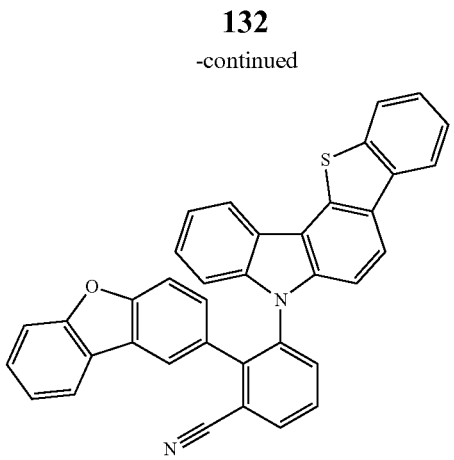
435 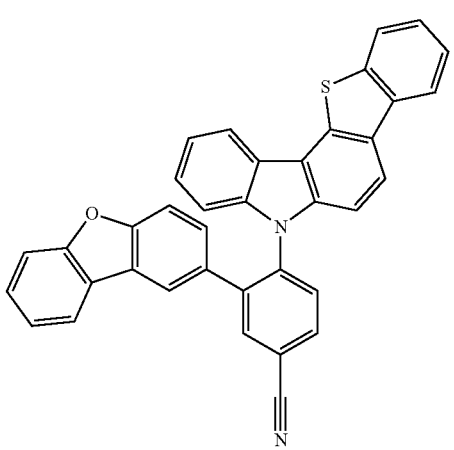
436 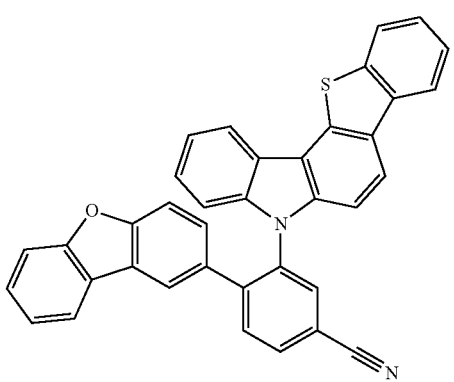
437 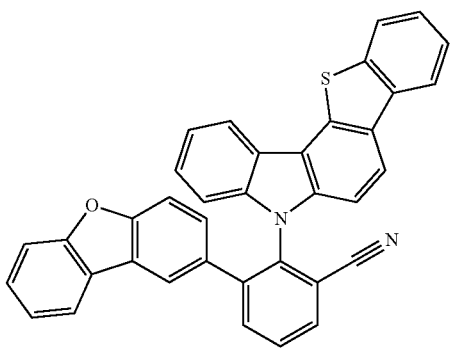

438
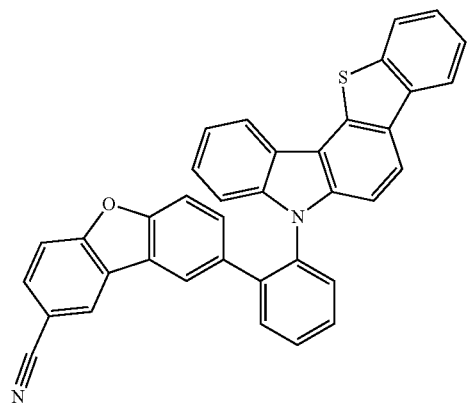
439
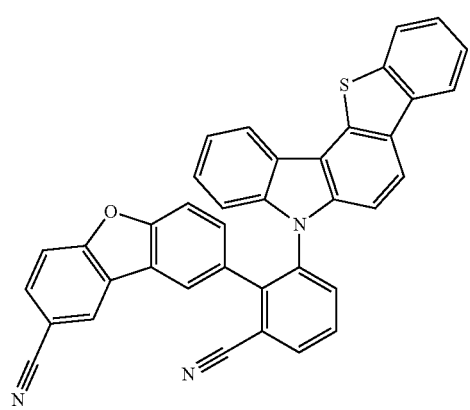
440
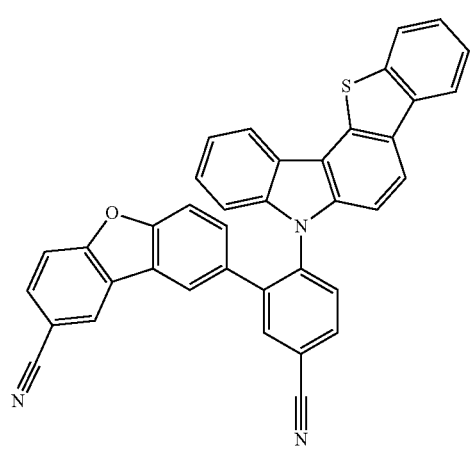
441
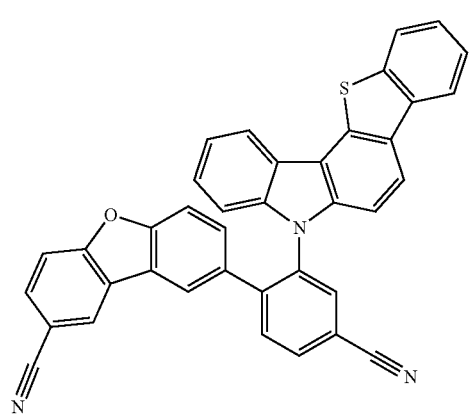
442
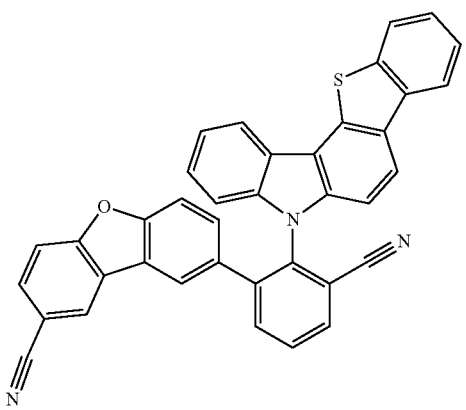
443
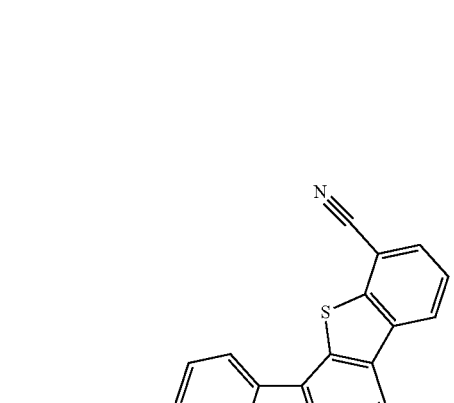
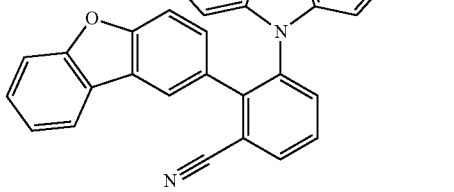
444
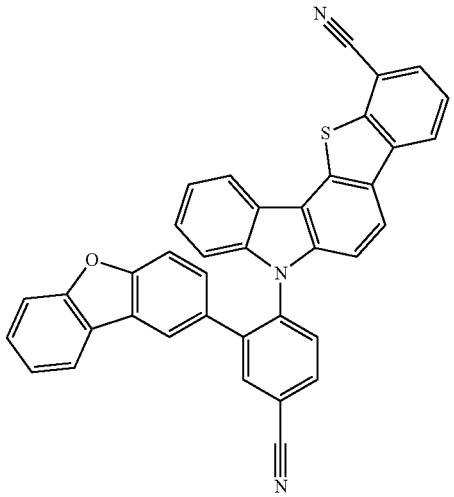

445
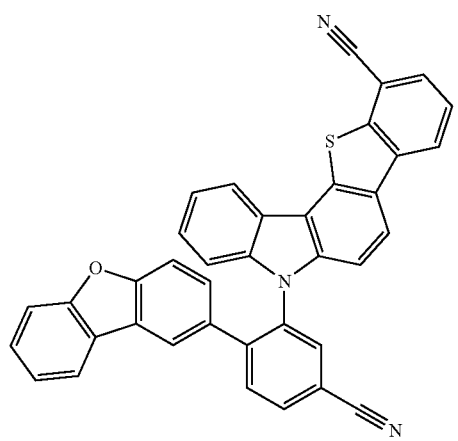
446
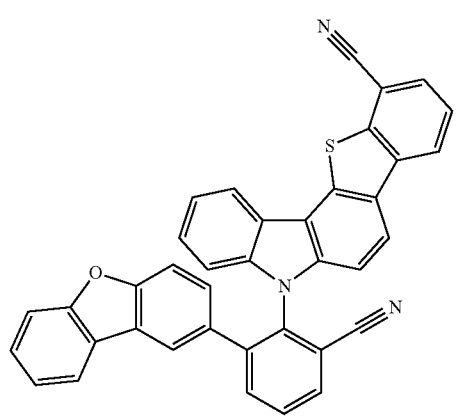
447
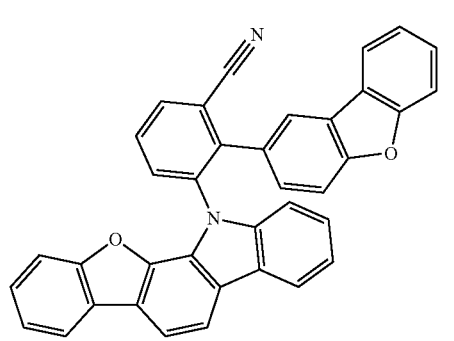
448
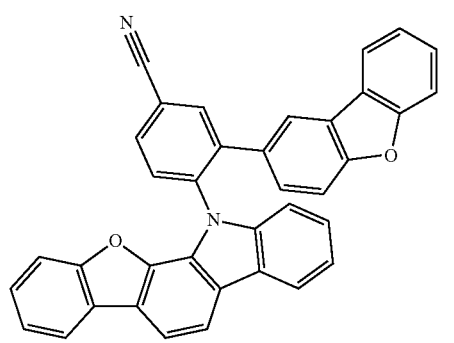
449
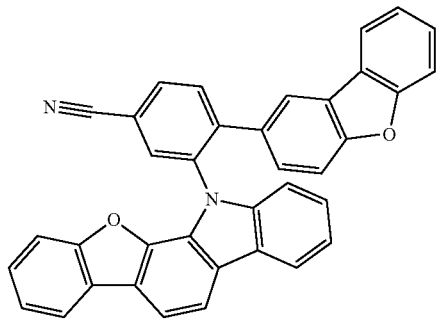
450
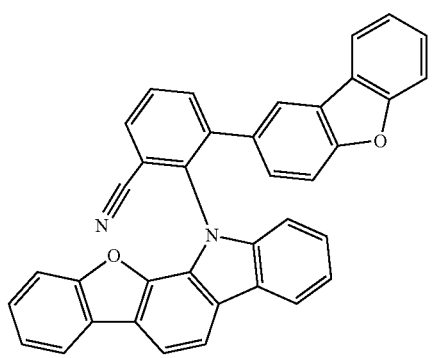
451
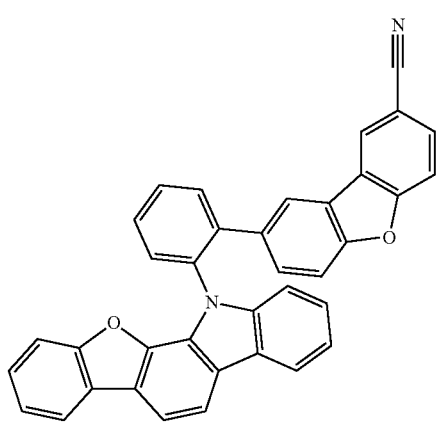
452
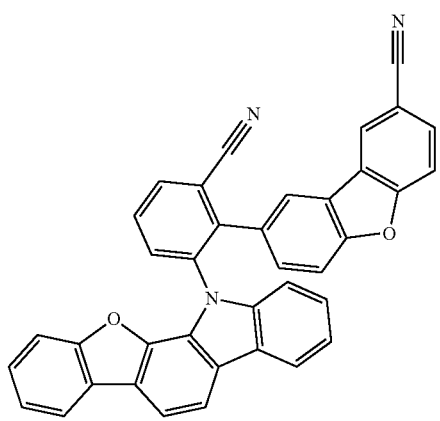

453
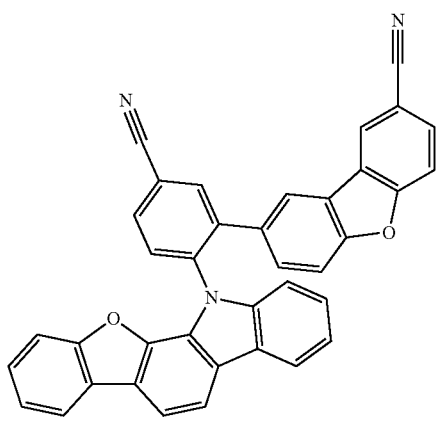
454
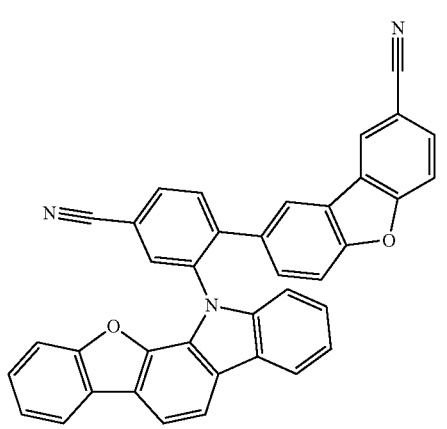
455
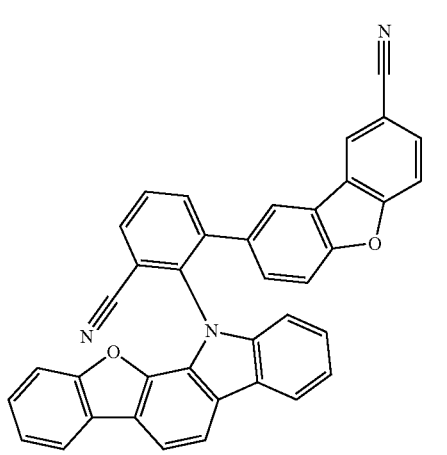
456
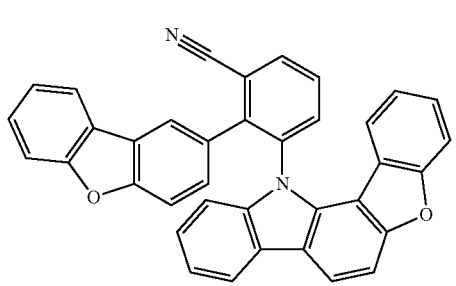
457
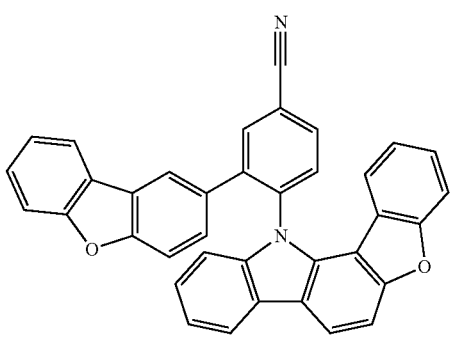
458
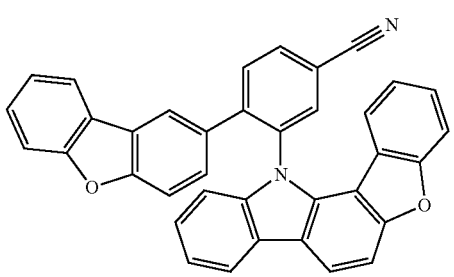
459
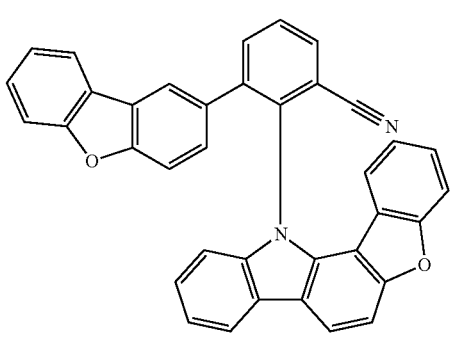
460
461

462
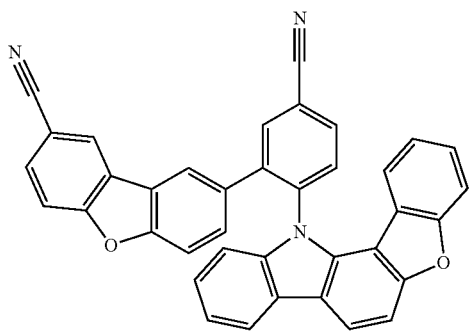
463
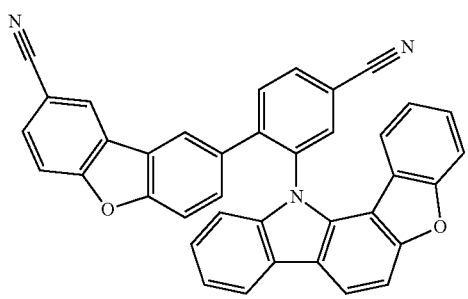
464
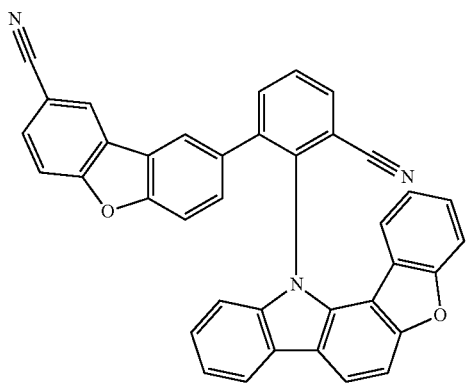
465
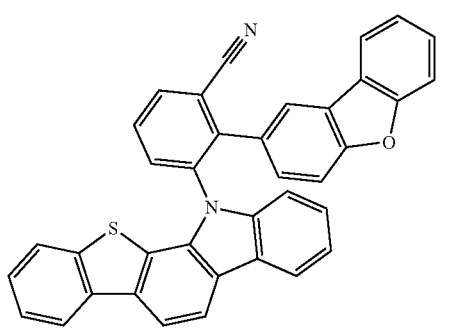
466
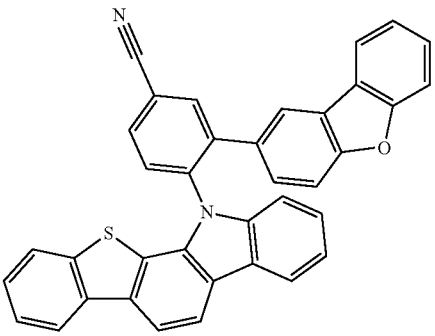
467
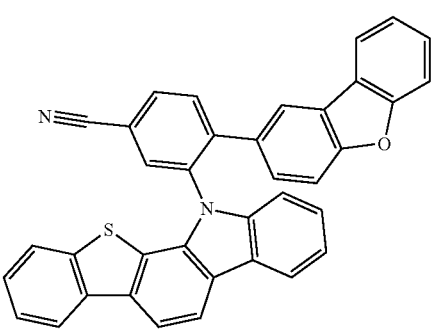
468
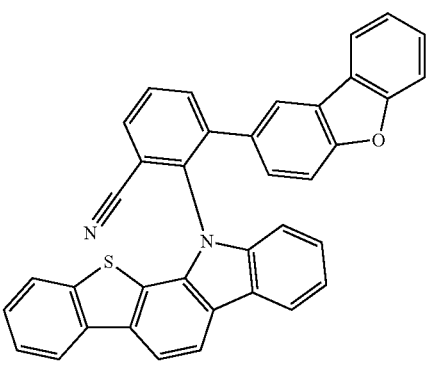
469
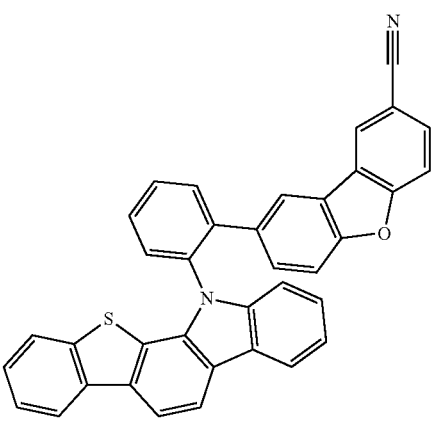

-continued
470
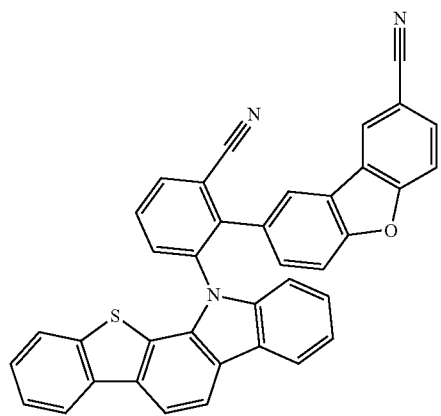
471
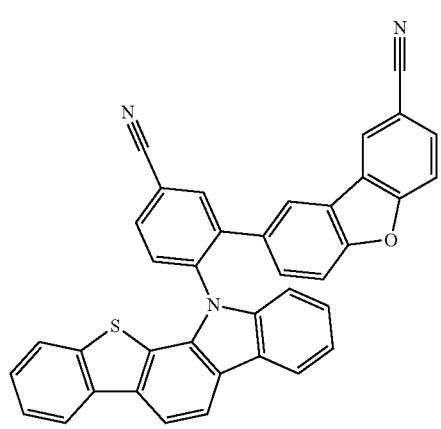
472
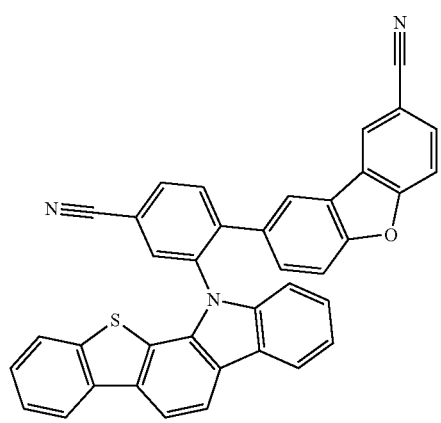
-continued
473
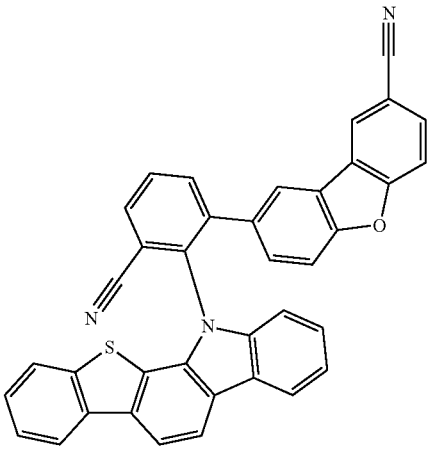
474
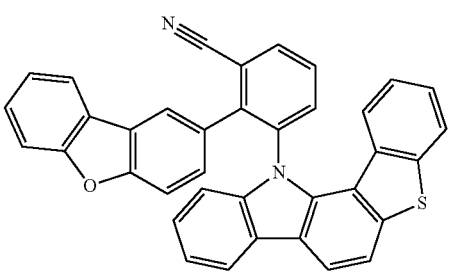
475
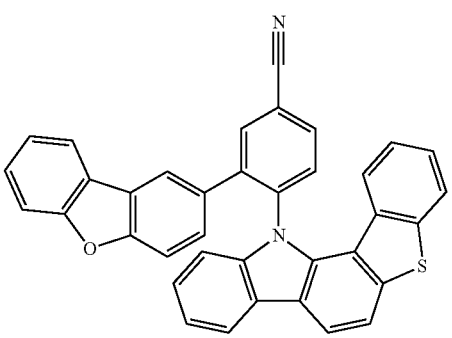
476
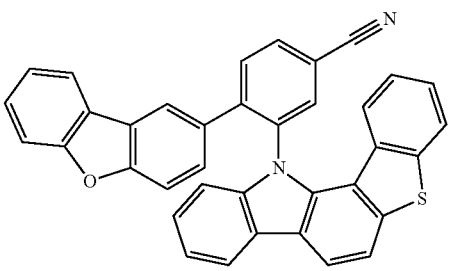
477
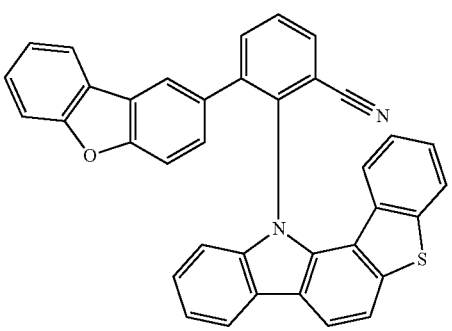

-continued

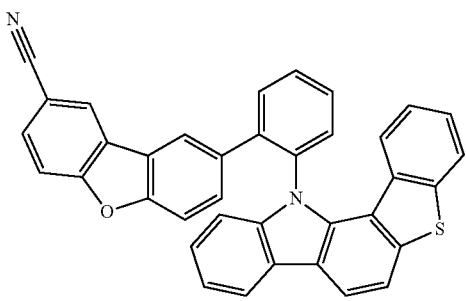
478

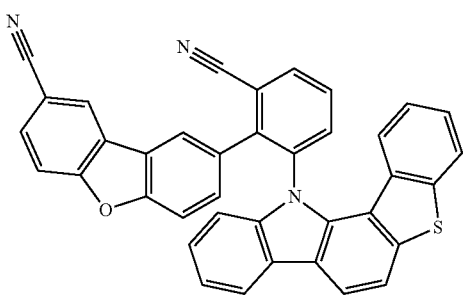
479

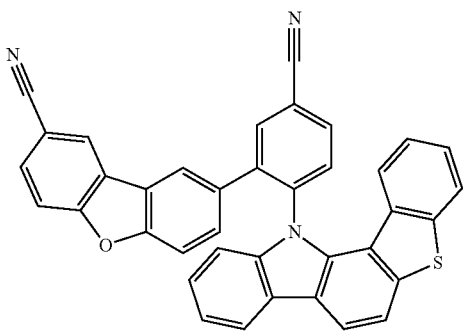
480

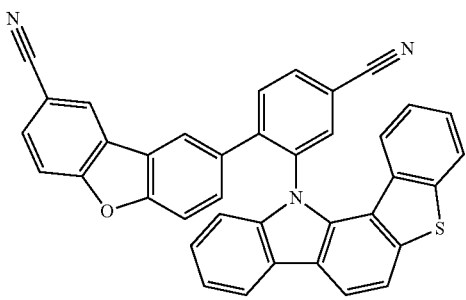
481

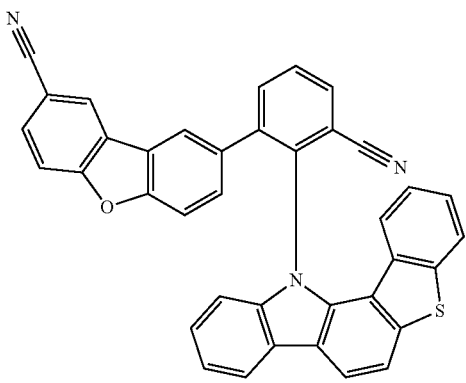
482

"Ring A" in the condensed cyclic compound represented by Formula 1 (see Formula 1' below) is linked to ring $A_5$ via "N", and "Ring B" is linked to a carbon atom of ring $A_5$, which is linked to "N" of "Ring A", in an ortho-position. In this regard, a conjugation length of the condensed cyclic compound represented by Formula 1 shortens, and thus the condensed cyclic compound represented by Formula 1 can have a high triplet energy level. As a result, while not wishing to be bound by theory, it is believed that the condensed cyclic compound represented by Formula 1 may have a triplet ($T_1$) energy level suitable for an electronic device, for example, a material of an organic light-emitting device (for example, a material for a host of an emission layer).

$X_2$ of "Ring B" in Formula 1 is O or S, and the condensed cyclic compound represented by Formula 1 includes 1, 2, 3 or 4 cyano groups as a substituent. Thus, electric characteristics (for example, HOMO, LUMO energy level, etc.) of the condensed cyclic compound represented by Formula 1 may be easily controlled to improve electric charge (for example, electron) mobility. The condensed cyclic compound represented by Formula 1 has 1, 2, 3 or 4 cyano groups as a substituent and thus, has an excellent heat resistance. As a result, the condensed cyclic compound represented by Formula 1 can have a HOMO/LUMO energy level suitable for an electronic device, for example, a material for an organic light-emitting device (for example, a material for a host of an emission layer, and a common layer), and can have a long lifespan.

Formula 1'

Ring A

Ring B

For example, HOMO, LUMO, $T_1$ and $S_1$ energy levels of Compounds 3, 4, 9, 16, 28, 408, 409, 413, 415, 421, 423, 424, 429, 437, 450, 459, B and C may be structurally optimized at a level of B3LYP/6-31G(d,p) by using a density functional theory (DFT) method of a Gaussian program and evaluated by simulation. The results thereof are shown in Table 1 below:

TABLE 1

| Compound No. | HOMO (eV) | LUMO (eV) | $T_1$ (eV) | $S_1$ (eV) |
|---|---|---|---|---|
| Compound 3 | −5.624 | −1.798 | 2.964 | 3.194 |
| Compound 4 | −5.544 | −1.636 | 3.096 | 3.202 |
| Compound 9 | −5.483 | −1.433 | 3.126 | 3.529 |
| Compound 16 | −5.669 | −1.793 | 3.079 | 3.176 |
| Compound 28 | −5.560 | −1.657 | 3.048 | 3.202 |
| Compound 408 | −5.920 | −1.606 | 3.119 | 3.900 |
| Compound 409 | −5.958 | −1.903 | 3.119 | 3.393 |
| Compound 413 | −5.491 | −1.685 | 2.950 | 3.121 |
| Compound 415 | −5.490 | −1.873 | 2.921 | 2.989 |

TABLE 1-continued

| Compound No. | HOMO (eV) | LUMO (eV) | $T_1$ (eV) | $S_1$ (eV) |
|---|---|---|---|---|
| Compound 421 | −5.429 | −1.694 | 3.000 | 3.172 |
| Compound 423 | −5.463 | −1.837 | 2.912 | 3.060 |
| Compound 424 | −5.378 | −1.681 | 3.004 | 3.065 |
| Compound 429 | −5.441 | −1.827 | 2.943 | 2.995 |
| Compound 437 | −5.426 | −1.694 | 2.969 | 3.100 |
| Compound 450 | −5.494 | −1.569 | 2.951 | 3.245 |
| Compound 459 | −5.472 | −1.714 | 2.988 | 3.082 |
| Compound B | −5.175 | −1.278 | 2.599 | 3.351 |
| Compound C | −5.543 | −1.811 | 2.912 | 3.271 |

Compound B

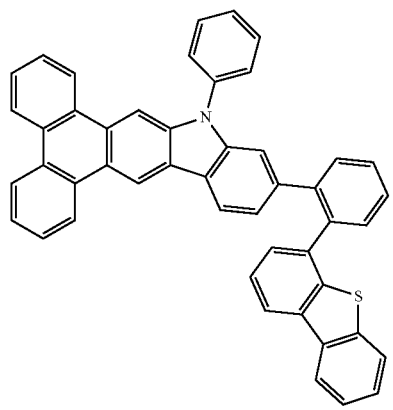

Compound C

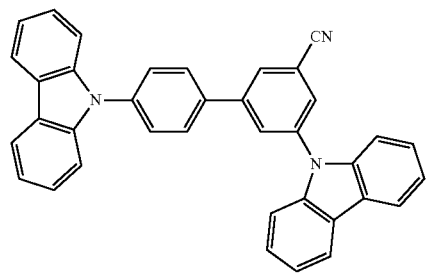

A method of synthesizing the condensed cyclic compound represented by Formula 1 may be understood by one of ordinary skill in the art by referring to Synthesis Examples described below.

In this regard, the condensed cyclic compound represented by Formula 1 may be suitable to be used as a material for an organic layer of an organic light-emitting device, for example, a host for an emission layer in the organic layer. According to another aspect, the organic light-emitting device may include:

a first electrode;

a second electrode; and an organic layer disposed between the first electrode and the second electrode, wherein the organic layer includes the emission layer and at least one condensed cyclic compound represented by Formula 1.

The organic light-emitting device includes the organic layer including the condensed cyclic compound represented by Formula 1, thereby having low driving voltage, high efficiency and long lifespan.

The condensed cyclic compound represented by Formula 1 may be used between a pair of electrodes in an organic light-emitting device. For example, the condensed cyclic compound may be included in at least one selected from:

i) an emission layer, ii) a hole transport region disposed between a first electrode and an emission layer (for example, at least one selected from a hole injection layer, a hole transport layer, and an electron blocking layer is included in the hole transport region), and iii) an electron transport region disposed between an emission layer and a second electrode (for example, at least one selected from a hole blocking layer, an electron transport layer, and an electron injection layer is included in the electron transport region).

For example, the condensed cyclic compound represented by Formula 1 may be included in the emission layer. Here, the condensed cyclic compound included in the emission layer may serve as a host, and the emission layer may further include a dopant (a fluorescent dopant, a phosphorescent dopant or a delayed fluorescent dopant). The emission layer may be a red emission layer, a green emission layer, or a blue emission layer respectively emitting red light, green light or blue light. According to an embodiment, the condensed cyclic compound represented by Formula 1 may be included in the emission layer, the emission layer may further include a phosphorescent dopant, and the emission layer may emit blue light.

The expression as used herein "(an organic layer) includes at least one condensed cyclic compound" may be understood as "(organic layer) may include one condensed cyclic compound represented by Formula 1 or two or more different condensed cyclic compounds represented by Formula 1".

For example, the organic layer may include only Compound 1 as the condensed cyclic compound. In this regard, Compound 1 may be included in the emission layer of the organic light-emitting device. Alternatively, the organic layer may include Compound 1 and Compound 2 as the condensed cyclic compounds. In this regard, Compound 1 and Compound 2 may be included in the same layer (for example, both Compound 1 and Compound 2 may be included in the emission layer), or in different layers.

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include a hole transport region disposed between the first electrode and the emission layer and an electron transport region disposed between the emission layer and the second electrode, wherein the hole transport region includes at least one selected from a hole injection layer, a hole transport layer and an electron blocking layer, and the electron transport region includes at least one selected from a hole blocking layer, an electron transport layer and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming a first electrode on the substrate. The first electrode 11 may be an anode. The material for the first electrode 11 may be selected from materials with a high work function so as to facilitate hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag) may be used herein.

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer may be formed on the first electrode 11 by using various methods such as vacuum-deposition, spin coating, casting, and Langmuir-Blodgett (LB) method.

When a hole injection layer is formed by vacuum-deposition, though the conditions may vary depending on a compound that is used as a hole injection material and a structure and thermal properties of a desired hole injection layer, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, but embodiments are not limited thereto.

When a hole injection layer is formed by spin coating, though the conditions may vary depending on a compound that is used as a hole injection material and a structure and thermal properties of a desired hole injection layer, the spin coating may be performed at a coating rate in a range of about 2,000 revolutions per minute (rpm) to about 5,000 rpm, and at a temperature in a range of about 80° C. to 200° C. for removing a solvent after the spin coating, but embodiments are not limited thereto.

The conditions for forming a hole transport layer and an electron blocking layer may be understood by referring to the conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

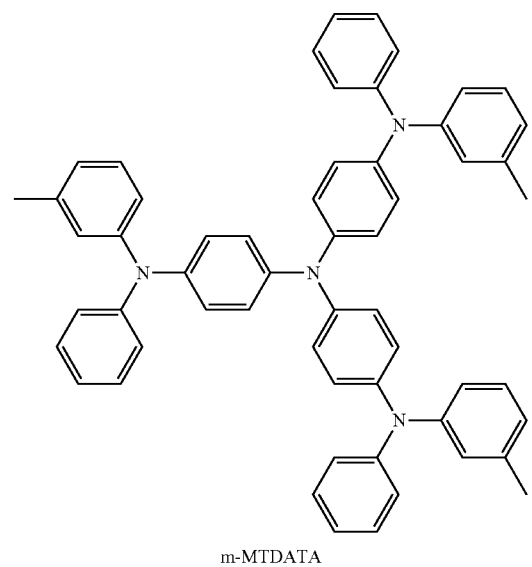

m-MTDATA

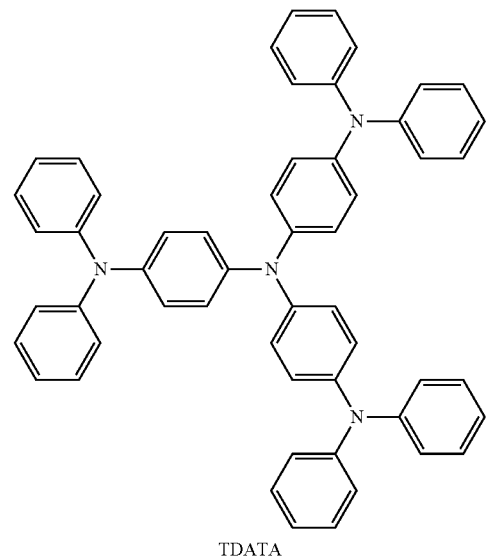

TDATA

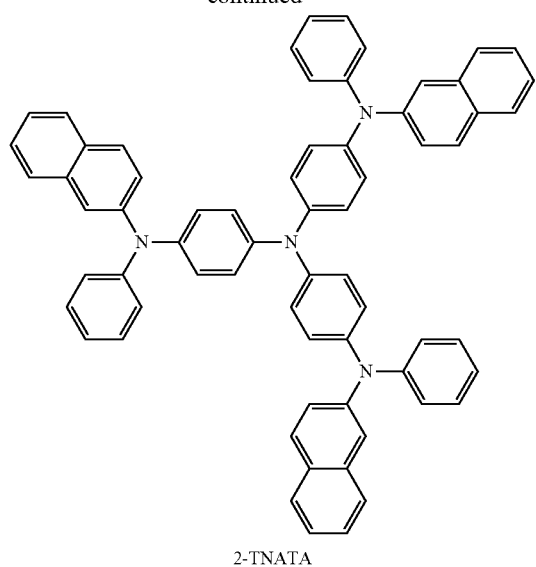
2-TNATA
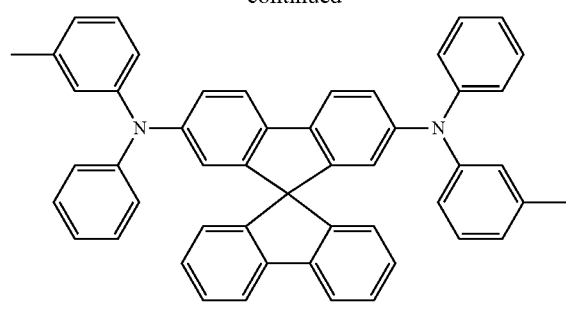
Spiro-TPD
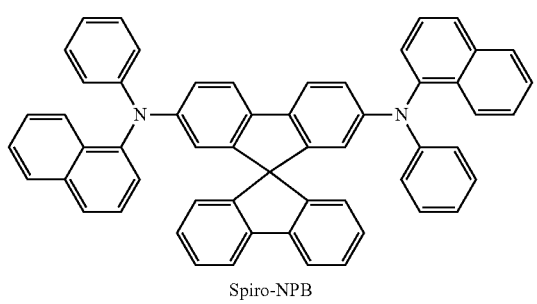
Spiro-NPB
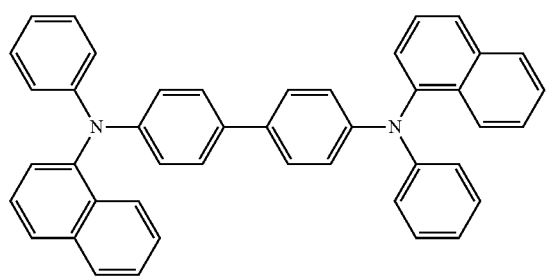
NPB
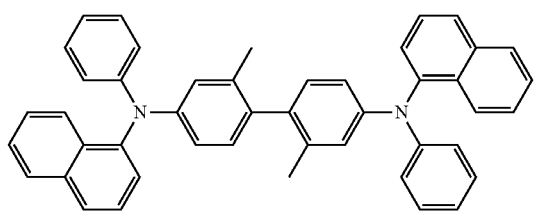
methylated NPB
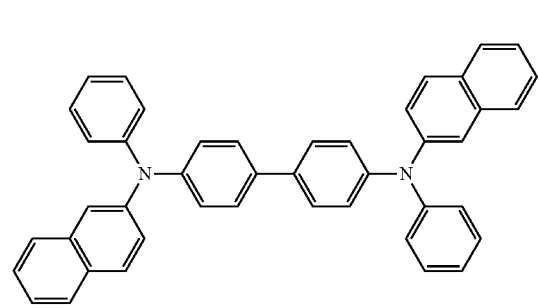
β-NPB
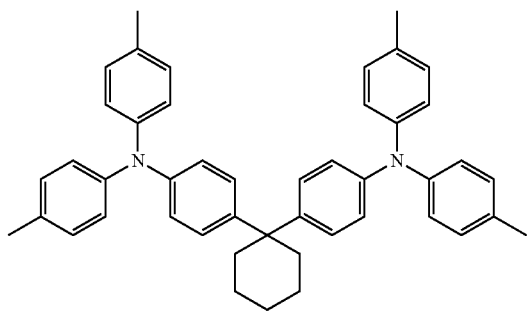
TAPC
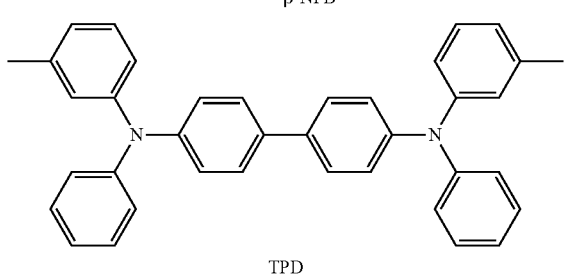
TPD
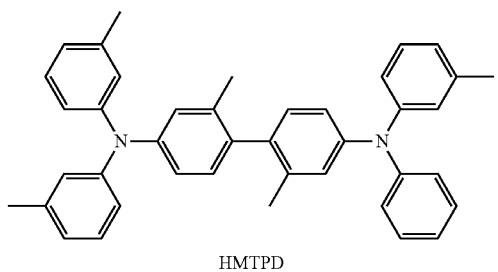
HMTPD -continued Formula 201

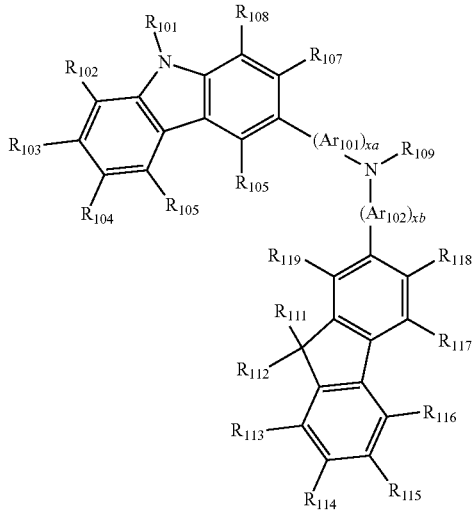

Formula 202

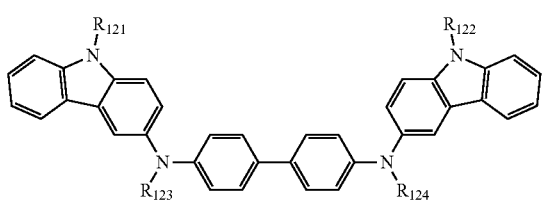

$Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group.

xa and xb in Formula 201 may each independently be an integer of 0 to 5, or may be 0, 1 or 2. For example, xa may be 1 and xb may be 0, but embodiments are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, etc.) and a $C_1$-$C_{10}$ alkoxy group (for example, a methoxy group, an ethoxy group, a propoxy group, butoxy group, a pentoxy group, etc.);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group and a pyrenyl group; and a phenyl group, a naphthyl group, an anthracenyl group, a fluorenyl group and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but embodiments are not limited thereto.

$R_{109}$ in Formula 201 may be selected from a phenyl group, a naphthyl group, an anthracenyl group and a pyridinyl group; and a phenyl group, a naphthyl group, an anthracenyl group and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group and a pyridinyl group.

According to an embodiment, the compound represented by Formula 201 may be represented by Formula 201A, but embodiments are not limited thereto:

Formula 201A

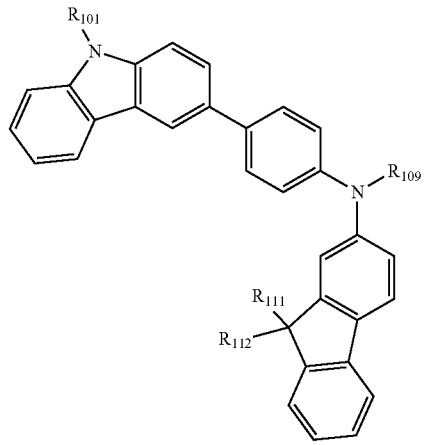

Descriptions of $R_{101}$, $R_{111}$, $R_{112}$ and $R_{109}$ in Formula 201A are the same as described herein.

For example, the compound represented by Formula 201 and the compound represented by Formula 202 may include Compounds HT1 to HT20, but embodiments are not limited thereto:
HT1
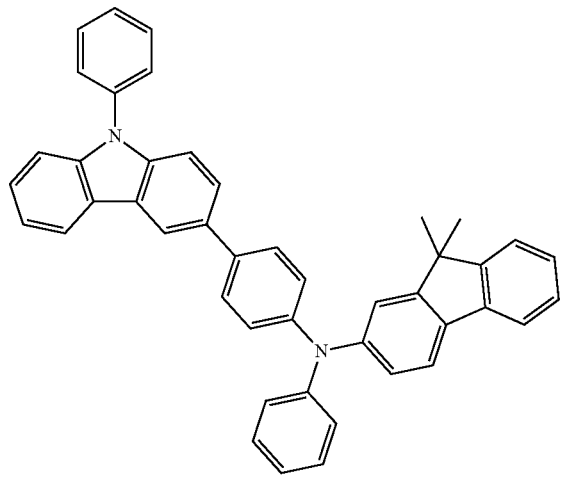
HT2
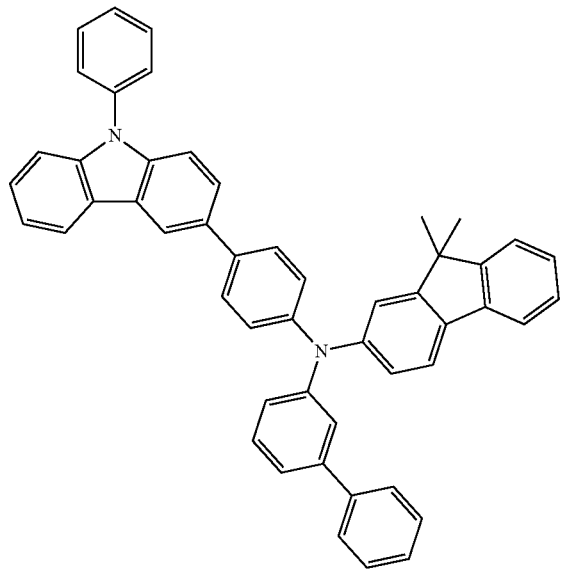
HT3
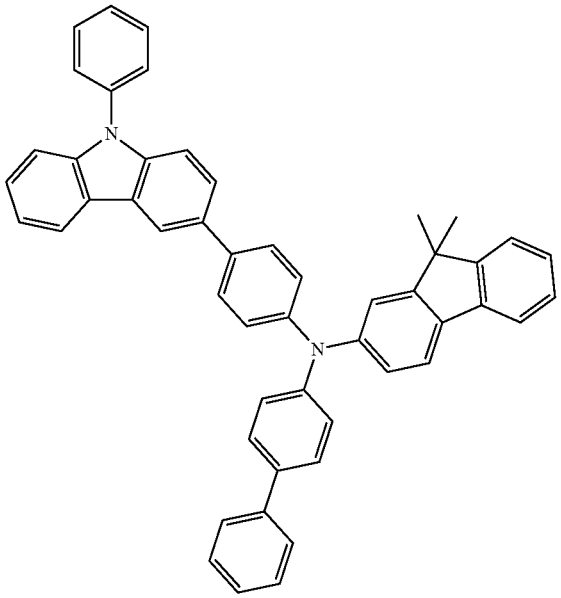
HT4
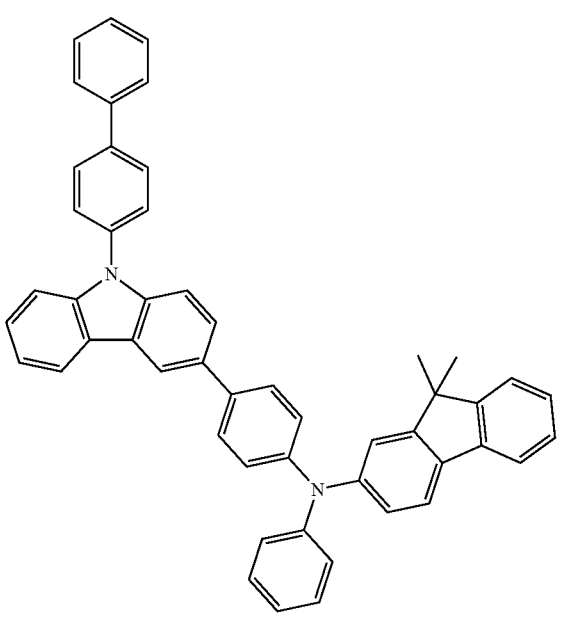

HT5
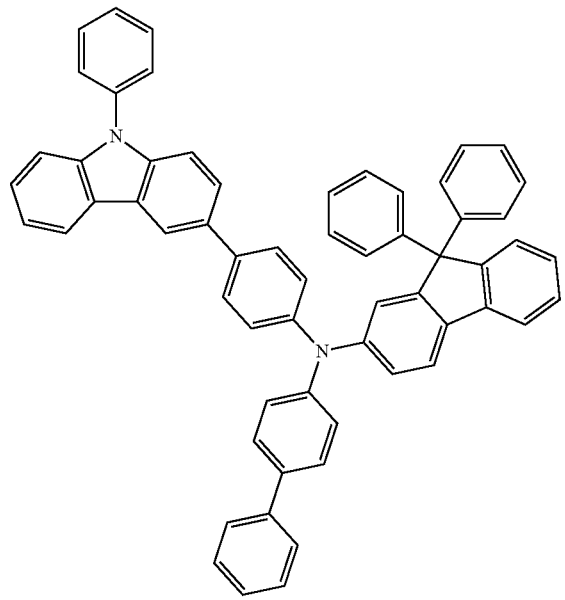
HT7
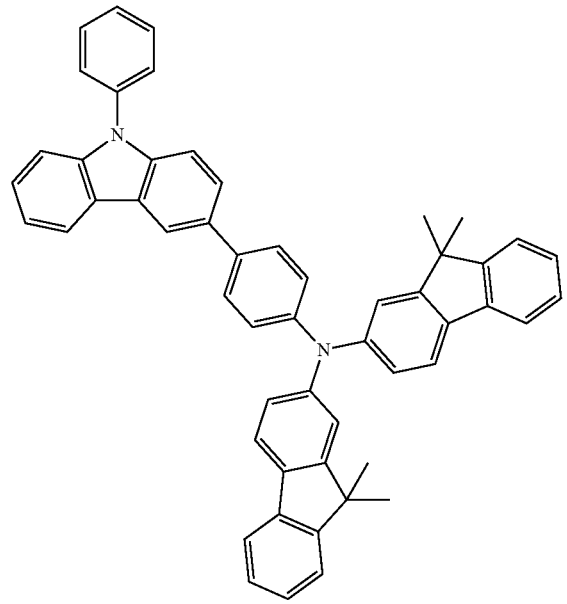
HT6
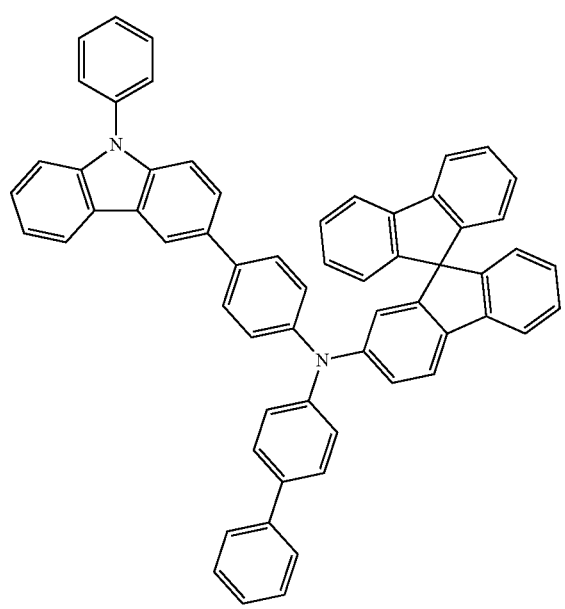
HT8
HT9
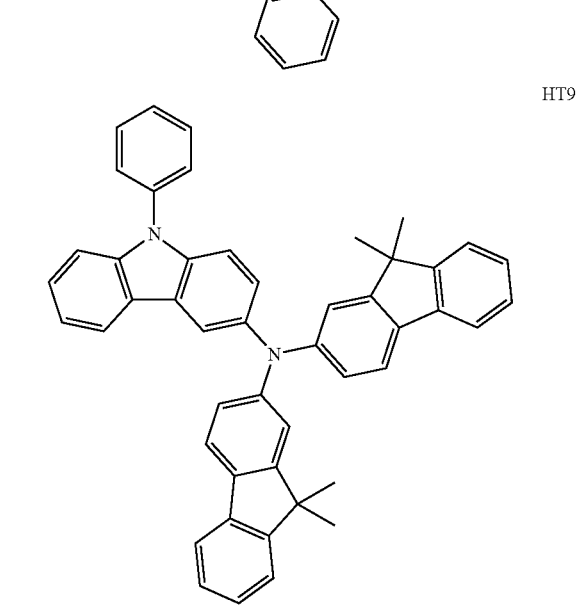

HT10
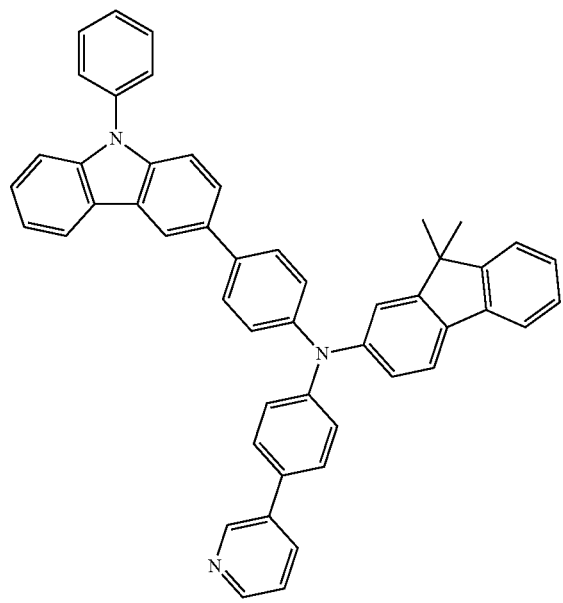
HT12
HT13
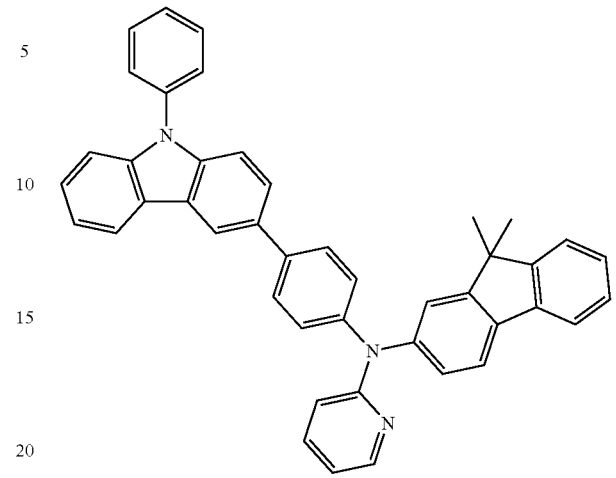
HT14
HT15
HT11
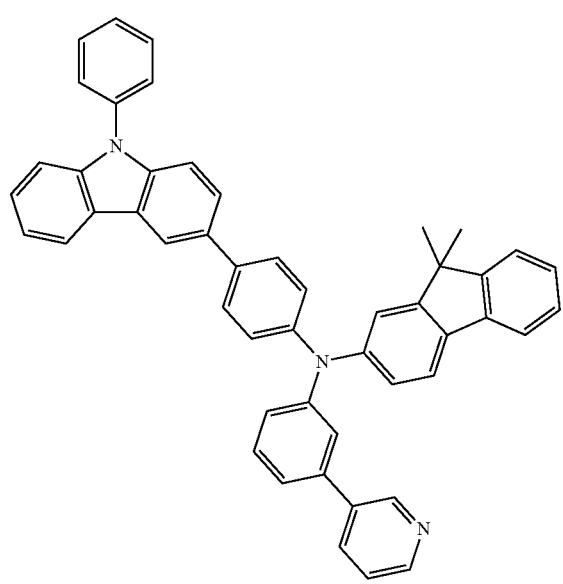

HT16

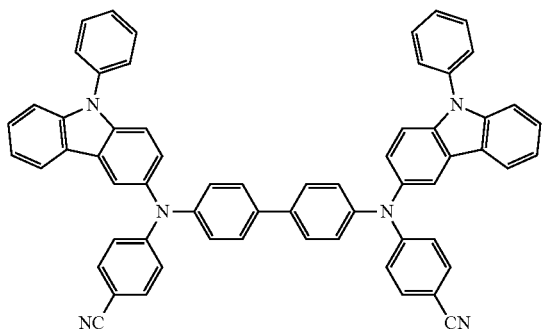

HT20

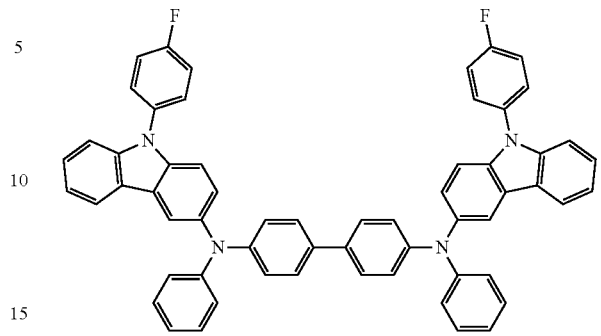

HT17

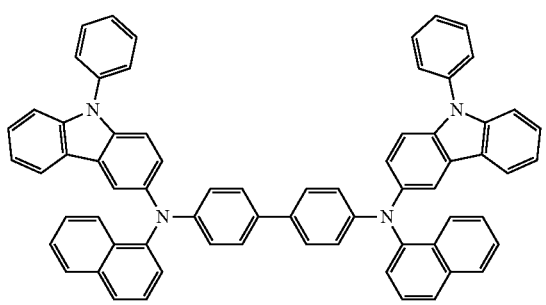

HT18

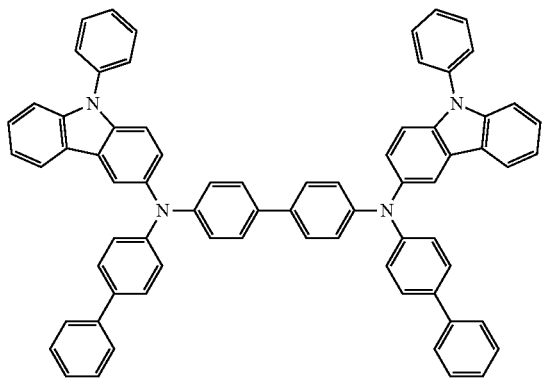

HT19

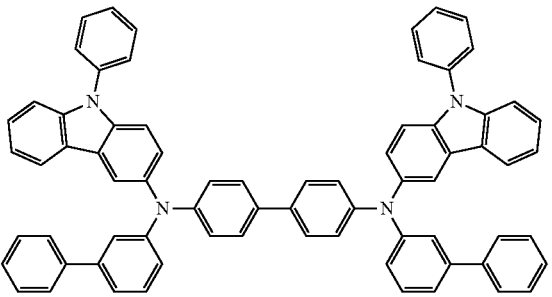

A thickness of the hole transport region may be in a range of about 100 Angstroms (Å) to about 10,000 Å, for example, about 100 Å to about 1,000 Å. When the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 and HP-1, but embodiments are not limited thereto.

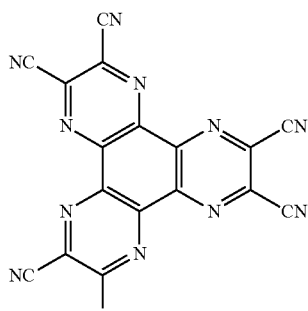

Compound HT-D1

-continued

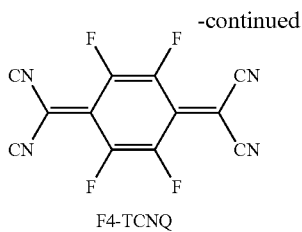

F4-TCNQ

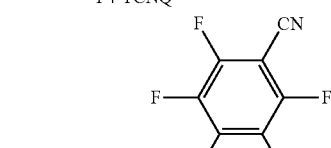

HP-1

The hole transport region may further include a buffer layer.

The buffer layer may compensate for an optical resonance distance according to a wavelength of light emitted from the emission layer to improve the efficiency of an organic light-emitting device.

An emission layer may be formed on the hole transport region by using various methods, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

The hole transport region may further include an electron blocking layer. The electron blocking layer may include a known material, for example, mCP, but embodiments are not limited thereto.

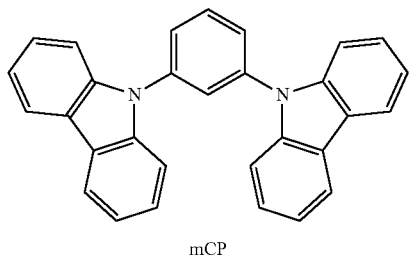 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the condensed cyclic compound represented by Formula 1. For example, the emission layer may include a host and a dopant, and the host may include the condensed cyclic compound represented by Formula 1.

A dopant in the emission layer may include at least one selected from a fluorescent dopant emitting light according to fluorescence emission mechanism, a phosphorescent dopant emitting light according to phosphorescence emission mechanism, and a delayed fluorescent dopant emitting light according to thermally activated delayed fluorescence emission mechanism.

According to an embodiment, a dopant in the emission layer may be a phosphorescent dopant, and the phosphorescent dopant may include an organometallic compound represented by Formula 81:

Formula 81

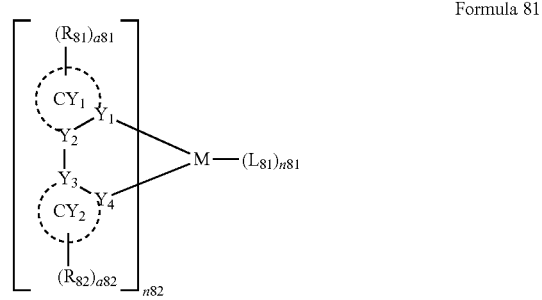

In Formula 81,

M may be selected from iridium (Ir), platinum (Pt), osmium (Os), titanium (Ti), zirconium (Zr), hafnium (Hf), europium (Eu), terbium (Tb) and thulium (Tm), $Y_1$ to $Y_4$ may each independently be carbon (C) or nitrogen (N), $Y_1$ and $Y_2$ may be linked to each other by a single bond or a double bond, and $Y_3$ and $Y_4$ may be linked to each other by a single bond or a double bond, $CY_1$ and $CY_2$ may each independently be a benzene, a naphthalene, a fluorene, a spiro-bifluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran or a dibenzothiophene, and $CY_1$ and $CY_2$ may be optionally further linked to each other by an organic linking group, $R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted C<sub>7</sub>-C<sub>60</sub> arylalkyl group, a substituted or unsubstituted C$_1$-C$_{60}$ heteroaryl group, a substituted or unsubstituted C$_1$-C$_{60}$ heteroaryloxy group, a substituted or unsubstituted C$_1$-C$_{60}$ heteroarylthio group, a substituted or unsubstituted C$_2$-C$_{60}$ heteroarylalkyl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$) and —B(Q$_6$)(Q$_7$), a81 and a82 may each independently be an integer of 1 to 5, n81 may be integer of 0 to 4, n82 may be 1, 2 or 3, and L$_{81}$ may be a monovalent organic ligand, a divalent organic ligand or a trivalent organic ligand. Q$_1$ to Q$_7$ may have the same definitions as Q$_1$ to Q$_3$ in —Si(Q$_1$)(Q$_2$)(Q$_3$) in Formula 1.

Descriptions of R$_{81}$ and R$_{82}$ may be the same as the description of R$_{11}$ provided herein.

The phosphorescent dopant may include at least one selected from Compounds PD1 to PD78, FIr6 and PtOEP, but embodiments are not limited thereto:

PD1

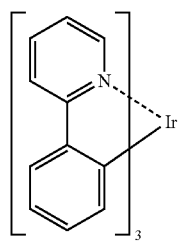

PD2

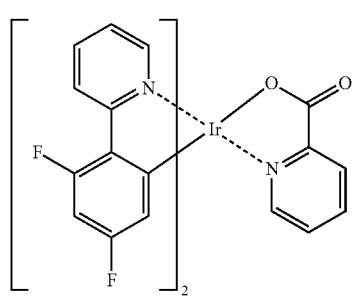

PD3

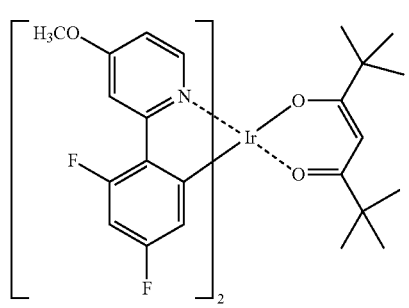

PD4

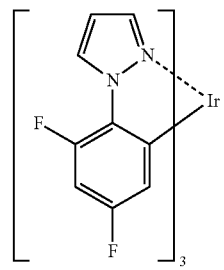

PD5

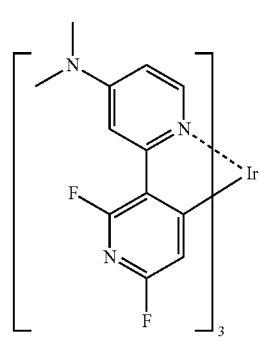

PD6

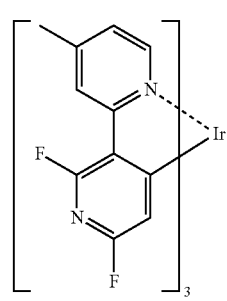

PD7

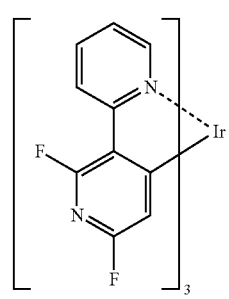

PD8

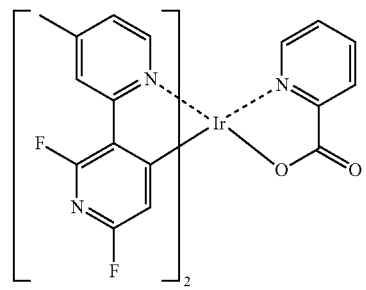

PD9 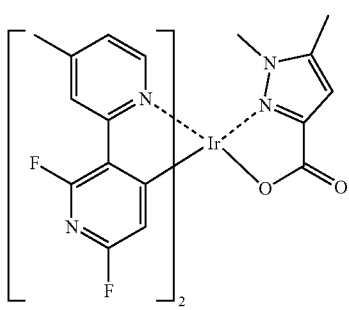
PD14 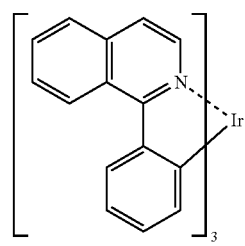
PD10 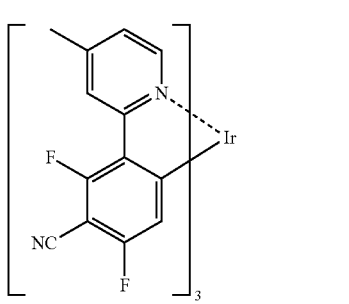
PD15 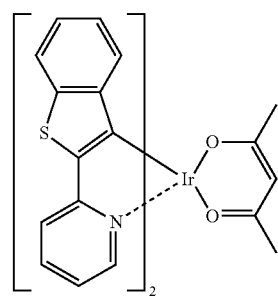
PD11 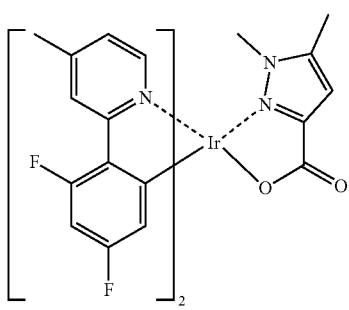
PD16 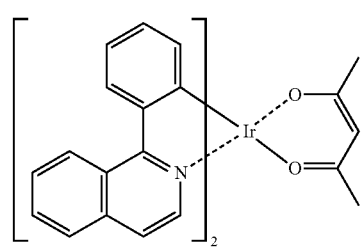
PD12 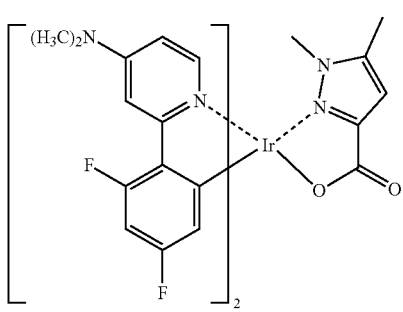
PD17 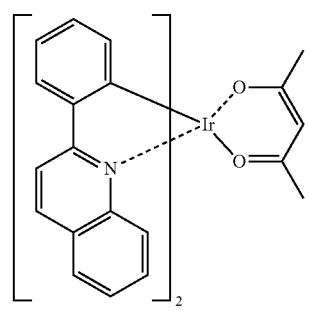
PD13 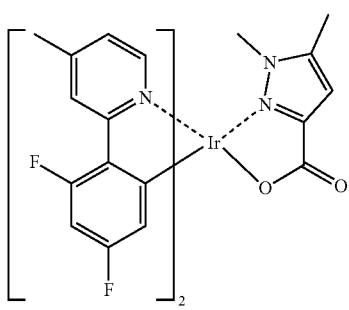
PD18 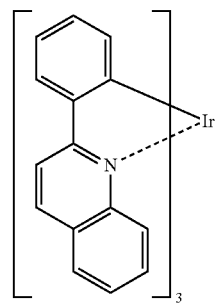

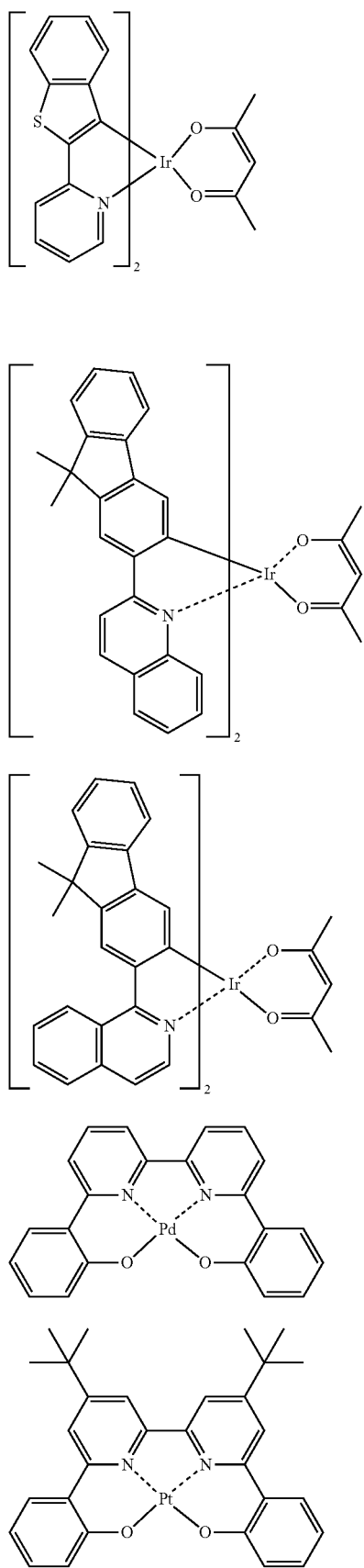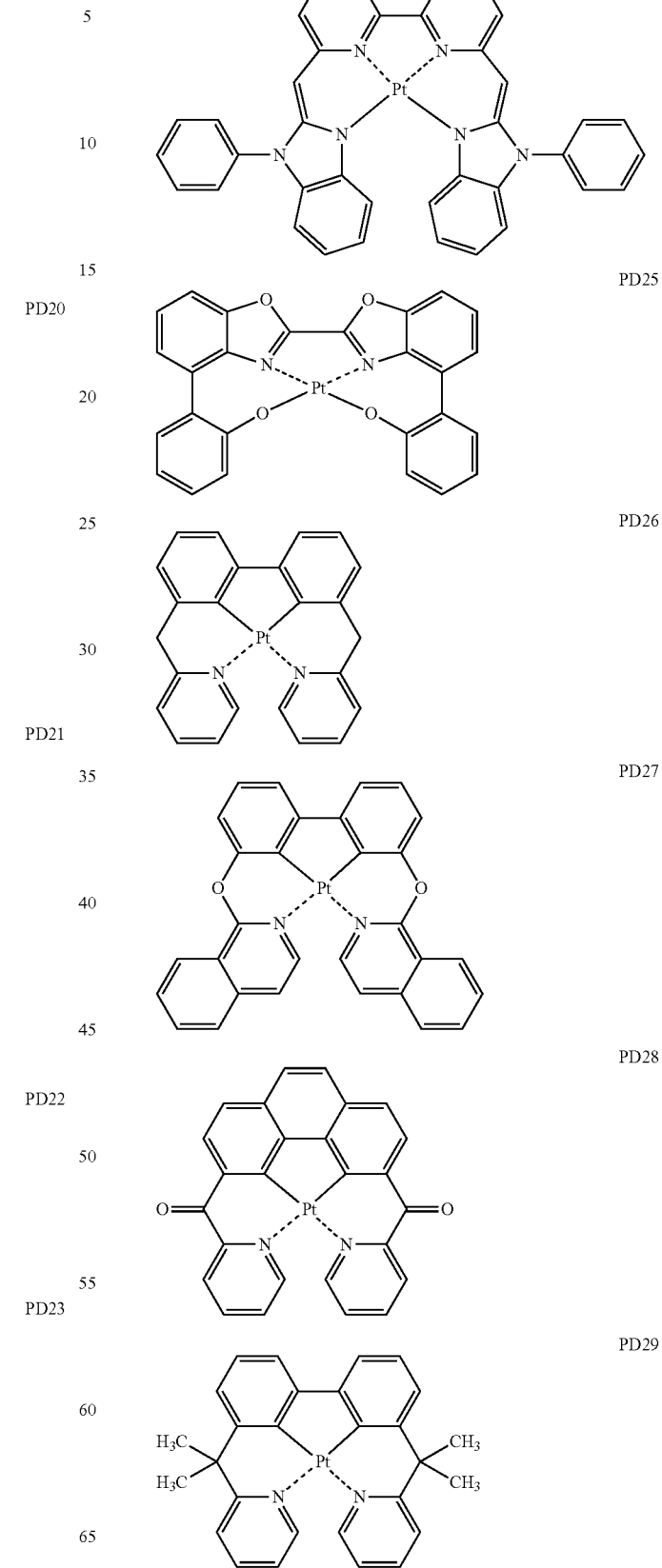

-continued
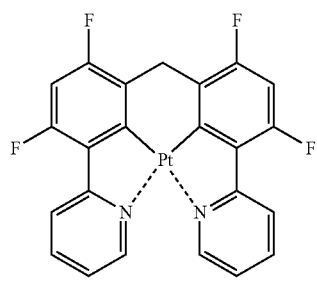
PD30
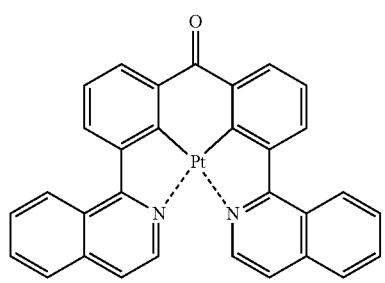
PD31
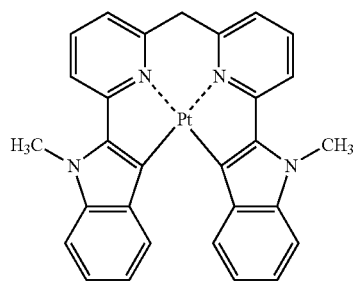
PD32
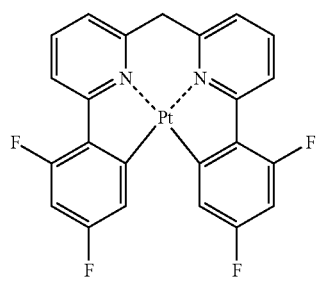
PD33
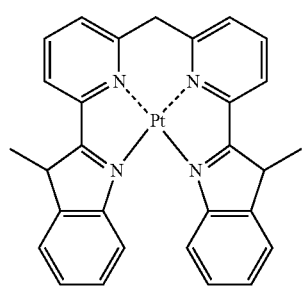
PD34
-continued
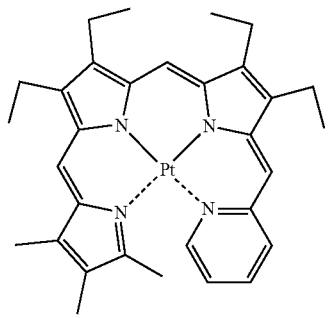
PD35
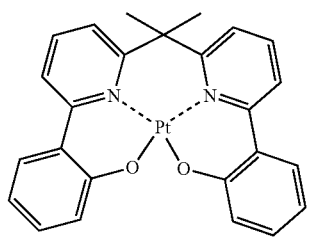
PD36
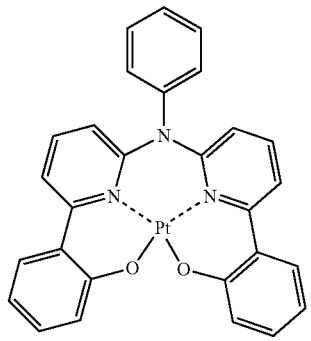
PD37
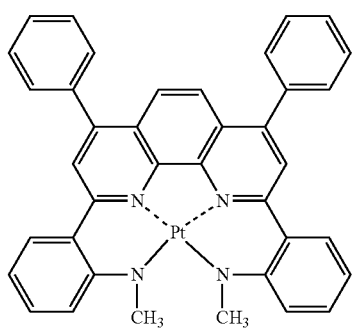
PD38
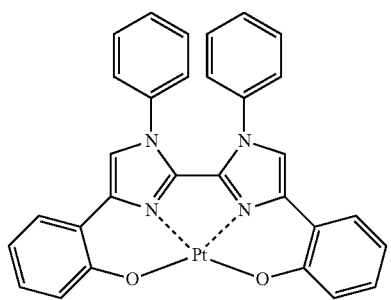
PD39

-continued
PD40
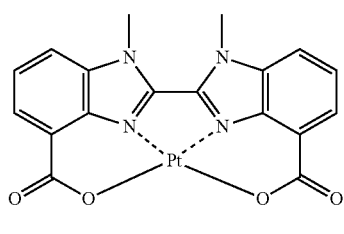
PD41
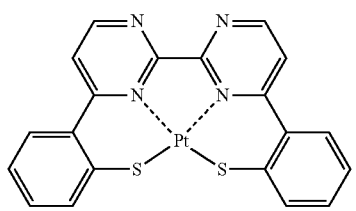
PD42
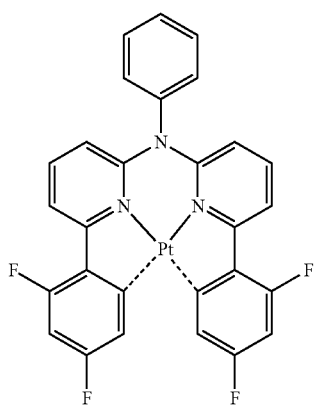
PD43
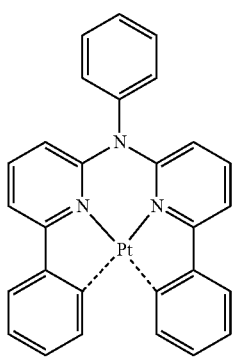
PD44
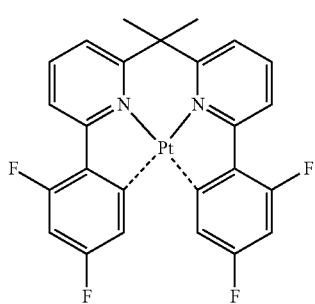
-continued
PD45
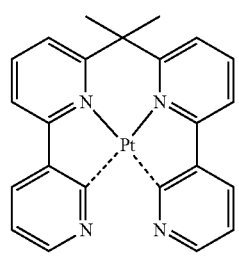
PD46
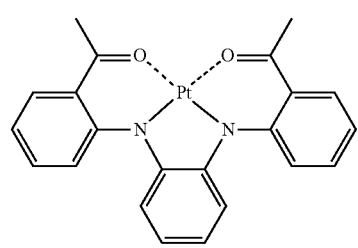
PD47
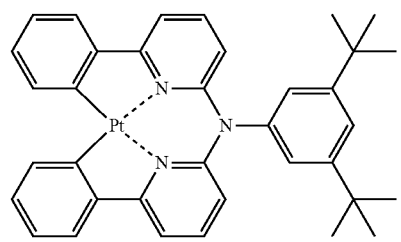
PD48
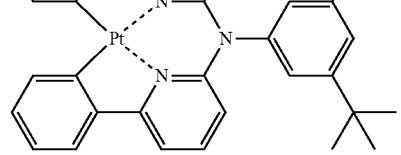
PD49
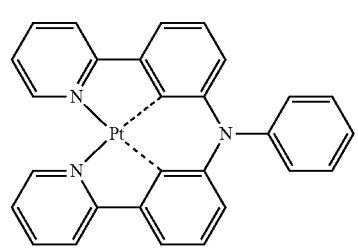
PD50
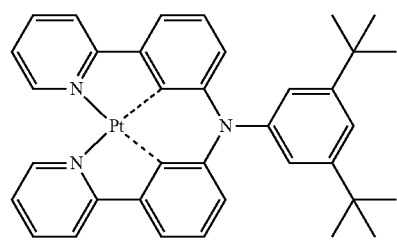

PD51 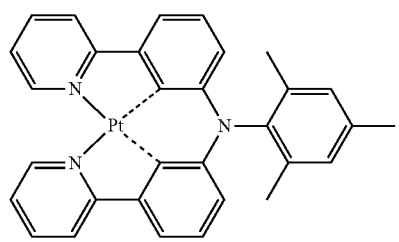
PD52 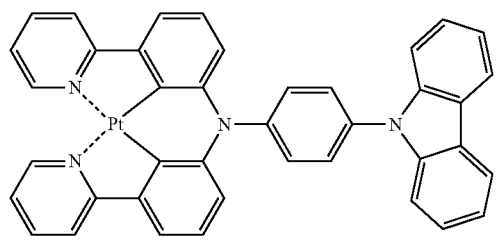
PD53 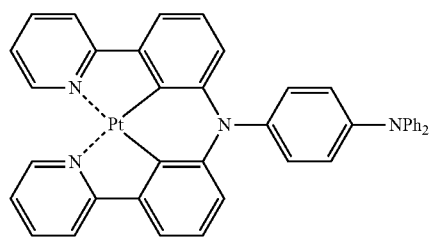
PD54 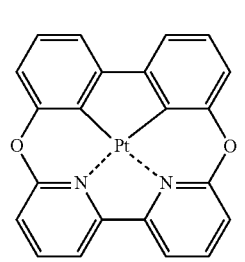
PD55 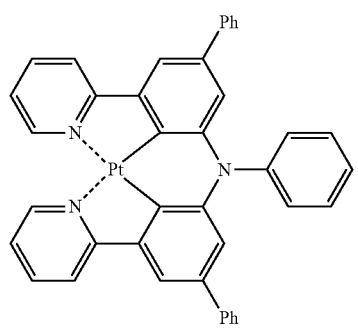
PD56 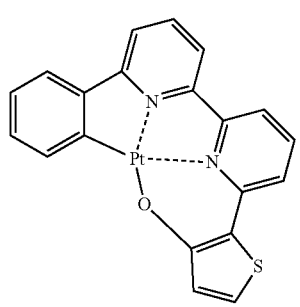
PD57 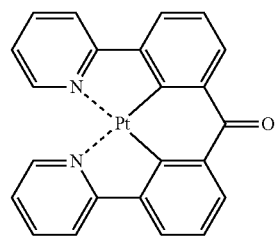
PD58 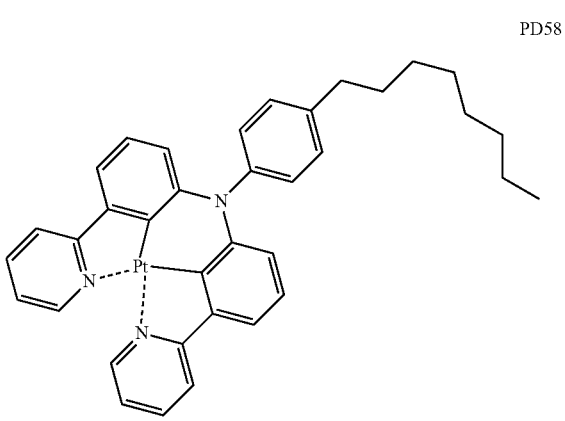
PD59 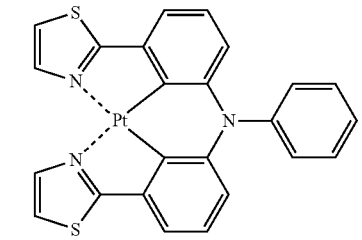
PD60 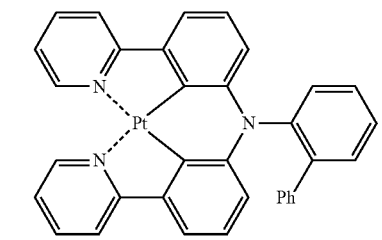
PD61 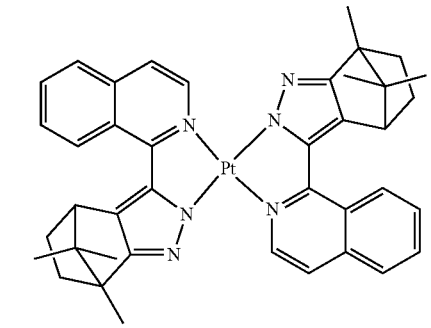

-continued
PD62
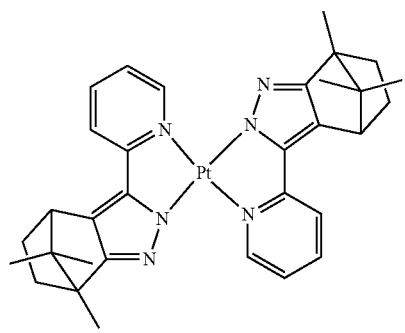
PD63
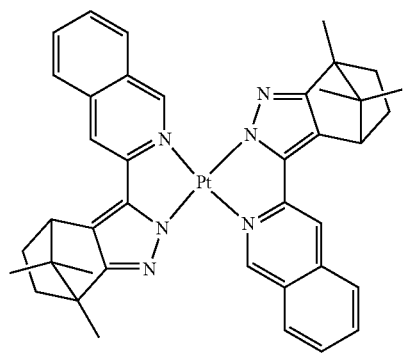
PD64
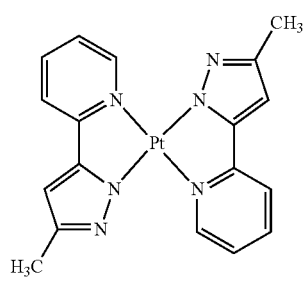
PD65
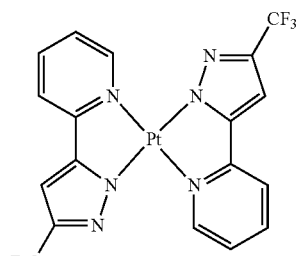
PD66
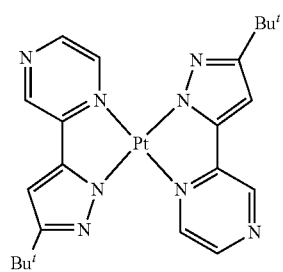
-continued
PD67
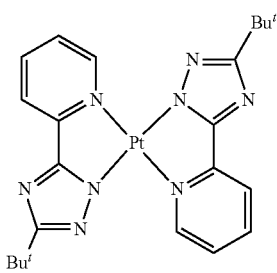
PD68
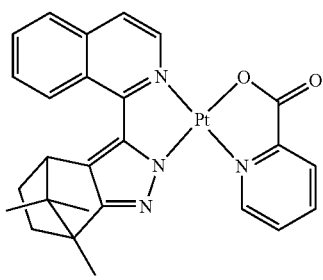
PD69
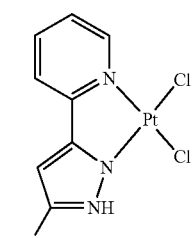
PD70
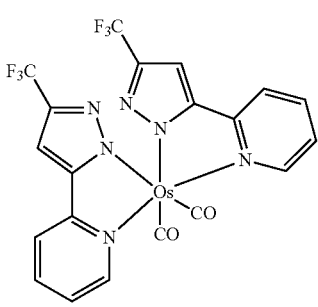
PD71
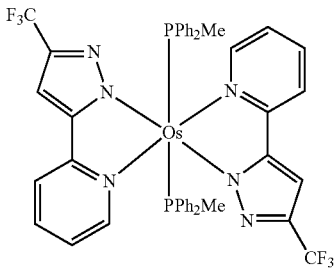

-continued

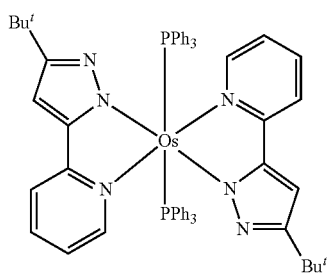

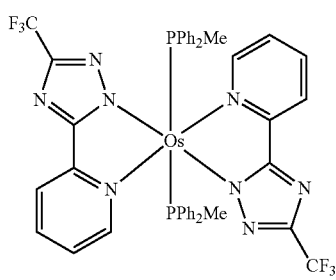

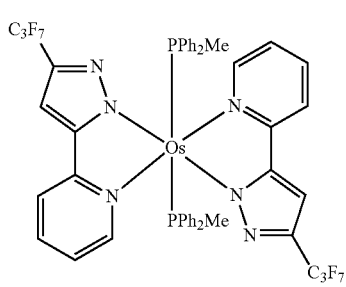

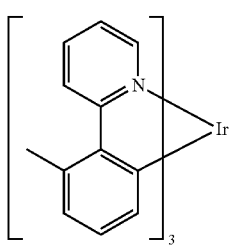

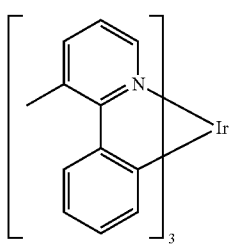

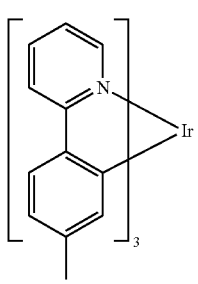

PD72

PD73

PD74

PD75

PD76

PD77

-continued

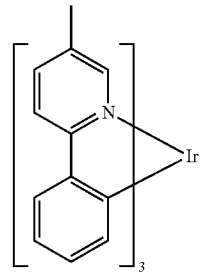

PD78

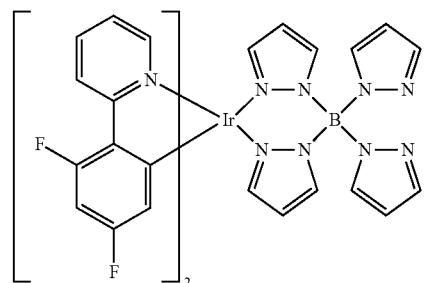

Flr6

In some embodiments, the phosphorescent dopant may include PtOEP:

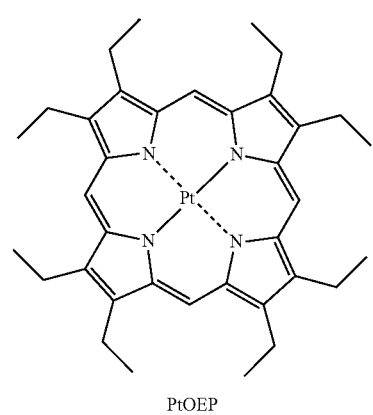

PtOEP

When the emission layer includes a host and a dopant, an amount of the dopant may be selected from a range of about 0.01 part by weight to about 20 parts by weight based on about 100 parts by weight of the host, but embodiments are not limited thereto.

A thickness of the emission layer may be in a range of about 100 Å to about 1000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer may be understood by referring to the conditions for forming the hole injection layer.

When the electron transport region includes a hole blocking layer, the hole blocking layer may, for example, include at least one of BCP, Bphen and TmPyPB, but is not limited thereto.

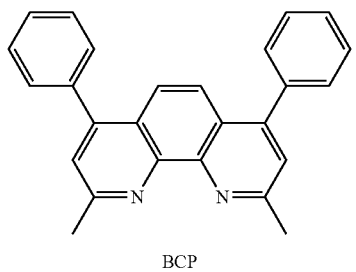

BCP

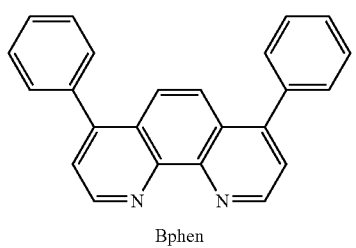

Bphen

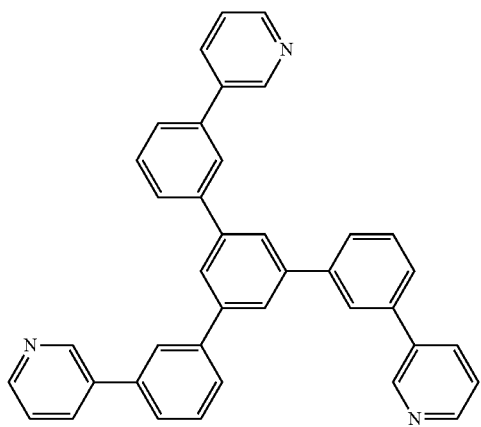

TmPyPB

A thickness of the hole blocking layer may be in a range of about 20 Å to about 1,000 Å, for example, about 30 Å to about 300 Å. While not wishing to be bound by theory, it is understood that when the thickness of the hole blocking layer is within this range, excellent hole blocking characteristics may be obtained without a substantial increase in driving voltage.

The electron transport layer may include at least one selected from BCP, BPhen, Alq3, BAlq, TAZ, and NTAZ.

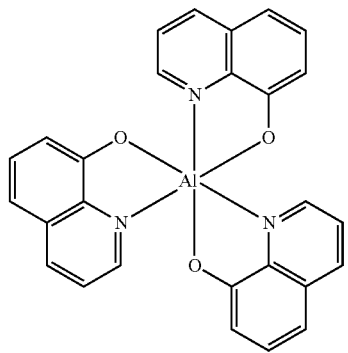

Alq3

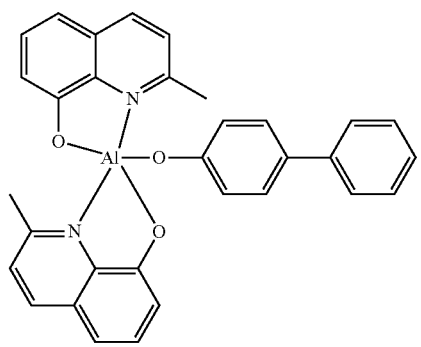

BAlq

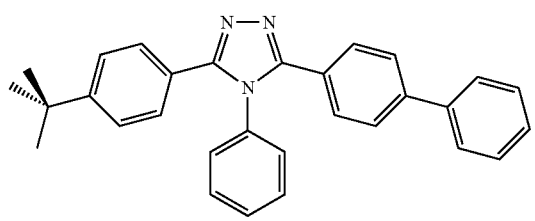

TAZ

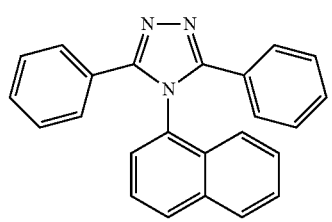

NTAZ

In some embodiments, the electron transport layer may include at least one selected from Compounds ET1 and ET2, but it is not limited thereto.

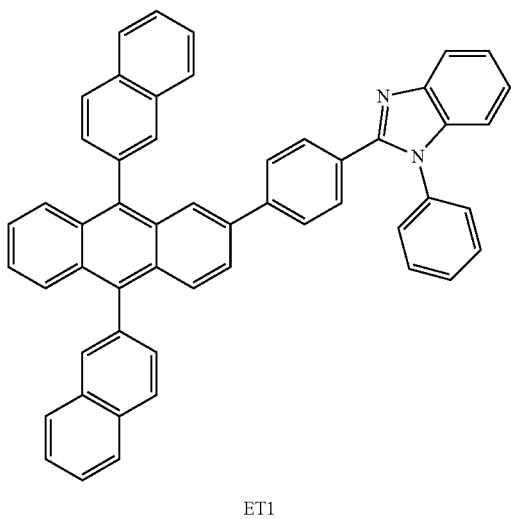

ET1

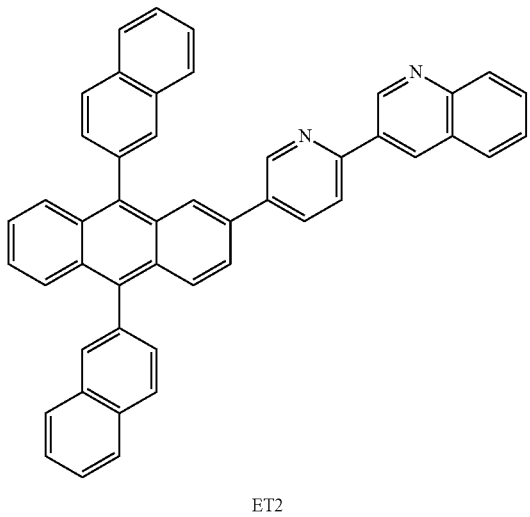

ET2

A thickness of the electron transport layer may be in a range of about 100 Å to about 1,000 Å, for example, about 150 Å to about 500 Å. While not wishing to be bound by theory, it is understood that when the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

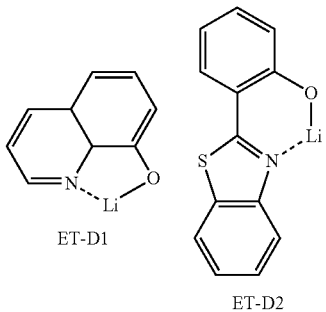

ET-D1

ET-D2

The electron transport region may include an electron injection layer (EIL) that facilitates electron injection from the second electrode 19.

The electron injection layer may include at least one selected from, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, an organic light-emitting device has been described with reference to FIG. 1, but embodiments are not limited thereto.

A $C_1$-$C_{60}$ alkyl group as used herein refers to a linear or branched aliphatic saturated hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as a $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a group formed by placing at least one carbon-carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by substituting at least one carbon triple bond in the middle or at the terminal of the $C_2$-$C_{60}$ alkyl group. Detailed examples thereof are an ethynyl group and a propynyl group.

A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent saturated monocyclic group including at least one hetero atom selected from N, O, P, Si and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in its ring, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, Si and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_2$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_{60}$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a heterocyclic aromatic system including at least one hetero atom selected from N, O, P, Si and S as a ring-forming atom and 1 to 60 carbon atoms. A $C_1$-$C_{60}$ heteroarylene group as used herein refers to a divalent group having a carbocyclic aromatic system including at least one hetero atom selected from N, O, P, Si and S as a ring-forming atom and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group), and a $C_7$-$C_{60}$ arylalkyl group as used herein indicates -$A_{104}A_{105}$ (wherein $A_{104}$ is the $C_6$-$C_{60}$ aryl group and $A_{105}$ is the $C_1$-$C_{60}$ alkyl group).

A $C_1$-$C_{60}$ heteroaryloxy group as used herein indicates —$OA_{106}$ (wherein $A_{106}$ is the $C_1$-$C_{60}$ heteroaryl group), a $C_1$-$C_{60}$ heteroarylthio group as used herein indicates —$SA_{107}$ (wherein $A_{107}$ is the $C_1$-$C_{60}$ heteroaryl group), and a $C_1$-$C_{60}$ heteroarylalkyl group as used herein indicates -$A_{108}A_{109}$ (wherein $A_{109}$ is the $C_1$-$C_{60}$ heteroaryl group and $A_{108}$ is the $C_1$-$C_{60}$ alkyl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic in the entire molecular structure. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group that has a plurality of rings condensed with each other, has a hetero atom selected from N, O, P, Si and S, other than carbon atoms (for example, the number of carbon atoms may be in a range of 1 to 60), as ring-forming atoms, wherein the molecular structure as a whole is non-aromatic in the entire molecular structure. The monovalent non-aromatic condensed heteropolycyclic group includes a carbazolyl group. A divalent non-aromatic condensed hetero-polycyclic group as used herein refers to a divalent group having the same structure as the monovalent non-aromatic condensed heteropolycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted monovalent non-aromatic condensed polycyclic group and substituted monovalent non-aromatic condensed heteropolycyclic group may be selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$), wherein $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{60}$ aryl group, the total number of carbon atoms in the resulting aryl substituted alkyl group is $C_7$-$C_{90}$.

The term "a biphenyl group" as used herein refers to a monovalent group in which two benzenes are linked to each other by a single bond.

The term "a terphenyl group" as used herein refers to a monovalent group in which three benzenes are linked to each other by a single bond.

Hereinafter, a compound and an organic light-emitting device according to an embodiment will be described in detail with reference to Synthesis Examples and Examples, however, the present inventive concept is not limited thereto. The expression "B was used instead of A" used in describing Synthesis Examples means that an amount of B used was identical to an amount of A used based on molar equivalence.

EXAMPLE

Synthesis Example 1

Synthesis of Compound 3

Compound 3 was synthesized according to the reaction scheme below.

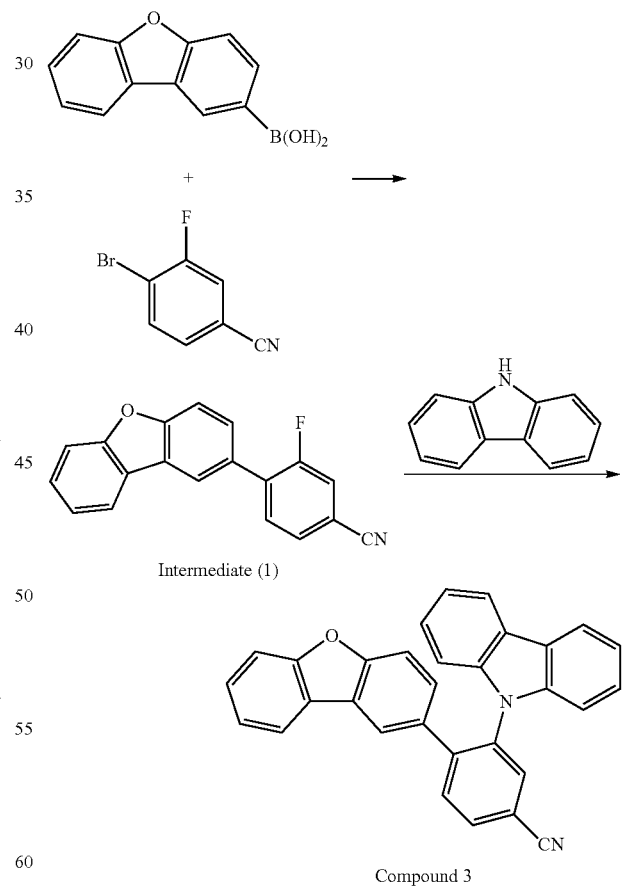

Synthesis of Intermediate (1)

10 grams (g) (47.2 millimoles (mmol)) of dibenzofuran-2-yl boronic acid, 9.43 g (47.2 mmol) of 4-bromo-3-fluorobenzonitrile, 10.9 g (9.4 mmol) of palladium tetrakis (triphenylphosphine) Pd(PPh$_3$)$_4$, and 19.6 g (141.5 mmol) of potassium carbonate (K$_2$CO$_3$) were added to 100 milliliters (ml) of tetrahydrofuran and 70 ml of distilled water, and the resulting mixture was heated and then refluxed. When the reaction was completed, the result was cooled to room temperature, and the organic layer was extracted with ethyl acetate, dried with anhydrous sodium sulfate (Na$_2$SO$_4$) and then concentrated. The product was separated by silica gel column chromatography (dichloromethane/hexane). A solid obtained from the above step was recrystallized (dichloromethane/methanol) to synthesize a white solid of Intermediate (1) (11.9 g, 41.4 mmol, yield 88%).

LC-Mass (calculated: 287.29 g/mol. found: [M+1]=288 g/mol)

Synthesis of Compound 3

20 ml of N,N-dimethylformamide was slowly added to 1.9 g (47.8 mmol) of sodium hydride (NaH) (60% in mineral oil) at 0° C., and the resulting mixture was stirred for 10 minutes. Then, 8 g (47.8 mmol) of carbazole was melted to 30 ml of N,N-dimethylformamide, and the resulting mixture was slowly added to the above reaction solution and stirred for 2 hours at room temperature. A mixture of 90 ml of N,N-dimethylformamide and 10.9 g (38.0 mmol) of Intermediate (1) was added to the above reaction solution. The resulting mixture was heated to 120° C. and refluxed. When the reaction was completed, the reaction solution was added to methanol/water to obtain a precipitate, and the precipitate was filtered, and washed with methanol. The result obtained from the above step was melted in hot toluene and filtered by silica gel to obtain a filtrate. The filtrate was concentrated to obtain a solid, and the solid was recrystallized (dichloromethane/methanol, ethyl acetate) twice to synthesize Compound 3 (8.9 g, 20.5 mmol, yield 54%).

MALDI-TOF Mass (calculated: 434.49 g/mol. found: 434.10 g/mol)

Synthesis Example 2

Synthesis of Compound 4

Compound 4 was synthesized in the same manner as in Synthesis Example 1, except that in synthesizing Intermediate (1), 3-bromo-2-fluorobenzonitrile was used instead of 4-bromo-3-fluorobenzonitrile (yield 52%).

MALDI-TOF Mass (calculated: 434.49 g/mol. found: 434.15 g/mol)

Synthesis Example 3

Synthesis of Compound 28

Compound 28 was synthesized in the same manner as in Synthesis Example 1, except that in synthesizing Intermediate (1), 3-bromo-2-fluorobenzonitrile was used instead of 4-bromo-3-fluorobenzonitrile, and dibenzothiophen-2-yl boronic acid was used instead of dibenzofuran-2-yl boronic acid (yield 47%).

MALDI-TOF Mass (calculated: 405.55 g/mol. found: 405.11 g/mol)

Synthesis Example 4

Synthesis of Compound 409

Compound 409 was synthesized in the same manner as in Synthesis Example 1, except that i) in synthesizing Intermediate (1), 3-bromo-2-fluorobenzonitrile was used instead of 4-bromo-3-fluorobenzonitrile, and ii) in synthesizing Compound 3, 9H-carbazole-3-carbonitrile was used instead of carbazole (yield 35%).

MALDI-TOF Mass (calculated: 459.50 g/mol. found: 459.18 g/mol)

Synthesis Example 5

Synthesis of Compound 413

Synthesis of Intermediate (2)

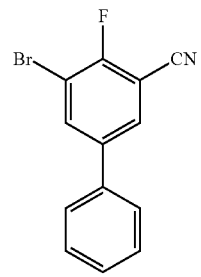

Intermediate (2)

3 g (24.6 mmol) of phenylboronic acid, 8.0 g (24.6 mmol) of 3-bromo-2-fluoro-5-iodobenzonitrile, 2.84 g (2.46 mmol) of palladium tetrakis(triphenylphosphine) (Pd(PPh$_3$)$_4$), and 10.2 g (73.8 mmol) of potassium carbonate (K$_2$CO$_3$) were added to 70 ml of tetrahydrofuran and 36 ml of distilled water, and the resulting mixture was heated and then refluxed. When the reaction was completed, the result was cooled to room temperature, and an organic layer was extracted with ethyl acetate, dried with anhydrous sodium sulfate (Na$_2$SO$_4$), and concentrated to perform a separation process by silica gel column chromatography(dichloromethane/hexane), thereby synthesizing Intermediate (2) (5.8 g, 21 mmol, yield 85%).

LC-Mass (calculated: 276.10 g/mol. found: [M+1]=277 g/mol)

Synthesis of Compound 413

Compound 413 was synthesized in the same manner as in Synthesis Example 1, except that, in synthesizing Intermediate (1), Intermediate (2) was used instead of 4-bromo-3-fluorobenzonitrile (yield 45%).

MALDI-TOF Mass (calculated: 510.58 g/mol. found: 510.17 g/mol)

Synthesis Example 6

Synthesis of Compound 415

Synthesis of Intermediate (2)-1

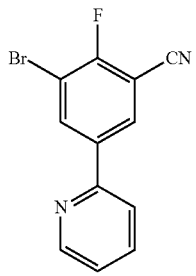

Intermediate (2)-1

Intermediate (2)-1 was synthesized in the same manner as Intermediate (2) in Synthesis Example 5, except that, in synthesizing Intermediate (2) of Synthesis Example 5, 2-pyridineboronic acid was used instead of phenylboronic acid.

Synthesis of Compound 415

Compound 415 was synthesized in the same manner as in Synthesis Example 1, except that, in synthesizing Intermediate (1), Intermediate (2)-1 was used instead of 4-bromo-3-fluorobenzonitrile (yield 23%).
MALDI-TOF Mass (calculated: 511.57 g/mol. found: 511.17 g/mol)

Synthesis Example 7

Synthesis of Compound 9

Compound 9 was synthesized in the same manner as in Synthesis Example 1, except that, in synthesizing Intermediate (1), 8-bromodibenzo[b,d]furan-2-carbonitrile was used instead of dibenzofuran-2-yl boronic acid, and 2-fluorophenylboronic acid was used instead of 4-bromo-3-fluorobenzonitrile (yield 32%).
MALDI-TOF Mass (calculated: 434.49 g/mol. found: 434.14 g/mol)

Synthesis Example 8

Synthesis of Compound 16

Compound 16 was synthesized in the same manner as in Synthesis Example 1, except that, in synthesizing Intermediate (1), 8-bromodibenzo[b,d]furan-2-carbonitrile was used instead of dibenzofuran-2-yl boronic acid, and 3-cyano-2-fluorophenylboronic acid was used instead of 4-bromo-3-fluorobenzonitrile (yield 40%).
MALDI-TOF Mass (calculated: 459.50 g/mol. found: 459.17 g/mol)

Synthesis Example 9

Synthesis of Compound 408

Compound 408 was synthesized in the same manner as in Synthesis Example 1, except that, i) in synthesizing Intermediate (1), 8-bromodibenzo[b,d]furan-2-carbonitrile was used instead of dibenzofuran-2-yl boronic acid, and ii) in synthesizing Compound 3, 9H-carbazole-3-carbonitrile was used instead of carbazole (yield 30%).
MALDI-TOF Mass (calculated: 459.50 g/mol. found: 459.15 g/mol)

Synthesis Example 10

Synthesis of Compound 421

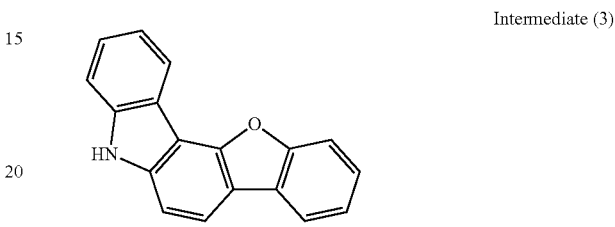

Intermediate (3)

Compound 421 was synthesized in the same manner as in Synthesis Example 1, except that, i) in synthesizing Intermediate (1), 2-bromo-3-fluorobenzonitrile was used instead of 4-bromo-3-fluorobenzonitrile, and ii) in synthesizing Compound 3, Intermediate (3) was used instead of carbazole and the reaction temperature was changed to 150° C. (yield 62%).
MALDI-TOF Mass (calculated: 524.57 g/mol. found: 524.17 g/mol)

Synthesis Example 11

Synthesis of Compound 423

Compound 423 was synthesized in the same manner as in Synthesis Example 1, except that, in synthesizing Compound 3, Intermediate (3) was used instead of carbazole and the reaction temperature was changed to 150° C. (yield 57%).
MALDI-TOF Mass (calculated: 524.57 g/mol. found: 524.16 g/mol)

Synthesis Example 12

Synthesis of Compound 424

Compound 424 was synthesized in the same manner as in Synthesis Example 1, except that, i) in synthesizing Intermediate (1), 3-bromo-2-fluorobenzonitrile was used instead of 4-bromo-3-fluorobenzonitrile, and ii) in synthesizing Compound 3, Intermediate (3) was used instead of carbazole and the reaction temperature was changed to 150° C. (yield 60%).
MALDI-TOF Mass (calculated: 524.57 g/mol. found: 524.17 g/mol)

Synthesis Example 13

Synthesis of Compound 429

Compound 429 was synthesized in the same manner as in Synthesis Example 1, except that, i) in synthesizing Intermediate (1), 8-bromodibenzo[b,d]furan-2-carbonitrile was used instead of dibenzofuran-2-yl boronic acid and 3-cyano- 2-fluorophenylboronic acid was used instead of 4-bromo-3-fluorobenzonitrile, and ii) in synthesizing Compound 3, Intermediate (3) was used instead of carbazole and the reaction temperature was changed to 150° C. (yield 33%).

MALDI-TOF Mass (calculated: 549.58 g/mol. found: 549.18 g/mol)

Synthesis Example 14

Synthesis of Compound 437

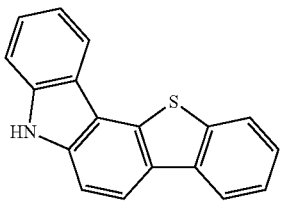

Intermediate (4)

Compound 437 was synthesized in the same manner as in Synthesis Example 1, except that, i) in synthesizing Intermediate (1), 3-bromo-2-fluorobenzonitrile was used instead of 4-bromo-3-fluorobenzonitrile, and ii) in synthesizing Compound 3, Intermediate (4) was used instead of carbazole and the reaction temperature was changed to 150° C. (yield 60%).

MALDI-TOF Mass (calculated: 540.63 g/mol. found: 540.17 g/mol)

Synthesis Example 15

Synthesis of Compound 450

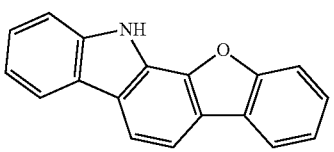

Intermediate (5)

Compound 450 was synthesized in the same manner as in Synthesis Example 1, except that, i) in synthesizing Intermediate (1), 3-bromo-2-fluorobenzonitrile was used instead of 4-bromo-3-fluorobenzonitrile, and ii) in synthesizing Compound 3, Intermediate (5) was used instead of carbazole and the reaction temperature was changed to 150° C. (yield 17%).

MALDI-TOF Mass (calculated: 524.57 g/mol. found: 524.19 g/mol)

Synthesis Example 16

Synthesis of Compound 459

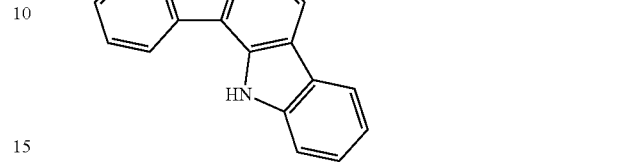

Intermediate (6)

Compound 459 was synthesized in the same manner as in Synthesis Example 1, except that, i) in synthesizing Intermediate (1), 3-bromo-2-fluorobenzonitrile was used instead of 4-bromo-3-fluorobenzonitrile, and ii) in synthesizing Compound 3, Intermediate (6) was used instead of carbazole and the reaction temperature was changed to 150° C. (yield 31%).

MALDI-TOF Mass (calculated: 524.57 g/mol. found: 524.18 g/mol)

Evaluation Example 1

Evaluation of Thermal Characteristics

Thermal analysis ($N_2$ atmosphere, temperature range: room temperature ~800° C. (10° C./min)-TGA, from room temperature to 400° C.-DSC, Pan Type: Pt Pan in disposable Al pan(TGA), disposable Al pan(DSC)) was performed on Compounds 3, 4, 413, 424 and A by using Thermo Gravimetric Analysis (TGA) and Differential Scanning calorimetry (DSC). The results thereof are shown in Table 2. Table 2 shows that Compounds 3, 4, 413 and 424 have an excellent thermal stability compared to Compound A.

TABLE 2

| Compound No. | Tg (° C.) | decomposition start temperature (° C.) |
|---|---|---|
| 3 | 89 | 292 |
| 4 | 83 | 285 |
| 413 | 106 | 362 |
| 424 | 129 | 393 |
| Compound A | 72 | 317 |

Compound A

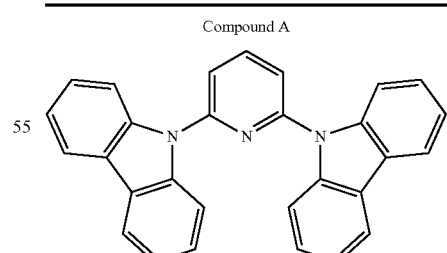

Example 1

A glass substrate having an indium tin oxide (ITO) electrode as a first electrode having a thickness of 1,500 Angstroms (Å) thereon was sonicated with distilled water and then further sonicated with solvent such as isopropyl alcohol, acetone, and methanol and dried to be placed in a plasma cleaner. Next, the glass substrate was cleaned for 5 minutes by using oxygen plasma and then mounted on a vacuum deposition apparatus.

Compound NPB was vacuum deposited on the ITO electrode of the glass substrate to form a hole transport layer having a thickness of 1,200 Å, and mCP was deposited on the hole transport layer to form an electron blocking layer having a thickness of 100 Å. As a result, a hole transport region was formed.

Compound 3 (host) and Compound FIr6 (dopant, 10 percent by weight (wt %)) were co-deposited on the hole transport region to form an emission layer having a thickness of 300 Å.

TmPyPB was vacuum deposited on the emission layer to form a hole blocking layer having a thickness of 100 Å, and Compound Alq$_3$ was deposited on the hole blocking layer to form an electron transport layer having a thickness of 250 Å. Then, LiF was deposited on the electron transport layer to form an electron injection layer having a thickness of 5 Å, and Al second electrode (cathode) having a thickness of 1,000 Å was formed on the electron injection layer, thereby manufacturing an organic light-emitting device.

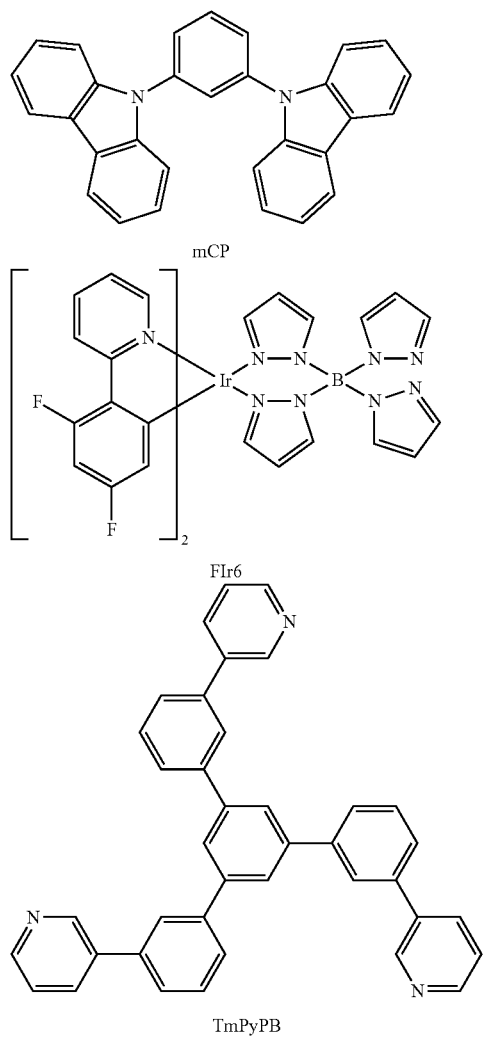

mCP

FIr6

TmPyPB

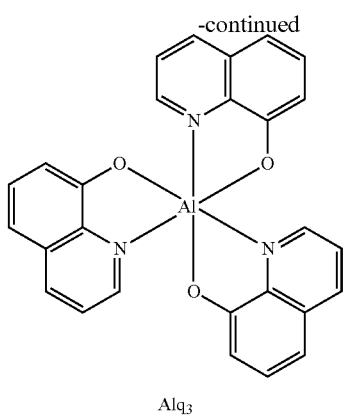

Alq$_3$

Examples 2 to 16 and Comparative Examples 1 to 4

Organic light-emitting devices were manufactured in the same manner as in Example 1, except that when forming an emission layer, Compounds in Table 3 were used as a host instead of Compound 3.

Evaluation Example 2

Characteristic Evaluation of Organic Light-emitting Device

The driving voltage, current efficiency and lifespan of each organic light-emitting device manufactured in Examples 1 to 16 and Comparative Examples 1 to 4 were evaluated by using a Keithley SMU 236 and a luminance meter PR650. In Table 3, the driving voltage and current efficiency of Examples 2 to 16 and Comparative Examples 1 to 4 were respectively expressed in a relative value compared to "100", which denotes the driving voltage and current efficiency of an organic light-emitting device in Example 1. Lifespan ($T_{95}$) in Table 3 refers to an amount of time (hour, hr) lapsed until luminance was decreased to 95% of its initial value, where the initial value was measured in 500 nit. Lifespan ($T_{95}$) of Examples 2 to 16 and Comparative Examples 1 to 4 was expressed in a relative value compared to "100", which denotes lifespan ($T_{95}$) of an organic light-emitting device in Example 1.

TABLE 3

| | host | driving voltage (V) (relative value) | current efficiency (cd/A) (relative value) | $T_{95}$ (hr) (relative value) |
|---|---|---|---|---|
| Example 1 | Compound 3 | 100 | 100 | 100 |
| Example 2 | Compound 4 | 88 | 108 | 171 |
| Example 3 | Compound 9 | 70 | 103 | 50 |
| Example 4 | Compound 16 | 77 | 114 | 58 |
| Example 5 | Compound 28 | 94 | 102 | 119 |
| Example 6 | Compound 408 | 72 | 94 | 75 |
| Example 7 | Compound 409 | 84 | 115 | 133 |
| Example 8 | Compound 413 | 91 | 110 | 171 |
| Example 9 | Compound 415 | 76 | 84 | 65 |
| Example 10 | Compound 421 | 67 | 83 | 143 |
| Example 11 | Compound 423 | 66 | 81 | 72 |
| Example 12 | Compound 424 | 63 | 89 | 105 |
| Example 13 | Compound 429 | 72 | 98 | 52 |
| Example 14 | Compound 437 | 63 | 94 | 80 |

TABLE 3-continued

| host | | driving voltage (V) (relative value) | current efficiency (cd/A) (relative value) | T$_{95}$ (hr) (relative value) |
|---|---|---|---|---|
| Example 15 | Compound 450 | 67 | 103 | 74 |
| Example 16 | Compound 459 | 65 | 79 | 53 |
| Comparative Example 1 | Compound A | 112 | 75 | 21 |
| Comparative Example 2 | Compound B | 109 | 62 | 27 |
| Comparative Example 3 | Compound C | 87 | 48 | 48 |
| Comparative Example 4 | Compound D | 101 | 78 | 25 |

TABLE 3-continued

| host | driving voltage (V) (relative value) | current efficiency (cd/A) (relative value) | T$_{95}$ (hr) (relative value) |
|---|---|---|---|

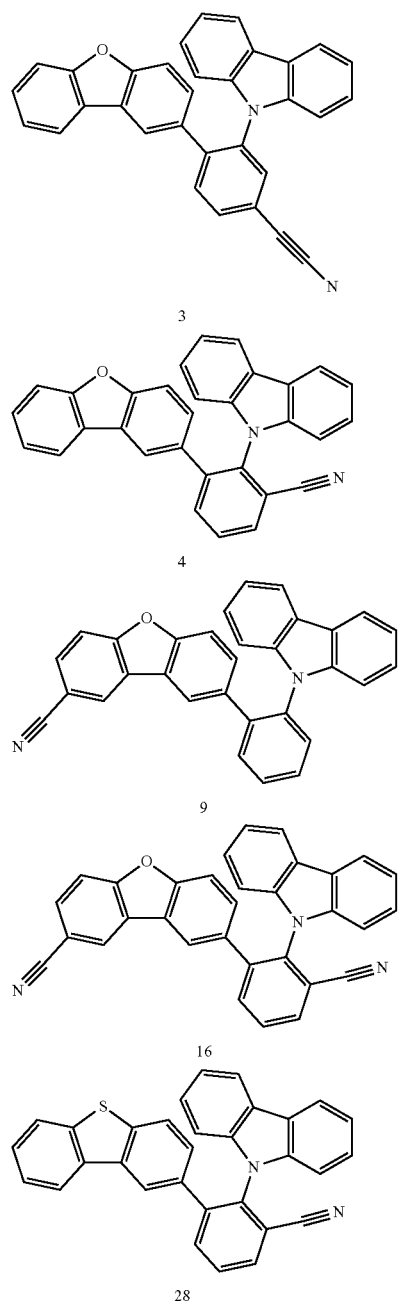

TABLE 3-continued
| host | driving voltage (V) (relative value) | current efficiency (cd/A) (relative value) | T$_{95}$ (hr) (relative value) |
|---|---|---|---|
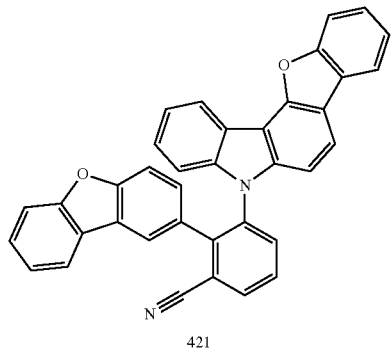 [SMILES: N#Cc1cccc(-n2c3ccccc3c3c4oc5ccccc5c4ccc32)c1-c1ccc2oc3ccccc3c2c1]
421
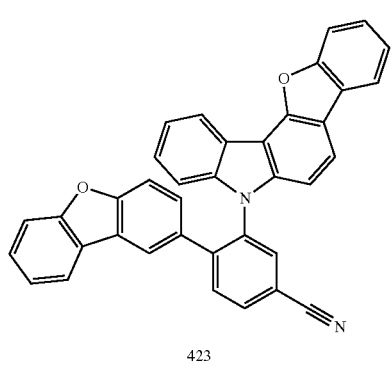 [SMILES: N#Cc1ccc(-c2ccc3oc4ccccc4c3c2)c(-n2c3ccccc3c3c4oc5ccccc5c4ccc32)c1]
423
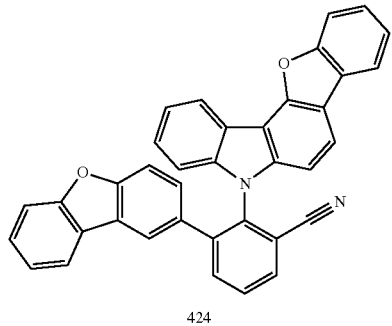 [SMILES: N#Cc1cccc(-c2ccc3oc4ccccc4c3c2)c1-n1c2ccccc2c2c3oc4ccccc4c3ccc21]
424
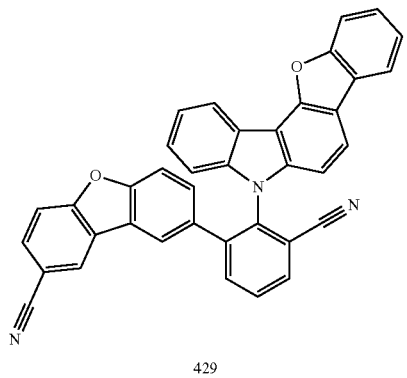 [SMILES: N#Cc1ccc2oc3ccc(-c4cccc(C#N)c4-n4c5ccccc5c5c6oc7ccccc7c6ccc54)cc3c2c1]
429
TABLE 3-continued
| host | driving voltage (V) (relative value) | current efficiency (cd/A) (relative value) | T$_{95}$ (hr) (relative value) |
|---|---|---|---|
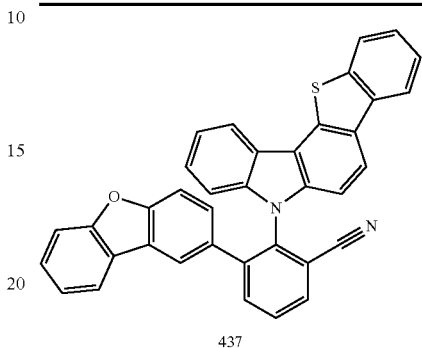
437
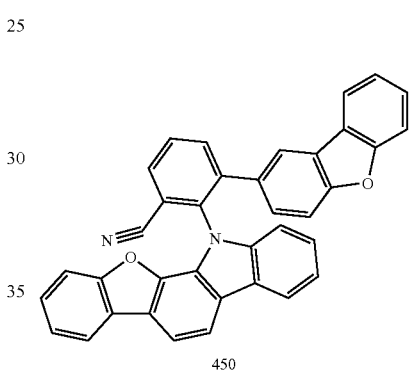
450
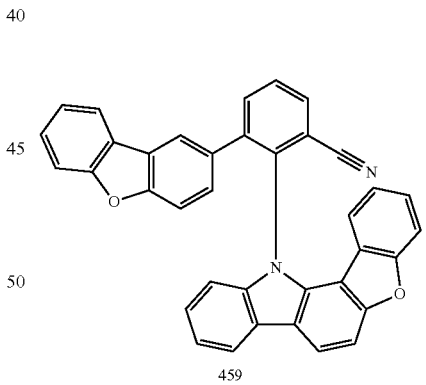
459
Compound A
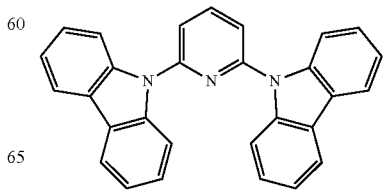

TABLE 3-continued

| host | driving voltage (V) (relative value) | current efficiency (cd/A) (relative value) | $T_{95}$ (hr) (relative value) |
|---|---|---|---|

Compound B

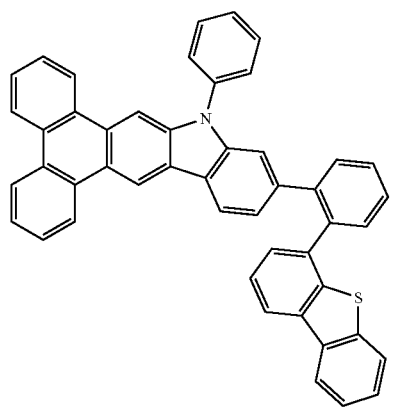

Compound C

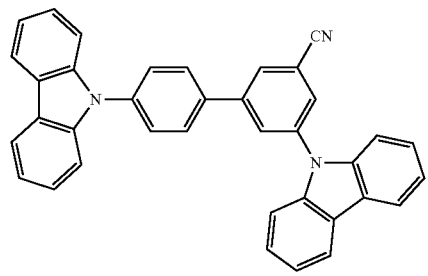

Compound D

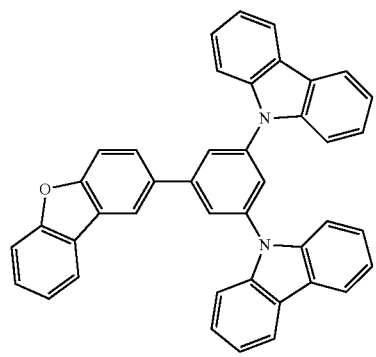

Table 3 shows that organic light-emitting devices in Examples 1 to 16 have lower or comparable driving voltage, higher efficiency and longer lifespan compared to organic light-emitting devices in Comparative Examples 1 to 4.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

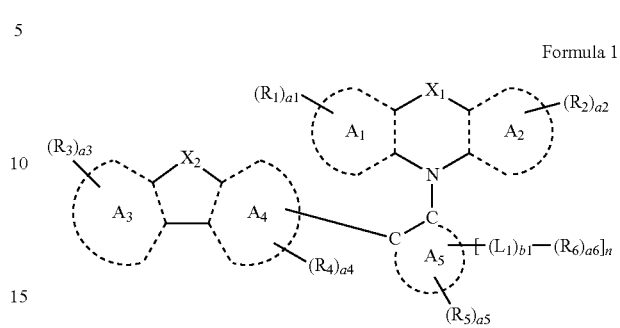

Formula 1 wherein, in Formula 1, $X_1$ is selected from a single bond, O, S, $N(R_{11})$ and $C(R_{12})(R_{13})$, $X_2$ is O or S, ring $A_1$ to ring $A_4$ are each independently a $C_5$-$C_{60}$ carbocyclic group or a $C_2$-$C_{60}$ heterocyclic group, ring $A_5$ is selected from a benzene, a pyridine, a pyrimidine, a pyrazine, a pyridazine and a triazine, provided that when n is 0, 1) ring $A_1$ to ring $A_5$ are not simultaneously a benzene, or
2) i) one or more of groups $R_1$ in the number of a1, ii) one or more groups $R_2$ in the number of a2, iii) one or more of groups $R_3$ in the number of a3, iv) one or more groups $R_4$ in the number of a4, v) one or more of groups $R_5$ in the number of a5, or vi) any combination thereof are each independently a cyano group-substituted $C_6$-$C_{10}$ aryl group, $R_1$ to $R_6$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$) and —B($Q_6$)($Q_7$), a1 is an integer of 1 to 4, a2 to a6 are each independently an integer of 0 to 4, $L_1$ is selected from a phenylene group, a pyridinylene group, a pyrimidinylene group, a pyrazinylene group, a pyridazinylene group and a triazinylene group; and a phenylene group, a pyridinylene group, a pyrimidinylene group, a pyrazinylene group, a pyridazinylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$), b1 is an integer of 1 to 3, n is an integer of 0 to 3, the number of cyano groups in Formula 1 is 1, 2, 3 or 4, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group and substituted monovalent non-aromatic condensed heteropolycyclic group is selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$), and —Si($Q_{31}$)($Q_{32}$)($Q_{33}$), —N($Q_{34}$)($Q_{35}$) and —B($Q_{36}$)($Q_{37}$); and $Q_1$ to $Q_{10}$, $Q_{11}$ to $Q_{17}$, $Q_{21}$ to $Q_{27}$ and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group and a substituted or unsubstituted monovalent non-aromatic condensed heteropolycyclic group.

2. The condensed cyclic compound of claim 1, wherein $X_1$ is a single bond.

3. The condensed cyclic compound of claim 1, wherein ring $A_1$ to ring $A_4$ are each independently selected from a benzene, a pyridine, a pyrimidine, a pyrazine, a pyridazine, a naphthalene, a quinoline, an isoquinoline, a quinoxaline, a quinazoline, a cinnoline, an indene, an indole, a benzofuran, a benzothiophene, a fluorene, a carbazole, a dibenzofuran and a dibenzothiophene.

4. The condensed cyclic compound of claim 1, wherein
ring $A_1$ and ring $A_2$ are each independently selected from
a benzene, a dibenzofuran and a dibenzothiophene, and
ring $A_3$ and ring $A_4$ are each independently selected from
a benzene, a fluorene, a carbazole, a dibenzofuran and
a dibenzothiophene.

5. The condensed cyclic compound of claim 1, wherein
$R_1$ to $R_6$ and $R_{11}$ to $R_{13}$ are each independently selected
from
a hydrogen, a deuterium, —F, —Cl, —Br, —I, a hydroxyl
group, a cyano group, a nitro group, an amino group, an
amidino group, a hydrazine group, a hydrazone group,
a carboxylic acid group or a salt thereof, a sulfonic acid
group or a salt thereof, a phosphoric acid group or a salt
thereof, a $C_1$-$C_{10}$ alkyl group and a $C_1$-$C_{10}$ alkoxy
group;
a $C_1$-$C_{10}$ alkyl group and a $C_1$-$C_{10}$ alkoxy group, each
substituted with at least one selected from a deuterium,
—F, —Cl, —Br, —I, a hydroxyl group, a cyano group,
a nitro group, an amino group, an amidino group, a
hydrazine group, a hydrazone group, a carboxylic acid
group or a salt thereof, a sulfonic acid group or a salt
thereof and a phosphoric acid group or a salt thereof;
a phenyl group, a naphthyl group, a pyridinyl group, a
pyrimidinyl group, a pyrazinyl group, a pyridazinyl
group and a triazinyl group;
a phenyl group, a naphthyl group, a pyridinyl group, a
pyrimidinyl group, a pyrazinyl group, a pyridazinyl
group and a triazinyl group, each substituted with at
least one selected from a deuterium, —F, —Cl, —Br,
—I, a hydroxyl group, a cyano group, a nitro group, an
amino group, an amidino group, a hydrazine group, a
hydrazone group, a carboxylic acid group or a salt
thereof, a sulfonic acid group or a salt thereof, a
phosphoric acid group or a salt thereof, a $C_1$-$C_{10}$ alkyl
group, a $C_1$-$C_{10}$ alkoxy group, a phenyl group, a
naphthyl group, a pyridinyl group, a pyrimidinyl group,
a pyrazinyl group, a pyridazinyl group, a triazinyl
group and —Si($Q_{31}$)($Q_{32}$)($Q_{33}$); and
—Si($Q_1$)($Q_2$)($Q_3$), and
$Q_1$ to $Q_3$ and $Q_{31}$ to $Q_{33}$ are each independently selected
from a hydrogen, a $C_1$-$C_{10}$ alkyl group, a $C_1$-$C_{10}$ alkoxy
group, a phenyl group, a naphthyl group, a pyridinyl
group, a pyrimidinyl group, a pyrazinyl group, a
pyridazinyl group and a triazinyl group.

6. The condensed cyclic compound of claim 1, wherein
$R_1$ to $R_6$ and $R_{11}$ to $R_{13}$ are each independently selected
from
a hydrogen, a deuterium, a cyano group, a $C_1$-$C_{10}$ alkyl
group and a $C_1$-$C_{10}$ alkoxy group;
a $C_1$-$C_{10}$ alkyl group and a $C_1$-$C_{10}$ alkoxy group, each
substituted with at least one selected from a deuterium
and a cyano group;
a phenyl group, a pyridinyl group, a pyrimidinyl group
and a triazinyl group;
a phenyl group, a pyridinyl group, a pyrimidinyl group
and a triazinyl group, each substituted with at least one
selected from a deuterium, a cyano group, a $C_1$-$C_{10}$
alkyl group, a $C_1$-$C_{10}$ alkoxy group, a phenyl group, a
pyridinyl group, a pyrimidinyl group, a triazinyl group
and —Si($Q_{31}$)($Q_{32}$)($Q_{33}$); and
—Si($Q_1$)($Q_2$)($Q_3$), and
$Q_1$ to $Q_3$ and $Q_{31}$ to $Q_{33}$ are each independently selected
from a hydrogen, a $C_1$-$C_{10}$ alkyl group, a $C_1$-$C_{10}$ alkoxy
group, a phenyl group, a pyridinyl group, a pyrimidinyl
group and a triazinyl group.

7. The condensed cyclic compound of claim 1, wherein
$L_1$ is selected from
a phenylene group, a pyridinylene group, a pyrimidinylene group and a triazinylene group; and
a phenylene group, a pyridinylene group, a pyrimidinylene group and a triazinylene group, each substituted
with at least one selected from a deuterium, a cyano
group, a $C_1$-$C_{10}$ alkyl group, a $C_1$-$C_{10}$ alkoxy group, a
phenyl group, a pyridinyl group, a pyrimidinyl group,
a triazinyl group and —Si($Q_8$)($Q_9$)($Q_{10}$), and
$Q_8$ to $Q_{10}$ are each independently selected from a hydrogen, a $C_1$-$C_{10}$ alkyl group, a $C_1$-$C_{10}$ alkoxy group, a
phenyl group, a pyridinyl group, a pyrimidinyl group
and a triazinyl group.

8. The condensed cyclic compound of claim 1, wherein
$L_1$ is selected from groups represented by Formulae 3-1 to
3-40:

Formula 3-1

Formula 3-2

Formula 3-3

Formula 3-4

Formula 3-5

Formula 3-6

Formula 3-7

Formula 3-8

-continued
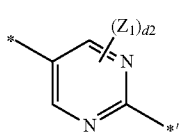
Formula 3-9
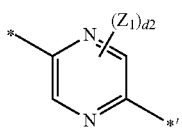
Formula 3-10
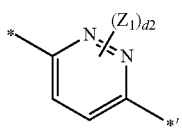
Formula 3-11
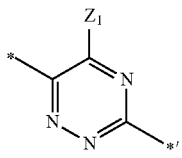
Formula 3-12
Formula 3-13
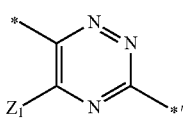
Formula 3-14
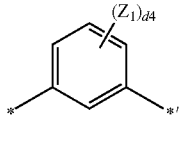
Formula 3-15
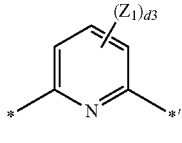
Formula 3-16
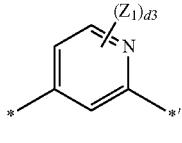
Formula 3-17
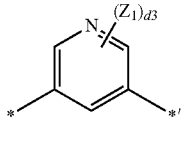
Formula 3-18
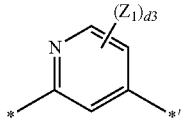
Formula 3-19
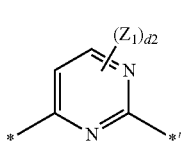
Formula 3-20
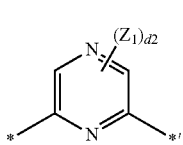
Formula 3-21
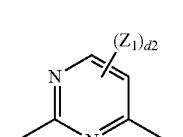
Formula 3-22
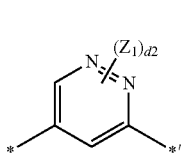
Formula 3-23
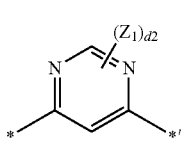
Formula 3-24
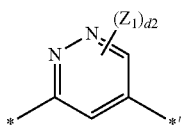
Formula 3-25
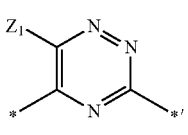
Formula 3-26
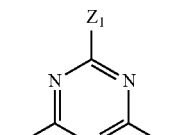
Formula 3-27
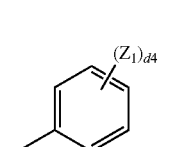
Formula 3-28
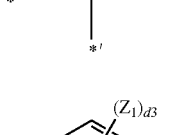
Formula 3-29
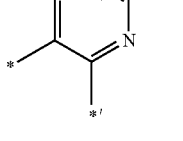

-continued

Formula 3-30
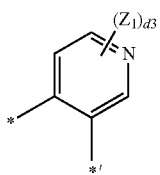

Formula 3-31
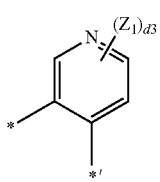

Formula 3-32
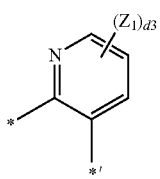

Formula 3-33
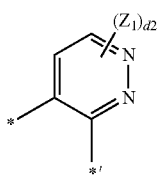

Formula 3-34
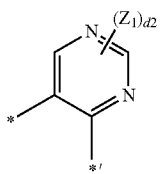

Formula 3-35
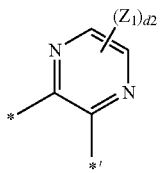

Formula 3-36
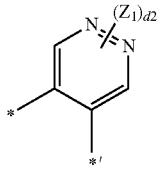

Formula 3-37
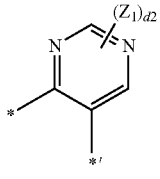

-continued

Formula 3-38
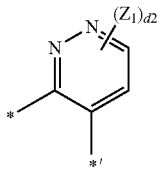

Formula 3-39
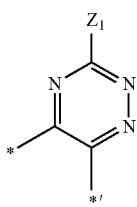

Formula 3-40
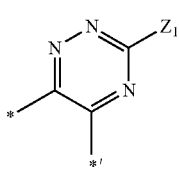

wherein, in Formulae 3-1 to 3-40, $Z_1$ is selected from a hydrogen, a deuterium, a cyano group, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$), $Q_8$ to $Q_{10}$ are each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group, d4 is an integer of 0 to 4, d3 is an integer of 0 to 3, d2 is an integer of 0 to 2, and each of * and *' is a binding site to a neighboring atom.

9. The condensed cyclic compound of claim 1, wherein n is 0 or 1.

10. The condensed cyclic compound of claim 1, wherein the condensed cyclic compound is represented by one of Formulae 1A to 1H:

Formula 1A
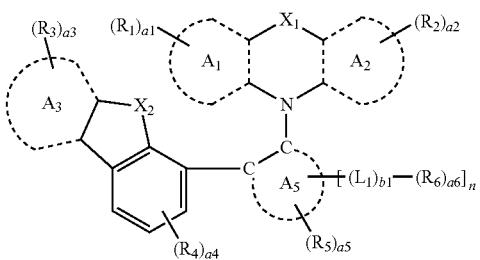

-continued

Formula 1B
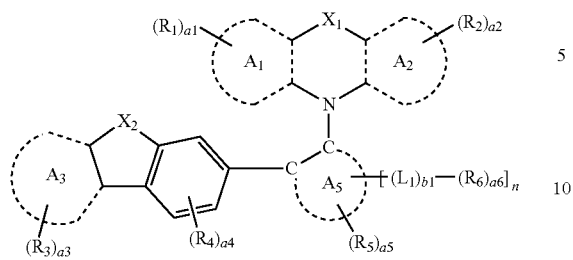

Formula 1C
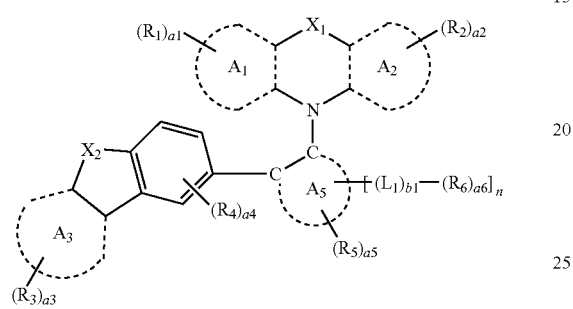

Formula 1D
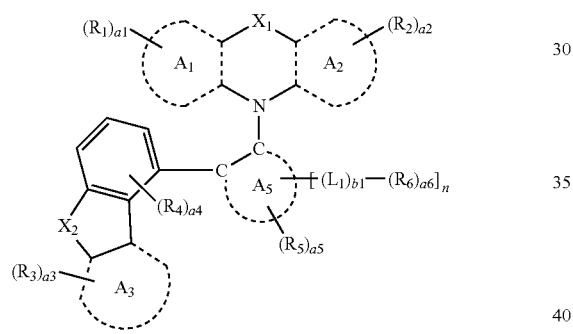

Formula 1E
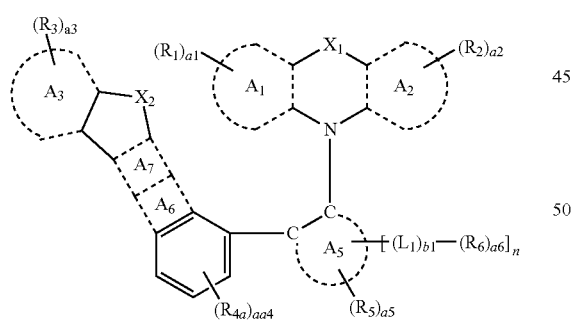

Formula 1F
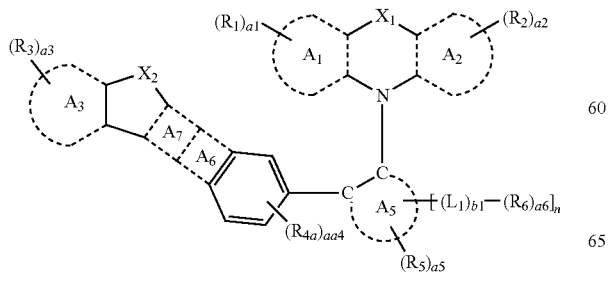

-continued

Formula 1G
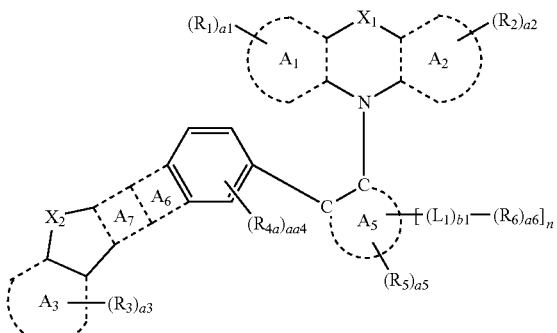

Formula 1H
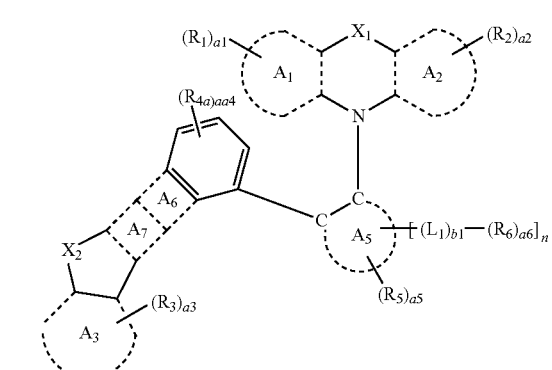

Formula 2A

Formula 2B

wherein, in Formulae 1A to 1H, 2A and 2B, $X_1$, $X_2$, ring $A_1$, ring $A_2$, ring $A_5$, $R_1$ to $R_6$, a1 to a6, $L_1$, b1 and n are the same as in claim 1, ring $A_3$ is selected from a benzene, a pyridine, a pyrimidine, a pyrazine, a pyridazine, an indene, an indole, a benzofuran, a benzothiophene, a fluorene, a carbazole, a dibenzofuran and a dibenzothiophene, ring $A_6$ is represented by Formula 2A, ring $A_7$ is represented by Formula 2B, $X_4$ is selected from O, S, $N(R_{4c})$ and $C(R_{4d})(R_{4e})$, $R_{4a}$ to $R_{4e}$ are the same as $R_4$, aa4 is an integer of 0 to 3, and ab4 is an integer of 0 to 2.

11. The condensed cyclic compound of claim 1, wherein the condensed cyclic compound is represented by one of Formulae 1-1 to 1-19:

Formula 1-1
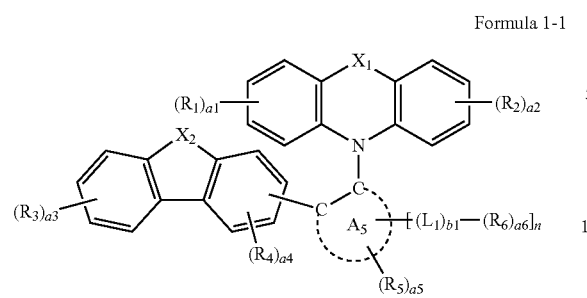
Formula 1-2
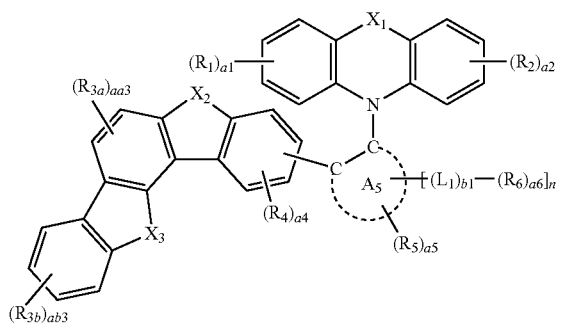
Formula 1-3
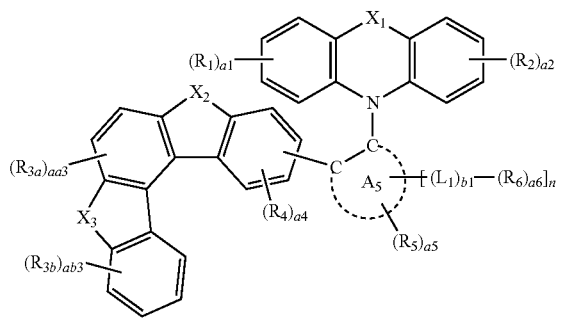
Formula 1-4
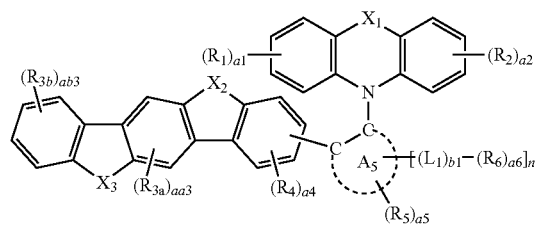
Formula 1-5
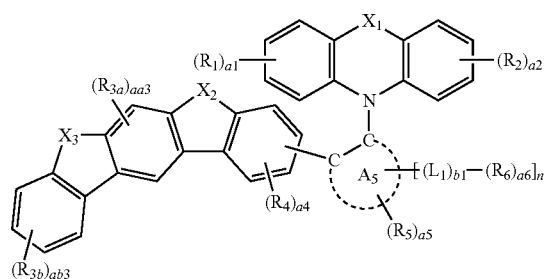
Formula 1-6
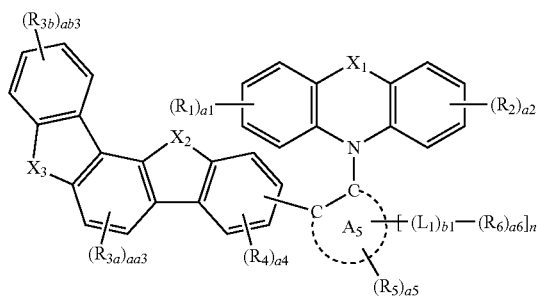
Formula 1-7
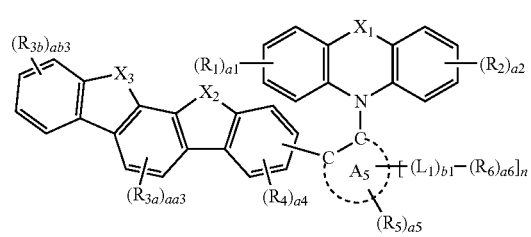
Formula 1-8
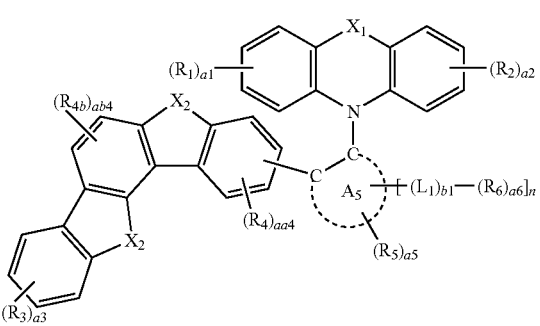
Formula 1-9
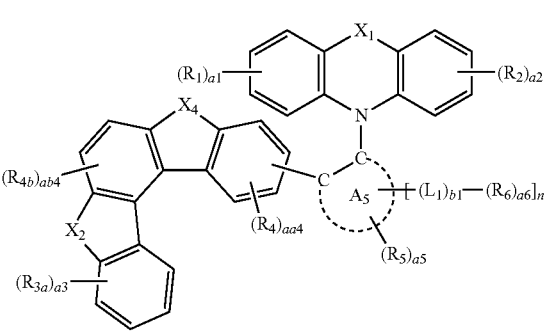
Formula 1-10
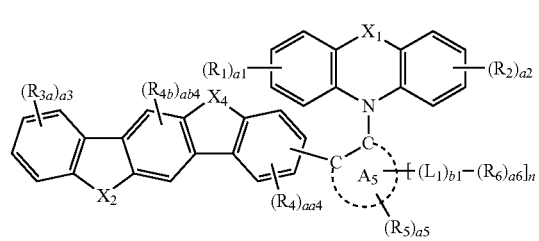

Formula 1-11
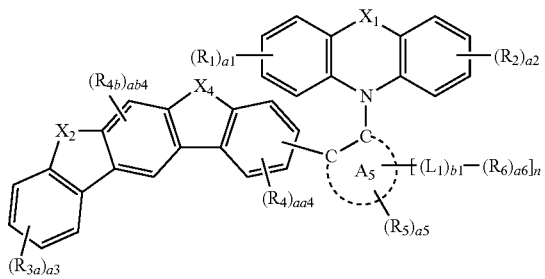

Formula 1-12
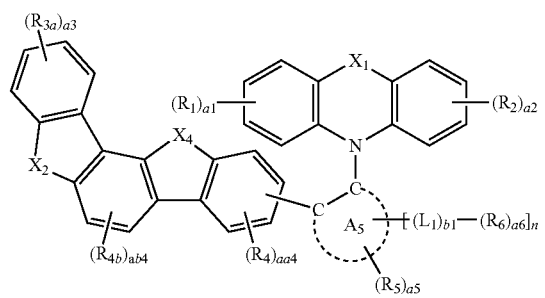

Formula 1-13
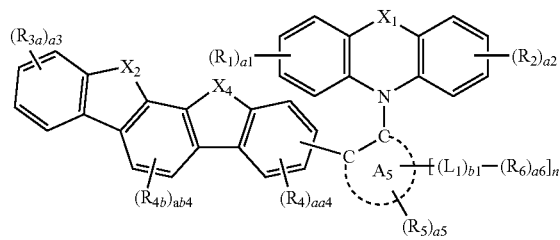

Formula 1-14
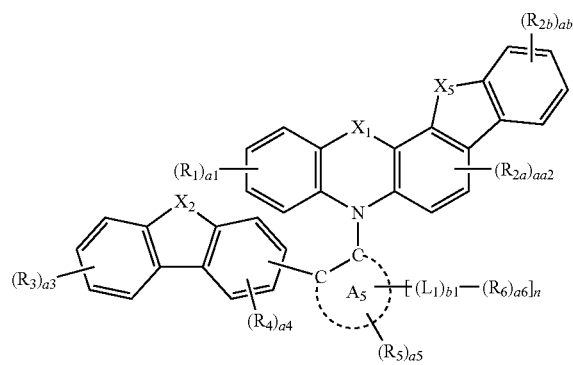

Formula 1-15
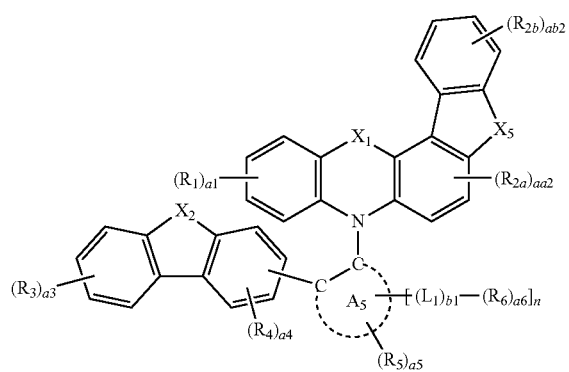

Formula 1-16
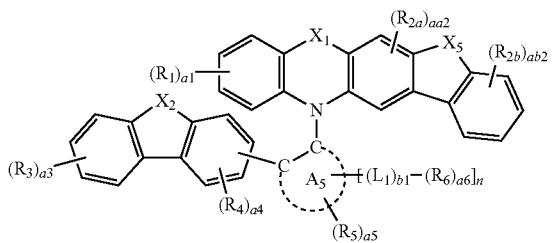

Formula 1-17
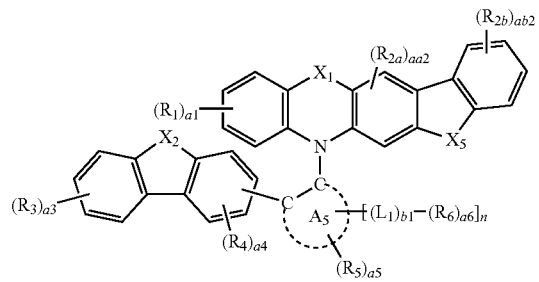

Formula 1-18
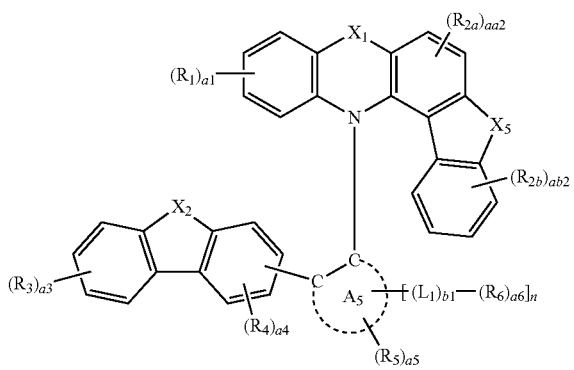

Formula 1-19
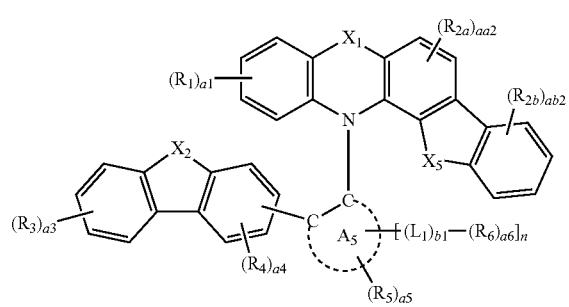

in Formulae 1-1 to 1-19,
$X_1$, $X_2$, ring $A_5$, $R_1$ to $R_6$, a1 to a6, $L_1$, b1 and n are the same as in claim 1,
$X_3$ is selected from O, S, $N(R_{3c})$ and $C(R_{3d})(R_{3e})$,
$X_4$ is selected from O, S, $N(R_{4c})$ and $C(R_{4d})(R_{4e})$,
$X_5$ is selected from O, S, $N(R_{2c})$ and $C(R_{2d})(R_{2e})$,
$R_{2a}$ to $R_{2e}$ are the same as the $R_2$,
$R_{3a}$ to $R_{3e}$ are the same as $R_3$,
$R_{4a}$ to $R_{4e}$ are the same as $R_4$,
aa2 and aa3 are each independently an integer of 0 to 2,
ab2 and ab3 are each independently an integer of 0 to 4,
aa4 is an integer of 0 to 3, and
ab4 is an integer of 0 to 2.

12. The condensed cyclic compound of claim 1, wherein the condensed cyclic compound is represented by one of Formulae 1(1) to 1(12):
Formula 1(1)
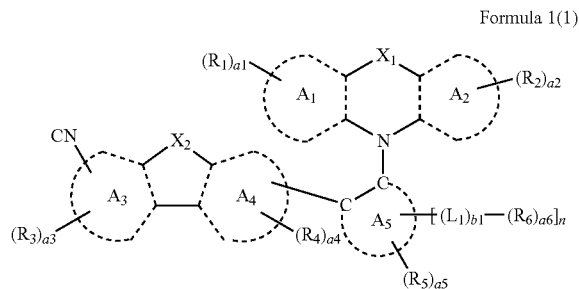
Formula 1(2)
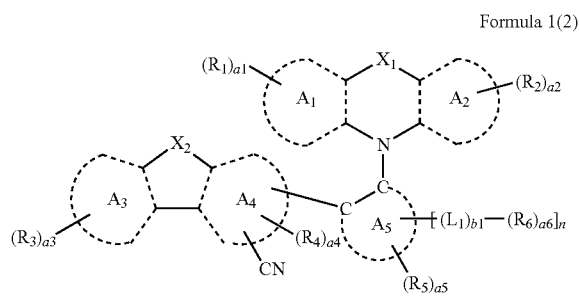
Formula 1(3)
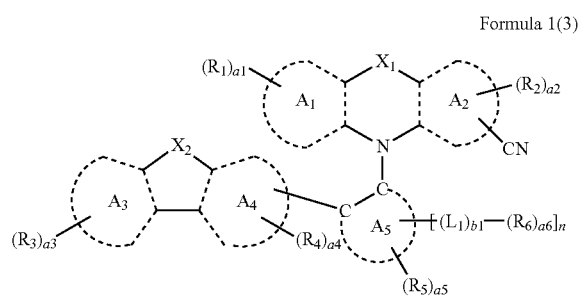
Formula 1(4)
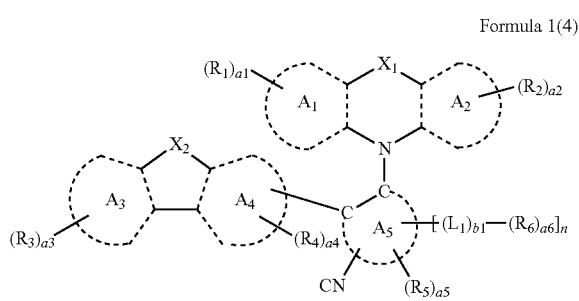
Formula 1(5)
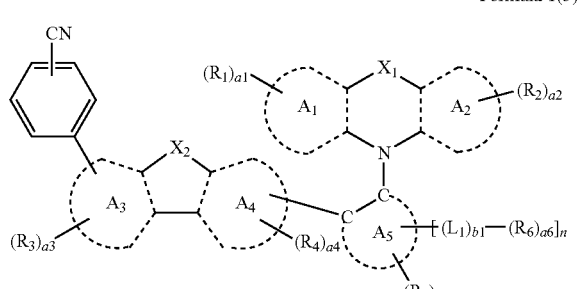
-continued
Formula 1(6)
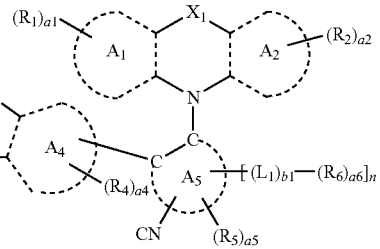
Formula 1(7)
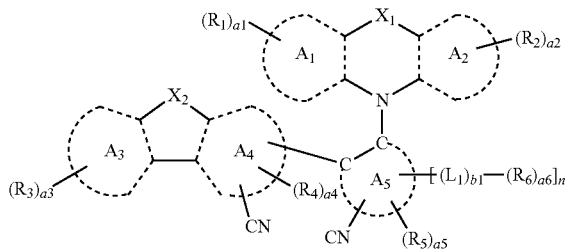
Formula 1(8)
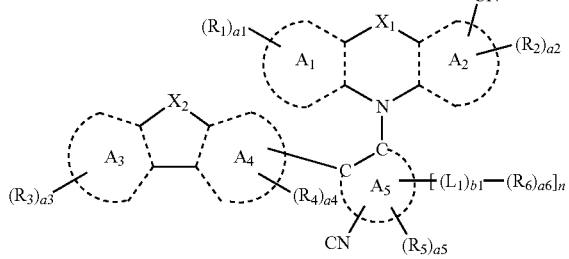
Formula 1(9)
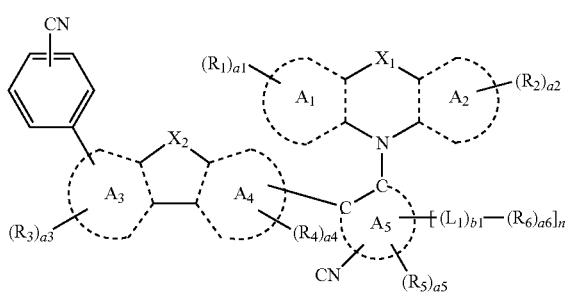
Formula 1(10)
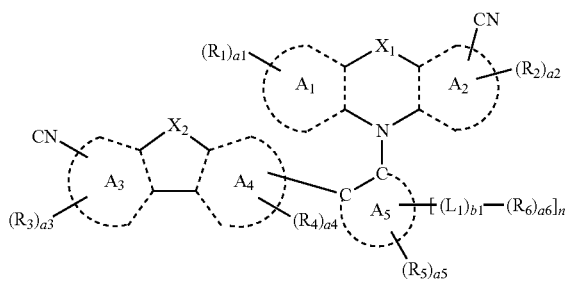

-continued

Formula 1(11)

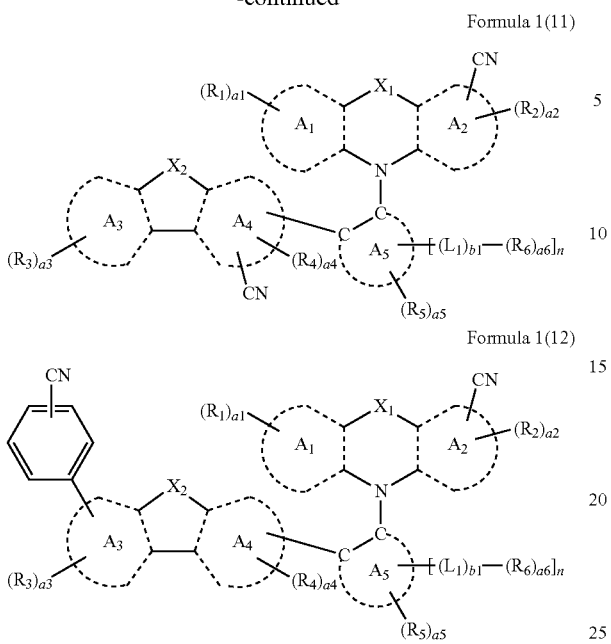

Formula 1(12)

wherein, in Formulae 1(1) to 1(12),
$X_1$, $X_2$, ring $A_1$ to ring $A_5$, $R_1$ to $R_6$, $L_1$, b1 and n are the same as in claim 1, and
a1 to a6 are each independently an integer of 0 to 3.

13. The condensed cyclic compound of claim 12, wherein
$X_1$ is a single bond,
ring $A_1$ and $A_2$ are each independently selected from a benzene, a dibenzofuran and a dibenzothiophene, and at least one of ring $A_1$ and $A_2$ is a benzene,
ring $A_3$ and $A_4$ are each independently selected from a benzene, a fluorene, a carbazole, a dibenzofuran and a dibenzothiophene, and at least one of ring $A_3$ and $A_4$ is a benzene,
ring $A_5$ is a benzene,
$R_1$ to $R_6$ are each independently selected from
a hydrogen, a deuterium, a $C_1$-$C_{10}$ alkyl group and a $C_1$-$C_{10}$ alkoxy group;
a $C_1$-$C_{10}$ alkyl group and a $C_1$-$C_{10}$ alkoxy group, each substituted with at least one deuterium;
a phenyl group, a pyridinyl group, a pyrimidinyl group and a triazinyl group;
a phenyl group, a pyridinyl group, a pyrimidinyl group and a triazinyl group, each substituted with at least one selected from a deuterium, a $C_1$-$C_{10}$ alkyl group, a $C_1$-$C_{10}$ alkoxy group, a phenyl group, a pyridinyl group, a pyrimidinyl group, a triazinyl group and —Si($Q_{31}$)($Q_{32}$)($Q_{33}$); and
—Si($Q_1$)($Q_2$)($Q_3$),
$L_1$ is selected from
a phenylene group, a pyridinylene group, a pyrimidinylene group and a triazinylene group; and
a phenylene group, a pyridinylene group, a pyrimidinylene group and a triazinylene group, each substituted with at least one selected from a deuterium, a $C_1$-$C_{10}$ alkyl group, a $C_1$-$C_{10}$ alkoxy group, a phenyl group, a pyridinyl group, a pyrimidinyl group, a triazinyl group and —Si($Q_8$)($Q_9$)($Q_{10}$),
b1 is 1 or 2,
n is 0 or 1, and $Q_1$ to $Q_3$, $Q_{31}$ to $Q_{33}$, and $Q_8$ to $Q_{10}$ are each independently selected from a hydrogen, a $C_1$-$C_{10}$ alkyl group, a $C_1$-$C_{10}$ alkoxy group, a phenyl group, a pyridinyl group, a pyrimidinyl group and a triazinyl group.

14. The condensed cyclic compound being one of Compounds 10 to 12, 47, 48, 50, 58 to 59, 61 to 64 and 75 to 482:

10

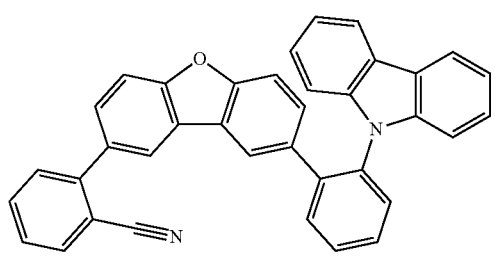

11

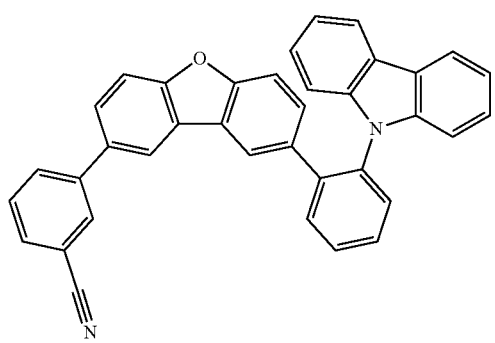

12

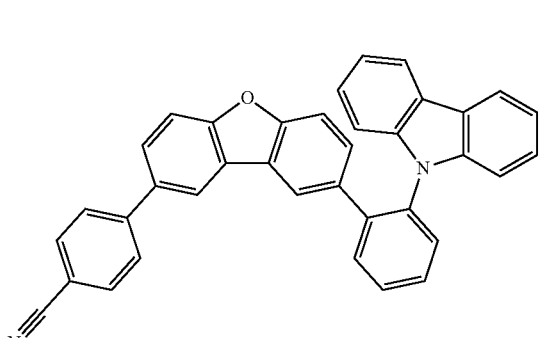

47

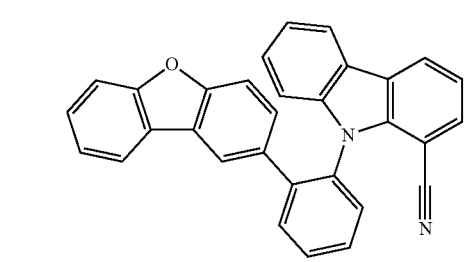

48
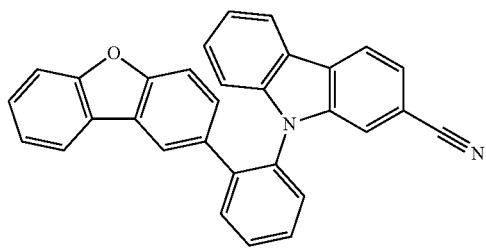
50
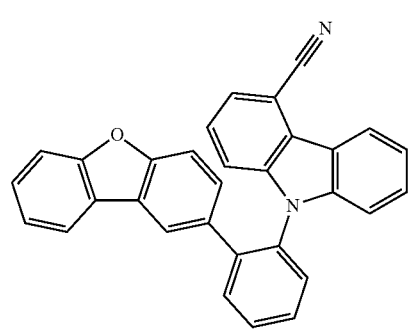
58
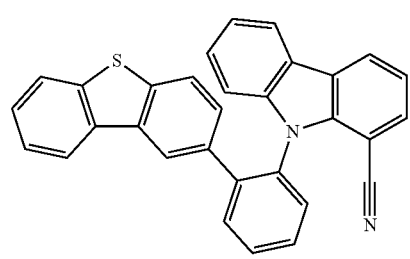
59
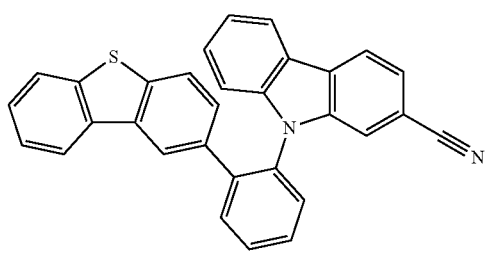
61
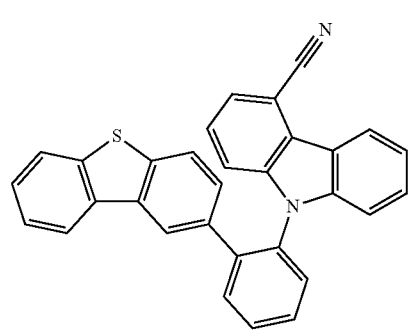
62
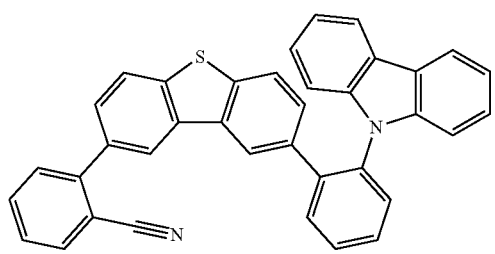
63
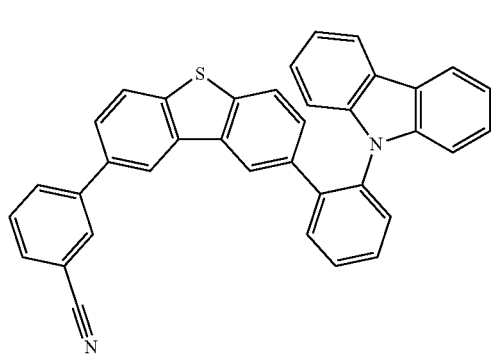
64
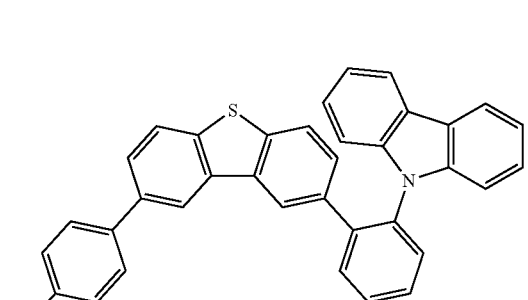
75
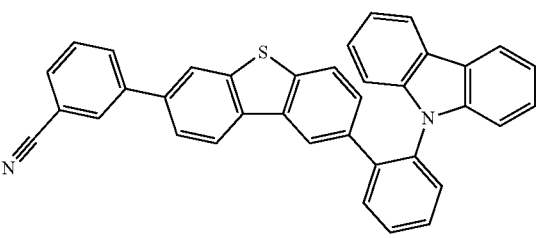
76
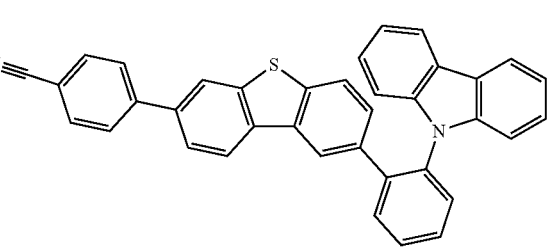

-continued
77
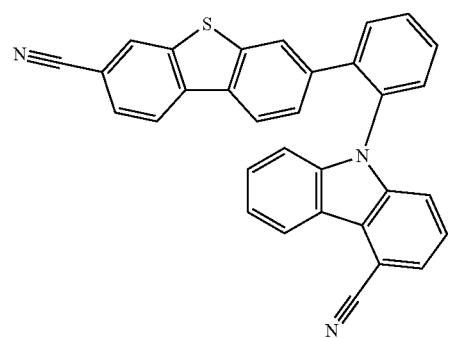
78
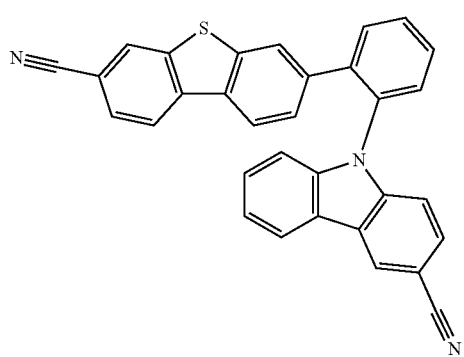
79
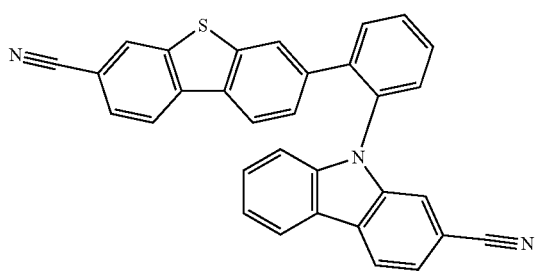
80
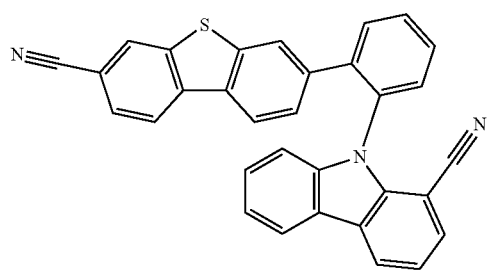
-continued
81
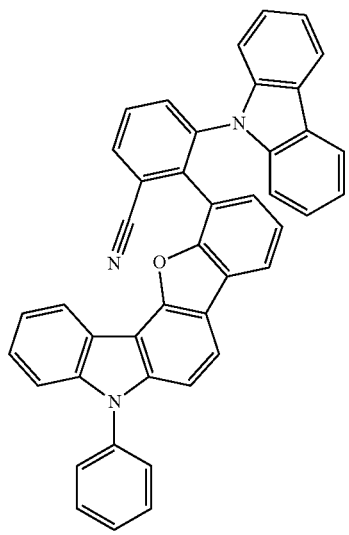
82
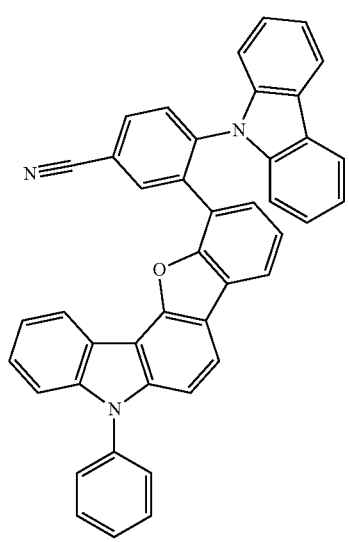
83
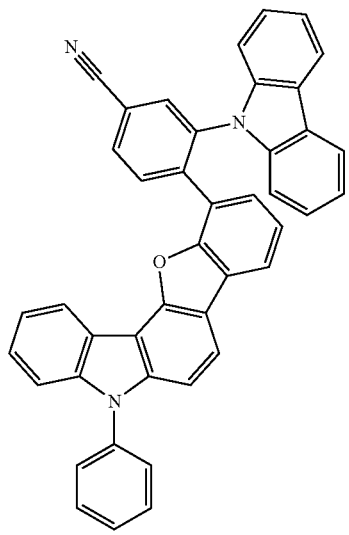

-continued
| | |
|---|---|
| 84 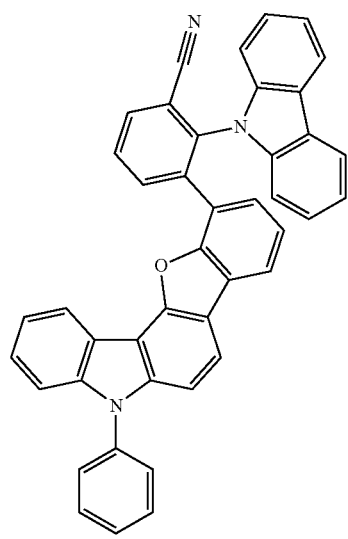 | 87 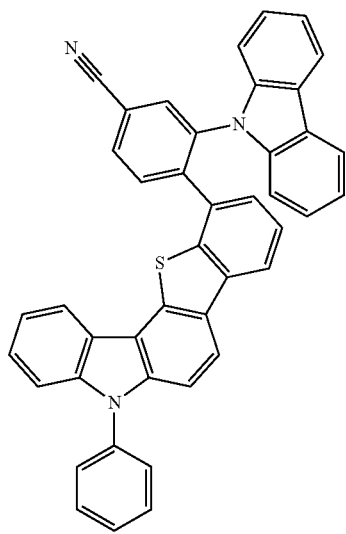 |
| 85 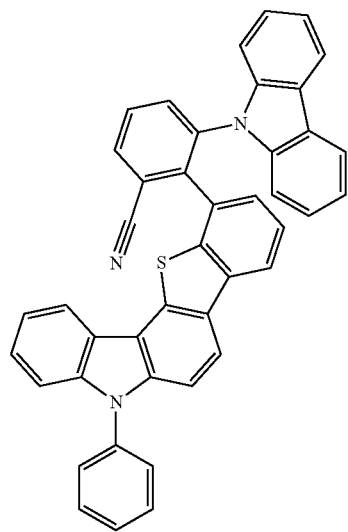 | 88 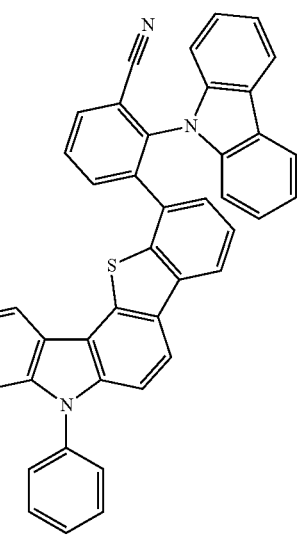 |
| 86 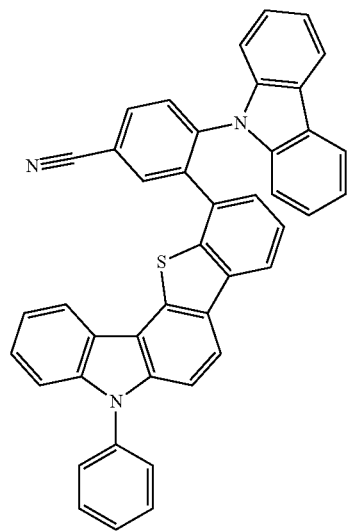 | 89 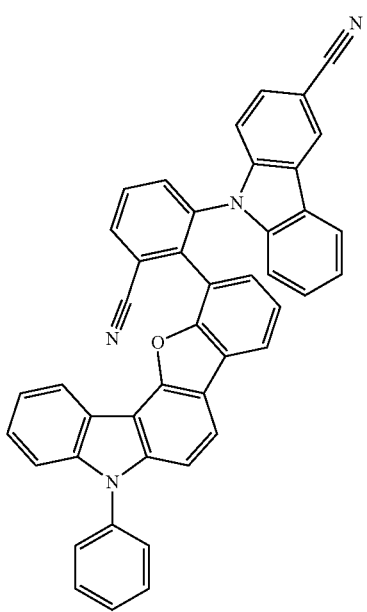 |

225
-continued
90
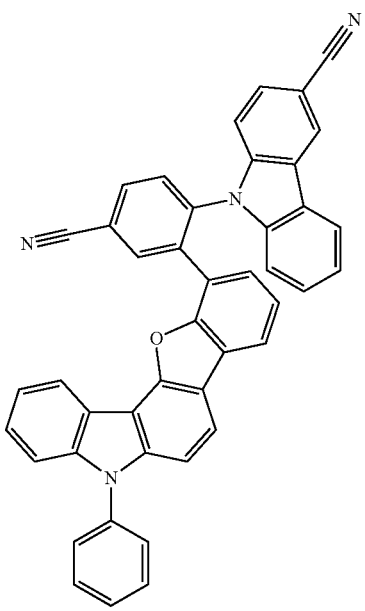
91
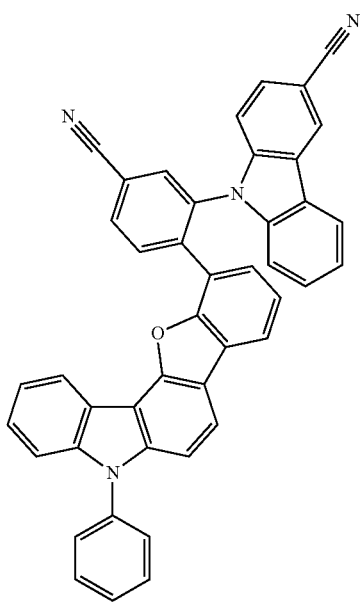
226
-continued
92
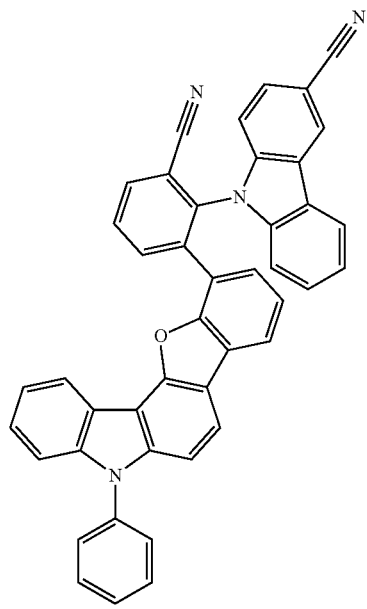
93
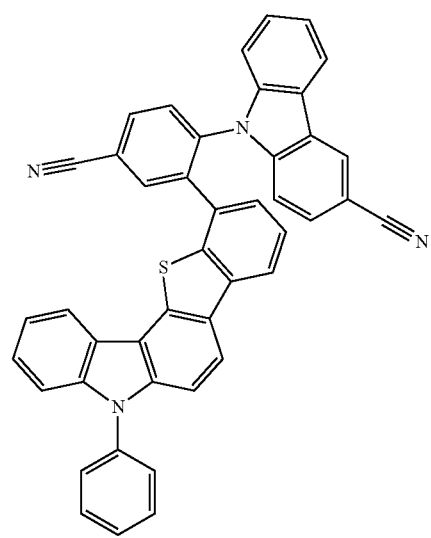
94

227
-continued
95
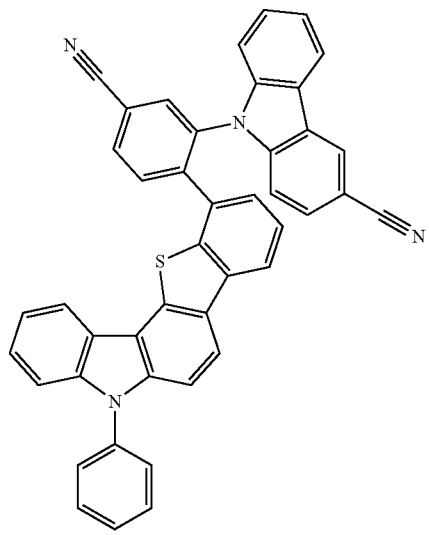
96
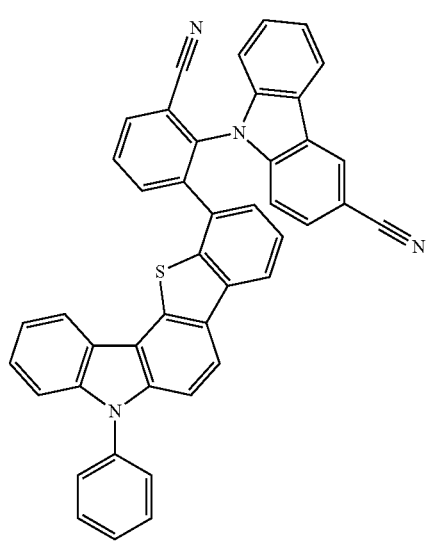
97
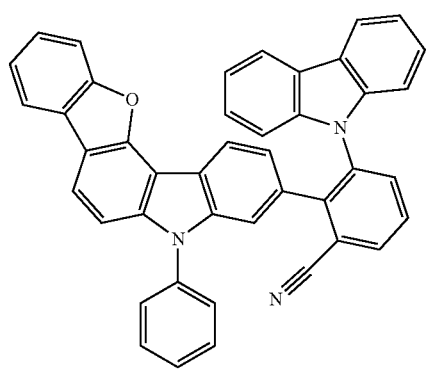
228
-continued
98
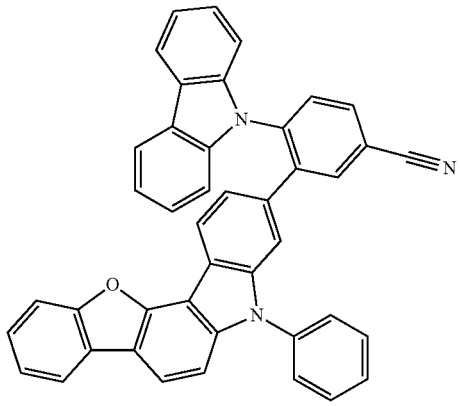
99
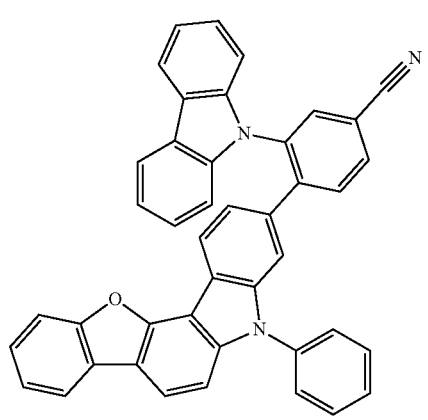
100
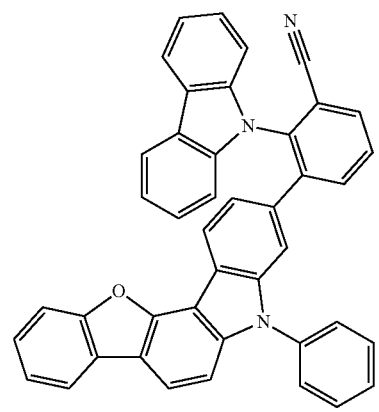
101
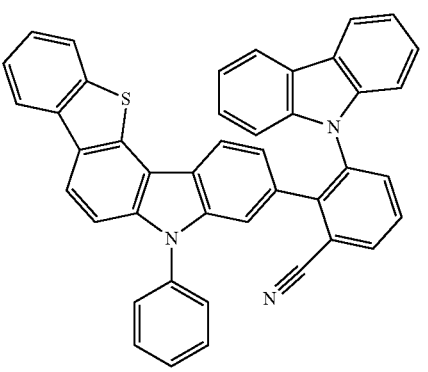

229
-continued
102
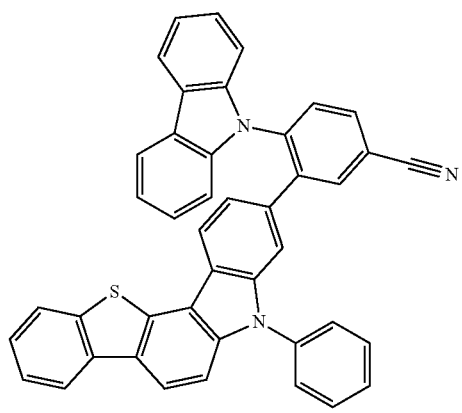
103
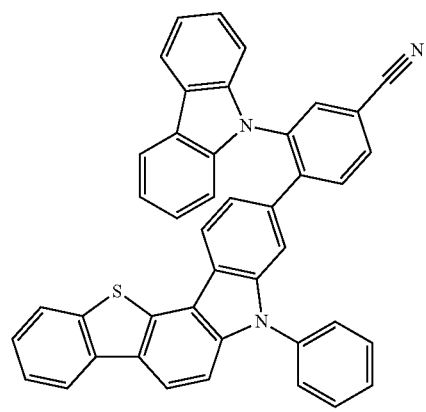
104
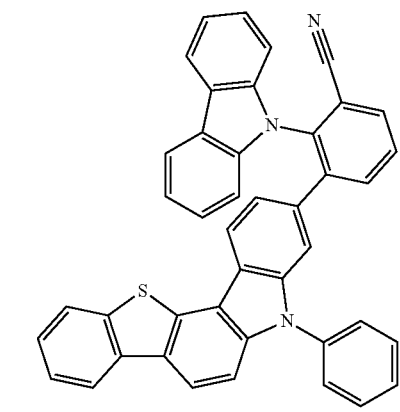
105
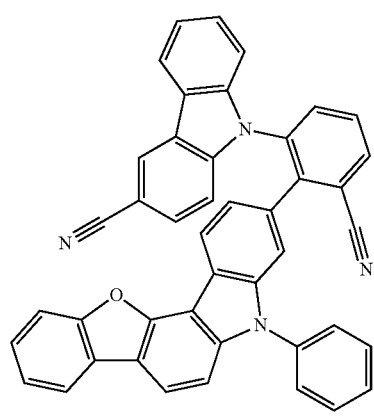
230
-continued
106
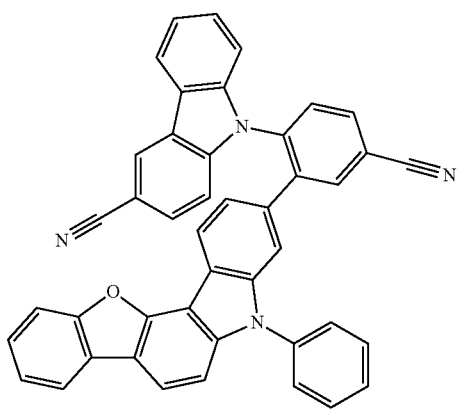
107
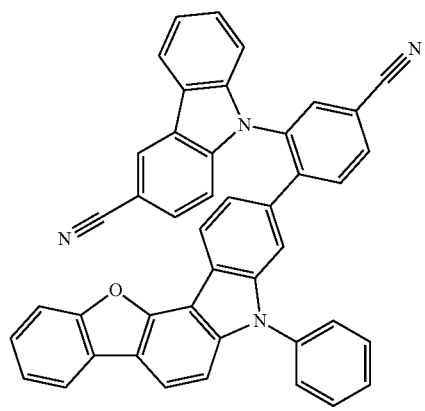
108
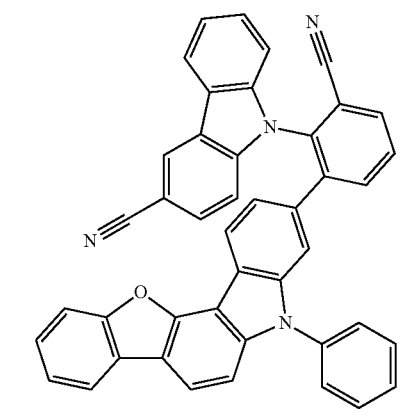
109
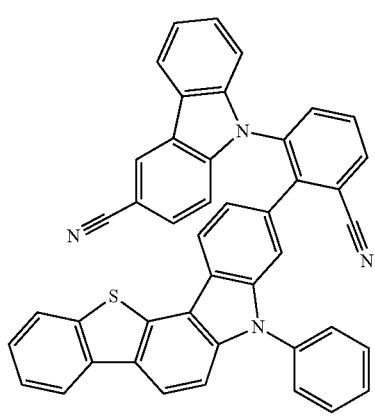

110
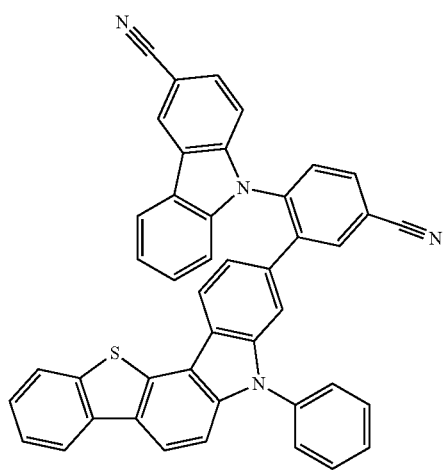
111
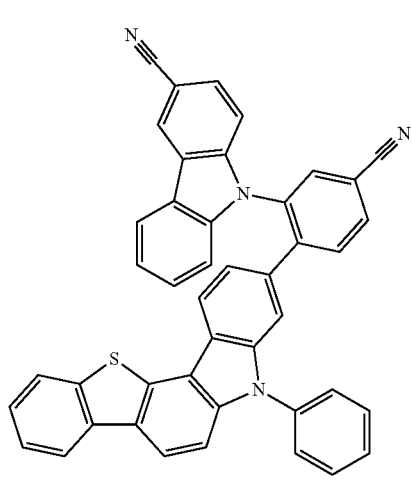
112
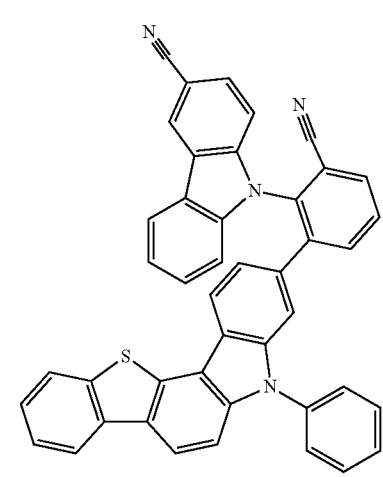
113
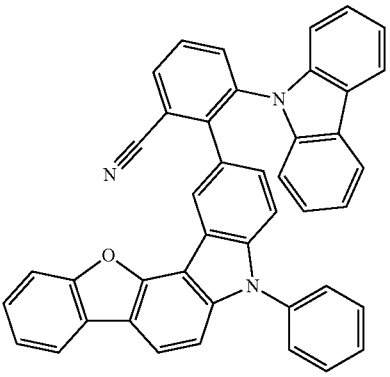
114
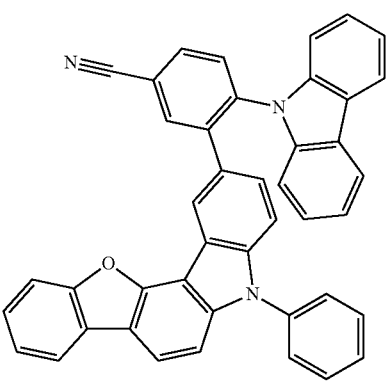
115
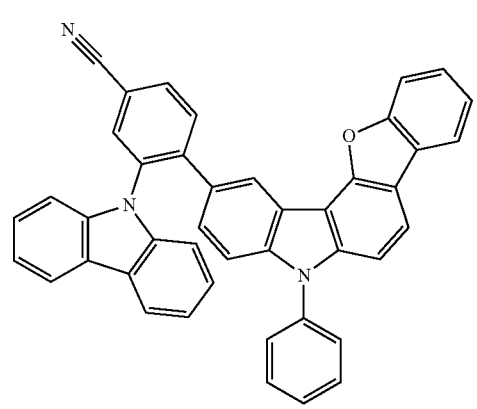
116
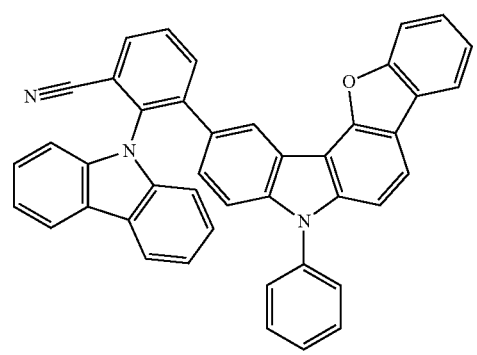

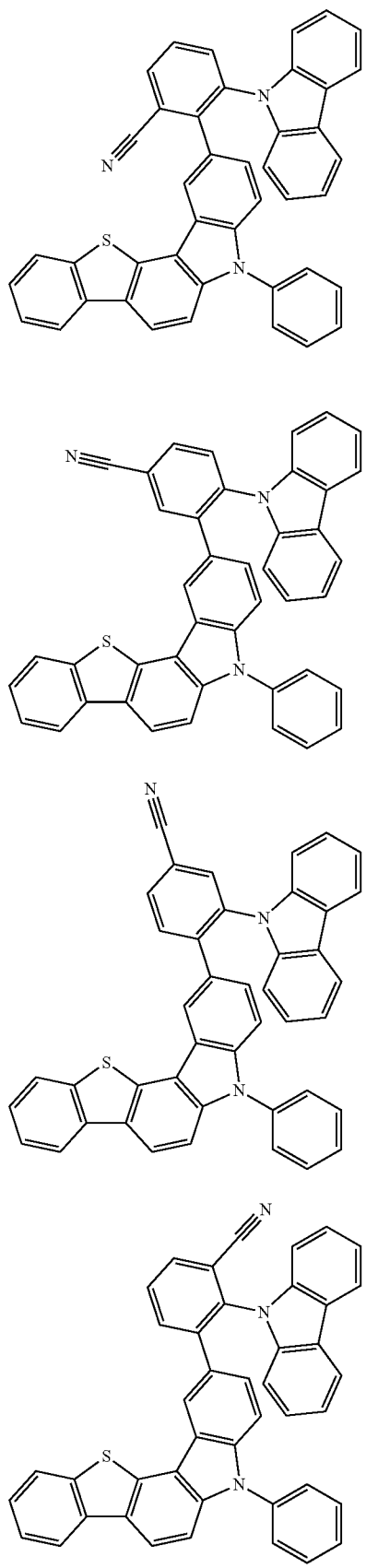

125
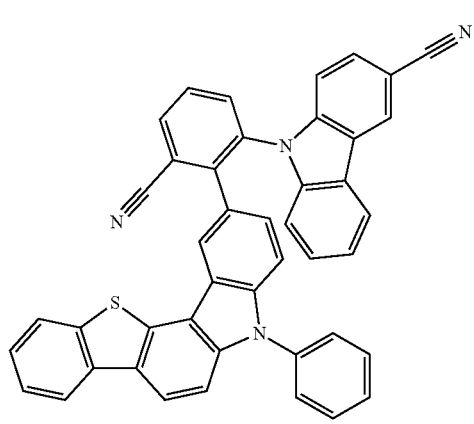
126
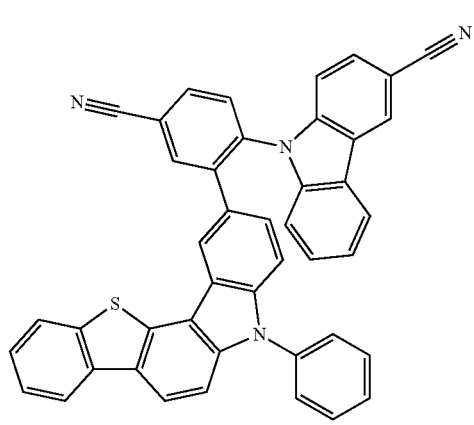
127
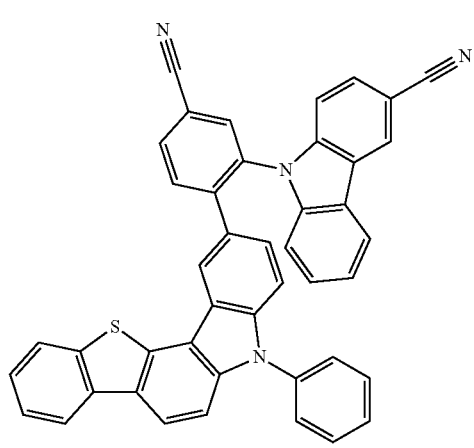
128
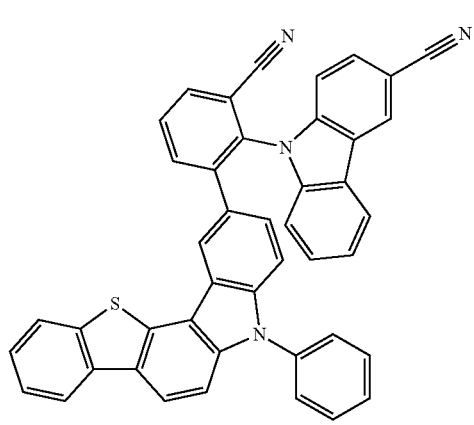
129
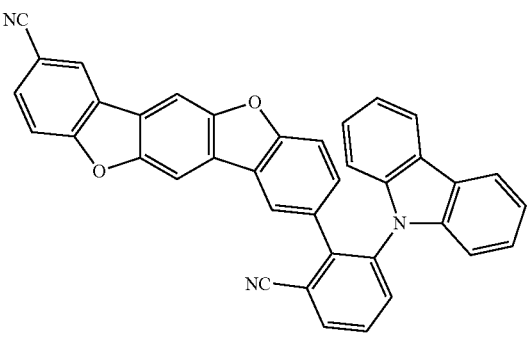
130
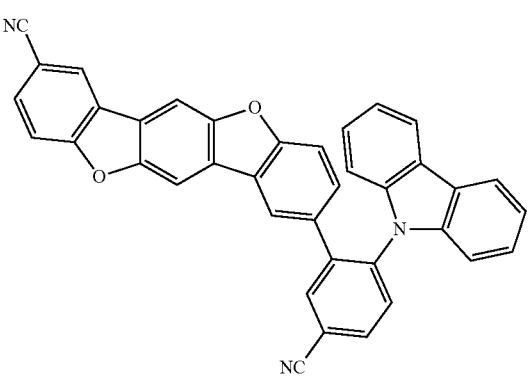
131
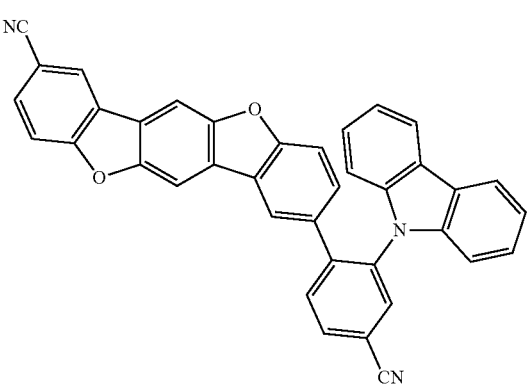
132
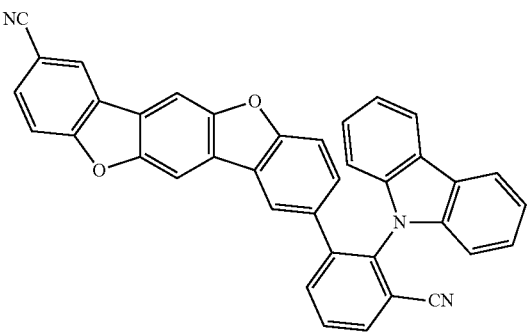

133
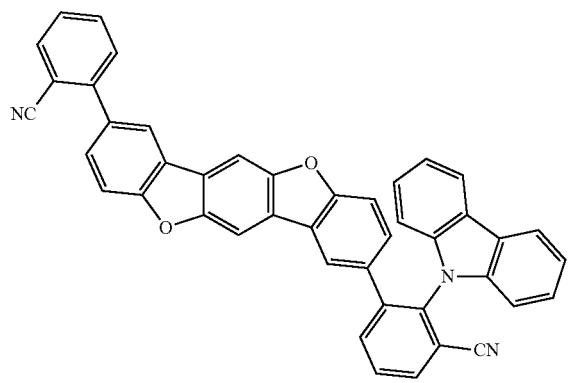
134
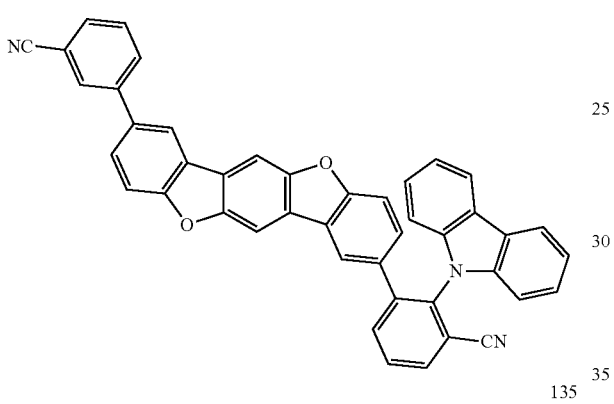
135
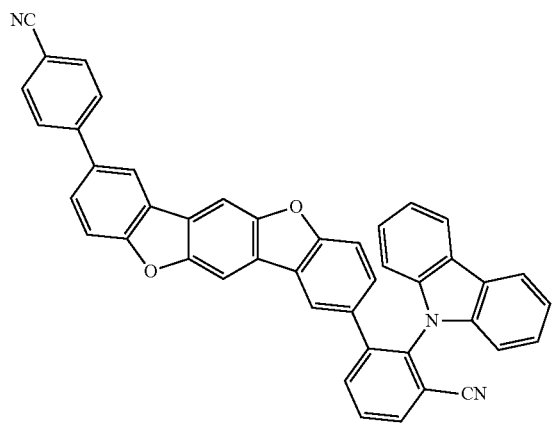
136
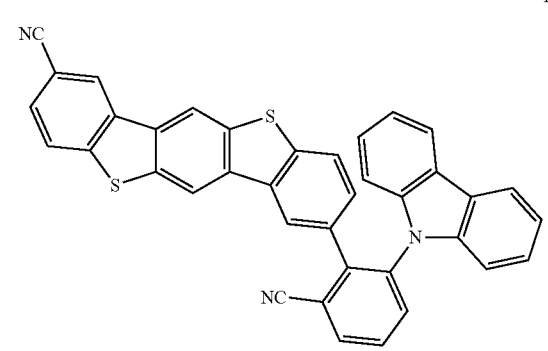
137
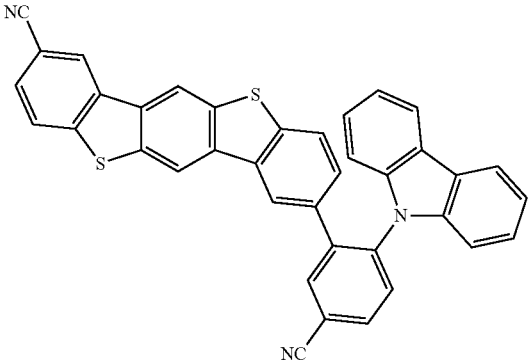
138
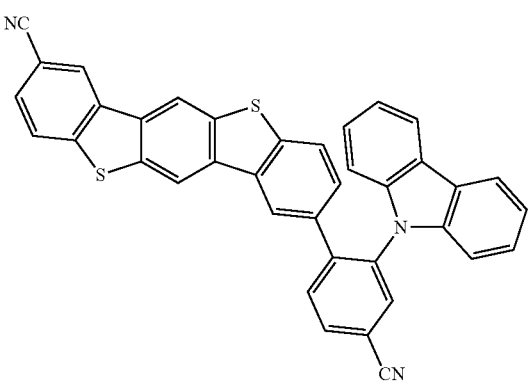
139
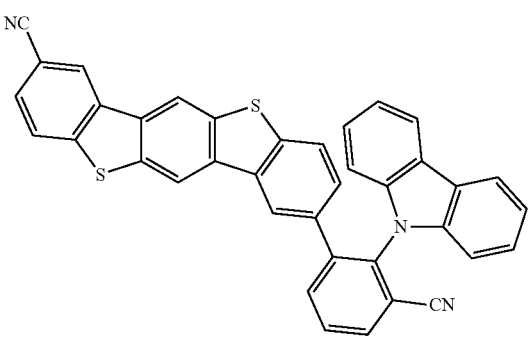
140
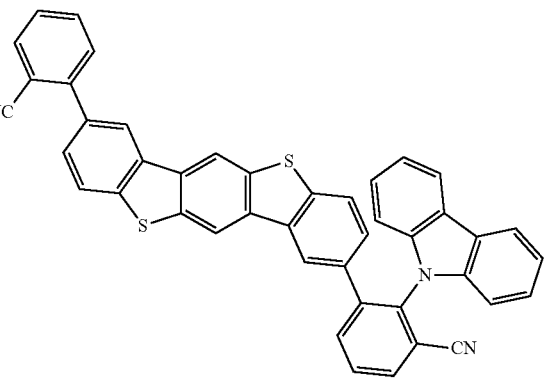

-continued
141
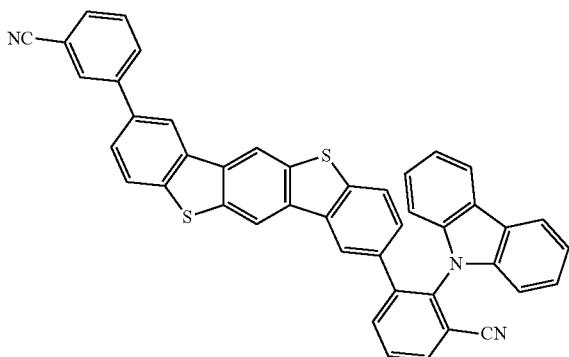
142
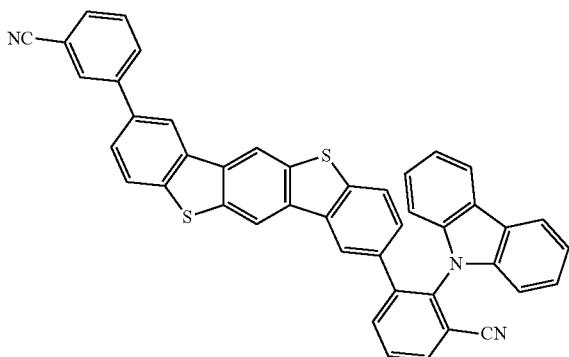
143
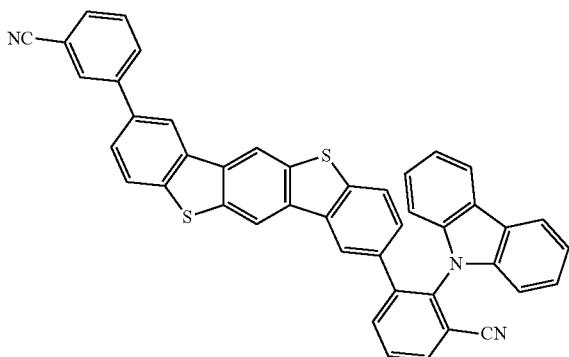
144
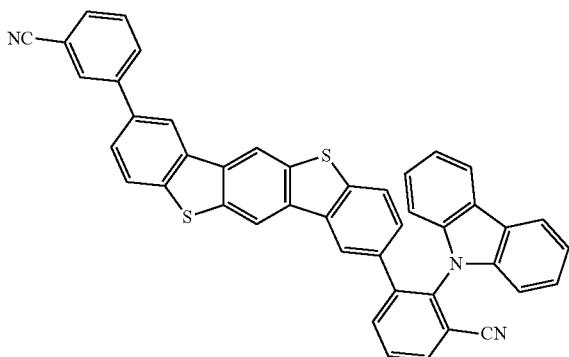
-continued
145
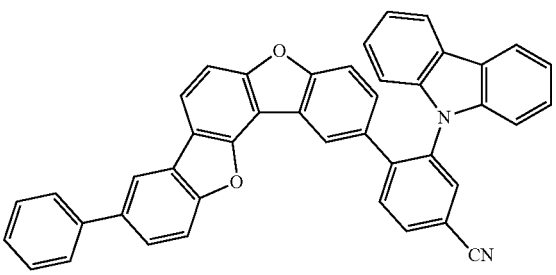
146
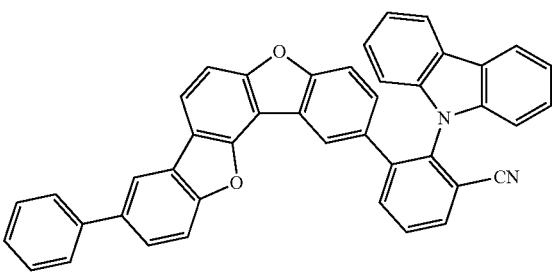
147
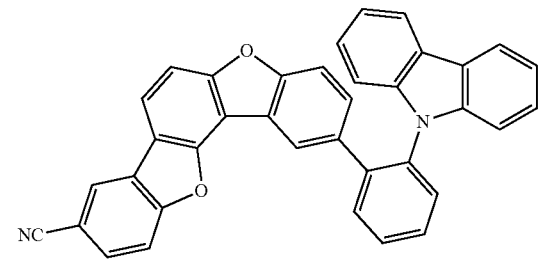
148
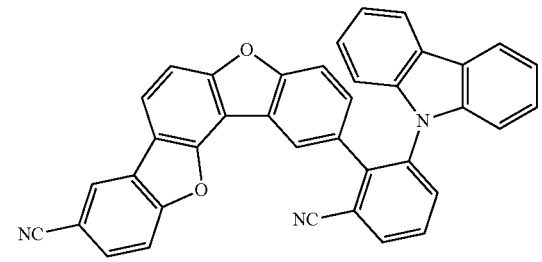
149
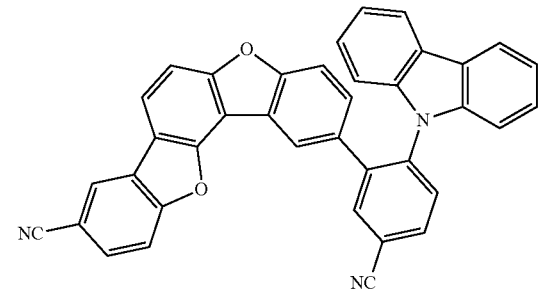

241
-continued
150
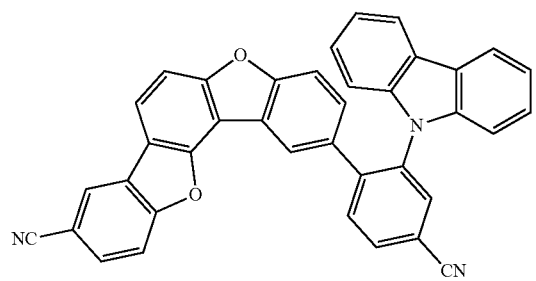
151
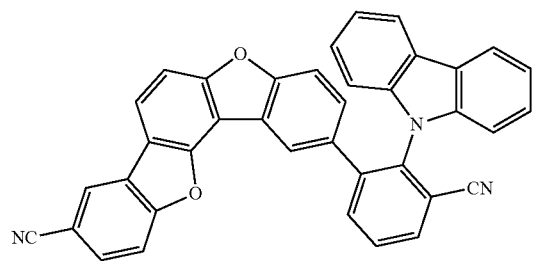
152
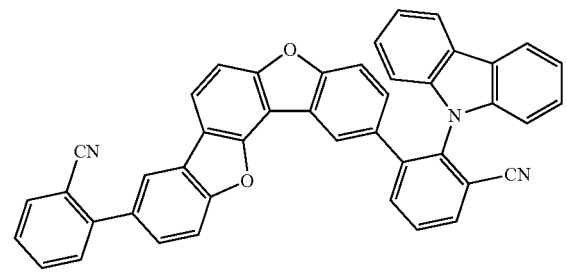
153
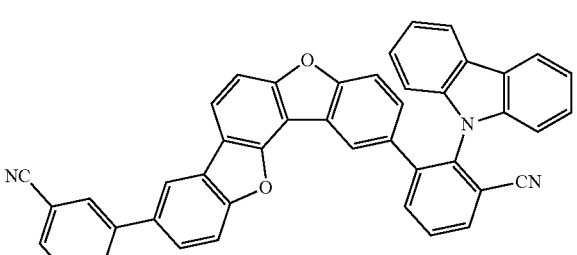
154
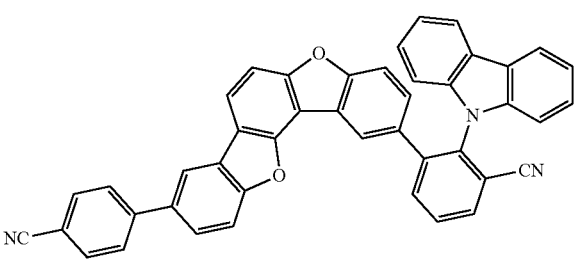
242
-continued
155
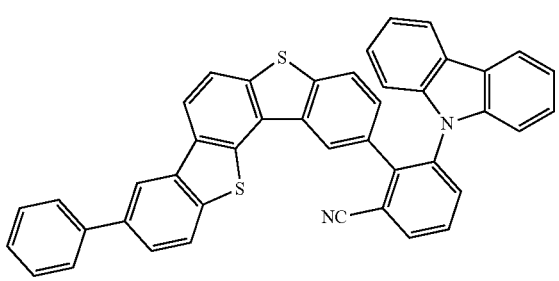
156
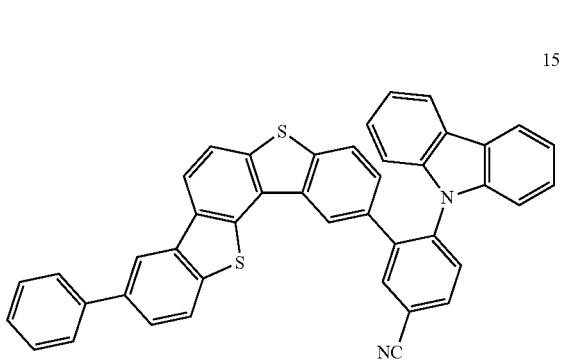
157
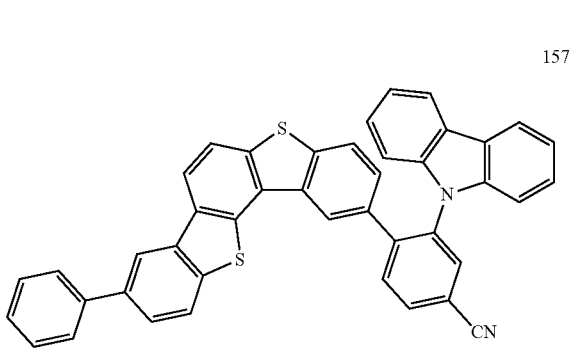
158
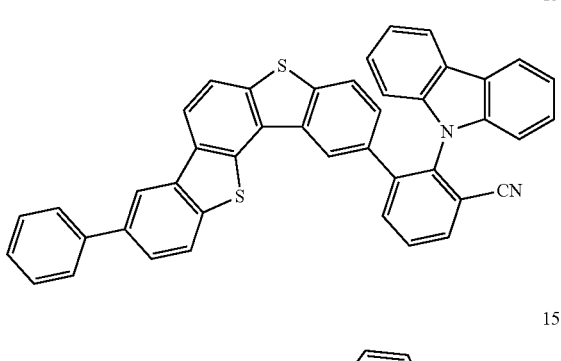
159
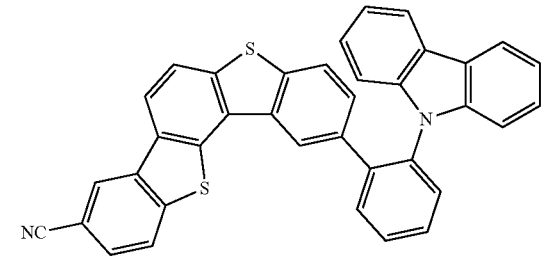

160
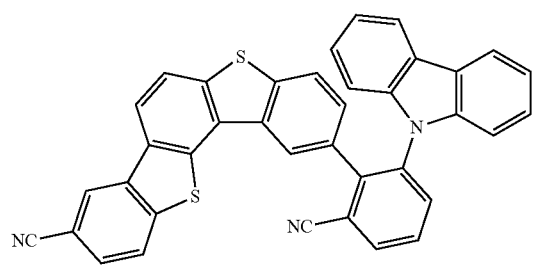
161
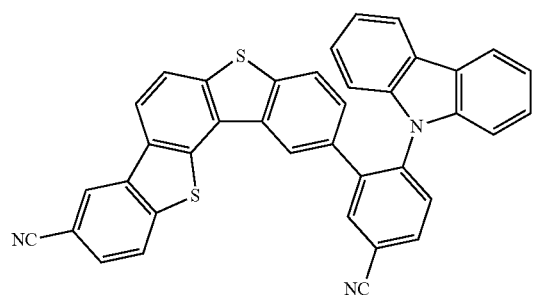
162
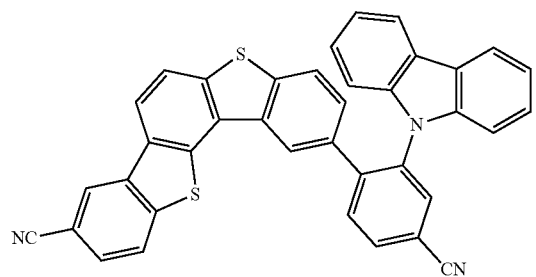
163
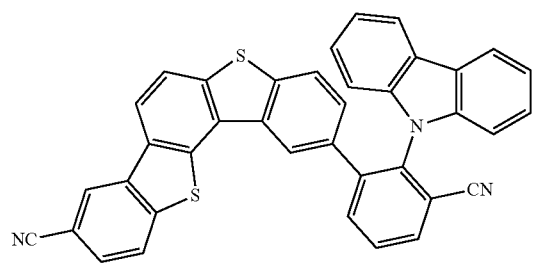
164
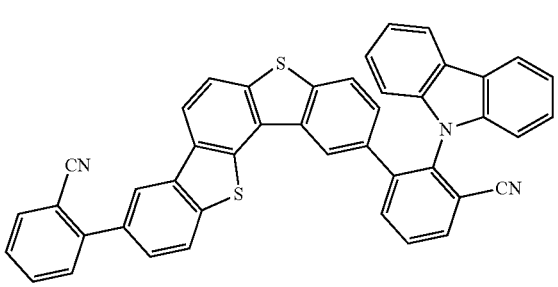
165
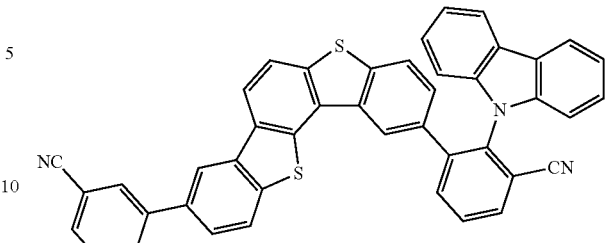
166
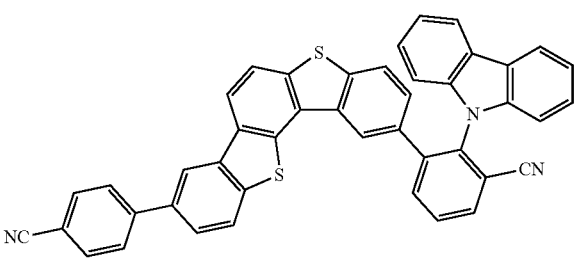
167
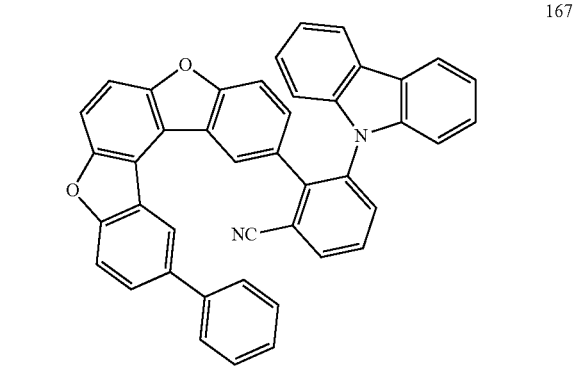
168
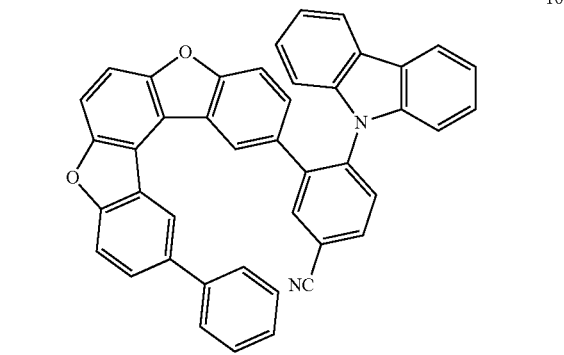
169
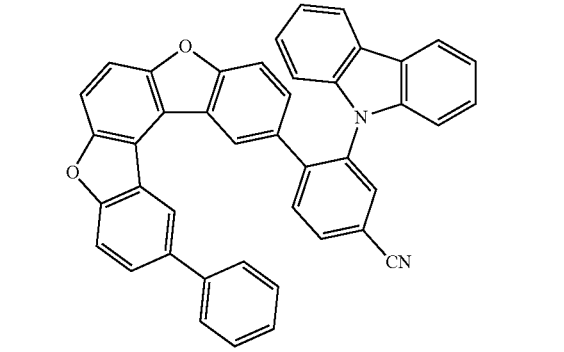

170
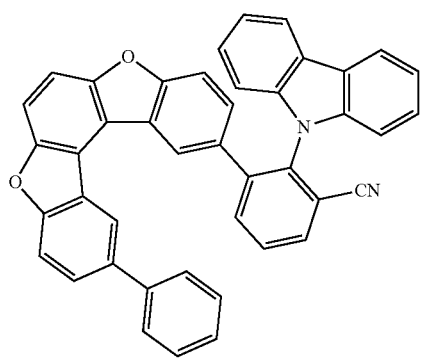
171
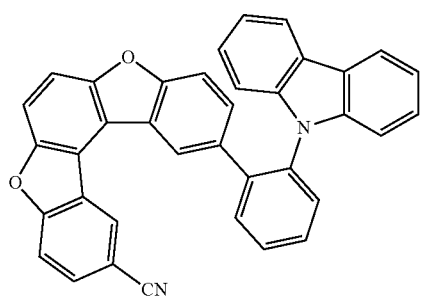
172
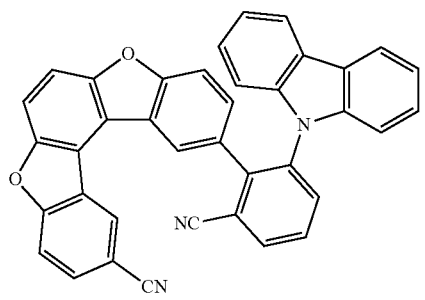
173
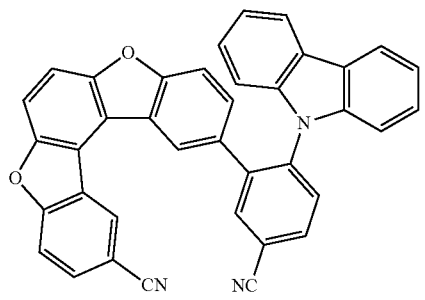
174
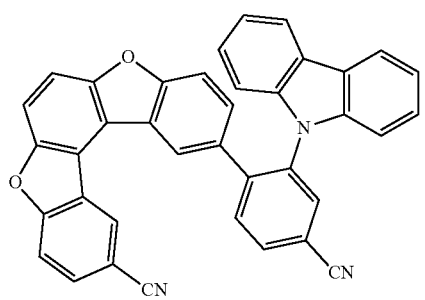
175
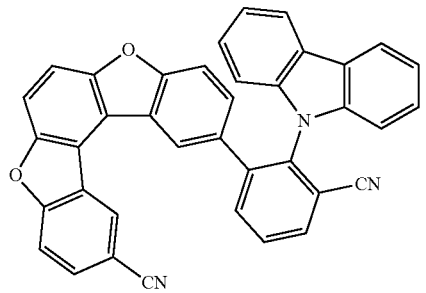
176
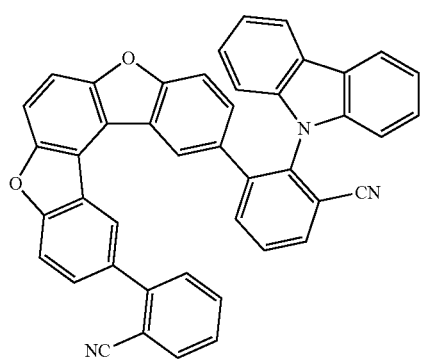
177
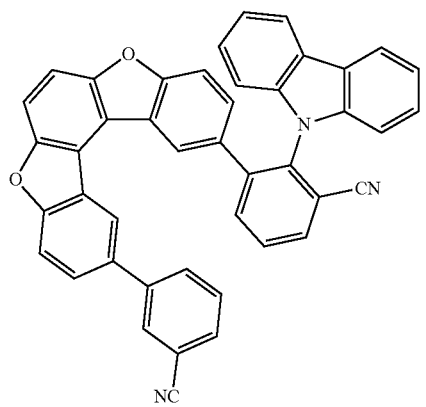
178
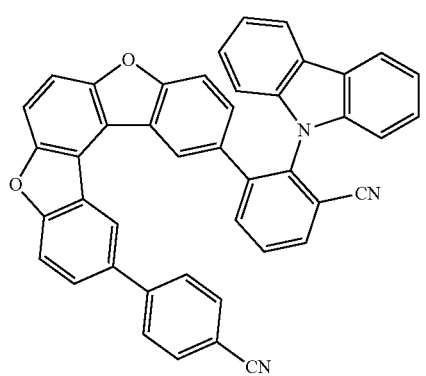

179
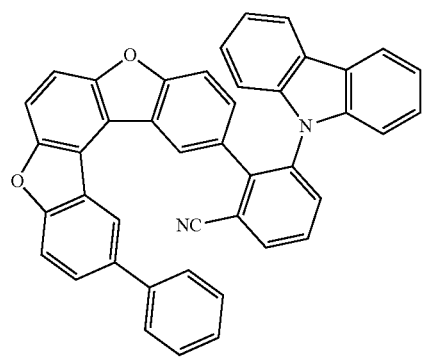
180
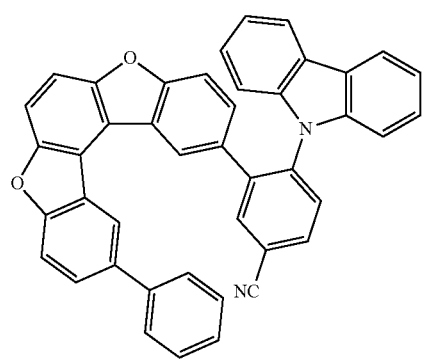
181
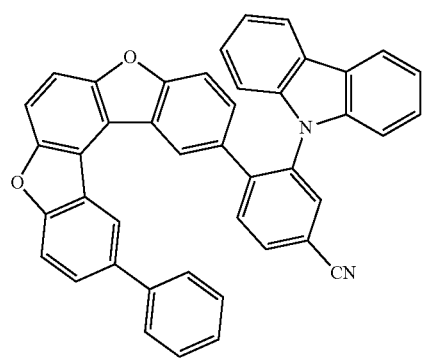
182
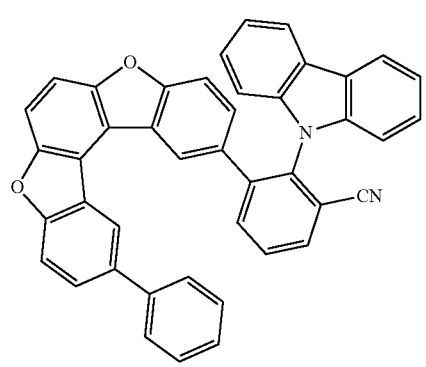
183
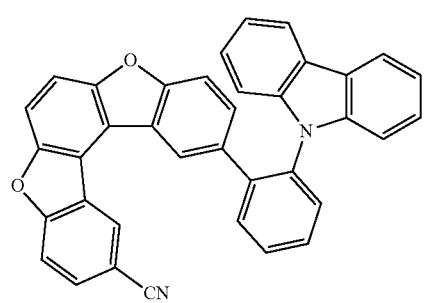
184
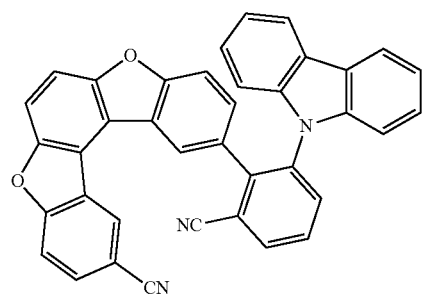
185
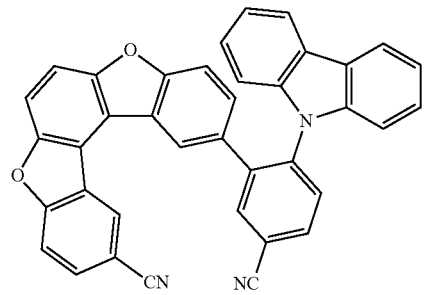
186
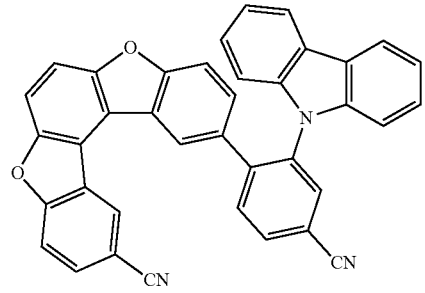
187
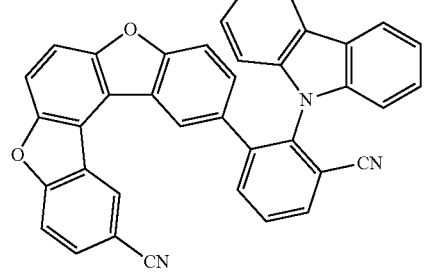

-continued
188
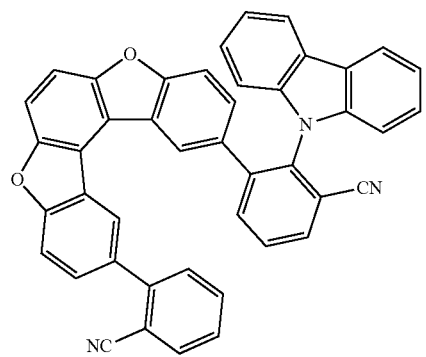
189
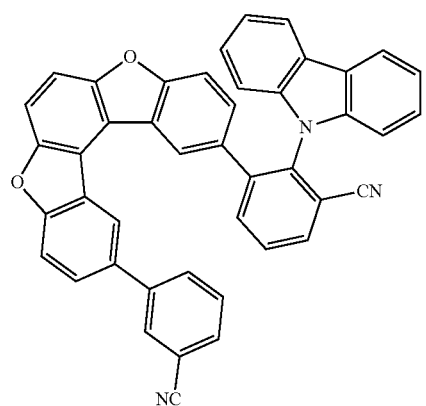
190
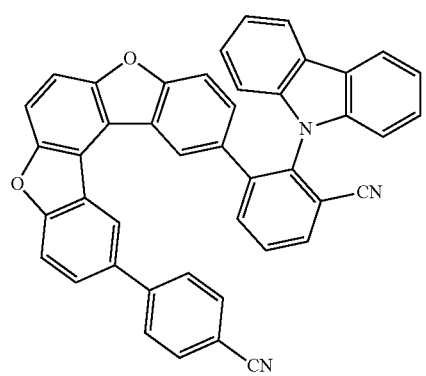
191
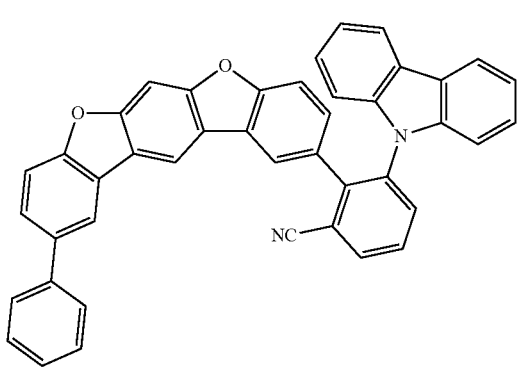
-continued
192
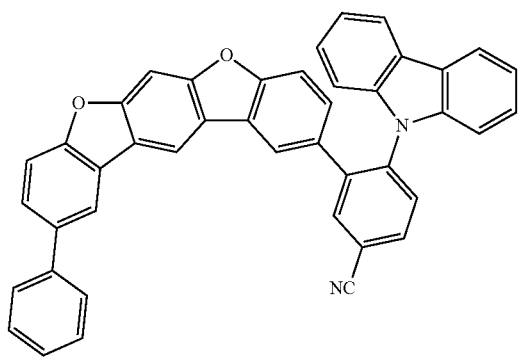
193
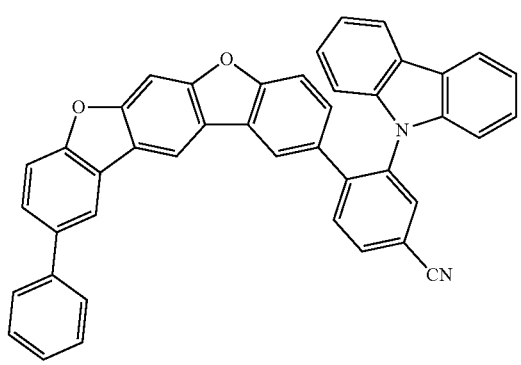
194
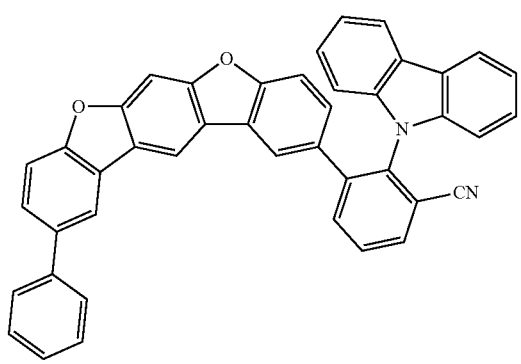
195
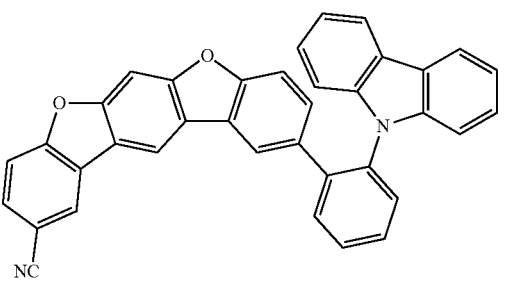

-continued
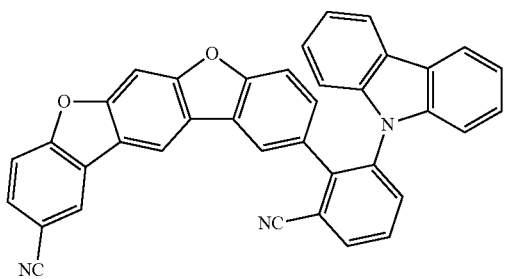
196
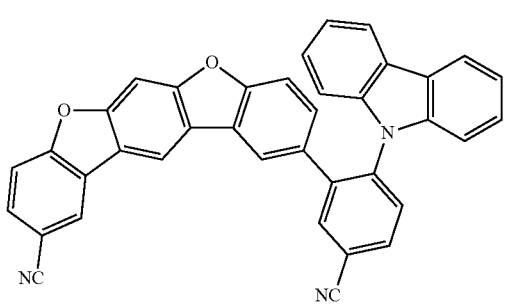
197
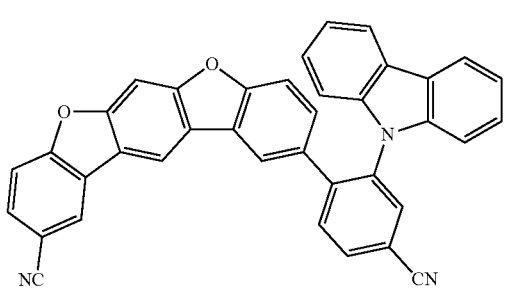
198
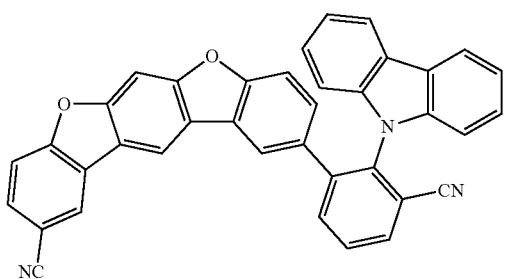
199
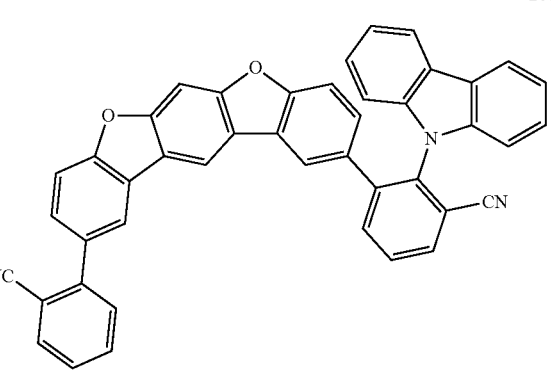
200
-continued
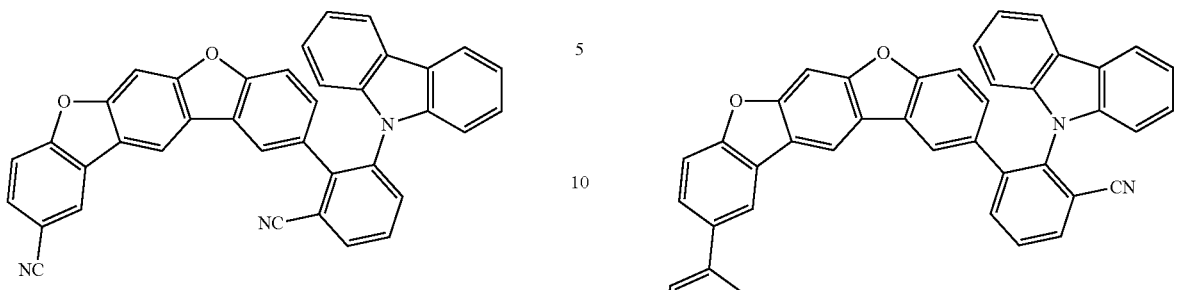
201
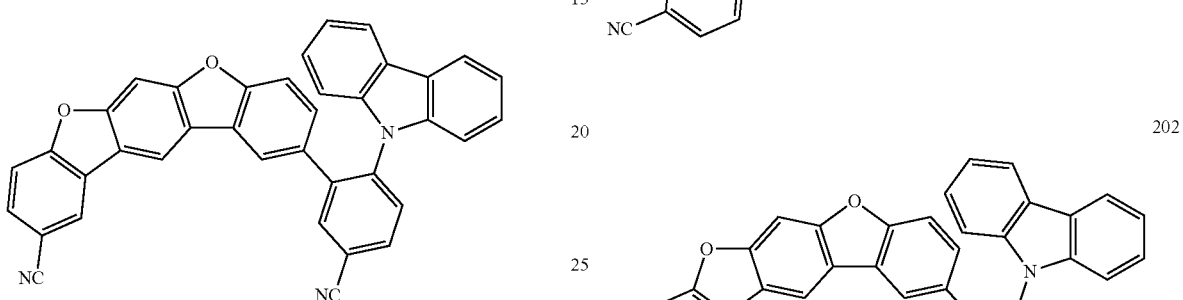
202
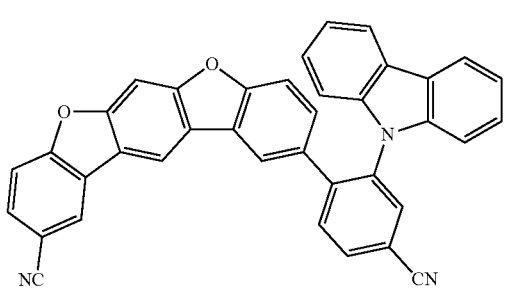
203
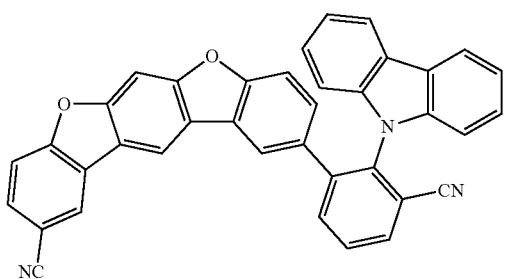
204
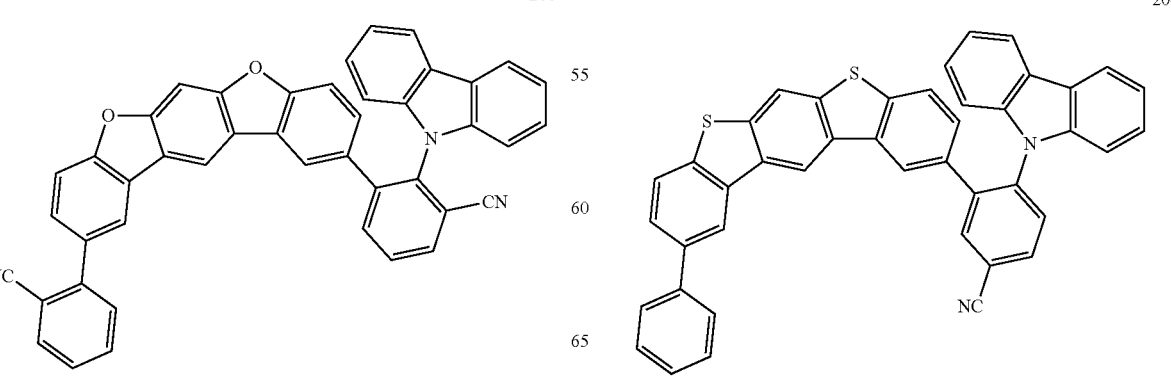

| 253 -continued | 254 -continued |
|---|---|
| 205 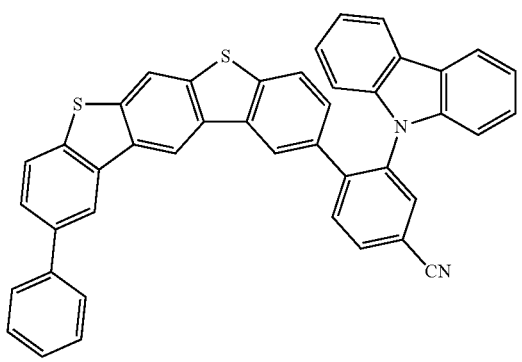 | 210 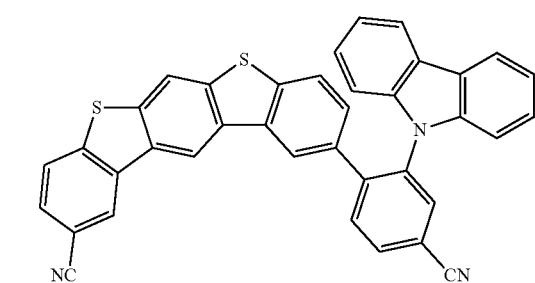 |
| 206 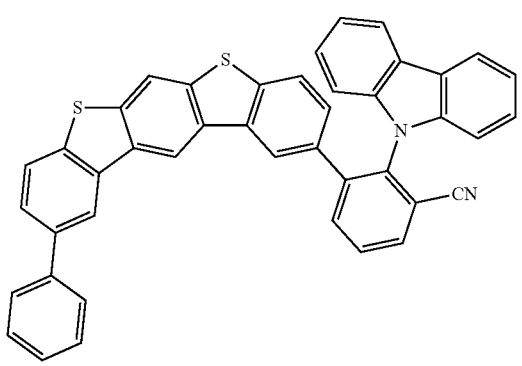 | 211 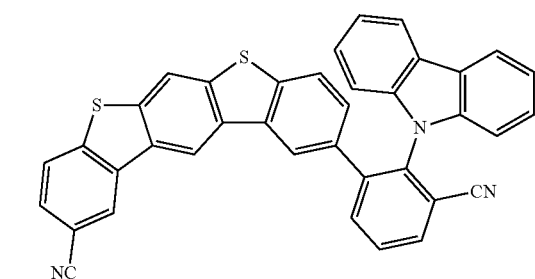 |
| 207 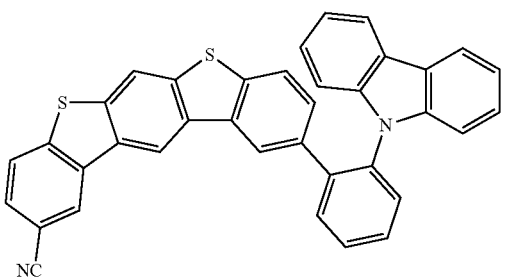 | 212 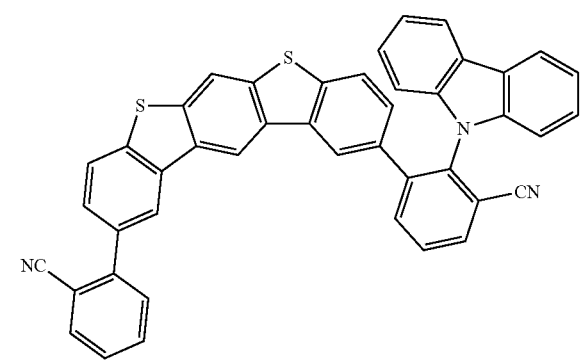 |
| 208 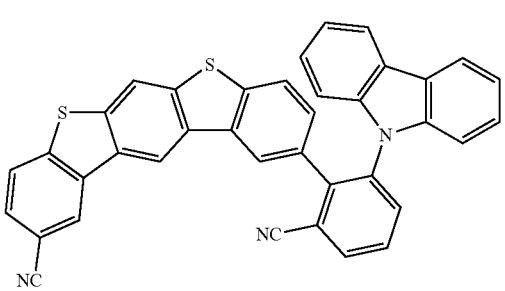 | 213 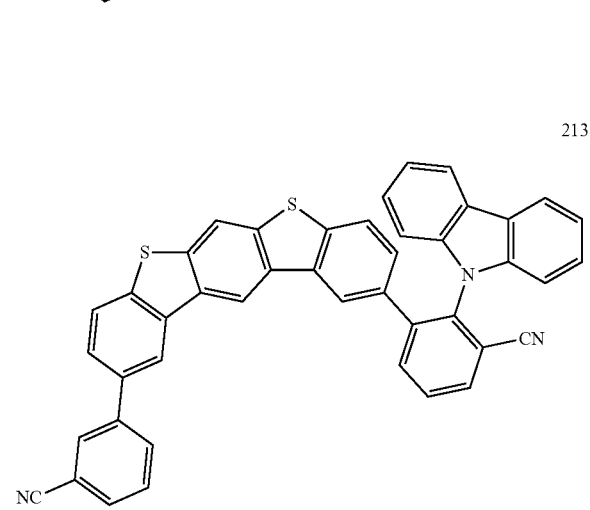 |
| 209 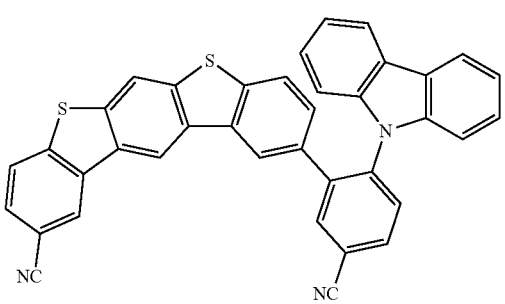 | |

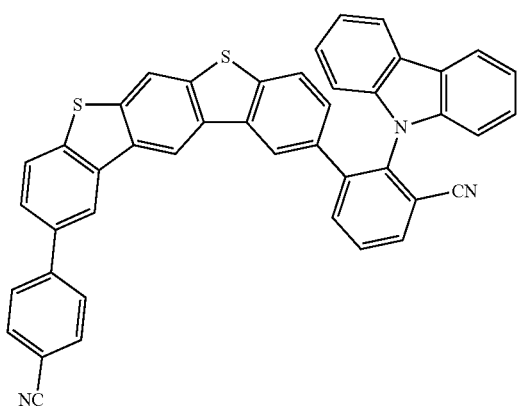
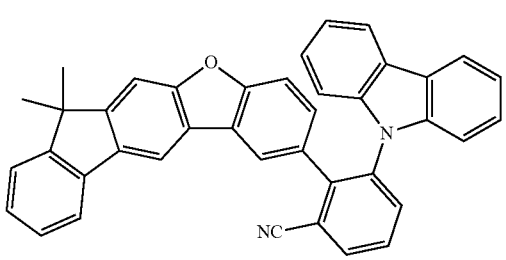
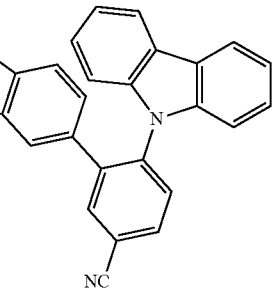
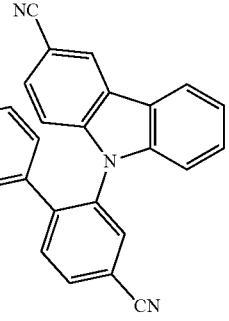
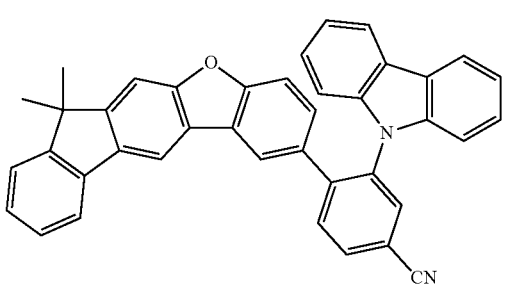
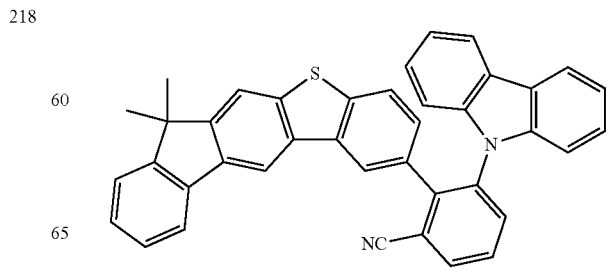

224
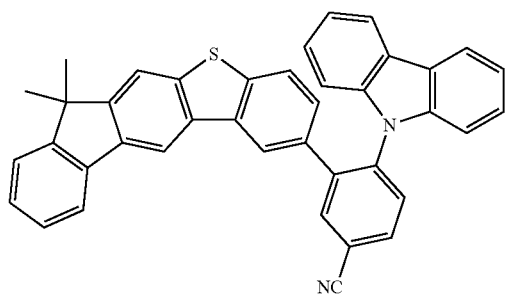
225
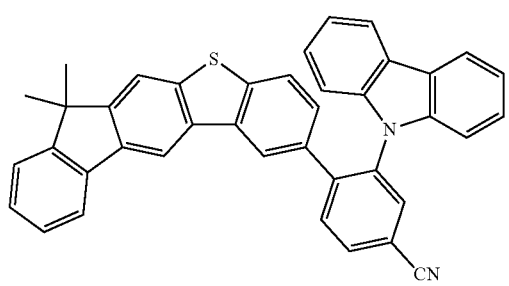
226
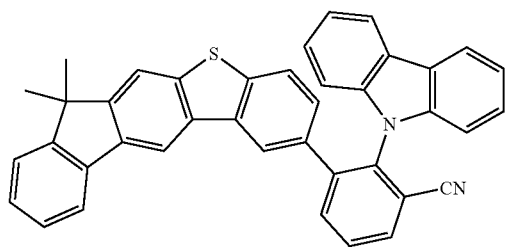
227
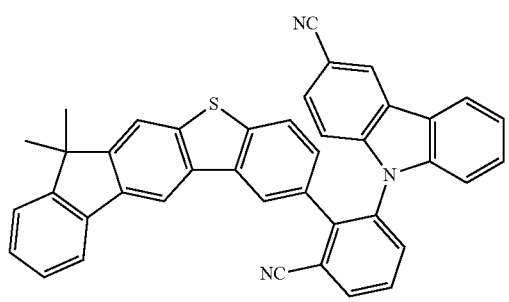
228
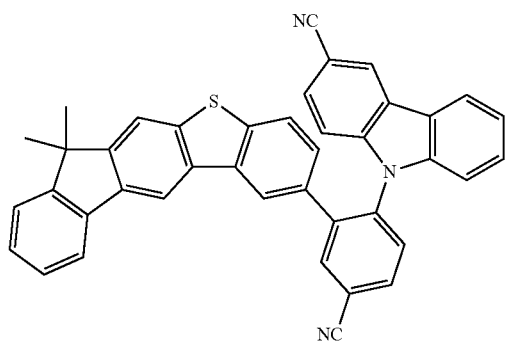
229
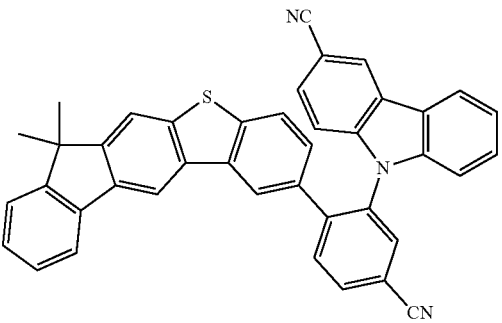
230
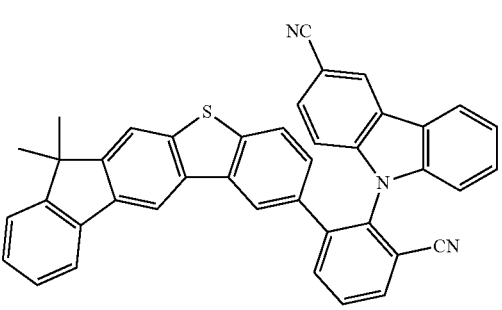
231
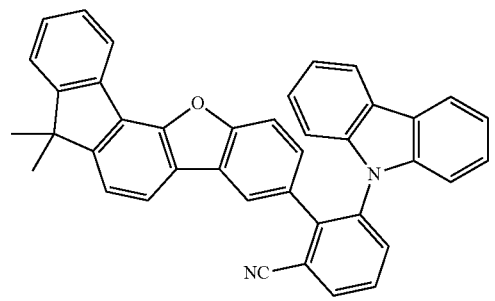
232
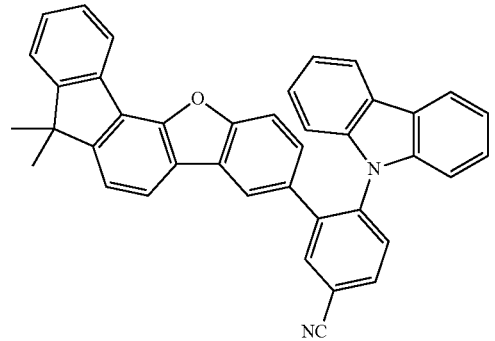
233
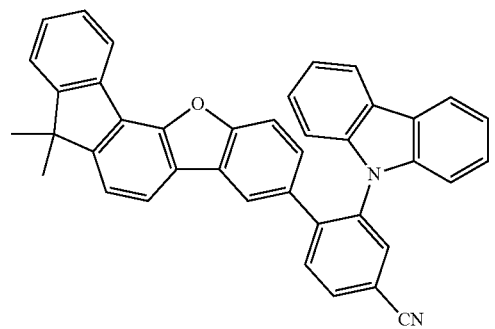

234
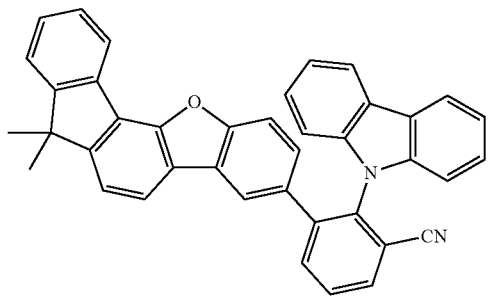
235
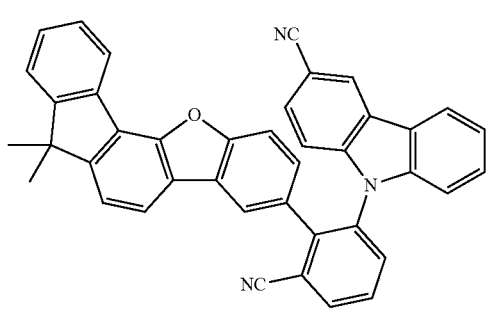
236
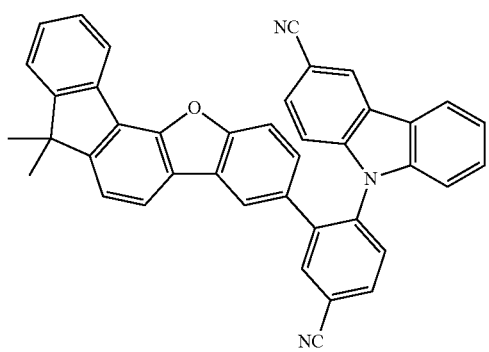
237
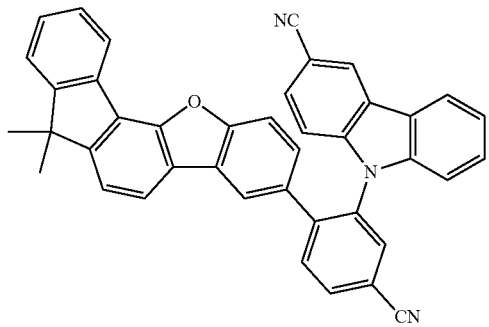
238
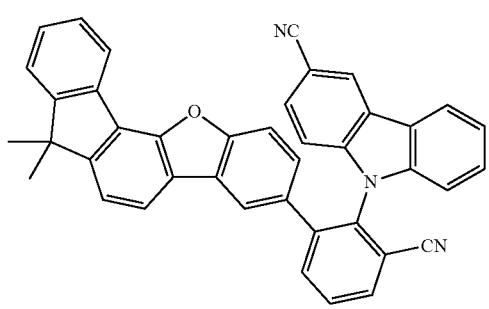
239
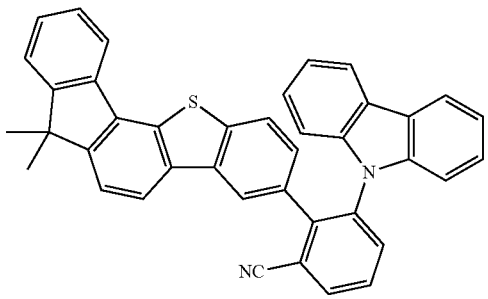
240
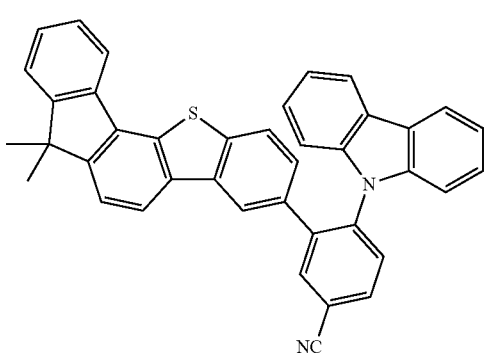
241
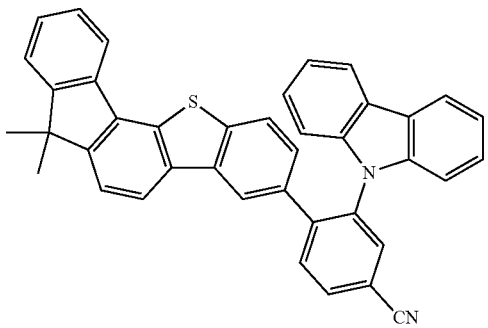
242
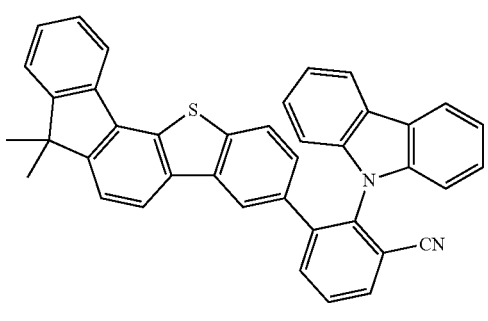
243
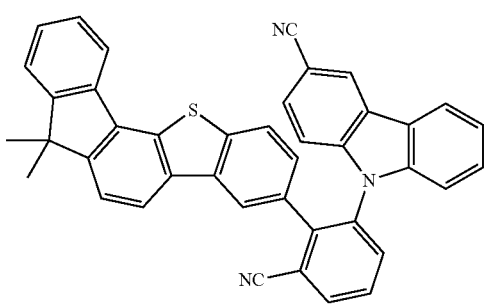

261
-continued
244
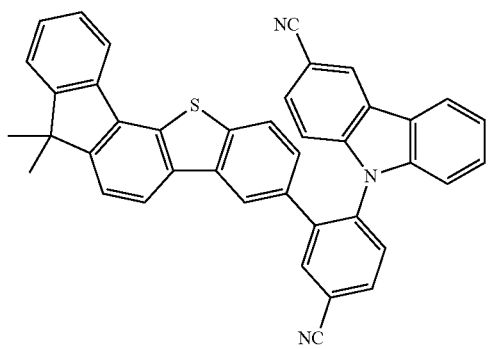
245
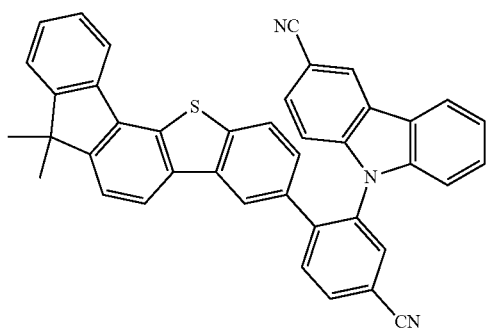
246
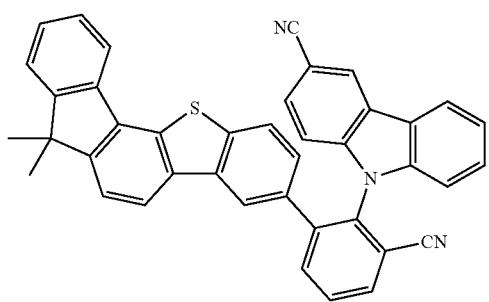
247
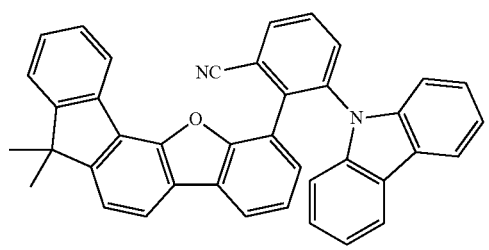
248
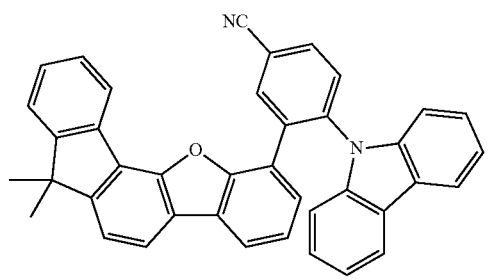
262
-continued
249
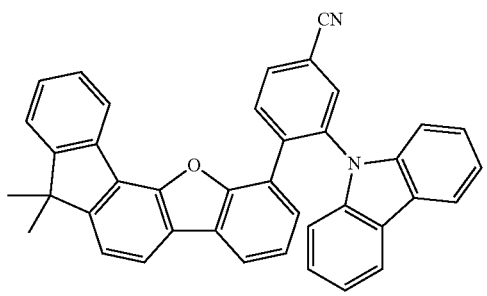
250
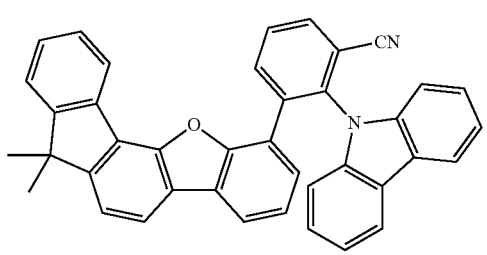
251
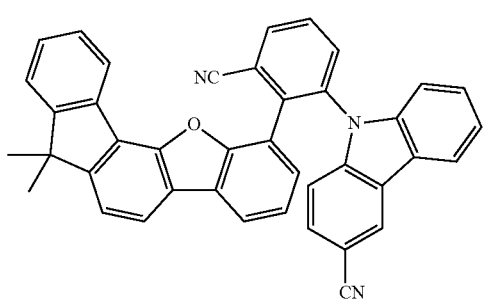
252
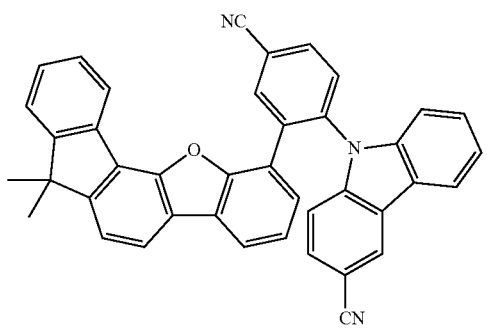
253
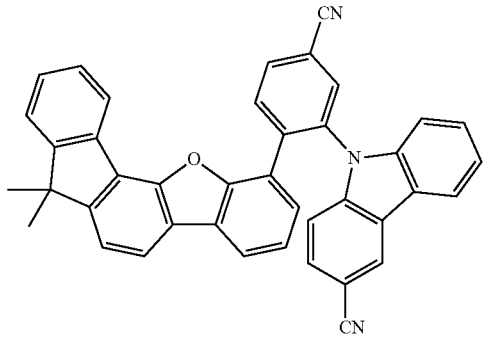

-continued
254
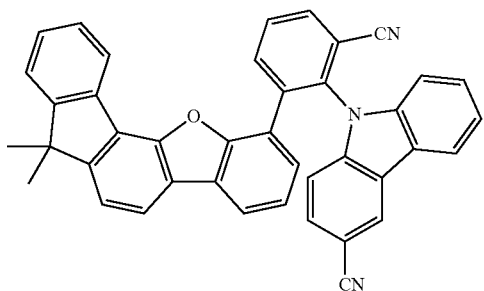
255
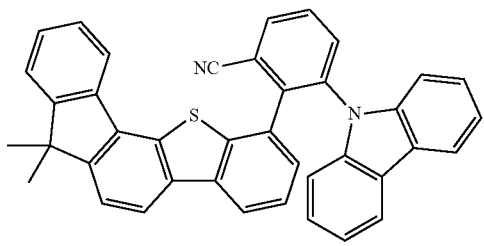
256
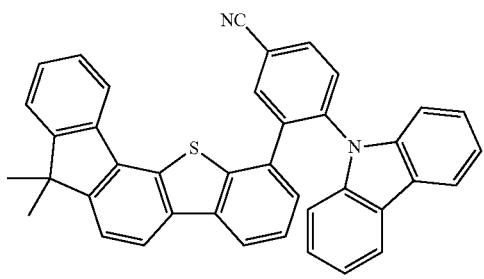
257
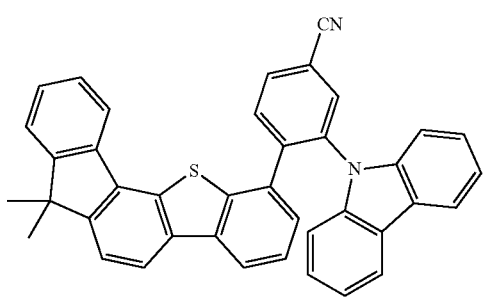
258
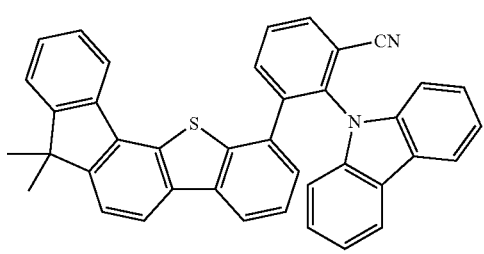
-continued
259
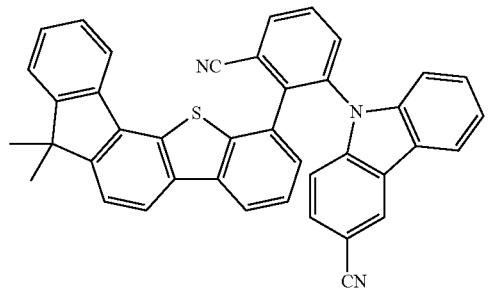
260
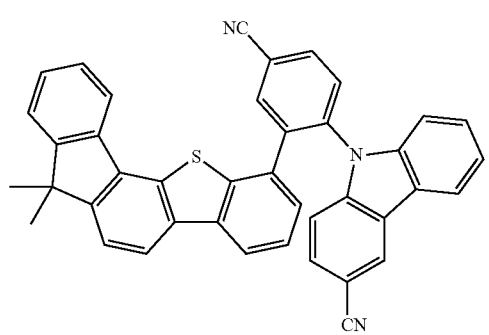
261
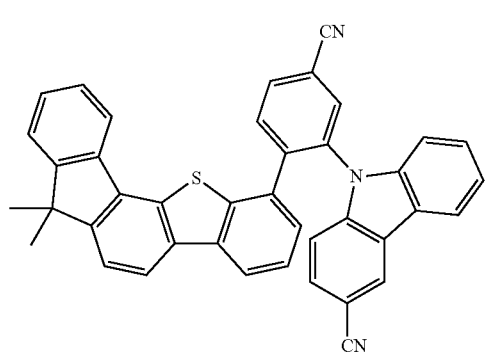
262
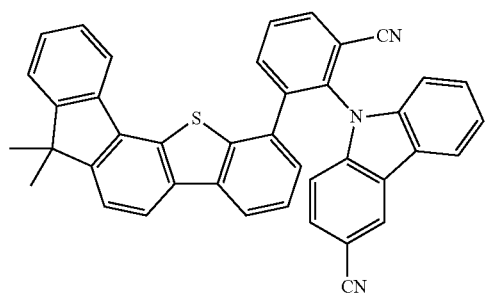
263
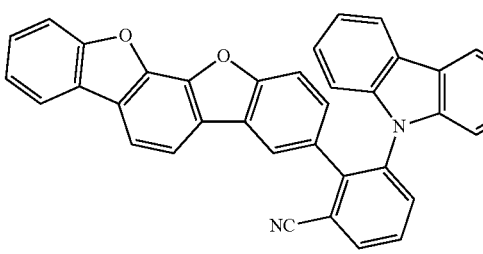

264
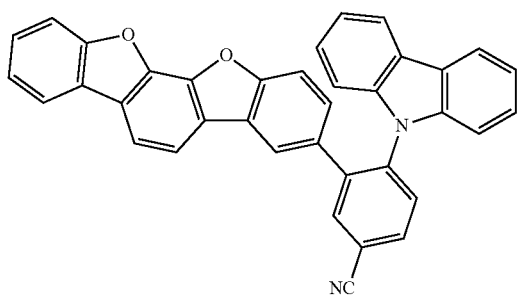
265
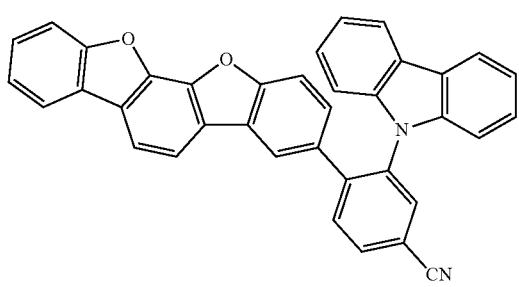
266
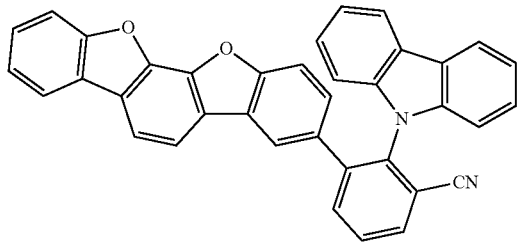
267
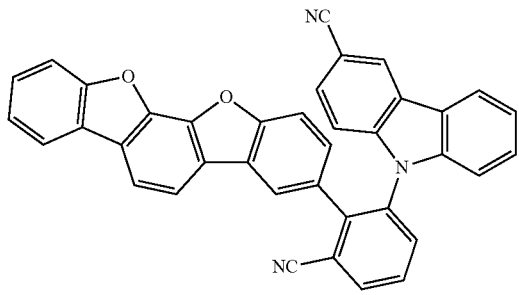
268
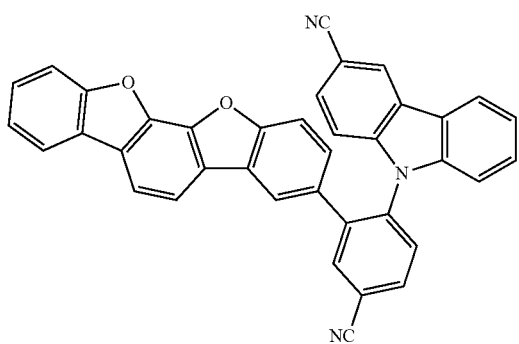
269
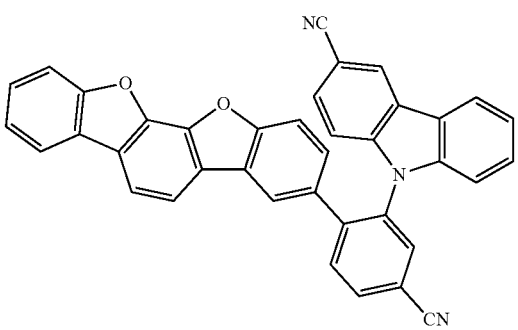
270
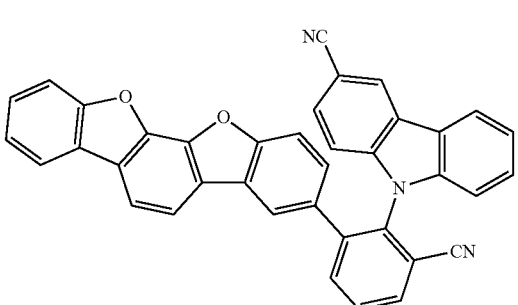
271
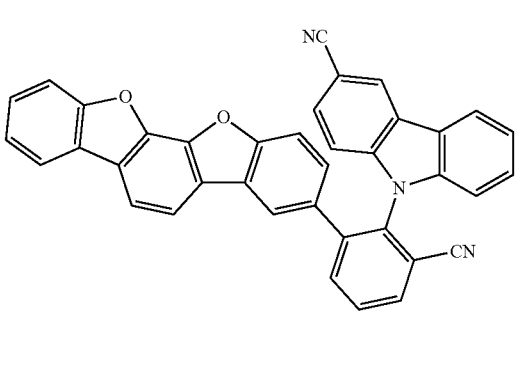
272
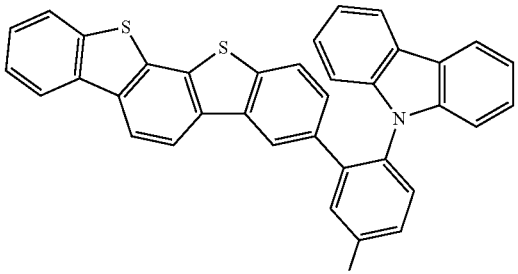
273
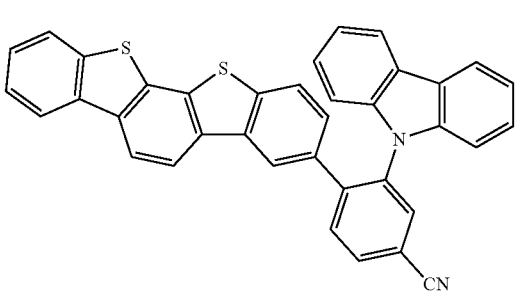

267
274
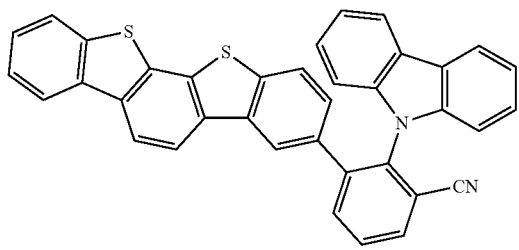
275
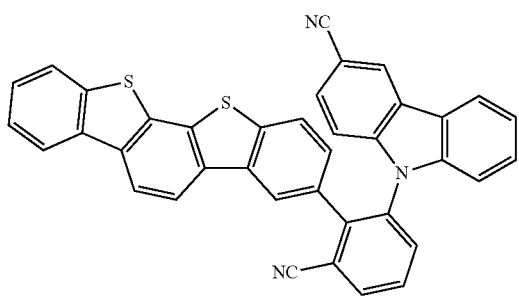
276
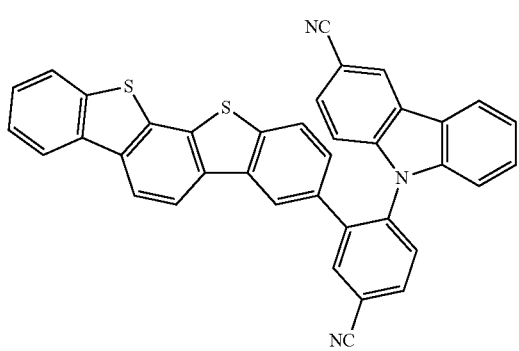
277
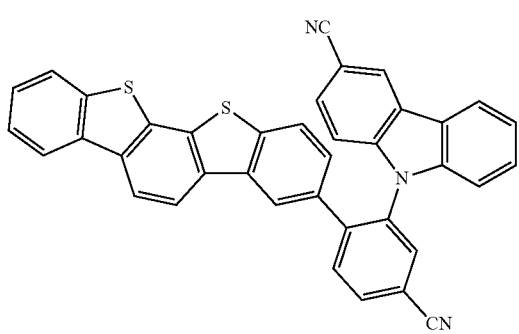
278
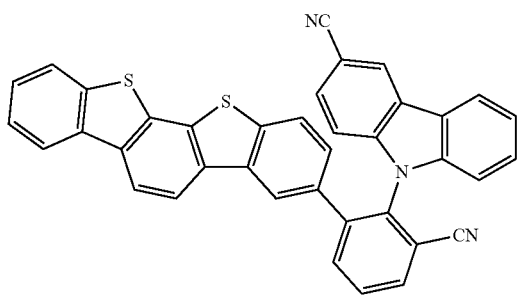
268
279
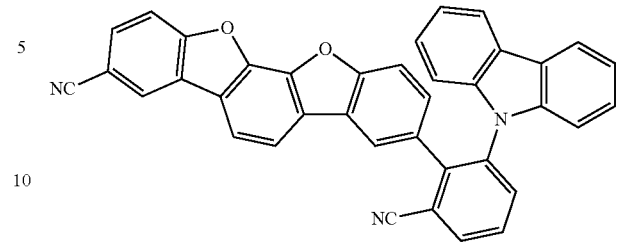
280
281
282
283

284
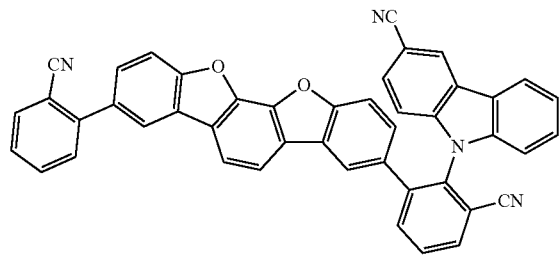
285
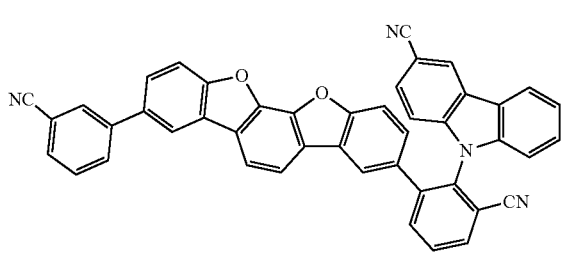
286
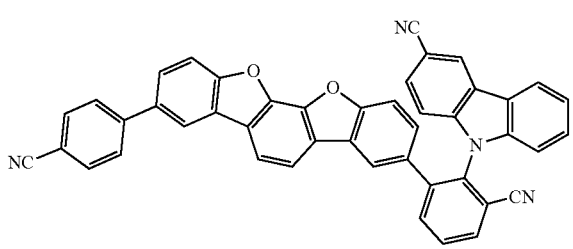
287
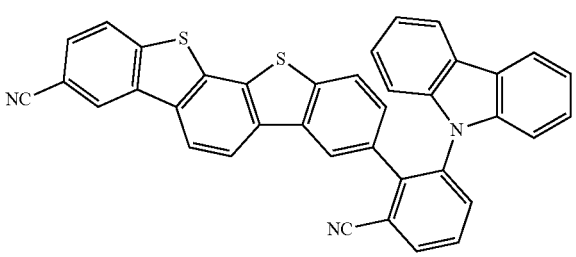
288
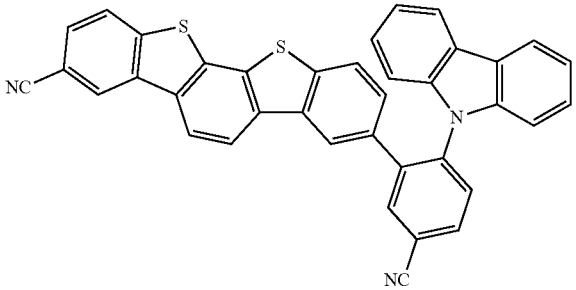
289
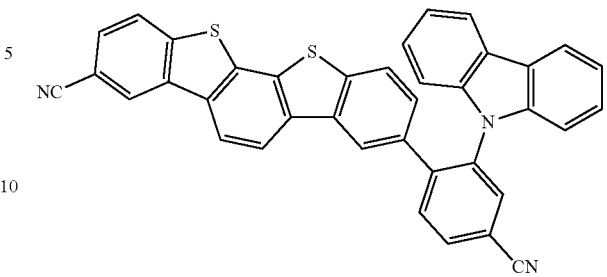
290
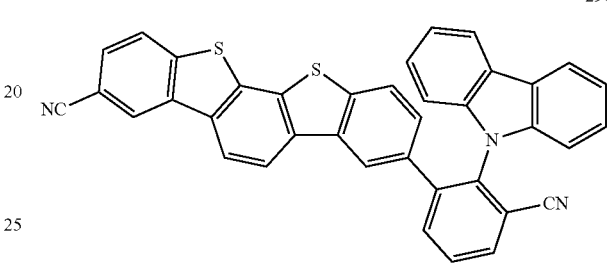
291
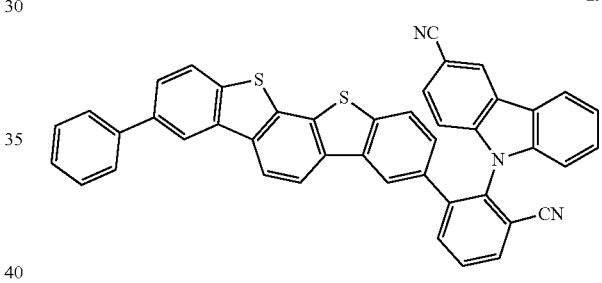
292
293
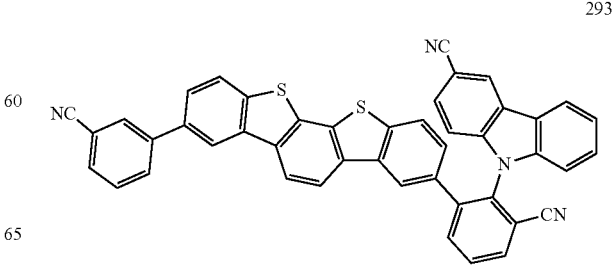

294
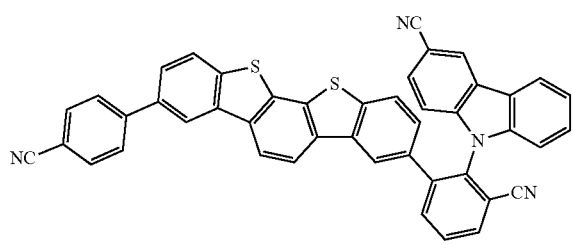
295
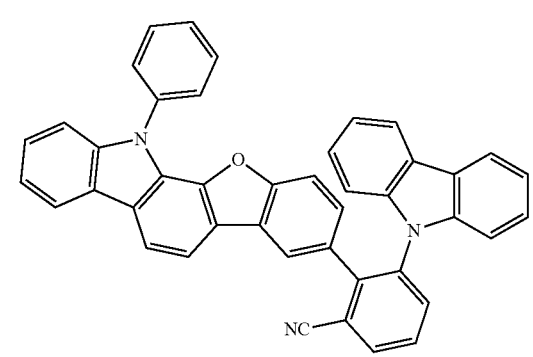
296
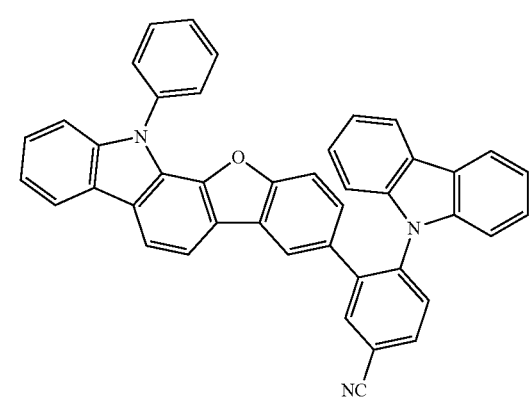
297
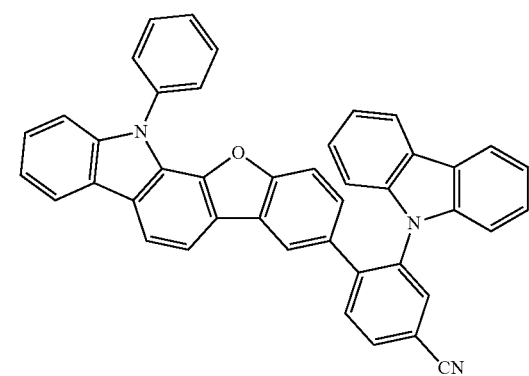
298
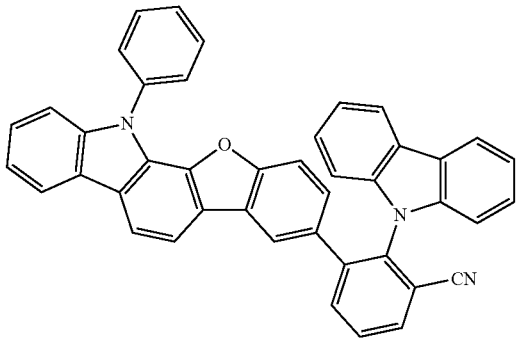
299
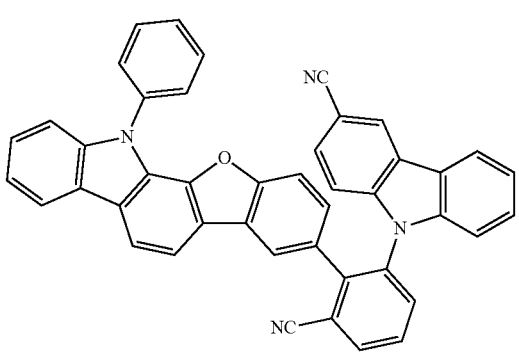
300
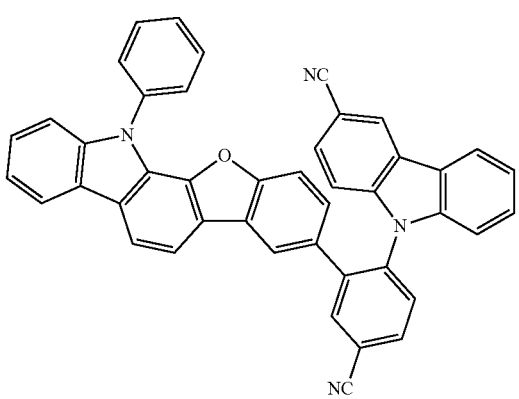
301
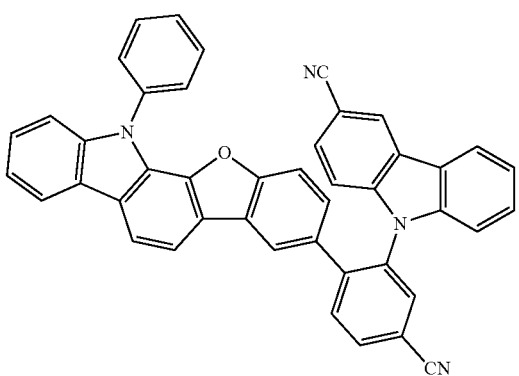

302
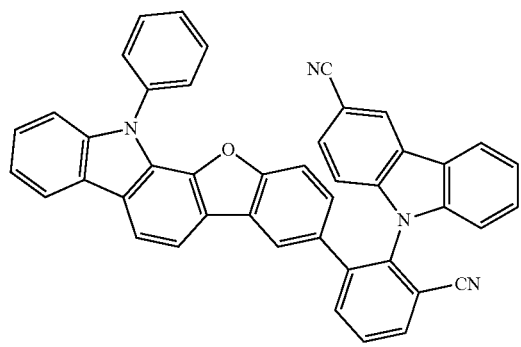
303
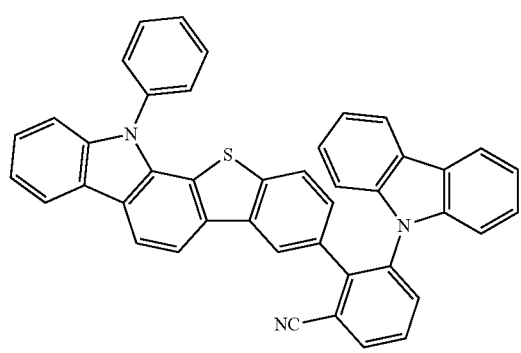
304
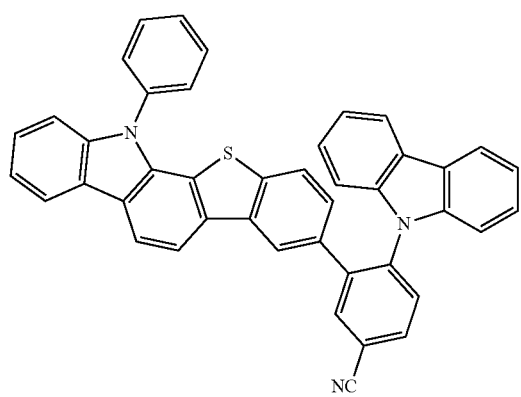
305
306
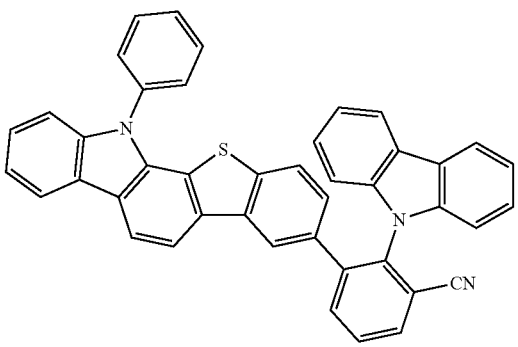
307
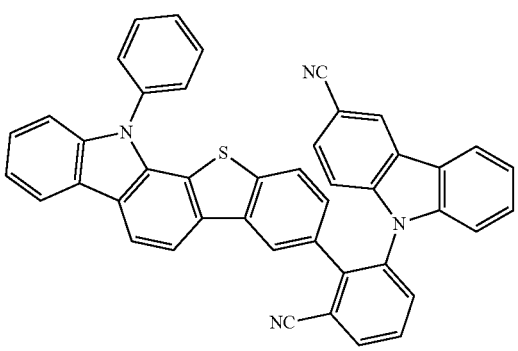
308
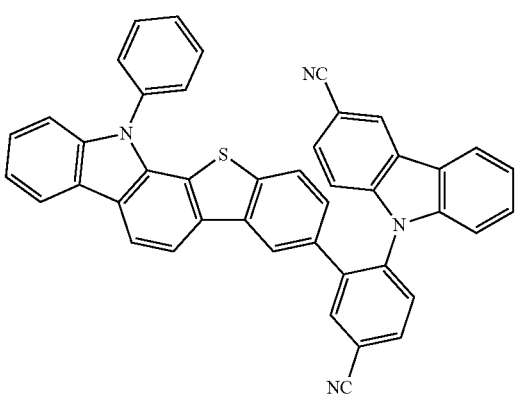
309
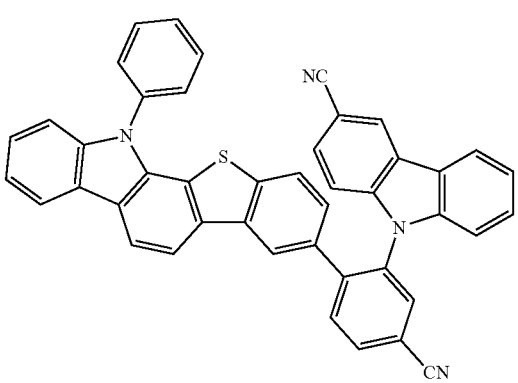

310 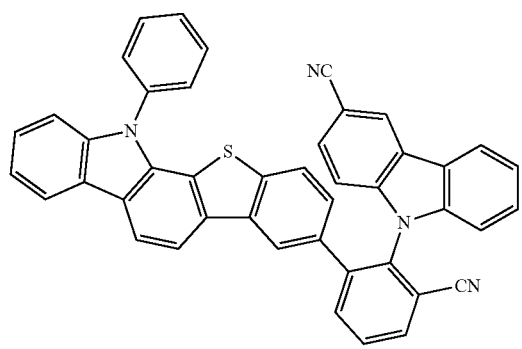
311 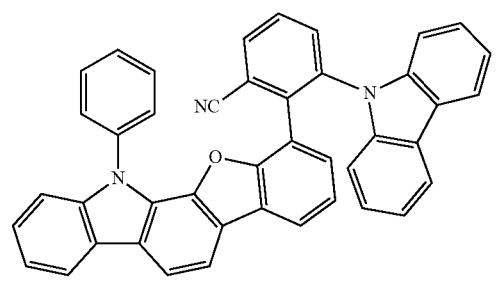
312 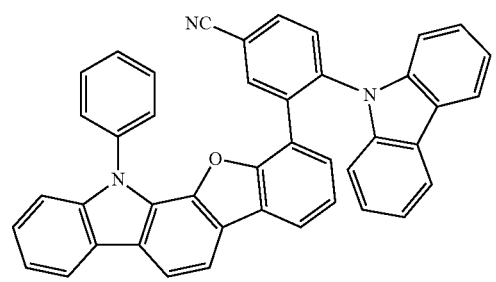
313 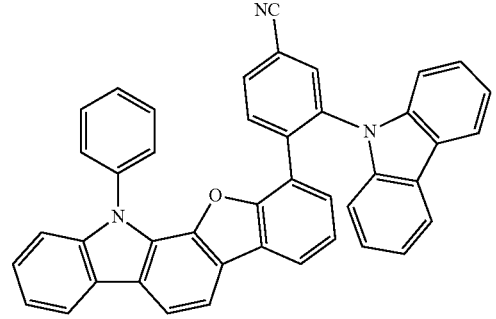
314 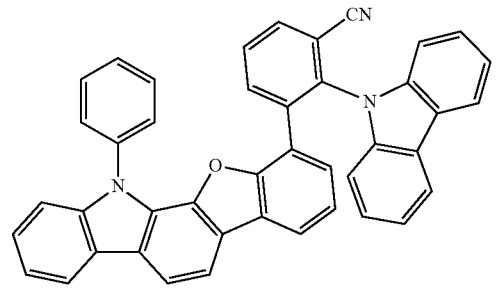
315 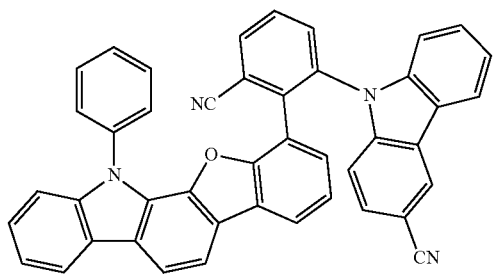
316 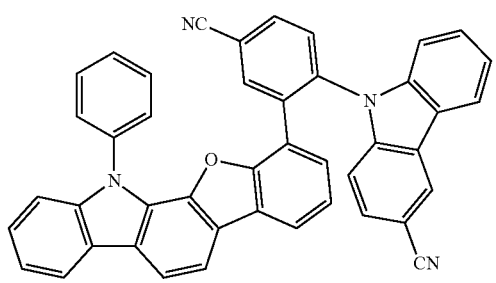
317 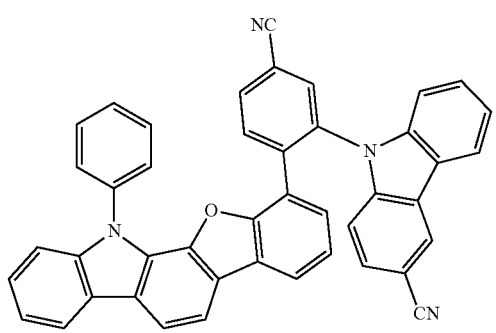
318 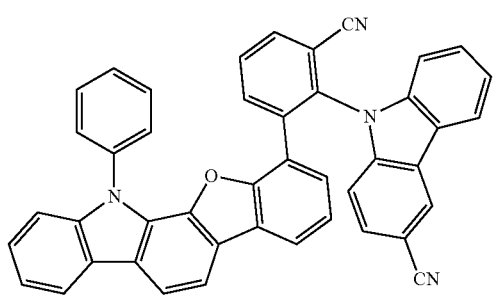
319 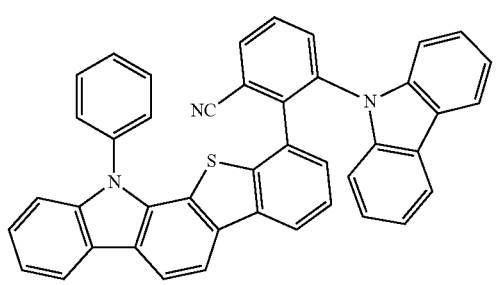

277
-continued
320
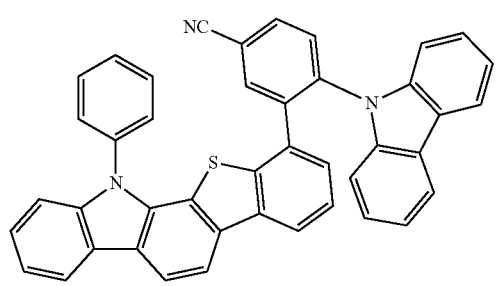
321
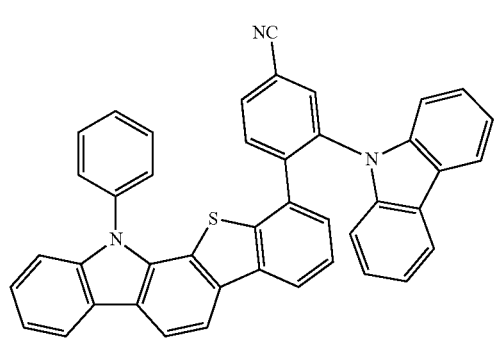
322
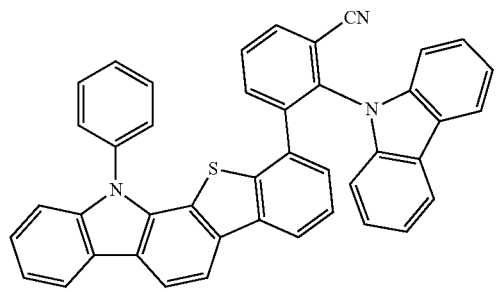
323
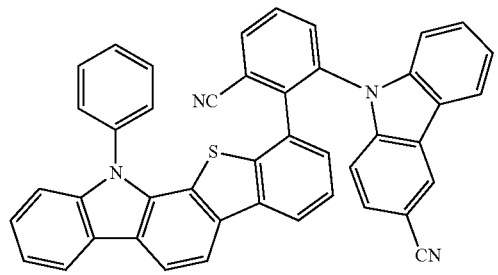
324
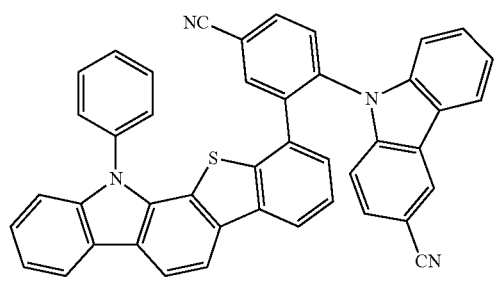
278
-continued
325
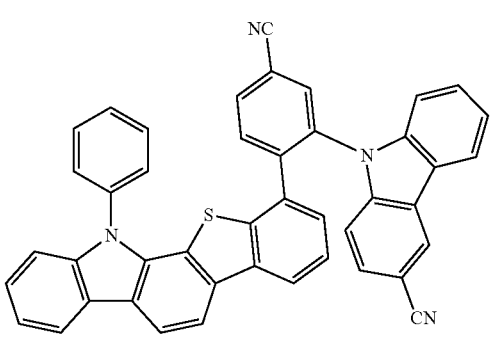
326
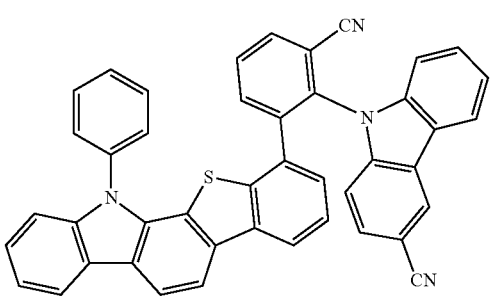
327
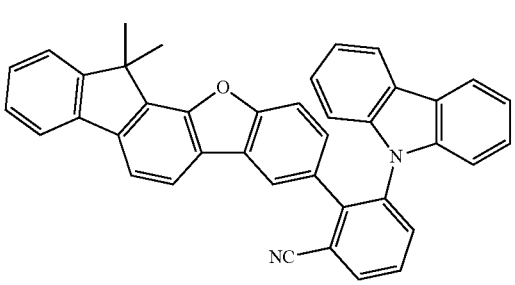
328
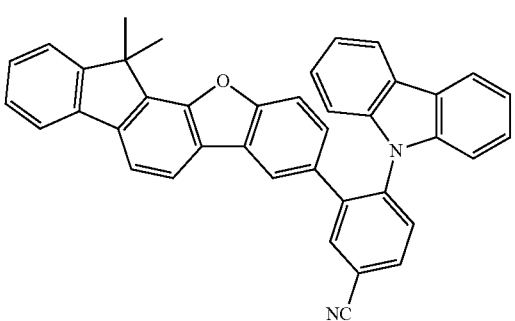
329
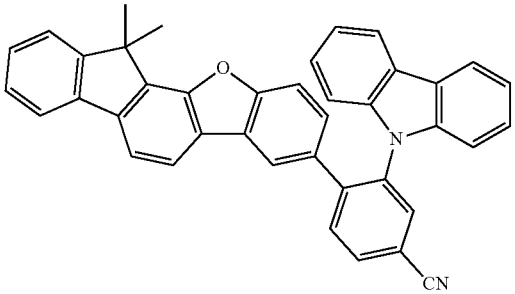

279
-continued
330
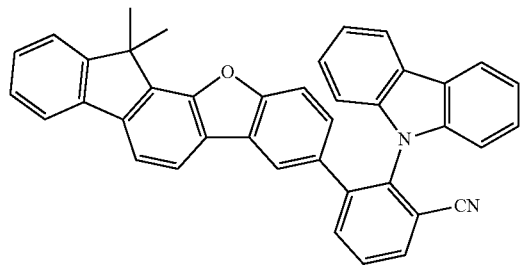
331
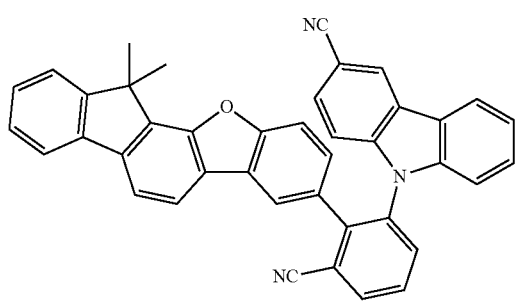
332
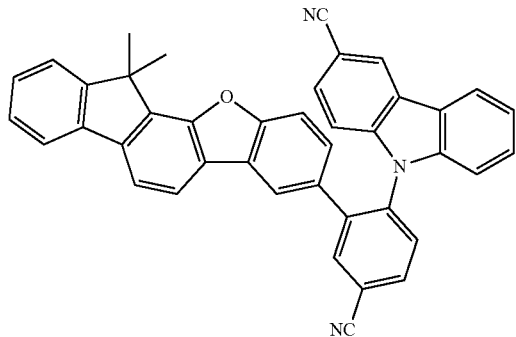
333
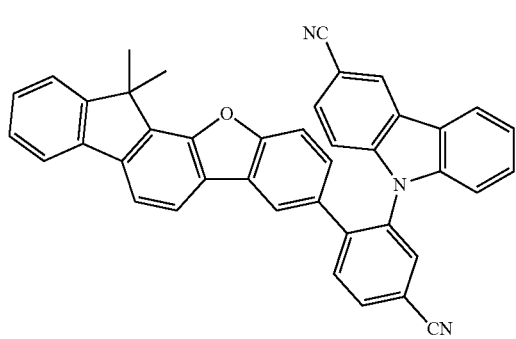
334
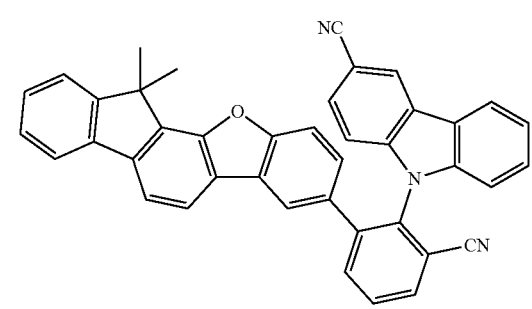
280
-continued
335
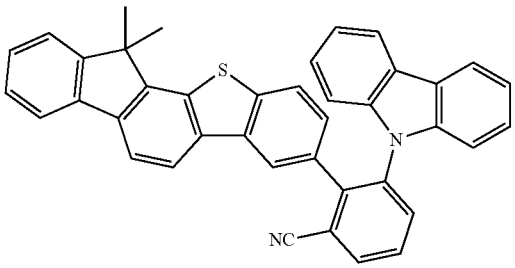
336
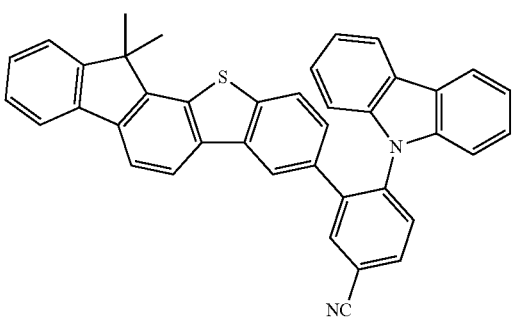
337
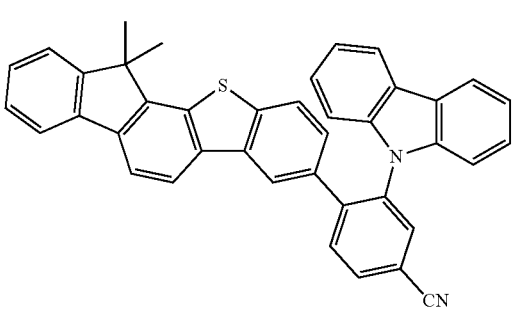
338
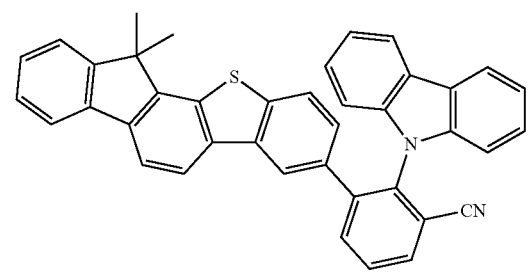
339
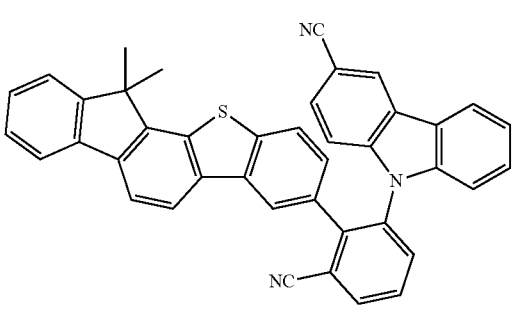

340
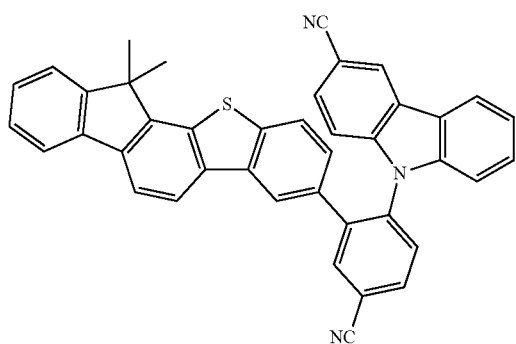
344
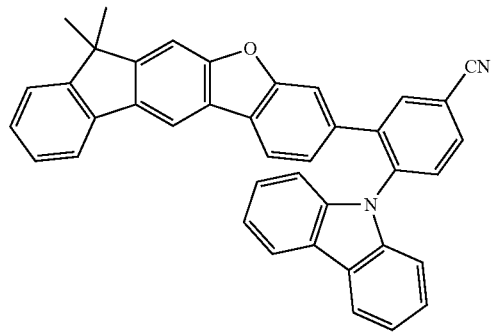
341
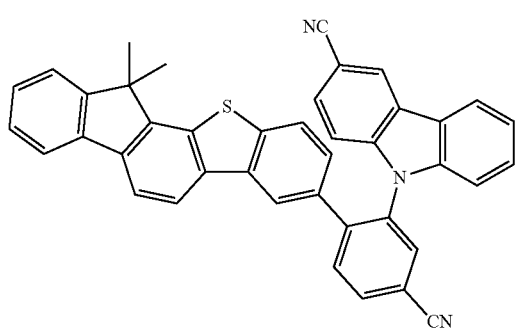
345
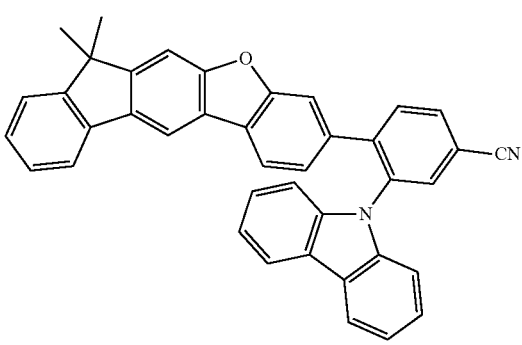
342
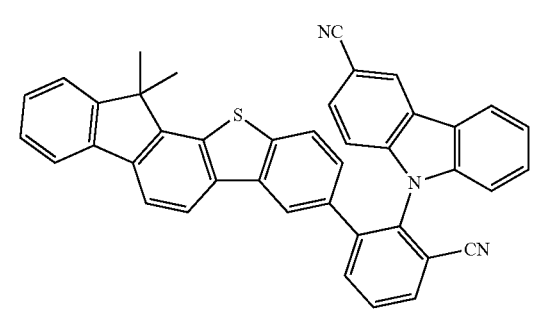
346
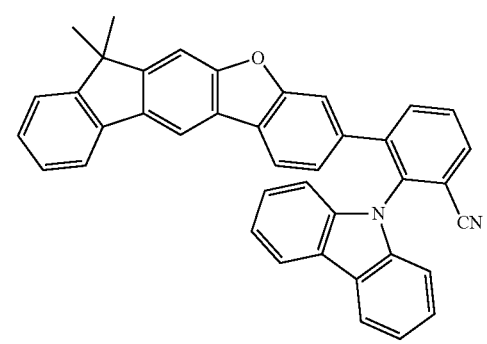
343
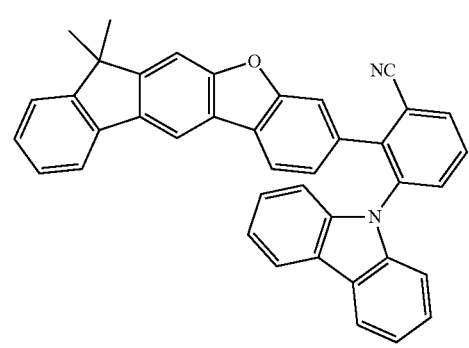
347
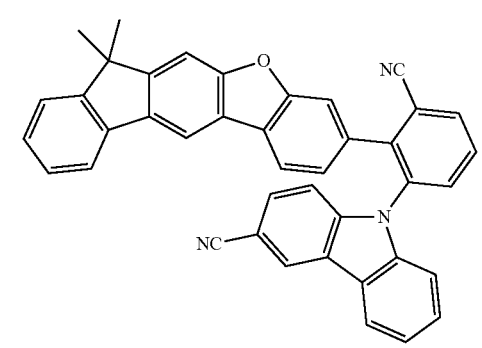

348
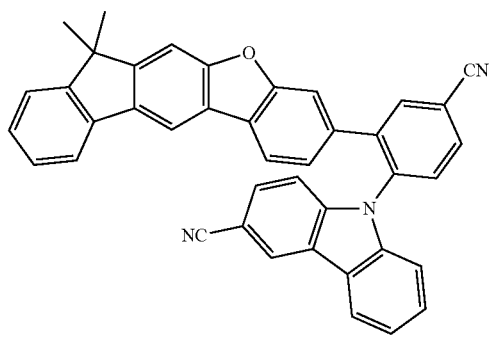
349
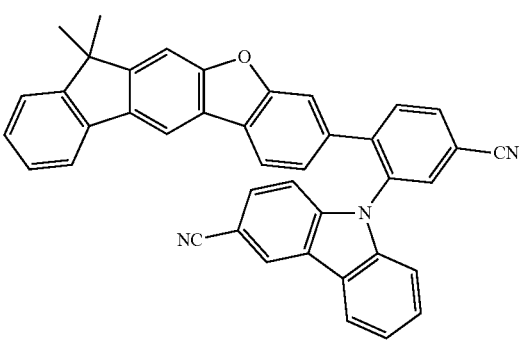
350
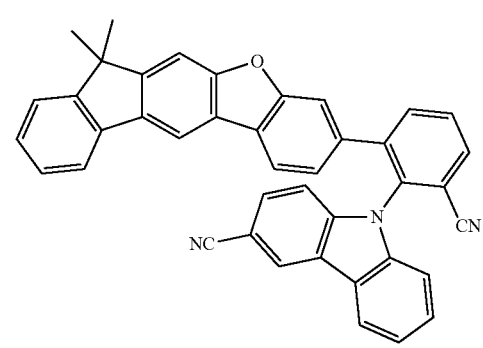
351
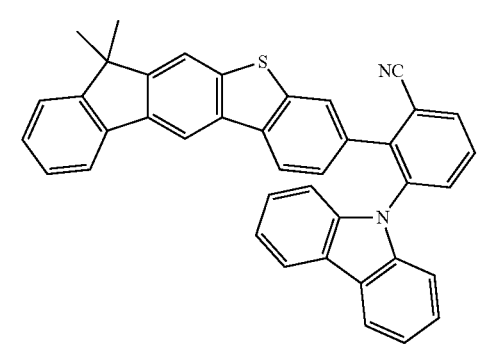
352
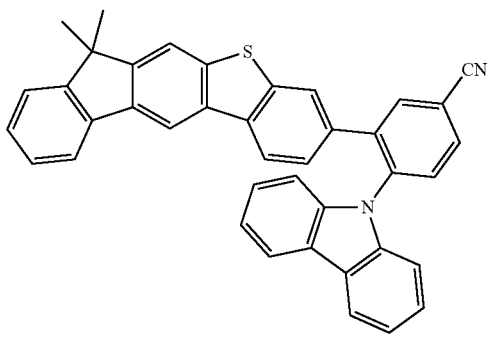
353
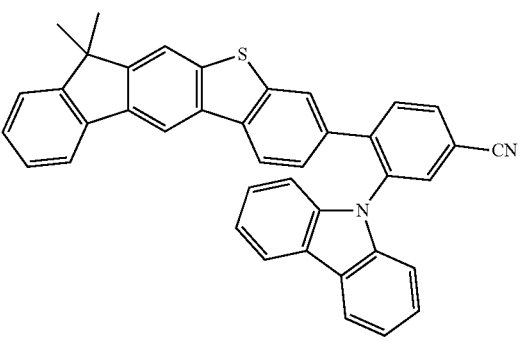
354
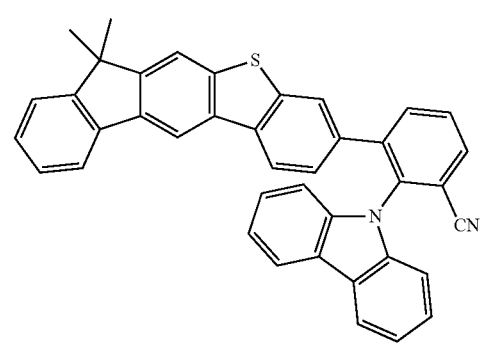
355
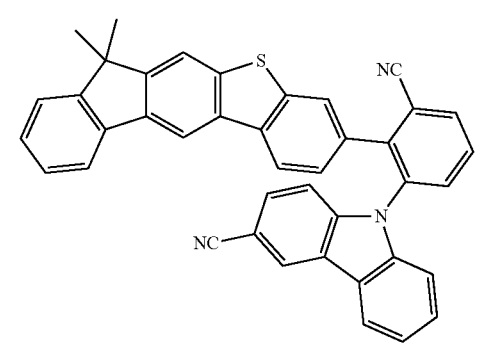

-continued
356
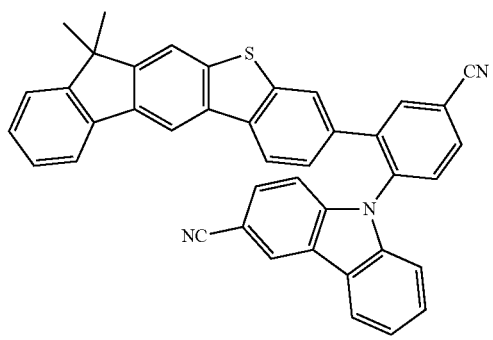
357
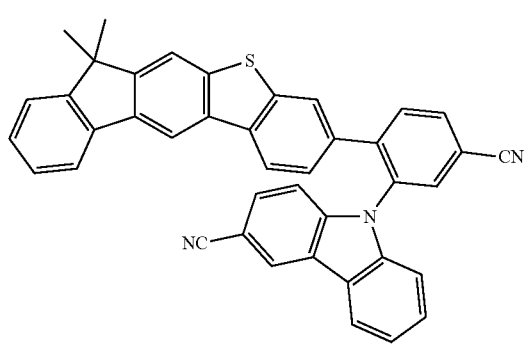
358
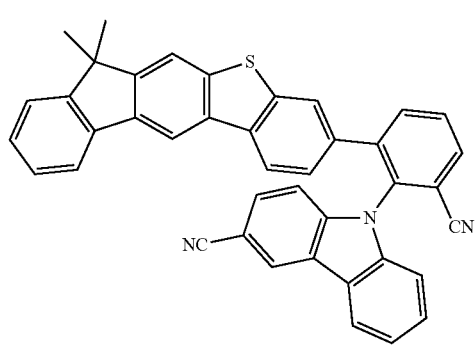
359
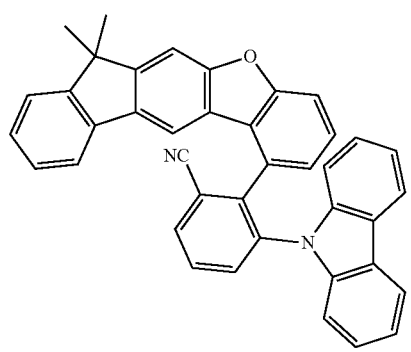
-continued
360
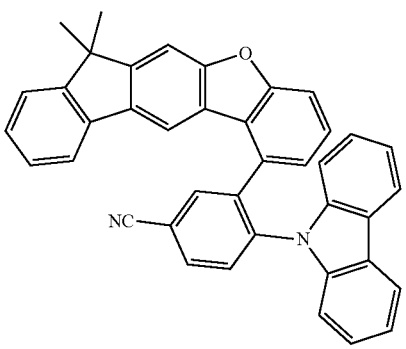
361
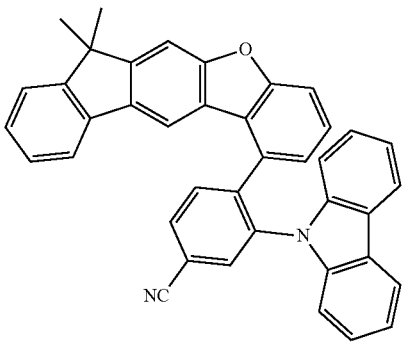
362
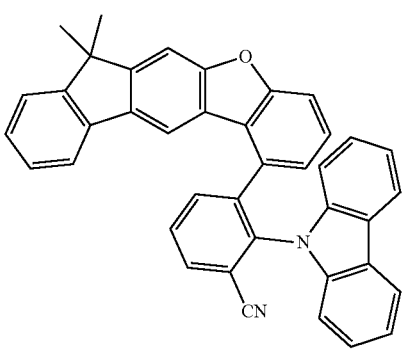
363
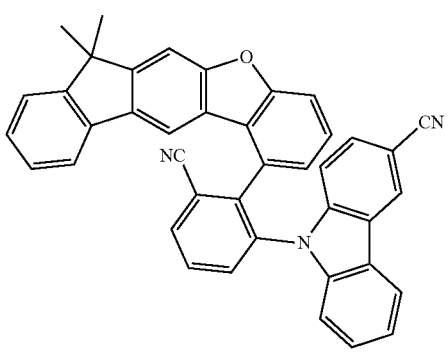

287
-continued
364
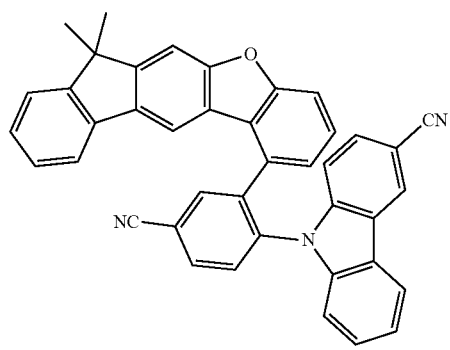
365
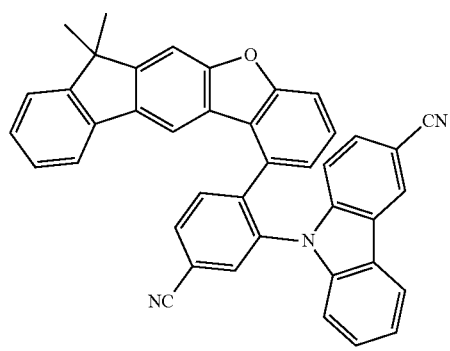
366
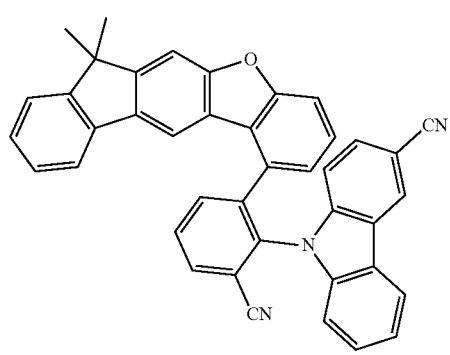
367
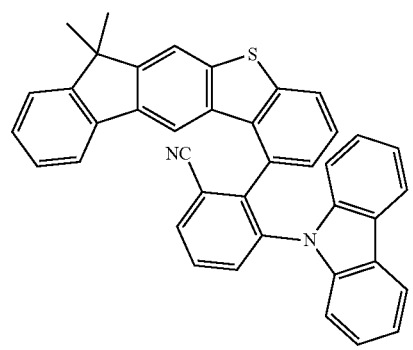
288
-continued
368
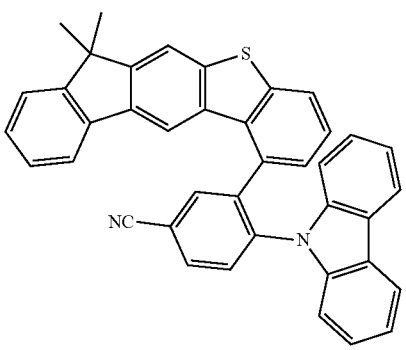
369
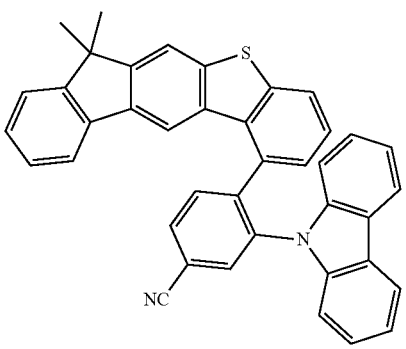
370
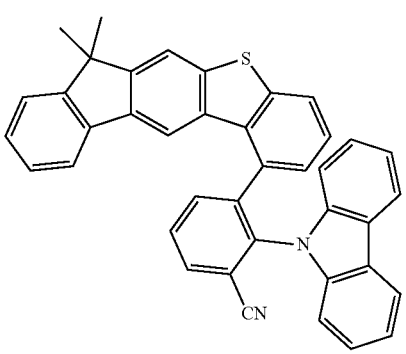
371
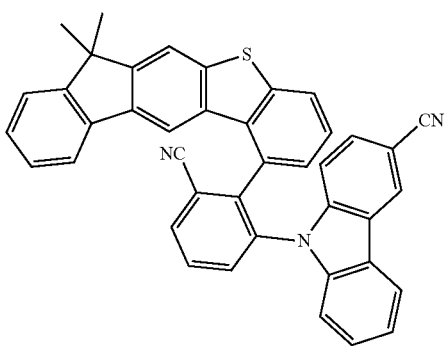

372
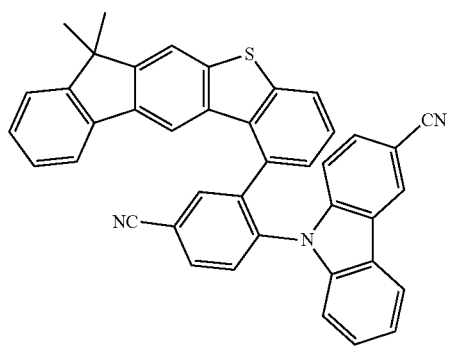
373
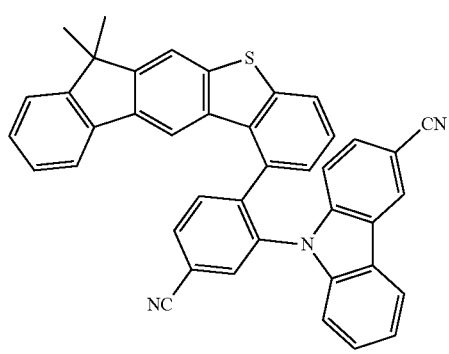
374
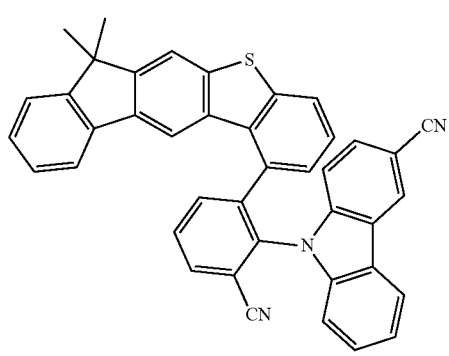
375
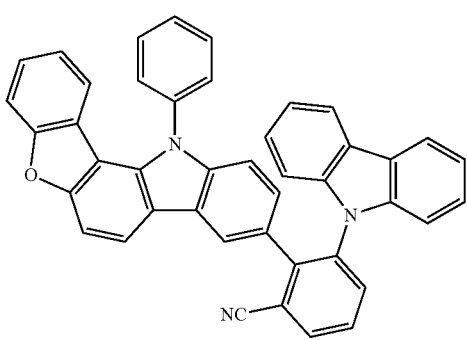
376
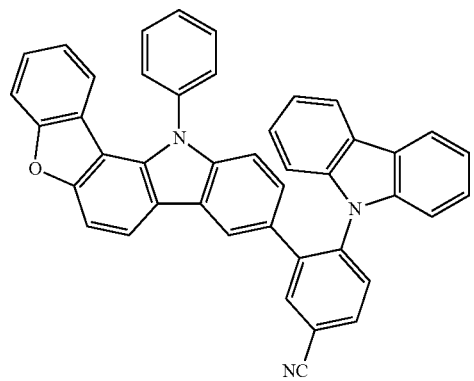
377
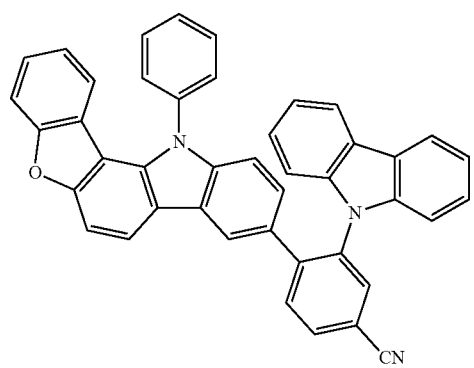
378
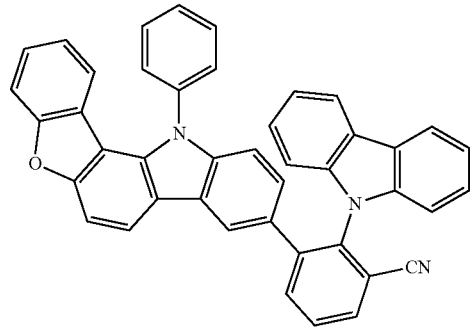
379
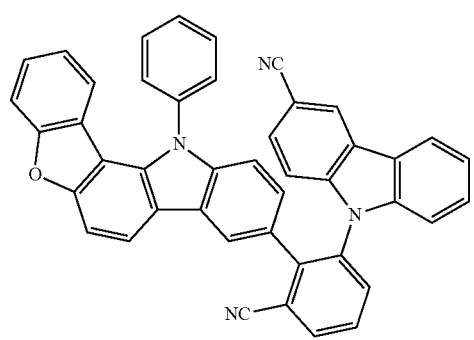

380
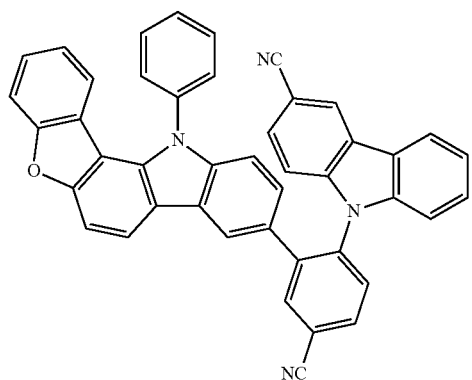
381
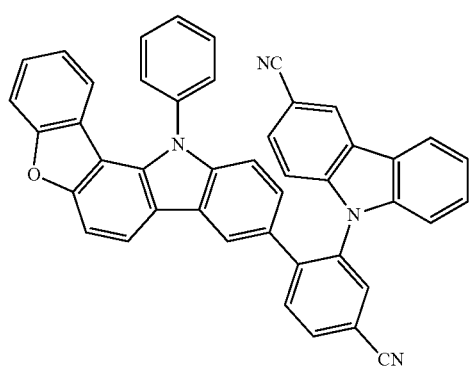
382
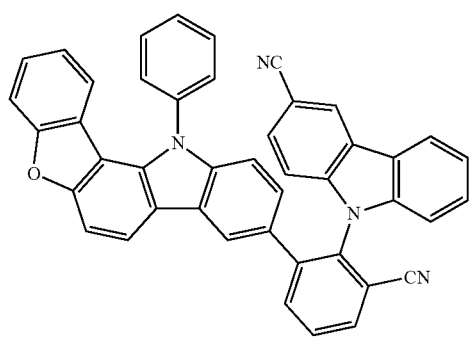
383
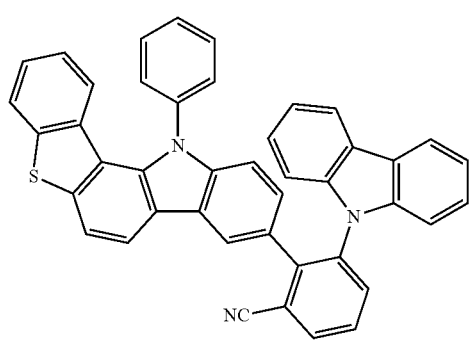
384
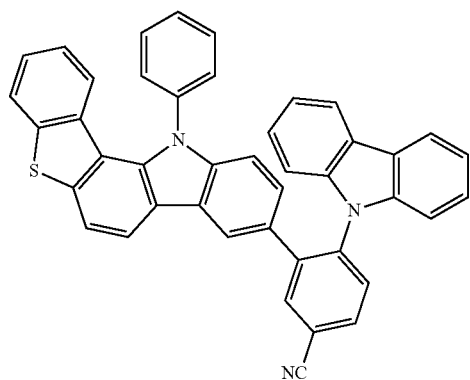
385
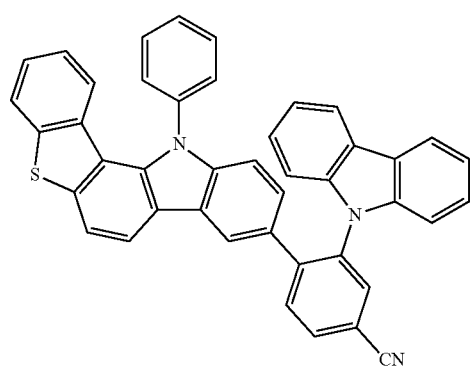
386
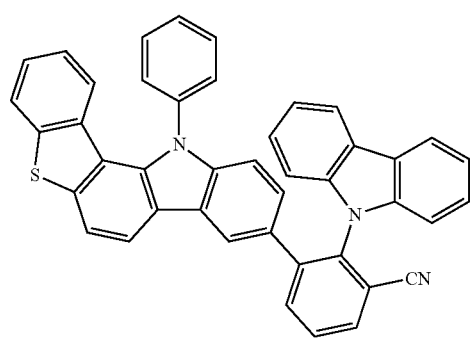
387
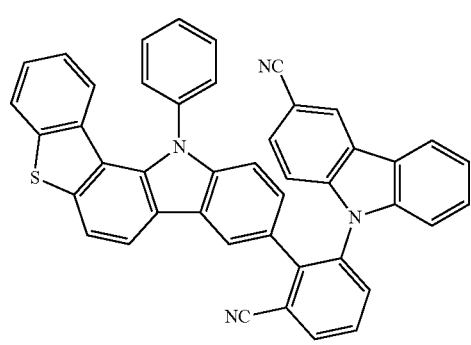

388
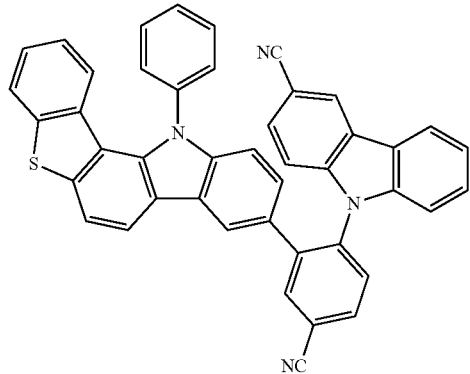
389
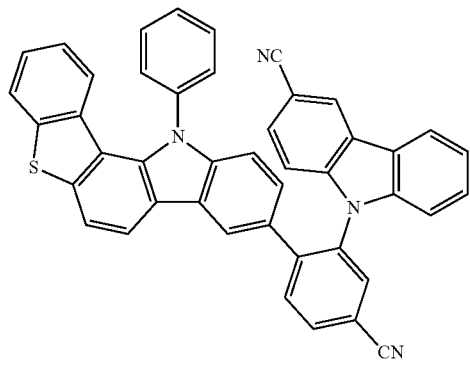
390
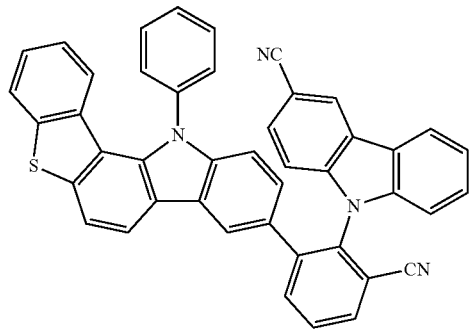
391
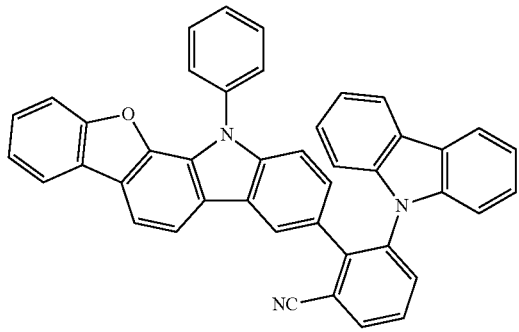
392
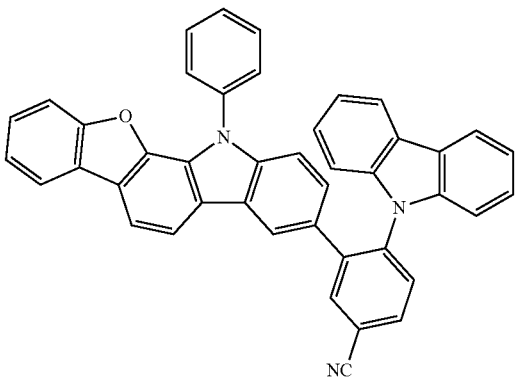
393
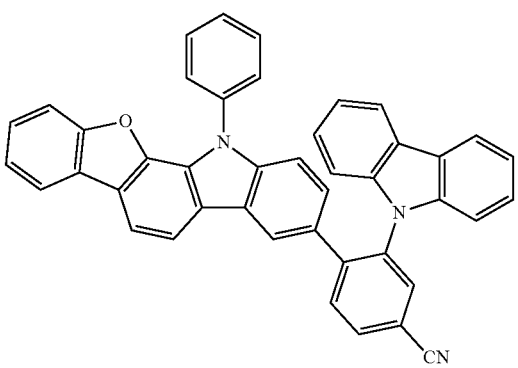
394
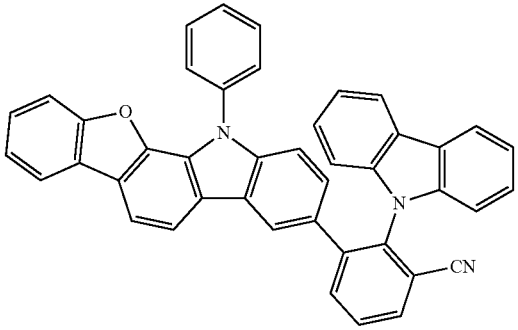
395
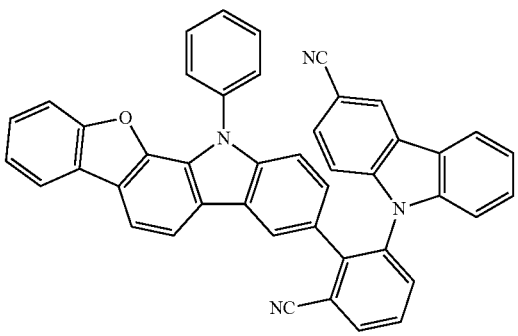

| 396 | 400 |
| 397 | 401 |
| 398 | 402 |
| 399 | 403 |

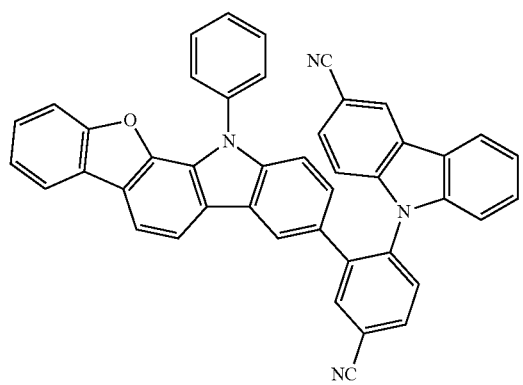
404
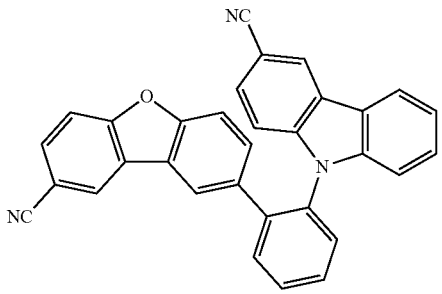
408
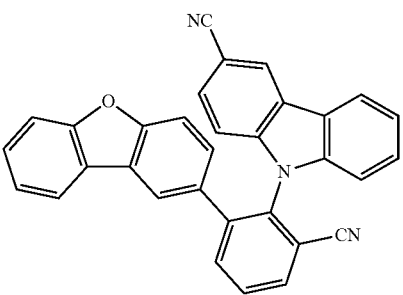
409
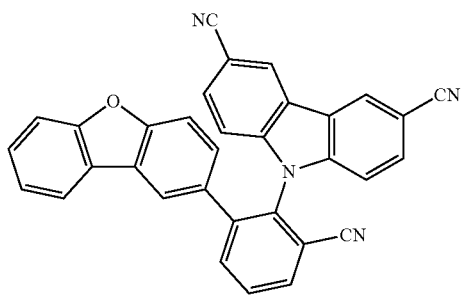
410
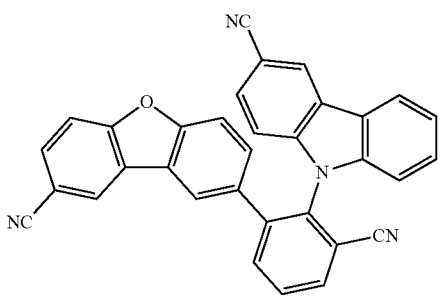
411
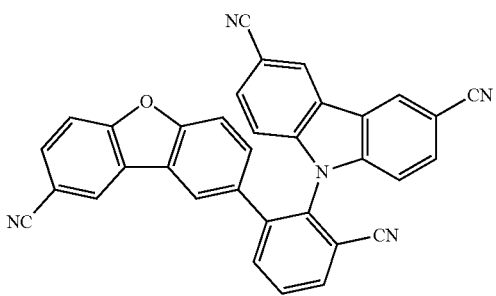
412

| 413 | 417 |
|---|---|
| 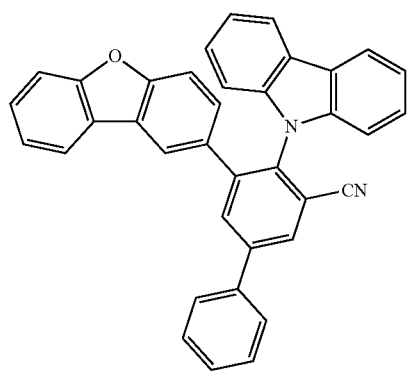 | 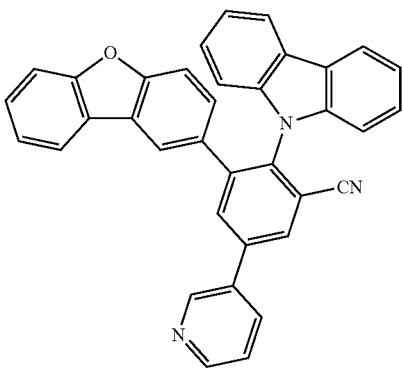 |
| 414 | 418 |
|---|---|
| 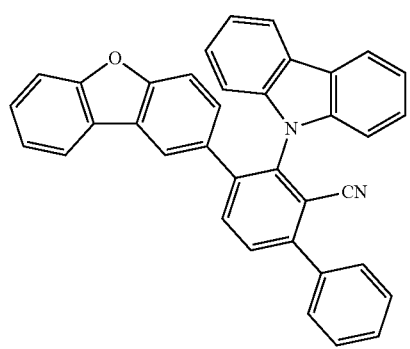 | 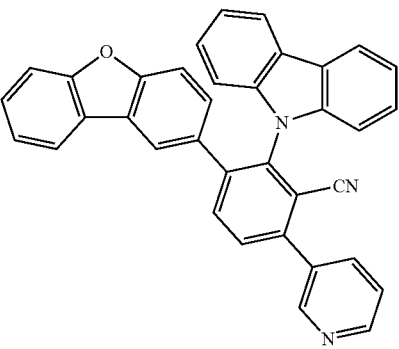 |
| 415 | 419 |
|---|---|
| 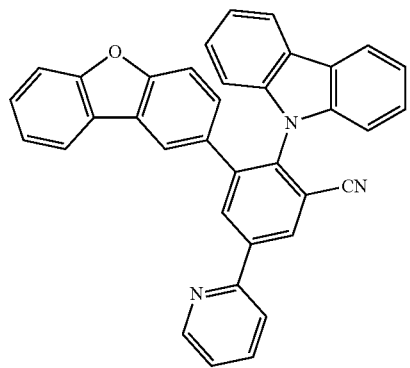 | 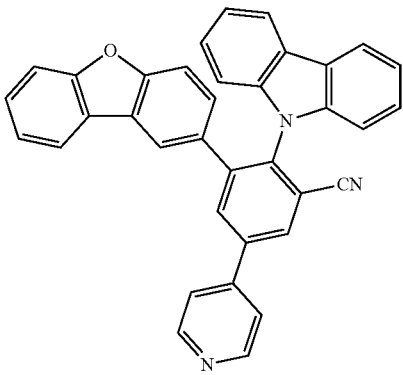 |
| 416 | 420 |
|---|---|
| 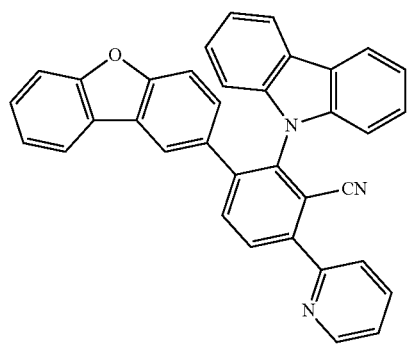 | 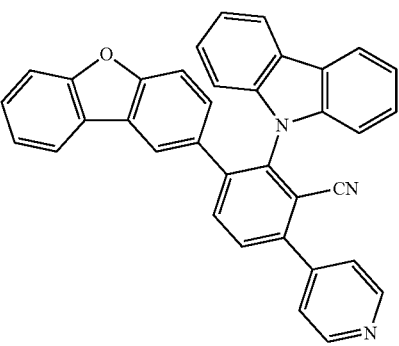 |

301
-continued
421
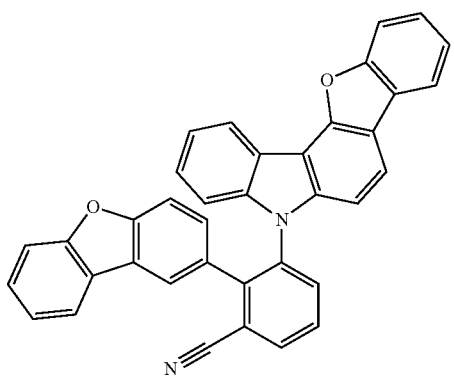
422
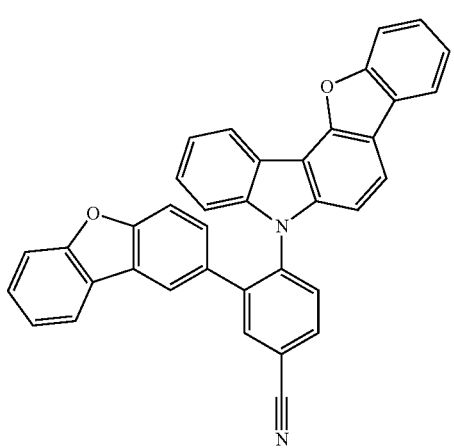
423
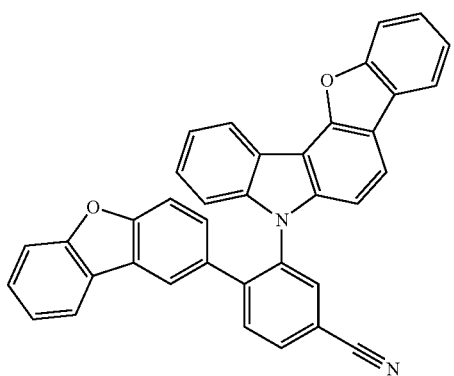
424
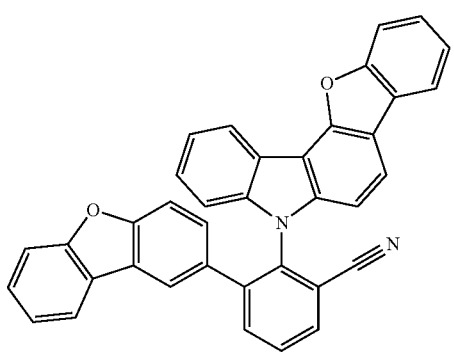
302
-continued
425
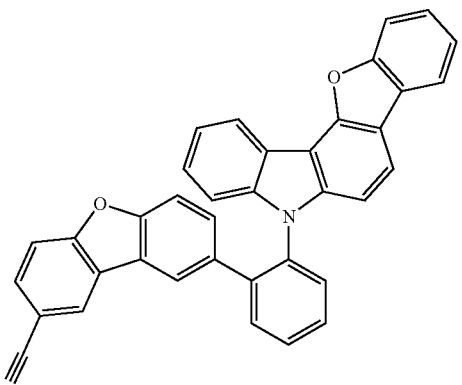
426
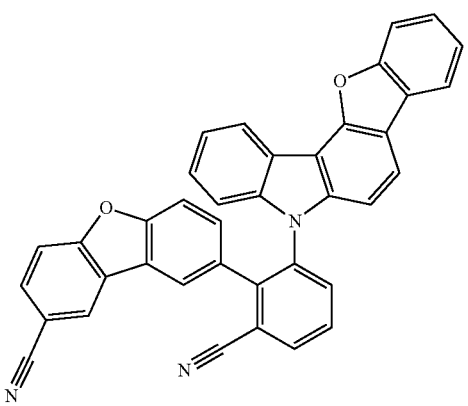
427
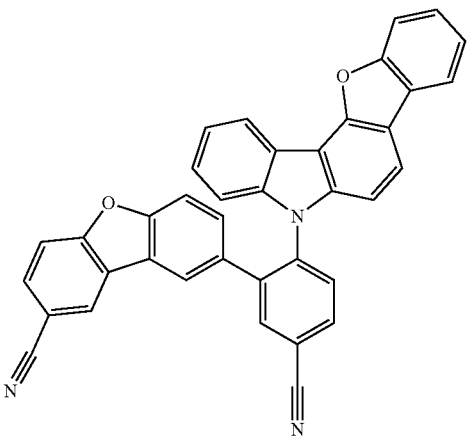
428
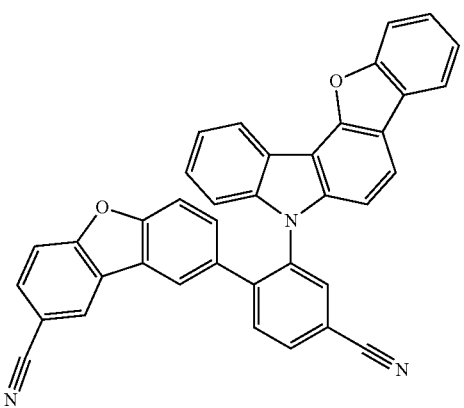

429
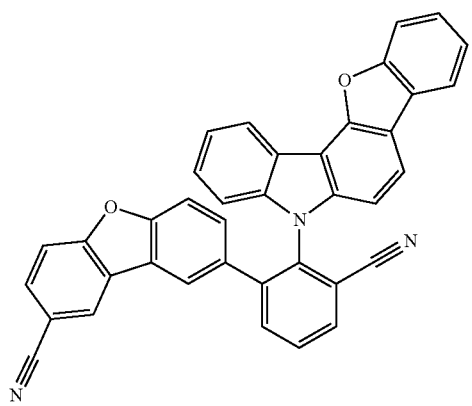
430
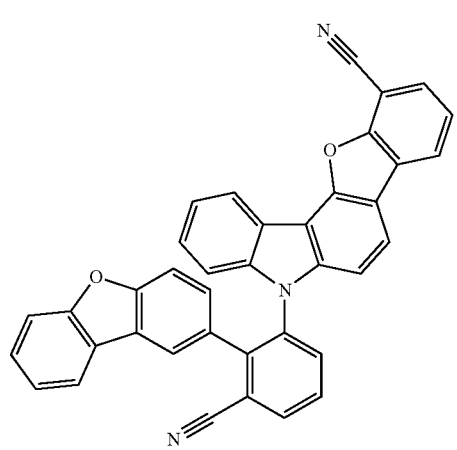
431
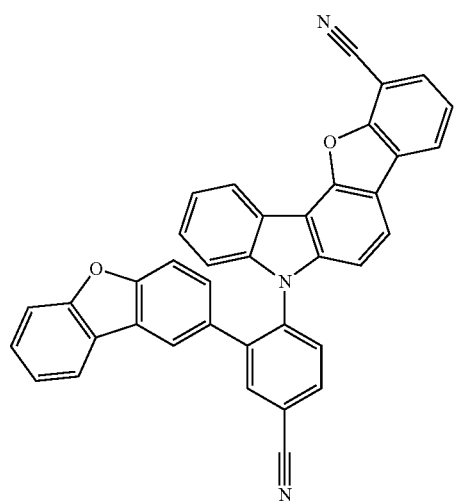
432
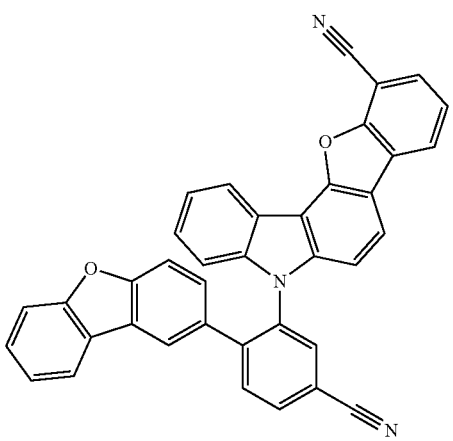
433
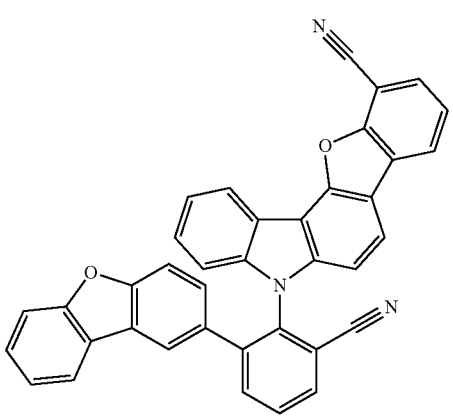
434
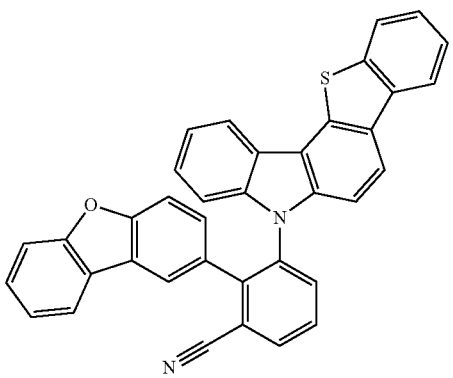
435
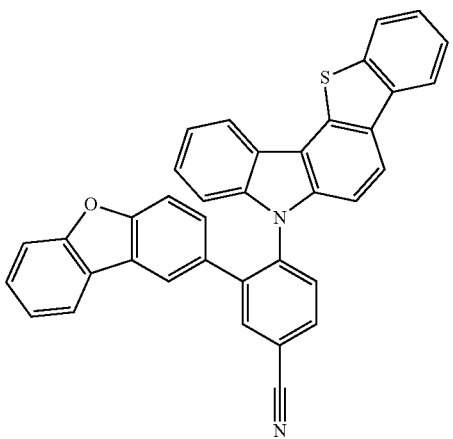

| 436 | 440 |
|---|---|
| 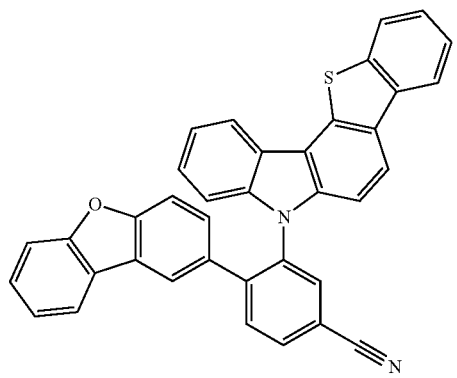 | 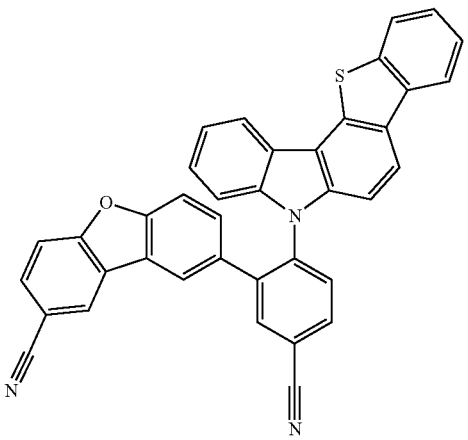 |
| 437 | |
|---|---|
| 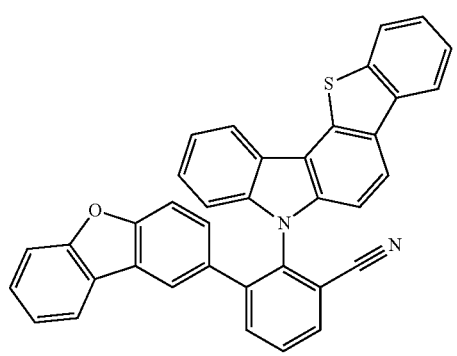 | |
| | 441 |
|---|---|
| | 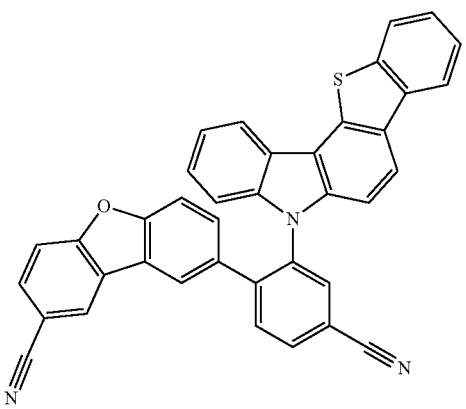 |
| 438 | |
|---|---|
| 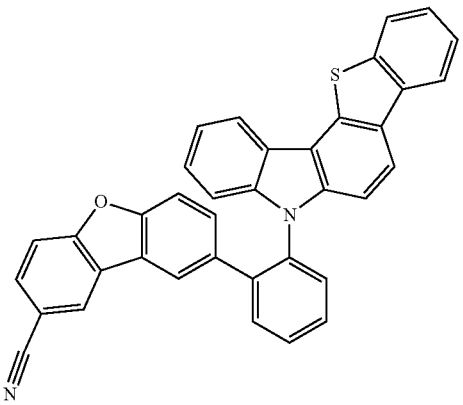 | |
| 439 | 442 |
|---|---|
| 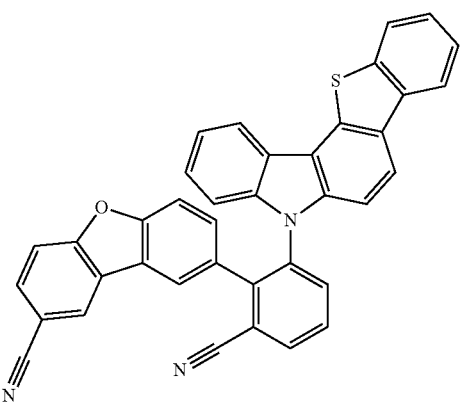 | 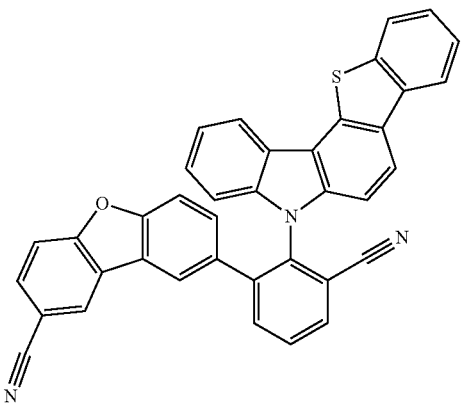 |

| 443 | 446 |
|---|---|
| 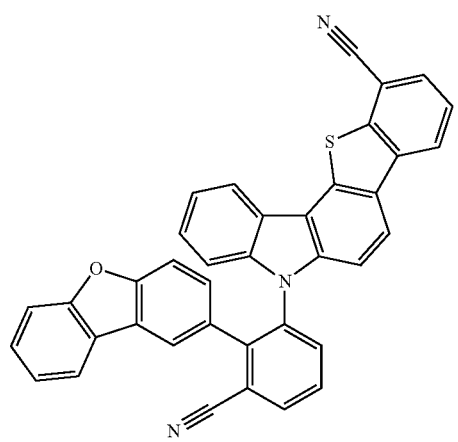 | 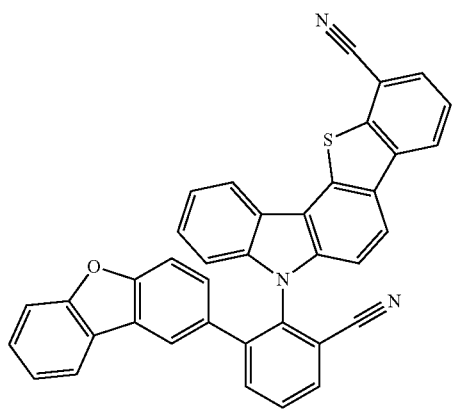 |
| 444 | 447 |
| 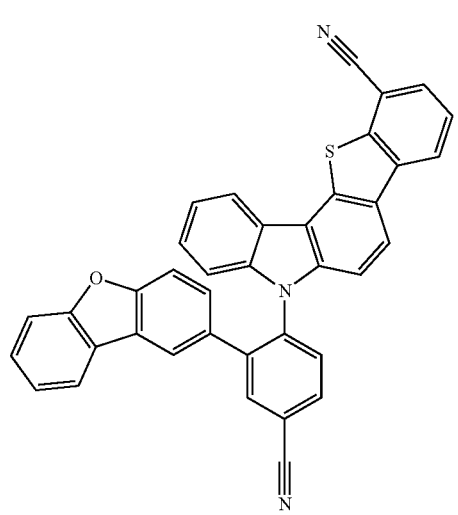 | 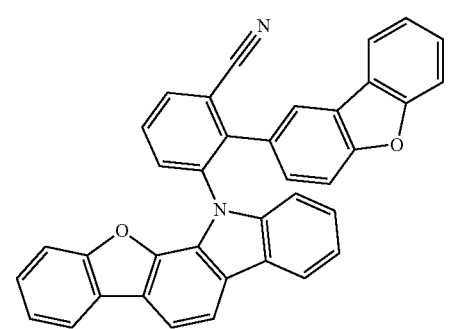 |
|  | 448 |
|  | 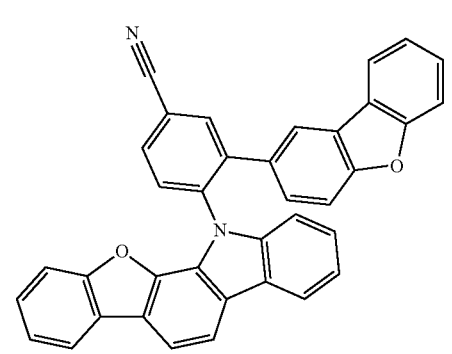 |
| 445 | 449 |
| 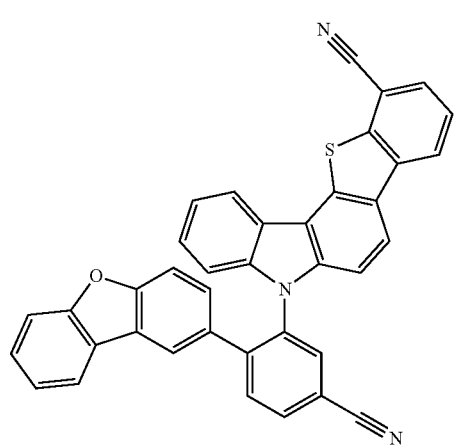 | 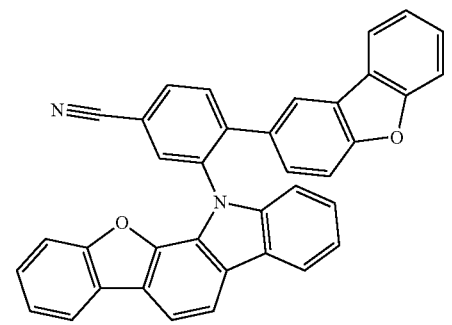 |

450
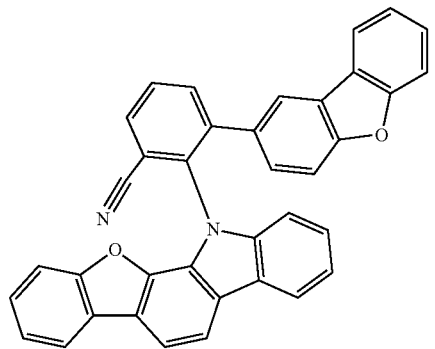
451
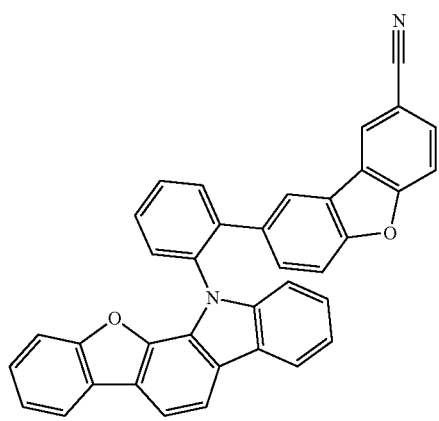
452
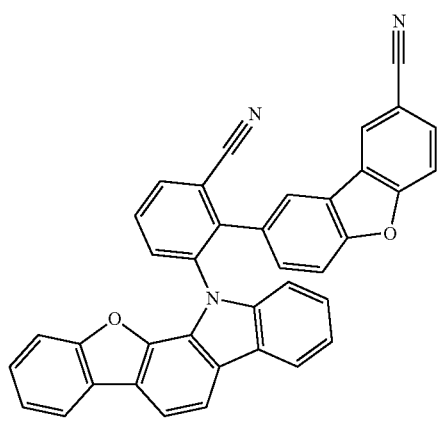
453
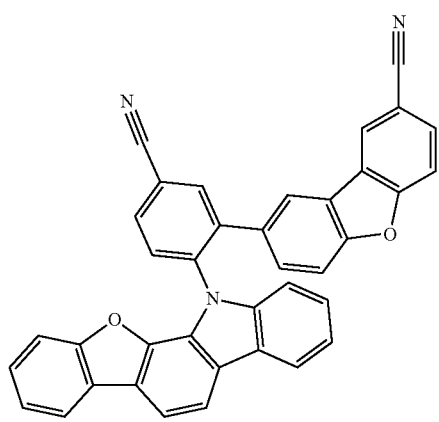
454
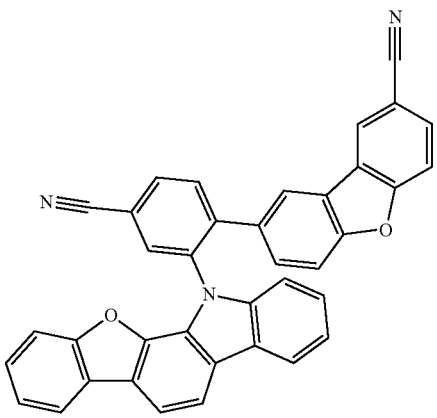
455
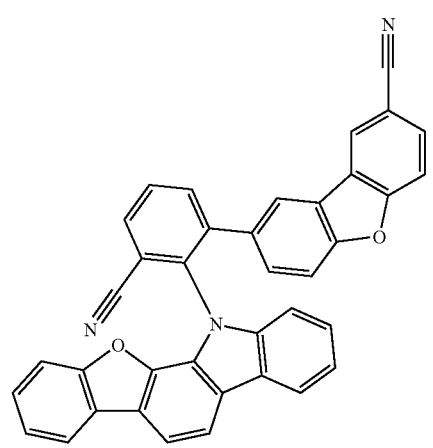
456
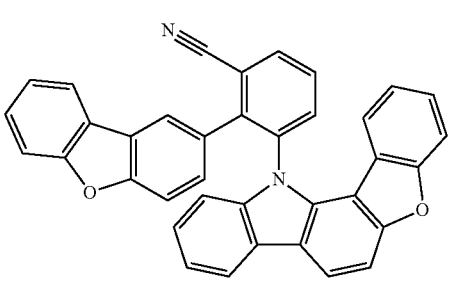
457
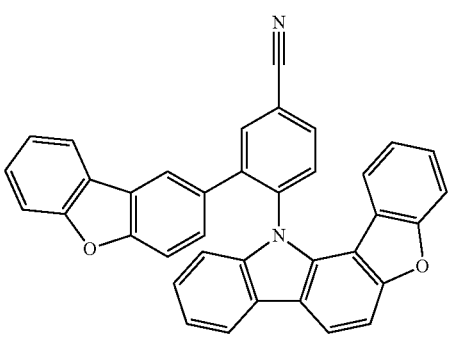

311
-continued
458
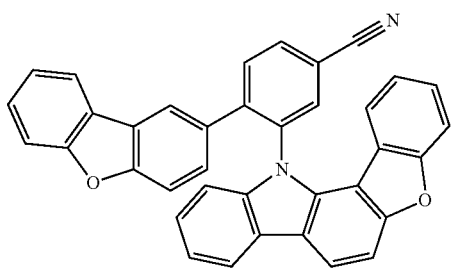
459
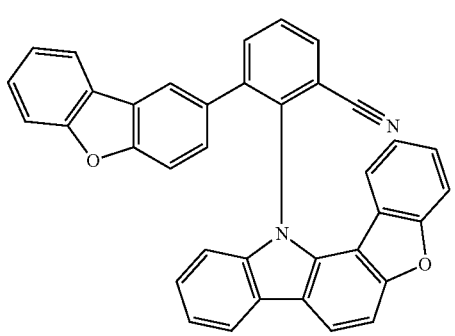
460
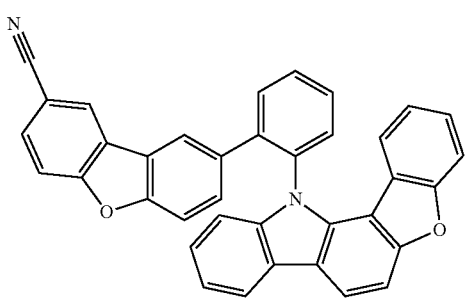
461
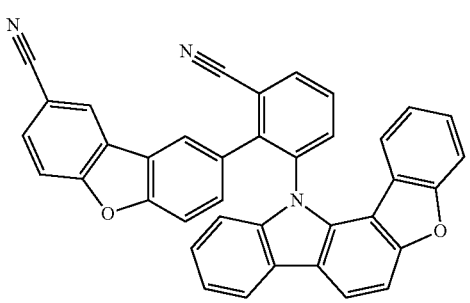
462
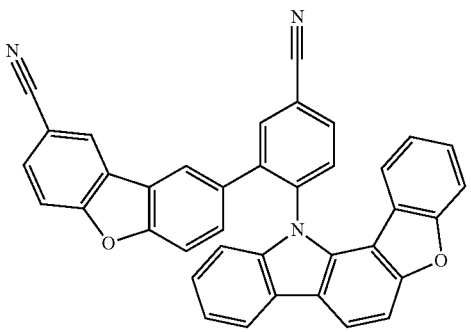
312
-continued
463
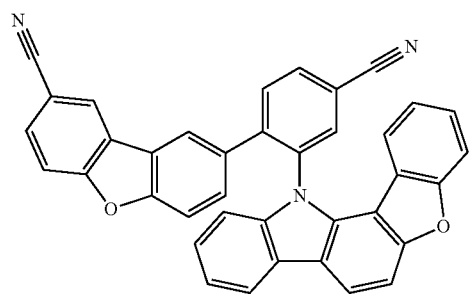
464
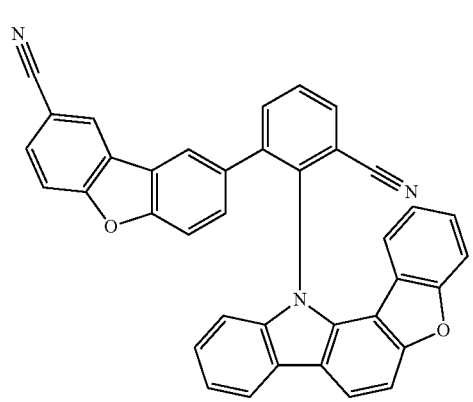
465
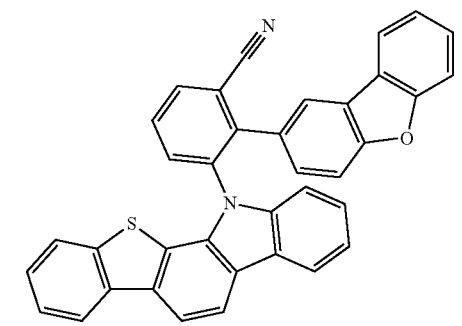
466
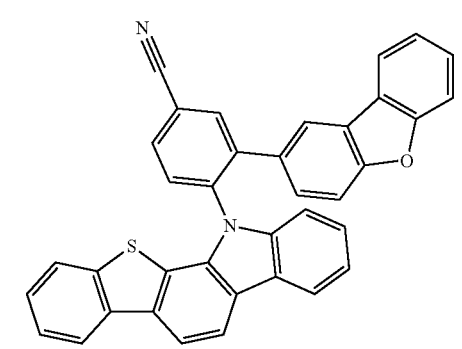

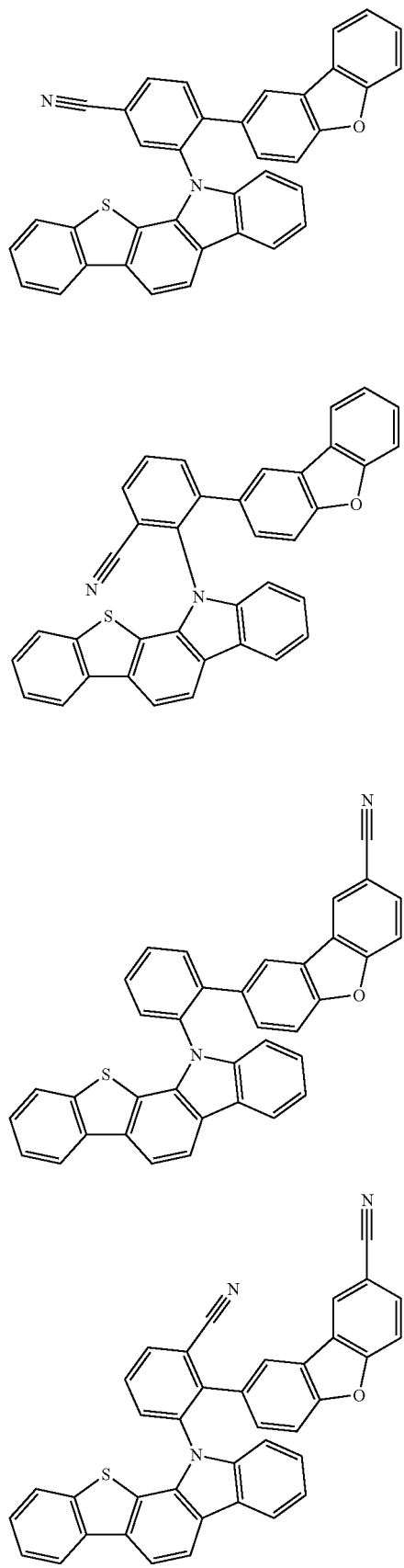
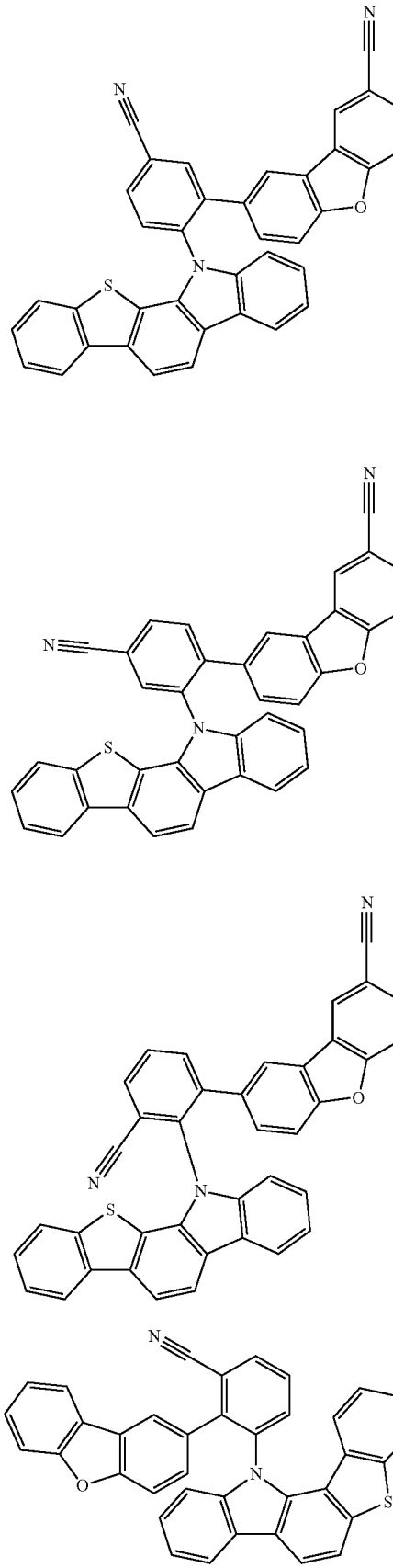

-continued

475 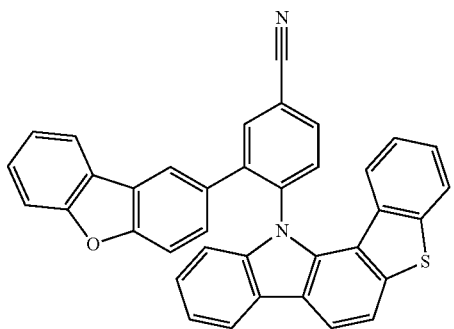

476 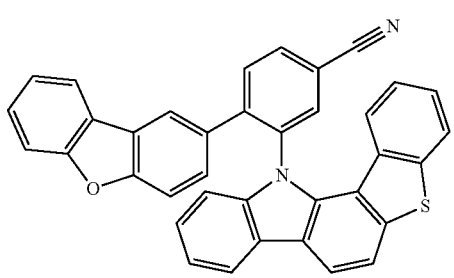

477 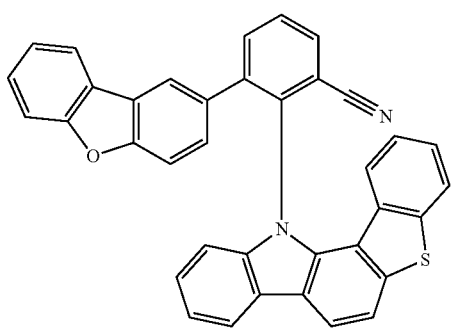

478 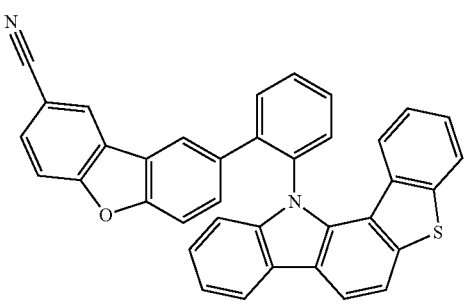

479 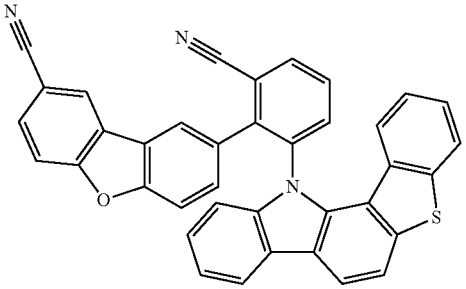

-continued

480 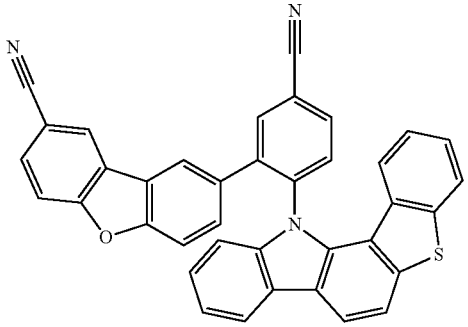

481 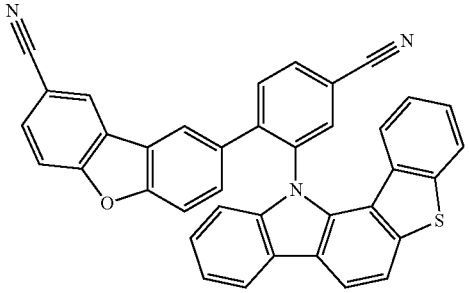

482 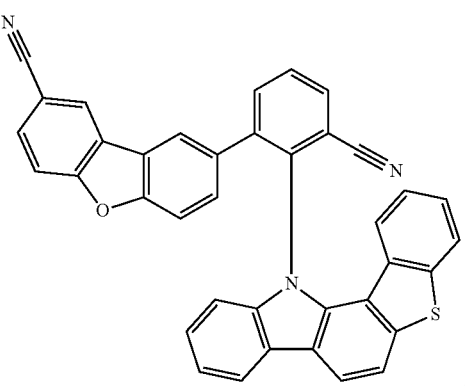

15. An organic light-emitting device comprising:
    a first electrode;
    a second electrode; and
    an organic layer disposed between the first electrode and the second electrode,
    wherein the organic layer comprises an emission layer and at least one condensed cyclic compound represented by Formula 1 of claim 1.
16. The organic light-emitting device of claim 15, wherein
    the first electrode is an anode,
    the second electrode is a cathode, and
    the organic layer comprises a hole transport region disposed between the first electrode and the emission layer, and an electron transport region disposed between the emission layer and the second electrode,
    wherein the hole transport region comprises at least one selected from a hole injection layer, a hole transport layer and an electron blocking layer, and
    wherein the electron transport region comprises at least one selected from a hole blocking layer, an electron transport layer and an electron injection layer.
17. The organic light-emitting device of claim 15, wherein the emission layer comprises the at least one condensed cyclic compound represented by Formula 1.

18. The organic light-emitting device of claim 15, wherein the emission layer comprises the at least one condensed cyclic compound represented by Formula 1 and a phosphorescent dopant,
wherein an amount of the at least one condensed cyclic compound is greater than an amount of the phosphorescent dopant.

19. The organic light-emitting device of claim 17, wherein the emission layer emits blue light.

20. A condensed cyclic compound represented by Formula 1:

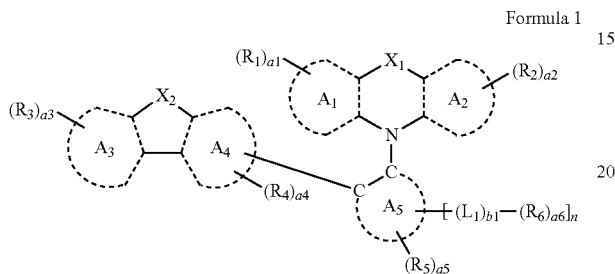

Formula 1 wherein, in Formula 1,
$X_1$ is selected from a single bond, O, S, $N(R_{11})$ and $C(R_{12})(R_{13})$,
$X_2$ is O or S,
ring $A_1$ to ring $A_4$ are each independently a $C_5$-$C_{60}$ carbocyclic group or a $C_2$-$C_{60}$ heterocyclic group,
ring $A_5$ is selected from a benzene, a pyridine, a pyrimidine, a pyrazine, a pyridazine and a triazine,
provided that when n is 0,
1) ring $A_1$ to ring $A_5$ are not simultaneously a benzene, or
2) i) one or more of groups $R_1$ in the number of a1, ii) one or more groups $R_2$ in the number of a2, iii) one or more of groups $R_3$ in the number of a3, iv) one or more groups $R_4$ in the number of a4, v) one or more of groups $R_5$ in the number of a5, or vi) any combination thereof are each independently a cyano group-substituted $C_6$-$C_{10}$ aryl group,
$R_1$ to $R_6$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$) and —B($Q_6$)($Q_7$),
a1 is an integer of 1 to 4,
a2 to a6 are each independently an integer of 0 to 4,
$L_1$ is selected from
a phenylene group, a pyridinylene group, a pyrimidinylene group, a pyrazinylene group, a pyridazinylene group and a triazinylene group; and
a phenylene group, a pyridinylene group, a pyrimidinylene group, a pyrazinylene group, a pyridazinylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$),
b1 is an integer of 1 to 3,
n is an integer of 0 to 3,
the number of cyano groups in Formula 1 is 2, 3 or 4,
provided that, when one group of $R_5$ in the number of a5 is a cyano group, one or more of groups $R_3$ in the number of a3 and one or more of groups $R_4$ in the number of a4 are not a cyano group,
at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group and substituted monovalent non-aromatic condensed heteropolycyclic group is selected from
a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;
a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$); and $Q_1$ to $Q_{10}$, $Q_{11}$ to $Q_{17}$, $Q_{21}$ to $Q_{27}$ and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group and a substituted or unsubstituted monovalent non-aromatic condensed heteropolycyclic group.

21. A condensed cyclic compound represented by Formula 1:

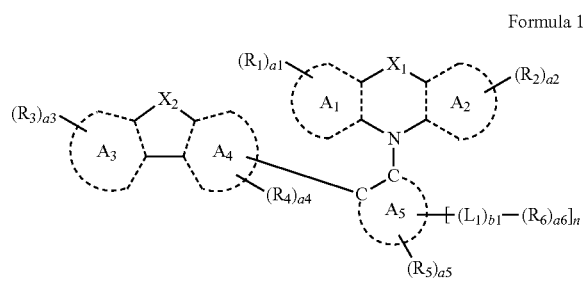

Formula 1 wherein, in Formula 1, $X_1$ is selected from a single bond, O, S, N($R_{11}$) and C($R_{12}$)($R_{13}$), $X_2$ O or S, ring $A_1$ to ring $A_4$ are each independently a $C_5$-$C_{60}$ carbocyclic group or a $C_2$-$C_{60}$ heterocyclic group, and at least one of ring $A_1$ to ring $A_4$ is each independently a fluorene, a carbazole, a dibenzofuran or a dibenzothiophene, ring $A_5$ is selected from a benzene, a pyridine, a pyrimidine, a pyrazine, a pyridazine and a triazine, $R_1$ to $R_6$ and $R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$) and —B($Q_6$)($Q_7$), a1 is an integer of 1 to 4, a2 to a6 are each independently an integer of 0 to 4, $L_1$ is selected from a phenylene group, a pyridinylene group, a pyrimidinylene group, a pyrazinylene group, a pyridazinylene group and a triazinylene group; and a phenylene group, a pyridinylene group, a pyrimidinylene group, a pyrazinylene group, a pyridazinylene group and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group and —Si($Q_8$)($Q_9$)($Q_{10}$), b1 is an integer of 1 to 3, n is an integer of 0 to 3, the number of cyano groups in Formula 1 is 1, 2, 3 or 4, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_1$-$C_{60}$ heteroaryloxy group, substituted $C_1$-$C_{60}$ heteroarylthio group, substituted $C_2$-$C_{60}$ heteroarylalkyl group, substituted monovalent non-aromatic condensed polycyclic group and substituted monovalent non-aromatic condensed heteropolycyclic group is selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$) and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_1$-$C_{60}$ heteroaryloxy group, a $C_1$-$C_{60}$ heteroarylthio group, a $C_2$-$C_{60}$ heteroarylalkyl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$) and —B($Q_{26}$)($Q_{27}$); and —Si($Q_{31}$)($Q_{32}$)($Q_{33}$), —N($Q_{34}$)($Q_{35}$) and —B($Q_{36}$)($Q_{37}$); and $Q_1$ to $Q_{10}$, $Q_{11}$ to $Q_{17}$, $Q_{21}$ to $Q_{27}$ and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted $C_2$-$C_{60}$ heteroarylalkyl group, a substituted or unsubstituted monovalent non-aromatic condensed polycyclic group and a substituted or unsubstituted monovalent non-aromatic condensed heteropolycyclic group.

* * * * *